(12) United States Patent
Mogi et al.

(10) Patent No.: US 8,759,365 B2
(45) Date of Patent: Jun. 24, 2014

(54) ORGANIC COMPOUNDS

(75) Inventors: Muneto Mogi, Cambridge, MA (US);
Toshio Kawanami, Cambridge, MA (US); Ken Yamada, Cambridge, MA (US); Kayo Yasoshima, Cambridge, MA (US); Hidetomo Imase, Cambridge, MA (US); Takahiro Miyake, Kobe (JP); Osamu Ohmori, Izunokuni (JP)

(73) Assignee: Novartis AG, Basel (CH)

( * ) Notice: Subject to any disclaimer, the term of this patent is extended or adjusted under 35 U.S.C. 154(b) by 240 days.

(21) Appl. No.: 12/745,105

(22) PCT Filed: Dec. 1, 2008

(86) PCT No.: PCT/EP2008/066537
§ 371 (c)(1),
(2), (4) Date: May 27, 2010

(87) PCT Pub. No.: WO2009/071509
PCT Pub. Date: Jun. 11, 2009

(65) Prior Publication Data
US 2010/0311750 A1 Dec. 9, 2010

Related U.S. Application Data

(60) Provisional application No. 60/991,891, filed on Dec. 3, 2007.

(51) Int. Cl.
| | |
|---|---|
| A61K 31/5377 | (2006.01) |
| A61K 31/506 | (2006.01) |
| A61K 31/41 | (2006.01) |
| A61K 31/40 | (2006.01) |
| C07D 413/14 | (2006.01) |
| C07D 405/14 | (2006.01) |
| C07D 401/12 | (2006.01) |
| C07D 401/14 | (2006.01) |
| C07D 403/12 | (2006.01) |
| C07D 207/14 | (2006.01) |

(52) U.S. Cl.
USPC ........ 514/275; 514/235.8; 514/423; 514/381; 544/122; 544/331; 544/332; 544/324; 548/251; 548/530

(58) Field of Classification Search
USPC ............... 514/275, 235.8, 423, 381; 544/122, 544/331, 332, 324; 548/251, 530
See application file for complete search history.

(56) References Cited

U.S. PATENT DOCUMENTS

| | | | |
|---|---|---|---|
| 2003/0096818 A1 | 5/2003 | Sikorski et al. |
| 2006/0063803 A1 | 3/2006 | Ruggeri et al. |
| 2006/0135551 A1 | 6/2006 | Baruah et al. |
| 2006/0148830 A1 | 7/2006 | Terakado et al. |
| 2006/0270675 A1 | 11/2006 | Groneberg et al. |
| 2006/0270705 A1 | 11/2006 | Yonemori et al. |
| 2007/0010529 A1 | 1/2007 | Takahashi et al. |
| 2007/0032485 A1 | 2/2007 | Kubota et al. |
| 2007/0173526 A1 | 7/2007 | Bell et al. |
| 2009/0118287 A1 | 5/2009 | Mogi et al. |
| 2009/0286790 A1 | 11/2009 | Imase et al. |
| 2009/0292125 A1 | 11/2009 | Okamoto et al. |

FOREIGN PATENT DOCUMENTS

| | | |
|---|---|---|
| EP | 0 987 251 B1 | 3/2000 |
| JP | 2009/051827 A | 3/2009 |
| JP | 2009/051828 A | 3/2009 |
| WO | WO 00/17165 A1 | 3/2000 |
| WO | WO 00/42011 A1 | 7/2000 |
| WO | WO 01/98344 A2 | 12/2001 |
| WO | WO 02/20016 A1 | 3/2002 |
| WO | WO 03/011837 A1 | 2/2003 |
| WO | 03045942 A2 | 6/2003 |
| WO | 03047569 A1 | 6/2003 |
| WO | WO 03047569 A1 * | 6/2003 |
| WO | WO 2004/031118 A1 | 4/2004 |
| WO | WO 2004050654 A1 * | 6/2004 |
| WO | WO 2004/101529 A1 | 11/2004 |
| WO | WO 2005/033082 A2 | 4/2005 |
| WO | WO 2005/044797 A1 | 5/2005 |

(Continued)

OTHER PUBLICATIONS

Biotechnology and Bioengineering, 1981, vol. XXIII, 1289-1296 by Voloch et al.* Ex parte Cao, Decision rendered by the Board of Patent Appeals and Interferences in U.S. Appl. No. 10/696,862 on Sep. 21, 2011.*
E. E. Stashenko et al: "Mass-spectrometric study of ring-substituted secondary and tertiary gamma-aminopiperidines" Khimiya Geterotsiklicheskikh Soedinenii, No. 3, pp. 380-387, Mar. 1990.

(Continued)

*Primary Examiner* — Joseph Kosack
*Assistant Examiner* — Matthew Coughlin
(74) *Attorney, Agent, or Firm* — Sophie Binet Cross

(57) ABSTRACT

The present invention provides a compound of formula (I): wherein the variants R1, R2, R3, R4, R6, R7 are as defined herein, and wherein said compound is an inhibitor of CETP, and thus can be employed for the treatment of a disorder or disease mediated by CETP or responsive to the inhibition of CETP.

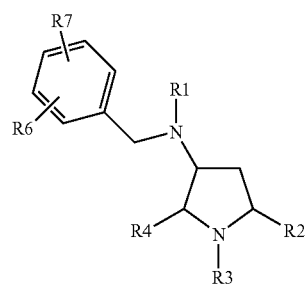

(I)

12 Claims, No Drawings

(56) References Cited

FOREIGN PATENT DOCUMENTS

| | | |
|---|---|---|
| WO | WO 2005/095409 A2 | 10/2005 |
| WO | WO 2005/097806 A1 | 10/2005 |
| WO | WO 2006/033002 A1 | 3/2006 |
| WO | WO 2006/134378 A1 | 12/2006 |
| WO | WO 2007/088999 A1 | 8/2007 |
| WO | WO 2007/107843 A1 | 9/2007 |
| WO | WO 2008/009435 A1 | 1/2008 |
| WO | WO 2009/059943 A1 | 5/2009 |
| WO | WO 2009/071701 A1 | 6/2009 |

OTHER PUBLICATIONS

N. S. Prostakov et al: "Benzylation of gamma-(N-arylamino)piperidines by the Wallach Method" Khimiya Geterotsiklicheskikh Soedinenii, vol. 8, 1988, pp. 1078-1083, XP009078378.

V. V. Kuznetsov et al: "I-Methyl(benzyl)-2,5-dimethyl-4-N-[4aryl(alkyl)amino]piperidines and their N-acyl derivatives" Khimiya Geterotsiklicheskikh Soedinenii, No. 7, pp. 949-953, Jul. 1987.

Vartanyan R S et al: "4-Anilides of 1-Substituted 2,5-Dimethylpiperidines: Synthesis and Analgesic Activity" Khimiko-Farmatsevticheskii Zhurnal, Moscow, RU, vol. 23, No. 5, 1989, pp. 562-565.

Weis R et al: "Synthesis of 2-substituted bamipine derivatives" Tetrahedron, Elsevier Science Publishers, Amsterdam, NL, vol. 59, No. 9, 2003, 1395-1402.

File Registry (STN), Jun. 25, 2009, RN:1160065-09-7.

Okumura et al., "Synthesis and Antiinflammatory Activity of a Series 1-Aryl-2-pyrrolidinone Derivatives," Journal of Medicinal Chemistry 9(3):315-319 (1966).

* cited by examiner

ORGANIC COMPOUNDS

This application is a U.S. national Phase filing of International Serial No. PCT/EP2008/066537 filed Dec. 1, 2008, and claims priority to the U.S. Provisional application Ser. No. 60/991,891 filed Dec. 3, 2007.

The present invention related to novel compound of formula (I):

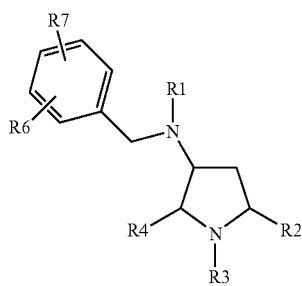

R1 is cycloalkyl, heterocyclyl, aryl, alkyl-O—C(O)—, alkanoyl, or alkyl, wherein each cycloalkyl, heterocyclyl, or aryl is optionally substituted with one to three substituents selected from alkyl, aryl, haloalkyl, hydroxy, halogen, nitro, carboxy, thiol, cyano, $HSO_3$—, cycloalkyl, alkenyl, alkoxy, cycloalkoxy, alkenyloxy, alkyl-O—C(O)—, alkanoyl, carbamoyl, alkyl-S—, alkyl-SO—, alkyl-$SO_2$—, amino, mono- or di-substituted (alkyl, cycloalkyl, aryl and/or aryl-alkyl-) amino, $H_2N$—$SO_2$—, or heterocyclyl, and wherein each alkanoyl, alkyl-O—C(O)—, alkyl, alkoxy, or heterocyclyl is further optionally substituted with one to three substituents selected from hydroxy, alkyl, halogen, nitro, carboxy, thiol, cyano, $HSO_3$—, cycloalkyl, alkenyl, alkoxy, cycloalkoxy, alkenyloxy, alkyl-O—C(O)—, alkanoyl, carbamoyl, alkyl-S—, alkyl-SO—, alkyl-$SO_2$—, amino, mono- or di-substituted (alkyl, cycloalkyl, aryl and/or aryl-alkyl-)amino, $H_2N$—$SO_2$—, or heterocyclyl;

R2 is hydrogen, alkyl, cycloalkyl, or cycloalkyl-alkyl-, wherein each alkyl, cycloalkyl or alkoxy is optionally substituted with one to three substituents selected from alkyl, alkoxy or halogen;

R3 is R8-O—C(O)—, (R8)(R9)N—C(O)—, R8-C(O)—, aryl, heterocyclyl or heteroaryl,
wherein R8 and R9 are independently hydrogen, alkyl, —C(O)O-alkyl, alkyl-O(O)C-alkyl-, amino-(O)C-alkyl-, cycloalkyl, aryl, heteroaryl, heterocyclyl, aryl-alkyl-, heteroaryl-alkyl-, heterocyclyl-alkyl-, cycloalkyl-alkyl-, alkyl-O—C(O)—, or carboxy, wherein each amino, alkyl, cycloalkyl, aryl, aryl-alkyl-, cycloalkyl-alkyl- or heteroaryl is optionally substituted with one to three substituents selected from alkyl, hydroxy, halogen, nitro, carboxy, thiol, cyano, $HSO_3$—, cycloalkyl, alkenyl, alkoxy, cycloalkoxy, alkenyloxy, alkyl-haloalkyl, alkyl-O—C(O)—, alkanoyl, carbamimidoyl, alkyl-S—, alkyl-SO—, alkyl-$SO_2$—, amino, $H_2N$—$SO_2$—, cycloalkyl, heterocyclyl, alkyl-O—C(O)-alkyl-, and HO—C(O)-alkyl-.

R8 and R9 may be taken together to form a 5 or 6-membered heterocyclyl or heteroaryl, which can be substituted with substituents selected from alkyl, hydroxy, halogen, nitro, carboxy, thiol, cyano, $HSO_3$—, cycloalkyl, alkenyl, alkoxy, cycloalkoxy, alkenyloxy, alkyl-haloalkyl, alkyl-O—C(O)—, alkanoyl, carbamimidoyl, alkyl-S—, alkyl-SO—, alkyl-$SO_2$—, amino, $H_2N$—$SO_2$—, HO—C(O)-alkyl-, acetyl, and heterocyclyl;

R4 is hydrogen, alkyl, alkoxy, cycloalkyl, aryl, heteroaryl, aryl-alkyl-, cycloalkyl-alkyl-, or heteroaryl-alkyl-, wherein each alkyl, cycloalkyl, aryl, heteroaryl, aryl-alkyl-, cycloalkyl-alkyl-, or heteroaryl-alkyl- is optionally substituted with one to three substituents selected from alkyl, hydroxy, halogen, haloalkyl, nitro, carboxy, thiol, cyano, $HSO_3$—, cycloalkyl, alkenyl, alkoxy, cycloalkoxy, haloalkoxy, alkenyloxy, alkyl-O—C(O)—, alkanoyl, carbamimidoyl, alkyl-S—, alkyl-SO—, alkyl-$SO_2$—, amino, mono- or di-substituted (alkyl, cycloalkyl, aryl and/or aryl-alkyl-) amino, $H_2N$—$SO_2$—, heterocyclyl;

R6 and R7 are independently hydrogen, alkyl, haloalkyl, halogen, cyano, nitro, hydroxy, amino, dialkylamino, or alkoxy, haloalkoxy; or R6 is aryl, heteroaryl, or alkyl-$S(O)_2$—, wherein each aryl or heteroaryl is optionally substituted with one to three substituents selected from alkyl, hydroxy, halogen, nitro, carboxy, thiol, cyano, $HSO_3$—, cycloalkyl, alkenyl, alkoxy, cycloalkoxy, alkenyloxy, alkyl-O—C(O)—, alkanoyl, carbamimidoyl, alkyl-S—, alkyl-SO—, alkyl-$SO_2$—, amino, $H_2N$—$SO_2$— heterocyclyl;

or a pharmaceutically acceptable salt thereof; or an optical isomer thereof; or a mixture of optical isomers.

The present invention also relates to a process for the preparation of these compounds, to the use of these compounds and to pharmaceutical preparations containing such a compound I in free form or in the form of a pharmaceutically acceptable salt.

Extensive pharmacological investigations have shown that the compounds I and their pharmaceutically acceptable salts, for example, have pronounced selectivity in inhibiting CETP (cholesteryl ester transfer protein). CETP is involved in the metabolism of any lipoprotein in living organisms, and has a major role in the reverse cholesterol transfer system. Namely, CETP has drawn attention as a mechanism for preventing accumulation of cholesterol in peripheral cells and preventing arteriosclerosis. In fact, with regard to HDL having an important role in this reverse cholesterol transfer system, a number of epidemiological researches have shown that a decrease in CE (cholesteryl ester) of HDL in blood is one of the risk factors of coronary artery diseases. It has been also clarified that the CETP activity varies depending on the animal species, wherein arteriosclerosis due to cholesterol-loading is hardly induced in animals with lower activity, and in reverse, easily induced in animals with higher activity, and that hyper-HDL-emia and hypo-LDL (low density lipoprotein)-emia are induced in the case of CETP deficiency, thus rendering the development of arteriosclerosis difficult, which in turn led to the recognition of the significance of blood HDL, as well as significance of CETP that mediates transfer of CE in HDL into blood LDL. While many attempts have been made in recent years to develop a drug that inhibits such activity of CETP, a compound having a satisfactory activity has not been developed yet.

DETAILED DESCRIPTION OF THE INVENTION

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. When an alkyl group includes one or more unsaturated bonds, it can be referred to as an alkenyl (double bond) or an alkynyl (triple bond) group. If the alkyl group can be substituted, it is preferably substituted by 1, 2 or 3 substituents selected from hydroxy, halogen, nitro, carboxy, thiol, cyano, $HSO_3$—, cycloalkyl, alkenyl, alkoxy, cycloalkoxy, alkenyloxy, alkoxycarbonyl, carbamimidoyl, alkyl-S—, alkyl-SO—, alkyl-$SO_2$—, amino, $H_2N$—$SO_2$—, alkanoyl, or heterocyclyl, more preferably selected from hydroxy, halogen, nitro, carboxy, thiol, cyano, alkoxy, or amino.

The term "aryl" refers to monocyclic or bicyclic aromatic hydrocarbon groups having 6-20 carbon atoms in the ring portion. Preferably, the aryl is a ($C_6$-$C_{10}$) aryl. Non-limiting examples include phenyl, biphenyl, naphthyl or tetrahydronaphthyl, most preferably phenyl, each of which may optionally be substituted by 1-4 substituents, such as alkyl, haloalkyl such as trifluoromethyl, cycloalkyl, halogen, hydroxy, alkoxy, alkyl-C(O)—O—, aryl-O—, heteroaryl-O—, amino, acyl, thiol, alkyl-S—, aryl-S—, nitro, cyano, carboxy, alkyl-O—C(O)—, carbamoyl, alkyl-S(O)—, sulfonyl, sulfonamido, heterocyclyl, alkenyl, haloalkoxy, cycloalkoxy, alkenyloxy, alkoxycarbonyl, alkyl-SO—, alkyl-$SO_2$—, amino, mono- or di-substituted (alkyl, cycloalkyl, aryl and/or aryl alkyl)amino or $H_2N$—$SO_2$.

Furthermore, the term "aryl" as used herein, refers to an aromatic substituent which can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-7, more preferably about 1-4 carbons.

As used herein, the term "acyl" refers to a group R—C(O)— of from 1 to 10 carbon atoms of a straight, branched, or cyclic configuration or a combination thereof, attached to the parent structure through carbonyl functionality. Such group can be saturated or unsaturated, and aliphatic or aromatic. Preferably, R in the acyl residue is alkyl, or alkoxy, or aryl, or heteroaryl. When R is alkyl then the moiety is referred to a alkanoyl. Also preferably, one or more carbons in the acyl residue may be replaced by nitrogen, oxygen or sulfur as long as the point of attachment to the parent remains at the carbonyl. Examples include but are not limited to, acetyl, benzoyl, propionyl, isobutyryl, t-butoxycarbonyl, benzyloxycarbonyl and the like. Lower acyl refers to acyl containing one to four carbons.

As used herein, the term "acylamino" refers to acyl-NH—, wherein "acyl" is defined herein.

As used herein, the term "carbamoyl" refers to $H_2$NC(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aryl-alkyl-NHC(O)—, alkyl(aryl-alkyl)-NC(O)— and the like.

As used herein, the term "sulfonyl" refers to R—$SO_2$—, wherein R is hydrogen, alkyl, aryl, hereoaryl, aryl-alkyl, heteroaryl-alkyl, aryl-O—, heteroaryl-O—, alkoxy, aryloxy, cycloalkyl, or heterocyclyl.

As used herein, the term "sulfonamido" refers to alkyl-S(O)$_2$—NH—, aryl-S(O)$_2$—NH—, aryl-alkyl-S(O)$_2$—NH—, heteroaryl-S(O)$_2$—NH—, heteroaryl-alkyl-S(O)$_2$—NH—, alkyl-S(O)$_2$—N(alkyl)-, aryl-S(O)$_2$—N(alkyl)-, aryl-alkyl-S(O)$_2$—N(alkyl)-, heteroaryl-S(O)$_2$—N(alkyl)-, heteroaryl-alkyl-S(O)$_2$—N(alkyl)- and the like.

As used herein, the term "alkoxycarbonyl" or "alkyl-O—C(O)—" refers to alkoxy-C(O)—, wherein alkoxy is defined herein.

As used herein, the term "alkanoyl" refers to alkyl-C(O)—, wherein alkyl is defined herein.

As used herein, the term "alkenyl" refers to a straight or branched hydrocarbon group having 2 to 20 carbon atoms and that contains at least one double bonds. The alkenyl groups preferably have about 2 to 8 carbon atoms.

As used herein, the term "alkenyloxy" refers to alkenyl-O—, wherein alkenyl is defined herein.

As used herein, the term "cycloalkoxy" refers to cycloalkyl-O—, wherein cycloalkyl is defined herein.

As used herein, the term "heterocyclyl" or "heterocyclo" refers to an optionally substituted, fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, piperazinyl, piperidinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

When heterocyclyl is aromatic, this moiety is referred to as "heteroaryl".

As used herein, the term "heteroaryl" refers to a 5-14 membered monocyclic- or bicyclic- or fused polycyclic-ring system, having 1 to 8 heteroatoms selected from N, O or S. Preferably, the heteroaryl is a 5-10 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl; each of which may optionally be substituted by 1-4 substituents, such as alkyl, haloalkyl such as trifluoromethyl, substituted or unsubstituted cycloalkyl, halogen, hydroxy, alkoxy, alkyl-C(O)—O—, aryl-O—, heteroaryl-O—, amino, acyl, thiol, alkyl-S—, aryl-S—, nitro, cyano, carboxy, alkyl-O—C(O)—, carbamoyl, alkyl-S(O)—, sulfonyl, sulfonamido, substituted or unsubstituted heterocyclyl, alkenyl, haloalkoxy, cycloalkoxy, alkenyloxy, alkoxycarbonyl, alkyl-SO—, alkyl-SO$_2$—, amino, mono- or di-substituted (alkyl, cycloalkyl, aryl and/or aryl alkyl)amino or H$_2$N—SO$_2$.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinolinyl, 1-, 3-, 4-, 5-, 6-, 7-, or 8-isoquinolinyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoquinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazepinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

A heteroaryl group may be mono-, bi-, tri-, or polycyclic, preferably mono-, bi-, or tricyclic, more preferably mono- or bicyclic.

The term "heterocyclyl" further refers to heterocyclic groups as defined herein substituted with 1, 2 or 3 substituents selected from the groups consisting of the following:

alkyl; haloalkyl, hydroxy (or protected hydroxy); halo; oxo, i.e., =O; amino, mono- or di-substituted (alkyl, cycloalkyl, aryl and/or aryl alkyl)amino such as alkylamino or dialkylamino; alkoxy; cycloalkyl; alkenyl; carboxy; heterocyclooxy, wherein heterocyclooxy denotes a heterocyclic group bonded through an oxygen bridge; alkyl-O—C(O)—; mercapto; HSO$_3$; nitro; cyano; sulfamoyl or sulfonamido; aryl; alkyl-C(O)—O—; aryl-C(O)—O—; aryl-S—; cycloalkoxy; alkenyloxy; alkoxycarbonyl; aryloxy; carbamoyl; alkyl-S—; alkyl-SO—, alkyl-SO$_2$—; formyl, i.e., HC(O)—; aryl-alkyl-; acyl such as alkanoyl; heterocyclyl and aryl substituted with alkyl, cycloalkyl, alkoxy, hydroxy, amino, alkyl-C(O)—NH—, alkylamino, dialkylamino or halogen.

As used herein, the term "cycloalkyl" refers to optionally substituted saturated or unsaturated monocyclic, bicyclic or tricyclic hydrocarbon groups of 3-12 carbon atoms, each of which may be substituted by one or more substituents, such as alkyl, halo, oxo, hydroxy, alkoxy, alkanoyl, acylamino, carbamoyl, alkyl-NH—, (alkyl)$_2$N—, thiol, alkylthio, nitro, cyano, carboxy, alkyl-O—C(O)—, sulfonyl, sulfonamido, sulfamoyl, heterocyclyl and the like. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "sulfamoyl" refers to H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aryl-alkyl-NHS(O)$_2$—, heteroaryl-alkyl-NHS(O)$_2$— and the like.

As used herein, the term "aryloxy" refers to both an —O-aryl and an —O— heteroaryl group, wherein aryl and heteroaryl are defined herein.

As used herein, the term "halogen" or "halo" refers to fluoro, chloro, bromo, and iodo.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Preferably, the polyhaloalkyl contains up to 12, 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "dialkylamino" refers to an to an amino group which is di-substituted by alkyl, whereby the alkyl can be the same or different, as defined herein. Preferably the dialkylamino can have the same alkyl substitutent. Non-limiting examples of dialkylamino include dimethylamino, diethylamino and diisopropylamino.

As used herein, the term "aryl alkyl" is interchangeable for "aryl-alkyl-", wherein aryl and alkyl are defined herein.

As used herein, the term "cycloalkyl-alkyl-" is interchangeable for "cycloalkyl alkyl", wherein cycloalkyl and alkyl are defined herein.

As used herein, the term "isomers" refers to different compounds that have the same molecular formula. Also as used herein, the term "an optical isomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which are not biologically or otherwise undesirable. Non-limiting examples of the salts include non-toxic, inorganic and organic base or acid addition salts of compounds of the present invention. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in *Remington's Pharmaceutical Sciences*, 20th ed., Mack Publishing Company, Easton, Pa., (1985).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329. Except insofar as any conventional carrier is incompatible with the active ingredient, its use in the therapeutic or pharmaceutical compositions is contemplated.

The term "therapeutically effective amount" of a compound of the present invention refers to an amount of the compound of the present invention that will elicit the biological or medical response of a subject, or ameliorate symptoms, slow or delay disease progression, or prevent a disease, etc. In a preferred embodiment, the "effective amount" refers to the amount that inhibits or reduces expression or activity of CETP.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "a disorder" or "a disease" refers to any derangement or abnormality of function; a morbid physical or mental state. See *Dorland's Illustrated Medical Dictionary*, (W.B. Saunders Co. 27th ed. 1988).

As used herein, the term "inhibition" or "inhibiting" refers to the reduction or suppression of a given condition, symptom, or disorder, or disease, or a significant decrease in the baseline activity of a biological activity or process. Preferably, the condition or symptom or disorder or disease is mediated by CETP activity or responsive to the inhibition of CETP.

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The following preferred embodiments of the moieties and symbols in formula I can be employed independently of each other to replace more general definitions and thus to define specially preferred embodiments of the invention, where the remaining definitions can be kept broad as defined in embodiments of the inventions defined above of below.

Various embodiments of the invention are described below. It will be appreciated that the features specified in each embodiment may be combined with other specified features, to provide further embodiments.

In one embodiment, the invention is related to a compound of formula I wherein
R1 is heterocyclyl, aryl, alkoxycarbonyl, alkanoyl, or alkyl, wherein each heterocyclyl or aryl is optionally substituted with one to three substituents selected from alkyl, haloalkyl, hydroxy, halogen, nitro, carboxy, thiol, cyano, HSO$_3$—, cycloalkyl, alkenyl, alkoxy, cycloalkoxy, alkenyloxy, alkoxycarbonyl, carbamoyl, alkyl-S—, alkyl-SO—, alkyl-SO$_2$—, amino, H$_2$N—SO$_2$—, alkanoyl, or heterocyclyl; and wherein each alkanoyl, alkoxycarbonyl, or alkyl is optionally substituted with one to three substituents selected from hydroxy, halogen, nitro, carboxy, thiol, cyano, HSO$_3$—, cycloalkyl, alkenyl, alkoxy, cycloalkoxy, alkenyloxy, alkoxycarbonyl, carbamoyl, alkyl-S—, alkyl-SO—, alkyl-SO$_2$—, amino, H$_2$N—SO$_2$—, alkanoyl, or heterocyclyl;
R2 is alkyl;
R3 is R8-O—C(O)—, (R8)(R9)N—C(O)—, R8-C(O)—, R8-S(O)$_2$—, alkyl, cycloalkyl, heteroaryl, or aryl-alkyl-;
R4 is hydrogen, aryl-alkyl-, cycloalkyl-alkyl- or heteroaryl-alkyl-, wherein each aryl, cycloalkyl or heteroaryl is optionally substituted with one to three substituents selected from alkyl, haloalkyl, hydroxy, halogen, nitro, carboxy, thiol, cyano, HSO$_3$—, cycloalkyl, alkenyl, alkoxy, haloalkoxy, cycloalkoxy, alkenyloxy, alkoxycarbonyl, alkyl-S—, alkyl-SO—, alkyl-SO$_2$—, amino, mono- or di-substituted (alkyl, cycloalkyl, aryl and/or aryl-alkyl-) amino; H$_2$N—SO$_2$—, or alkanoyl;
R6 and R7 are independently hydrogen, alkyl, haloalkyl, halogen, cyano, nitro, hydroxy, dialkylamino or alkoxy; or
R6 is aryl or heteroaryl;
R8 is hydrogen, alkyl, cycloalkyl, aryl, aryl-alkyl- or cycloalkyl-alkyl-; or
a pharmaceutically acceptable salt thereof; or an optical isomer thereof; or a mixture of optical isomers.
Preferred Definitions for R1

Preferably, R1 is heterocyclyl, aryl, alkoxycarbonyl, alkanoyl, or alkyl, wherein each heterocyclyl or aryl is optionally substituted with one to three substituents selected from alkyl, haloalkyl, hydroxy, halogen, nitro, carboxy, thiol, cyano, HSO$_3$—, cycloalkyl, alkenyl, alkoxy, cycloalkoxy, alkenyloxy, alkoxycarbonyl, carbamoyl, alkyl-S—, alkyl-SO—, alkyl-SO$_2$—, amino, H$_2$N—SO$_2$—, alkanoyl, or heterocyclyl; and wherein each alkanoyl, alkoxycarbonyl, or alkyl is optionally substituted with one to three substituents selected from hydroxy, halogen, nitro, carboxy, thiol, cyano, HSO$_3$—, cycloalkyl, alkenyl, alkoxy, cycloalkoxy, alkenyloxy, alkoxycarbonyl, carbamoyl, alkyl-S—, alkyl-SO—, alkyl-SO$_2$—, amino, H$_2$N—SO$_2$—, alkanoyl, or heterocyclyl. More preferably, R1 is heterocyclyl, such as heteroaryl, alkanoyl or alkoxycarbonyl, wherein each heterocyclyl is optionally substituted with one to three substituents selected from alkyl, hydroxy, halogen, nitro, carboxy, thiol, cyano, HSO$_3$—, cycloalkyl, alkenyl, alkoxy, cycloalkoxy, alkenyloxy, alkoxycarbonyl, carbamoyl, alkyl-S—, alkyl-SO—, alkyl-SO$_2$—, amino, H$_2$N—SO$_2$—, alkanoyl, or heterocyclyl, more preferably alkyl, hydroxy, halogen, carboxy, alkoxy, amino, alkanoyl or heterocyclyl. Preferred examples for the heterocyclyl substituent of the heterocyclyl moiety for R1 is a 5- to 6-membered ring containing at least one heteroatom selected from O, N or S, more preferably N, most preferably it has more than one nitrogen in the ring, such as pyrazole and tetrazole.

A preferred meaning of variable R1 is heteroaryl as preferably represented by formulae

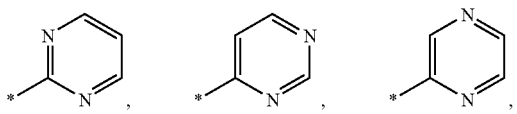 [SMILES: *c1ncccn1 ; "," ; *c1ccncn1 ; "," ; *c1cnccn1 ; ","]

or pyridyl, especially

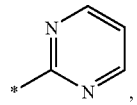

which are each unsubstituted or substituted by $C_1$-$C_4$-alkyl, especially methyl or halo, especially Br, or is $C_1$-$C_4$-alkoxycarbonyl, $C_1$-$C_4$-alkyl-carbonyl, or is heterocyclyl such as pyrrolidyl, piperidyl, piperazinyl, pyrazoyl, methylpyrazoyl or morpholinyl, especially methylpyrazoyl. For example R1 may be

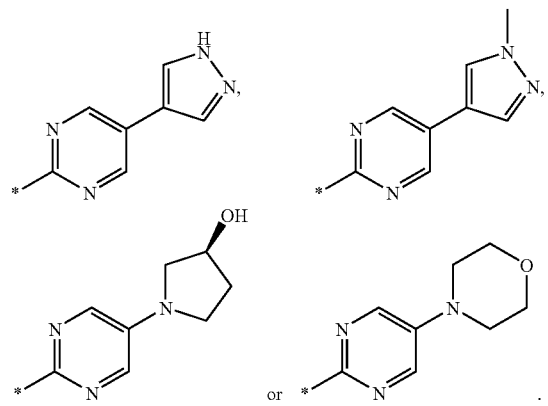

Preferred Definitions for R2

Preferably, R2 is straight chain or branched $C_1$-$C_6$ alkyl as defined herein. Examples include methyl, ethyl, isopropyl, n-propyl, isobutyl, n-butyl or sec-butyl, more preferably ethyl or isobutyl, most preferably ethyl.
Preferred Definitions for R3

Preferably R3 is alkyl-O—C(O)—, cycloalkyl-O—C(O)—, aryl-alkyl-O—C(O)—, (alkyl)$_2$N—C(O)—, alkanoyl, aryl-alkyl-C(O)—, alkyl-S(O)$_2$—, aryl-S(O)$_2$—, alkyl, aryl-alkyl-, or heteroaryl.

Preferred examples of alkyl-O—C(O)— include moieties where alkyl is selected from straight chain or branched, preferably branched, $C_1$-$C_6$ alkyl as defined herein, such as methyl, ethyl, isopropyl, isobutyl or tert-butyl, most preferably isopropyl.

Preferred examples of cycloalkyl-O—C(O)— include moieties where cycloalkyl is selected from $C_3$ to $C_{12}$ cycloalkyl as defined herein, such as cyclohexyl or adamantyl.

Preferred examples of aryl-alkyl-O—C(O)— include moieties where aryl is selected from $C_6$ to $C_{20}$ aryl as defined herein, such as phenyl or naphthyl, more preferably phenyl. Preferred examples of aryl-alkyl-include benzyl, phenethyl, more preferably benzyl.

Preferred examples of (alkyl)$_2$N—C(O)— include moieties where alkyl is selected from straight chain or branched, preferably straight chain, $C_1$-$C_6$ alkyl as defined herein, such as methyl, ethyl, isopropyl, isobutyl or tert-butyl, most preferably methyl or ethyl.

Preferred examples of alkanoyl include moieties where alkyl is selected from straight chain or branched, preferably branched, $C_1$-$C_6$ alkyl as defined herein, such as methyl, ethyl, isopropyl, isobutyl or tert-butyl, most preferably tert-butyl.

Preferred examples of aryl-alkyl-C(O)— include moieties where aryl is selected from $C_6$ to $C_{20}$ aryl as defined herein, such as phenyl or naphthyl, more preferably phenyl. Preferred examples of aryl-alkyl-include benzyl, phenethyl, more preferably benzyl.

Preferred examples of alkyl-S(O)$_2$— include moieties where alkyl is selected from straight chain or branched, preferably branched, $C_1$-$C_6$ alkyl as defined herein, such as methyl, ethyl, isopropyl, isobutyl or tert-butyl, most preferably methyl.

Preferred examples of aryl-S(O)$_2$— include moieties where aryl is selected from $C_6$ to $C_{20}$ aryl as defined herein, such as phenyl or naphthyl, more preferably phenyl.

Preferred examples of alkyl include moieties where alkyl is selected from straight chain or branched, preferably branched, $C_1$-$C_6$ alkyl as defined herein, such as methyl, ethyl, isopropyl, isobutyl or tert-butyl.

Preferred examples of aryl-alkyl-include moieties where aryl is selected from $C_6$ to $C_{20}$ aryl as defined herein, such as phenyl or naphthyl, more preferably phenyl. Preferred examples of aryl-alkyl-include benzyl, phenethyl, more preferably benzyl.

Preferred examples of heteroaryl include where heteroaryl is selected from substituted or unsubstituted pyridyl or pyrimidyl, more preferably substituted pyrimidyl.

Most preferably, R3 is alkyl-O—C(O)— as defined herein.

Preferred Definitions for R4

Preferably R4 is hydrogen, alkyl, cycloalkyl, aryl, heteroaryl, aryl-alkyl-, cycloalkyl-alkyl- or heteroaryl-alkyl-, more preferably hydrogen, aryl-alkyl-, cycloalkyl-alkyl- or heteroaryl-alkyl-, wherein each alkyl, is optionally substituted with one to three substituents selected from hydroxy, halogen, nitro, carboxy, thiol, cyano, HSO$_3$—, cycloalkyl, alkenyl, alkoxy, haloalkoxy, cycloalkoxy, alkenyloxy, alkoxycarbonyl, alkyl-S—, -alkyl-SO—, alkyl-SO$_2$—, amino, mono- or di-substituted (alkyl, cycloalkyl, aryl and/or aryl-alkyl-) amino; H$_2$N—SO$_2$—, or alkanoyl, and wherein each aryl, cycloalkyl or heteroaryl is optionally substituted with one to three substituents selected from alkyl, haloalkyl, hydroxy, halogen, nitro, carboxy, thiol, cyano, HSO$_3$—, cycloalkyl, alkenyl, alkoxy, haloalkoxy, cycloalkoxy, alkenyloxy, alkoxycarbonyl, alkyl-S—, alkyl-SO—, alkyl-SO$_2$—, amino, mono- or di-substituted (alkyl, cycloalkyl, aryl and/or aryl-alkyl-) amino; H$_2$N—SO$_2$—, or alkanoyl.

More preferably R4 is hydrogen, benzyl, or cycloalkyl-CH$_2$—, wherein each benzyl or cycloalkyl is optionally substituted with one to three substituents selected from alkyl, haloalkyl, hydroxy, halogen, nitro, carboxy, thiol, cyano, HSO$_3$—, alkoxy, haloalkoxy, amino, mono- or di-substituted (alkyl, cycloalkyl, aryl and/or aryl-alkyl-) amino; H$_2$N—SO$_2$—, or alkanoyl.

Most preferably, R4 is hydrogen or benzyl.

Preferred Definitions for R6 and R7

Preferably, R6 and R7 are independently hydrogen, alkyl, haloalkyl, halogen, or alkoxy.

More preferably, R6 and R7 are independently hydrogen, alkyl or haloalkyl, such as trifluoromethyl.

In one embodiment, one of R6 and R7 is hydrogen and the other is a group as defined herein other than hydrogen.

In another preferred embodiment, both R6 and R7 are the same and are as defined herein, most preferably trifluoromethyl.

The positions of R6 and R7 on the phenyl ring are preferably as follows:

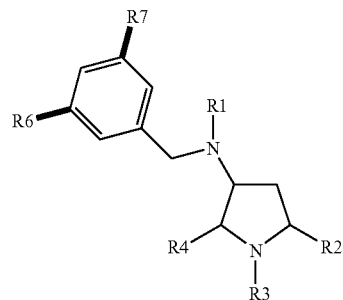

Any asymmetric carbon atom on the compounds of the present invention can be present in the (R)-, (S)- or (R,S)-configuration, preferably in the (R)- or (S)-configuration. Substituents at atoms with unsaturated bonds may, if possible, be present in cis-(Z)- or trans-(E)-form. Therefore, the compounds of the present invention can be in the form of one of the possible isomers or mixtures thereof, for example, as substantially pure geometric (cis or trans) isomers, diastereomers, optical isomers (antipodes), racemates or mixtures thereof.

Preferred isomers of the compound of the present invention can be represented by the following formula:

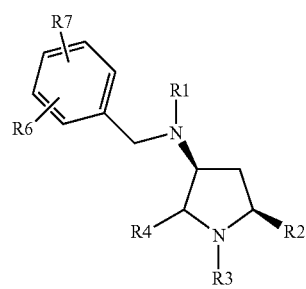

in particular:

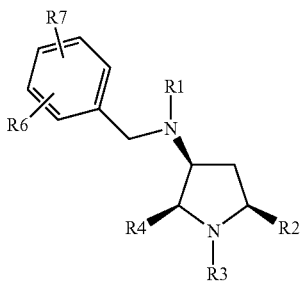

Any resulting mixtures of isomers can be separated on the basis of the physicochemical differences of the constituents, into the pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, the pyrrolidine moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Finally, compounds of the present invention are either obtained in the free form, as a salt thereof, or as prodrug derivatives thereof.

When a basic group is present in the compounds of the present invention, the compounds can be converted into acid addition salts thereof, in particular, acid addition salts with the pyrazole moiety or morpholine moiety of the structure, preferably pharmaceutically acceptable salts thereof. These are formed, with inorganic acids or organic acids. Suitable inorganic acids include but are not limited to, hydrochloric acid, sulfuric acid, a phosphoric or hydrohalic acid. Suitable organic acids include but are not limited to, carboxylic acids, such as $(C_1-C_4)$alkanecarboxylic acids which, for example, are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, organic sulfonic acids, such as $(C_1-C_4)$alkylsulfonic acids, e.g., methanesulfonic acid; or arylsulfonic acids which are unsubstituted or substituted, e.g., by halogen. Preferred are salts formed with hydrochloric acid, methanesulfonic acid and maleic acid.

When an acidic group is present in the compounds of the present invention, the compounds can be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

When both a basic group and an acid group are present in the same molecule, the compounds of the present invention can also form internal salts.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds are inactive or have low activity compared to the corresponding active drug compound, that contains one or more protective groups and are converted to an active form by metabolism or solvolysis. Both the active drug form and any released metabolic products should have acceptably low toxicity. Typically, the formation of active drug compound involves a metabolic process or reaction that is one of the follow types:

1. Oxidative reactions, such as oxidation of alcohol, carbonyl, and acid functions, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-delakylation, oxidative O- and S-delakylation, oxidative deamination, as well as other oxidative reactions.
2. Reductive reactions, such as reduction of carbonyl groups, reduction of alcoholic groups and carbon-carbon double bonds, reduction of nitrogen-containing functions groups, and other reduction reactions.
3. Reactions without change in the state of oxidation, such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. See, Cheng et al., U.S.20040077595, application Ser. No. 10/656, 838. Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxy groups with lipophilic carboxylic acids, or of carboxylic acid groups with alcohols, e.g., aliphatic alcohols. Wermuth, *The Practice of Medicinal Chemistry*, Ch. 31-32, Ed. Werriuth, Academic Press, San Diego, Calif., 2001.

Exemplary prodrugs are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

In view of the close relationship between the compounds, the compounds in the form of their salts and the pro-drugs, any reference to the compounds of the present invention is to be understood as referring also to the corresponding pro-drugs of the compounds of the present invention, as appropriate and expedient.

Furthermore, the compounds of the present invention, including their salts, can also be obtained in the form of their hydrates, or include other solvents used for their crystallization.

The compounds of the present invention have valuable pharmacological properties. The compounds of the present invention are useful as inhibitors for cholesteryl ester transfer protein (CETP). CETP is a 74 KD glycopeptide, it is secreted by the liver and is a key player in facilitating the transfer of lipids between the various lipoproteins in plasma. The primary function of CETP is to redistribute cholesteryl esters (CE) and triglycerides between lipoproteins. See Assmann, G et al., "HDL cholesterol and protective factors in atherosclerosis," *Circulation*, 109: 1118-1114 (2004). Because most triglycerides in plasma originate in VLDLs and most CEs are formed in HDL particles in the reaction catalyzed by lecithin: cholesterol acyltransferase, activity of CETP results in a net mass transfer of triglycerides from VLDLs to LDLs and HDLs and a net mass transfer of CEs from HDLs to VLDLs and LDLs. Thus, CETP potentially decreases HDL-C levels, increases LDL-cholesteryl (LDL-C) levels and reduces HDL and LDL particles size, and inhibition of CETP could be a therapeutic strategy for raising HDL-cholesteryl (HDL-C), have a favorable impact on the lipoprotein profile, and reduce the risk of cardiovascular diseases. Accordingly, the compounds of the present invention as CETP inhibitors are useful for the delay of progression and/or treatment of a disorder or disease that is mediated by CETP or responsive to inhibition of CETP. Disorders, conditions and diseases that can be treated with the compounds of the present invention include but are not limited to, hyperlipidemia, arteriosclerosis, atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorder, coronary heart disease, coronary artery disease, coronary vascular disease, angina, ischemia, heart ischemia, thrombosis, cardiac infarction such as myocardial infarction, stroke, peripheral vascular disease, reperfusion injury, angioplasty restenosis, hypertension, congestive heart failure, diabetes such as type II diabetes mellitus, diabetic vascular complications, obesity, infection or egg embryonation of schistosoma, or endotoxemia etc.

Additionally, the present invention provides:

a compound of the present invention as described herein above for use as a medicament;

the use of a compound of the present invention as described herein above for the preparation of a pharmaceutical composition for the delay of progression and/or treatment of a disorder or disease mediated by CETP, or responsive to inhibition of CETP.

the use of a compound of the present invention as described herein above for the preparation of a pharmaceutical composition for the delay of progression and/or treatment of a disorder or disease selected from hyperlipidemia, arteriosclerosis, atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorder, coronary heart disease, coronary artery disease, coronary vascular disease, angina, ischemia, heart ischemia, thrombosis, cardiac infarction such as myocardial infarction, stroke, peripheral vascular disease, reperfusion injury, angioplasty restenosis, hypertension, congestive heart failure, diabetes such as type II diabetes mellitus, diabetic vascular complications, obesity or endotoxemia etc.

The compounds of formula (I) can be prepared by the procedures described in the following sections.

Generally, the compounds of formula (I) can be prepared according to the following general procedures and schemes. In all these Schemes the variants R1, R2, R3, R4, R5, R6, R7 and R8 have the meaning as set forth herein unless defined otherwise.

1. General Procedure A: Using Alkoxypyrrolidine A1

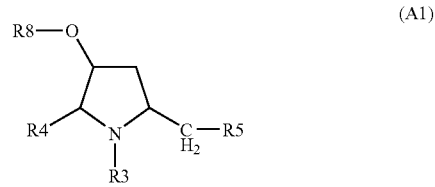

(A1)

1.1. Route AI when R4 is Hydrogen:

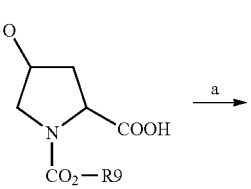

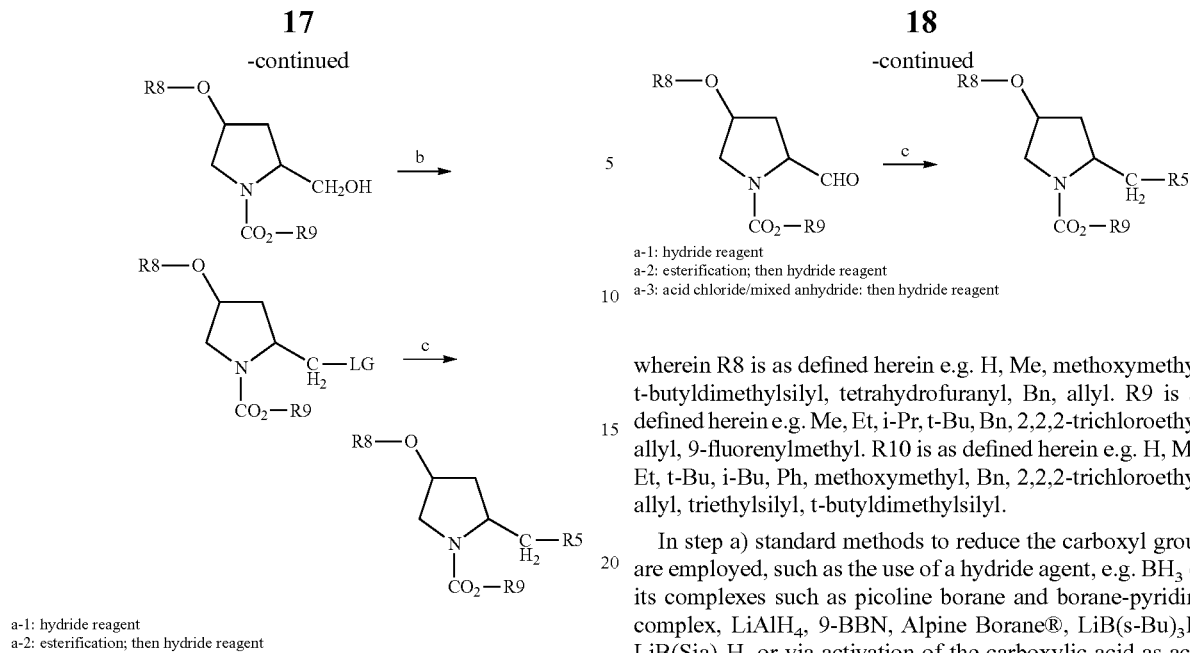

a-1: hydride reagent
a-2: esterification; then hydride reagent
a-3: acid chloride/mixed anhydride: then hydride reagent wherein R8 is as defined herein e.g. H, Me, methoxymethyl, t-butyldimethylsilyl, tetrahydrofuranyl, Bn, allyl. R9 is as defined herein e.g. Me, Et, i-Pr, t-Bu, Bn, 2,2,2-trichloroethyl, allyl, 9-fluorenylmethyl.

In step a) standard methods to reduce the carboxylic acid are employed, such as the use of a hydride agent, e.g. $BH_3$ or its complexes such as picoline borane and borane-pyridine, $LiAlH_4$, 9-BBN, Alpine Borane®, $LiB(s-Bu)_3H$, $LiB(Sia)_3H$, or via activation of the carboxylic acid as acid chloride, mixed anhydride or ester followed by reduction by a hydride reagent such as $NaBH_4$.

In step b) standard methods for the conversion of the alcohol to a leaving group (LG; e.g. a mesylate, tosylate, or bromide) are employed. The methods include the use of MsCl/base or TsCl/base or $SOCl_2$ or $NBS/PPh_3$ or $CBr_4/PPh_3$ or $Tf_2O$ using conditions well known in the art.

In step c) standard conditions for nucleophilic substitution are employed, such as R5Mx (Mx; e.g. Li, MgCl, MgBr, or MgI) in the presence of CuI (R5=alkyl), or a hydride reagent (R5=H).

a-1: hydride reagent
a-2: esterification; then hydride reagent
a-3: acid chloride/mixed anhydride: then hydride reagent wherein R8 is as defined herein e.g. H, Me, methoxymethyl, t-butyldimethylsilyl, tetrahydrofuranyl, Bn, allyl. R9 is as defined herein e.g. Me, Et, i-Pr, t-Bu, Bn, 2,2,2-trichloroethyl, allyl, 9-fluorenylmethyl. R10 is as defined herein e.g. H, Me, Et, t-Bu, i-Bu, Ph, methoxymethyl, Bn, 2,2,2-trichloroethyl, allyl, triethylsilyl, t-butyldimethylsilyl.

In step a) standard methods to reduce the carboxyl group are employed, such as the use of a hydride agent, e.g. $BH_3$ or its complexes such as picoline borane and borane-pyridine complex, $LiAlH_4$, 9-BBN, Alpine Borane®, $LiB(s-Bu)_3H$, $LiB(Sia)_3H$, or via activation of the carboxylic acid as acid chloride, mixed anhydride or ester followed by reduction by a hydride reagent such as NaBH4.

In step b) standard methods to oxidize the alcohol are employed, such as the use of a chromium complex (e.g. PDC, PCC or Na2Cr2O7), Pr4NRuO4, Raney nickel, NCS/TEMPO, a hypervalent iodine reagent (e.g. Dess-Martin periodinane, PhI(OAc)2/TEMPO), NCS/DMS/base or a DMSO based reagent (e.g. DMSO/DCC/H3PO4, DMSO/oxalyl chloride/base or DMSO/SO3/pyridine).

Alternatively, step a) and b) can be replaced by conversion to acid chloride followed by such as reduction with LiAl(OtBu)3 or hydrogenolysis with H2 and Pd—BaSO4, by conversion to thiolester followed by Et3SiH/Pd—C reduction, by conversion to amide followed by reduction with a hydride reagent e.g. LiAlH4, DIBAL, LiAl(O-t-Bu)3, disiamylborane or Ph2SiH2-Ti(OiPr)4, by treatment of the carboxylic acid with Li in MeNH2 or NH3 followed by hydrolysis, or by reduction of the carboxylic ester with a hydride reagent e.g. DIBAL or LiAlH4-Et2NH.

In step c) standard methods for the conversion of aldehyde are employed, such as the use of Tebbe reagent or Wittig reagent or Horner-Wadsworth-Emmons reagents, and followed by hydrogenation of the double bond with a suitable reducing agent (e.g. Pd/C, Pd(OH)2, PtO2, or Raney nickel using conditions well known in the art).

1.2. Route AII when R4 is Hydrogen:

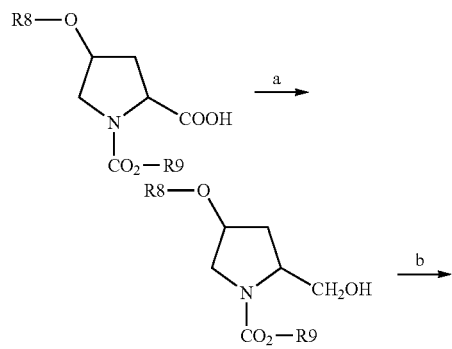

1.3. Route AIII when R4 is Hydrogen:

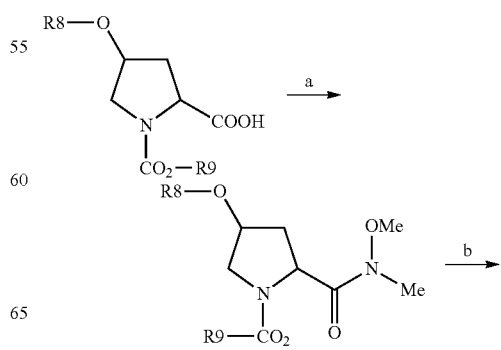

-continued

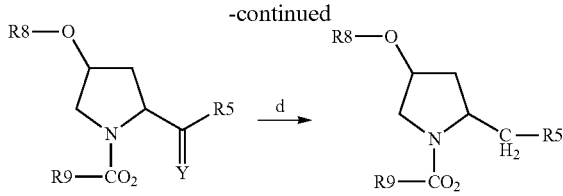

wherein R8 is as defined herein e.g. H, Me, MOM, TBS, tetrahydrofuranyl, Bn, allyl. R9 is as defined herein e.g. Me, Et, i-Pr, t-Bu, Bn, 2,2,2-trichloroethyl, allyl. Y=O or S.

In step a) N-methoxy-N-methyl amide (called Weinreb amide) are prepared by employing N,O-dimethylhydroxylamine with the use of activating reagent (e.g. DCC, thionyl chloride or oxalyl chloride) of carboxylic acid.

In step b) standard methods to alkylation are employed, such as R5Mx (Mx; e.g. Li, MgCl, MgBr, MgI).

In step c) standard methods for the deoxygenation of ketone are employed, such as:
i) the use of Raney nickel following preparation of thiocarbonyl group or thioacetal
ii) Wolff-Kishner reaction condition
iii) Clemmensen reduction condition 1.4. Route AIV when R4 is Hydrogen:

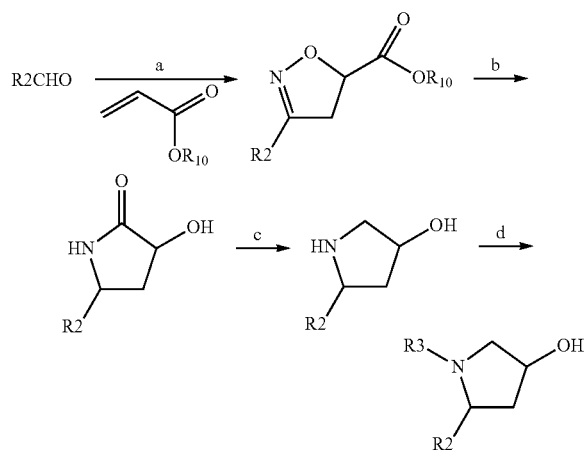

In step a) standard methods for 1,3-dipolar cycloaddition of nitrile oxide are employed, such as using i) HONH$_2$ [oxime formation] ii) either simultaneous treatment with or stepwise treatment via nitrile formation with Chloramine T, alpha, beta-unsaturated ester (see above) whereby R10 is for example Me, Et.

In step b) standard methods for hydrogenation of isoxazoline with a suitable reducing agent (e.g. Pd/C, Pd(OH)2, PtO2, Raney nickel or Mg using conditions well known in the art), followed by the cyclization to give gamma-lactam.

In step c) standard methods to reduce the amide group are employed to give the corresponding amine, such as the use of a hydride agent, e.g. BH$_3$ or its complexes such as picoline borane and borane-pyridine complex, LiAlH$_4$, 9-BBN, Alpine Borane®, LiB(s-Bu)$_3$H, LiB(Sia)$_3$H, NaBH(OAc)3, NaBH3CN, NaBH4 or LiBH4.

In step d) standard methods for the introduction of R3 which are defined in the claims are employed to protect amine part from undesired reaction.

1.5. Route AV:

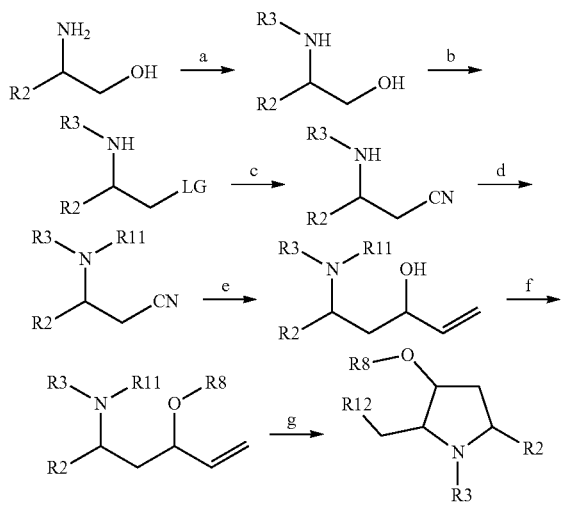

e-1) DIBAL; H3O+; then vinylMx
e-2) VinylMx; H3O+; then hydride reagent wherein R8 is as defined herein e.g. H, Me, MOM, TBS, tetrahydrofuranyl, Bn, allyl. R11 is as defined herein e.g. H, MOM, Bn, TMS, TBS, allyl. Mx is e.g. MgBr, MgI, MgCl, Li, also combination with Cu species.

Conversion of R3, R8 and R11 can be effected by standard functional group manipulation as well known in the art or as specifically described herein (except for H as R3, R8 or R11).

In step b) standard methods for the conversion of the alcohol to a leaving group (LG; e.g. mesylate, tosylate, or bromide) are employed. The methods include the use of MsCl/base or TsCl/base or SOCl$_2$ or NBS/PPh$_3$ or CBr$_4$/PPh$_3$ or Tf$_2$O using conditions well known in the art.

In step c) standard methods for the nucleophilic substitution reaction with CN anion species (e.g. NaCN, KCN) were employed.

In step g) cyclization reaction with R12X (R12 is substituted or unsubstituted aryl, or substituted or unsubstituted alkyl, X=halogen or OMs, OTs, OTf) was conducted in the presence of cat. Pd species, an additional ligand and a base. An illustrative example of this chemistry is outlined in Organic Letters, 2007, Vol. 9, pp. 457-460.

1.6. Route AVI:

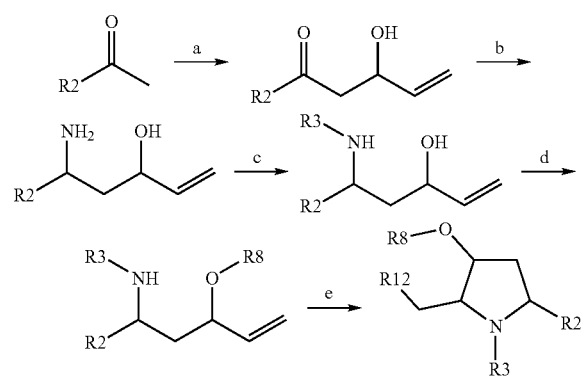

wherein R8 is as defined herein e.g. H, Me, MOM, TBS, tetrahydrofuranyl, Bn, allyl.

Conversion of R3 and R8 can be effected by standard functional group manipulation as well known in the art or as specifically described herein (except for H as R4, R8).

In step a) standard methods for aldol reaction with acrolein are employed in the presence of a strong base such as NaH, KOtBu, LHMDS or LDA.

In step b) standard methods for the introduction of the primary amine are employed, such as using:

an NH$_3$ equivalent [e.g. NH$_3$/EtOH, NH$_4$Cl, NH$_4$OH], a hydride reagent [e.g. NaBH(OAc)$_3$, NaBH$_3$CN or a combination of Ti(OiPr)$_4$ with hydride agents such as NaBH$_4$]

i) either simultaneous treatment with or stepwise treatment via imine formation with BnNH$_2$, a hydride reagent (see above), ii) cat. Hydrogenation a treatment with BnNH$_2$ under cat. Hydrogenation condition i) either simultaneous treatment with or stepwise treatment via imine formation with PMBNH$_2$, hydride reagent (see above), ii) CAN or DDQ (oxidative debenzylation) or TFA i) either simultaneous treatment with or stepwise treatment via imine formation with Ph$_2$CHNH$_2$ (benzhydrylamine), hydride reagent (see above), ii) deprotection with TFA/Et$_3$SiH or cat. Hydrogenation i) RONH$_2$ [oxime formation] ii) Na or BH$_3$ or cat. hydrogenation (e.g. Ra—Ni, Pd—C, Pt—C) [reduction of oxime] whereby R is for example benzyl, p-methoxybenzyl, or allyl.

i) a hydride reagent [reduction to alcohol] ii) Mitsunobu condition using PPh$_3$, DEAD, N$_3$ anion or mesylation with MsCl and base then N$_3$ anion or bromination with conditions such as NBS/PPh$_3$, PBr$_3$/PPh$_3$, CBr$_4$/PPh$_3$ then N$_3$ anion or PBr$_3$/PPh$_3$ then N$_3$ anion iii) PR$_3$ or cat. Hydrogenation [reduction of azide] whereby R is for example ethyl or phenylIn step c) standard methods for the nucleophilic substitution reaction with CN anion species (e.g. NaCN, KCN) are employed.

In step e) cyclization reaction with R12X (R12 is substituted or unsubstituted aryl, or substituted or unsubstituted alkyl, X=halogen or OMs, OTs, OTf) is performed in the presence of cat. Pd species, an additional ligand and a base. An illustrative example of this chemistry is outlined in Organic Letters, 2007, Vol. 9, pp. 457-460.

1.7. Route AVII:

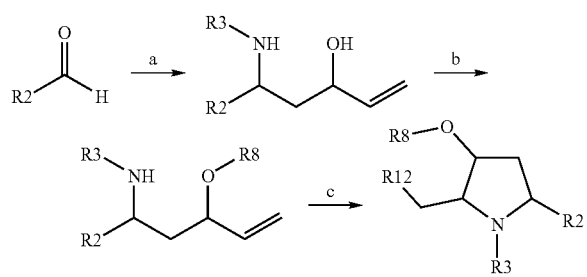

wherein R8 is as defined herein e.g. H, Me, MOM, TBS, tetrahydrofuranyl, Bn, allyl. Mx is e.g. MgBr, MgI, MgCl, Li, also combination with ZnCl$_2$ or Cu species.

Conversion of R3 and R8 can be effected by standard functional group manipulation as well known in the art or as specifically described herein (except for H as R3, R8).

In step a) standard methods for the introduction of the aminoalcohol are employed, such as using:

i) RNH2 [imine formation: e.g. R=Boc, alkylsulfinyl, alkoxy] ii) AllylMx (see above) iii) acidic hydrolysis (e.g. HCl aq) iv) protection with R3 source v) ozone oxidation followed by reduction (e.g. PPh3 or DMS) vi) VinylMx (Mx is e.g. MgBr, MgI, MgCl, Li, also combination with Zn or Cu species).

i) RNH2 [imine formation: e.g. R=Boc, alkylsulfinyl, alkoxy] ii) 3-ButenylMx (see above) iii) allylic oxidation (e.g. SeO2)

In step c) cyclization reaction with R12X (R12 is substituted or unsubstituted aryl, or substituted or unsubstituted alkyl, X=halogen or OMs, OTs, OTf) is performed in the presence of cat. Pd species, an additional ligand and a base. An illustrative example of this chemistry is outlined in Organic Letters, 2007, Vol. 9, pp. 457-460

1.8. Route AVIII:

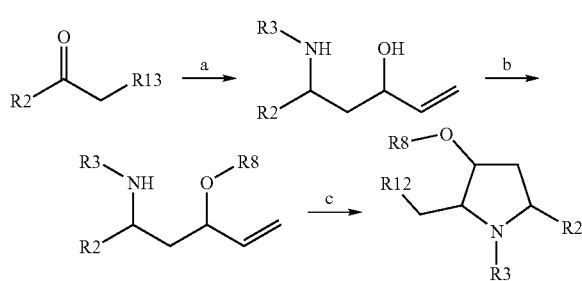

wherein R8 is as defined herein e.g. H, Me, MOM, TBS, tetrahydrofuranyl, Bn, allyl. R13 is an electron withdrawing group (e.g. CHO, COOMe, COOEt, COOBn, CN).

Conversion of R3 and R8 can be effected by standard functional group manipulation as well known in the art or as specifically described herein (except for H as R3, R8).

In step a) standard methods for the introduction of the aminoalcohol are employed, such as using:

i) RR'NH [imine formation: e.g. R=H, Bn, Boc, alkylsulfinyl, alkoxy, siloxy; R'=H, Bn, Boc, alkylsulfinyl, alkoxy, siloxy] in the presence of a Lewis acid ii) Reduction of R13 (except for R13=CHO) to give the corresponding aldehyde iii) VinylMx (Mx is e.g. MgBr, MgI, MgCl, Li, also combination with Zn or Cu species).

In step c) cyclization reaction with R12X (R12 is substituted or unsubstituted aryl, or substituted or unsubstituted alkyl, X=halogen or OMs, OTs, OTf) is performed in the presence of cat. Pd species, an additional ligand and a base. An illustrative example of this chemistry is outlined in Organic Letters, 2007, Vol. 9, pp. 457-460.

1.9. Route AIX:

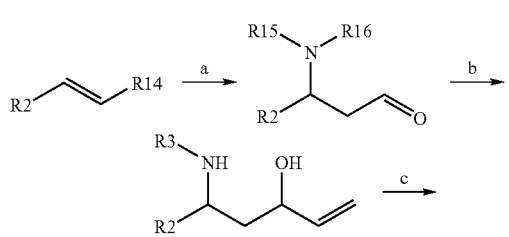

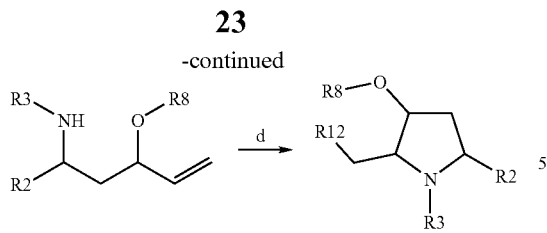

wherein R8 is as defined herein e.g. H, Me, MOM, TBS, tetrahydrofuranyl, Bn, allyl. R14 is an electron withdrawing group (e.g. COOMe, COOEt, COOBn, CN)

Conversion of R3, R8 can be effected by standard functional group manipulation as well known in the art or as specifically described herein (except for H as R3, R8).

In step a) standard methods for aza-Michael reaction are employed, such as using:
  MacMillan's method (see: Journal of the American Chemical Society, 2006, Vol. 128, No. 29, pp. 9328-9329) when R14 is CHO.
  Badia's method (see: The Journal of Organic Chemistry, 2004, Vol. 69, No. 7, 2588-2590, and references cited therein) when R14 is e.g. dialkyl or diaryl amide or alkyl ester, followed by reduction for the preparation of the corresponding aldehyde.

In step c) standard method for the addition of VinylMx (Mx is e.g. MgBr, MgI, MgCl, Li, also combination with Zn or Cu species) are employed.

In step d) cyclization reaction with R12X (R12 is substituted or unsubstituted aryl, or substituted or unsubstituted alkyl, X=halogen or OMs, OTs, OTf) is performed in the presence of cat. Pd species, an additional ligand and a base. An illustrative example of this chemistry is outlined in Organic Letters, 2007, Vol. 9, pp. 457-460.

1.10. Route AX:
  Compounds of formula (A1) can be prepared following the synthetic route outlined in WO2006002004 A1 either directly or analogously.

1.11. Route AXI:
  Compounds of formula (A1) can be prepared following the synthetic route outlined in Synlett, 2001, No. 10, 1602-1604 either directly or analogously.

1.12. Route AXII:
  Compounds of formula (A1) can be prepared following the synthetic route outlined in The Journal of Organic Chemistry, 1194, Vol. 59, No. 8, 1958-1960 either directly or analogously.

1.13. Route AXIII:
  Compounds of formula (A1) can be prepared following the synthetic route outlined in Journal of Medicinal Chemistry, 2006, Vol. 49, No. 15, pp. 4745-4761 either directly or analogously.

Using any of the routes AI to AXIII above, the alkoxypyrrolidine A1 can be converted into the compound of formula (I) using one of the routes AXIV, AXV or AXVI shown below.

1.14. Route AXIV:

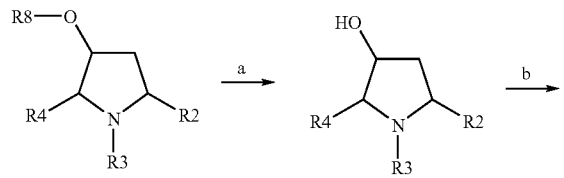

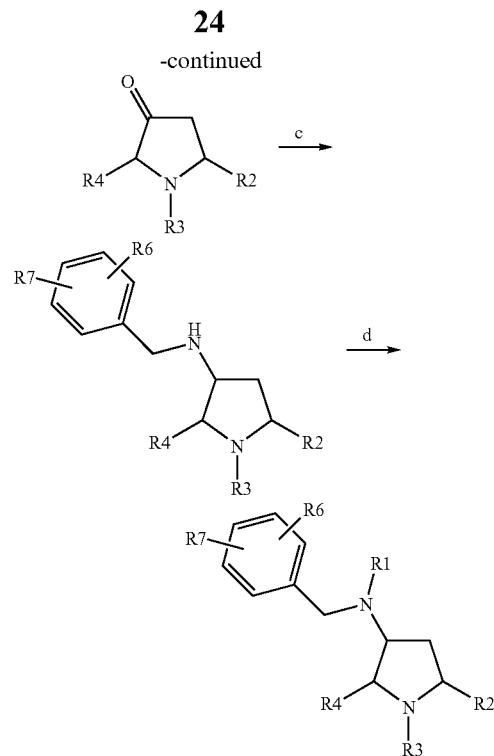

In step a) Removal of R8 can be effected by standard functional group manipulation as well known in the art or as specifically described herein.

In step b) standard methods to oxidize the alcohol are employed, such as the use of a chromium complex (e.g. PDC, PCC or $Na_2Cr_2O_7$), $Pr_4NRuO_4$, Raney nickel, NCS/TEMPO, a hypervalent iodine reagent (e.g. Dess-Martin periodinane, PhI(OAc)$_2$/TEMPO), NCS/DMS/base or a DMSO based reagent (e.g. DMSO/DCC/$H_3PO_4$, DMSO/oxalyl chloride/base or DMSO/SO$_3$/pyridine).

In step c) standard methods for reductive amination are employed, such as ArCH$_2$NH$_2$, hydride reagent [ex. NaBH(OAc)$_3$, NaBH$_3$CN, NaBH$_3$CN, NaBH$_4$, LiBH$_4$, BH$_3$, picoline borane, borane-pyridine complex]; or Ti(OiPr)$_4$; then hydride reagent such as NaBH(OAc)$_3$, NaBH$_3$CN, NaBH$_4$, LiBH$_4$, borane, picoline borane, borane-pyridine complex, LiAlH$_4$, 9-BBN, Alpine Borane®, LiB(s-Bu)$_3$H, LiB(Sia)$_3$H; or imine formation catalyzed or uncatalyzed by acid followed by reduction by hydride agents (see above).

In step d) group R1 is introduced by usual functional group manipulation in the amine, such as alkylation, carbamate formation, urea formation, $S_{RN}1$ substitution, aryl amination and reductive amination.

The group R3 may be modified at an appropriate stage to have the desired definition as set forth in the claims by standard nitrogen protecting group chemistry as known in the art or as described herein.

1.15. Route AXV:

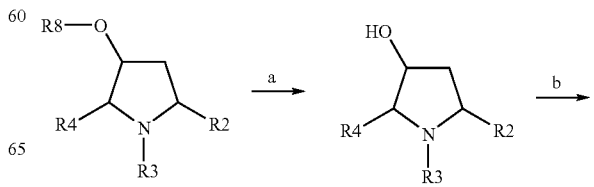

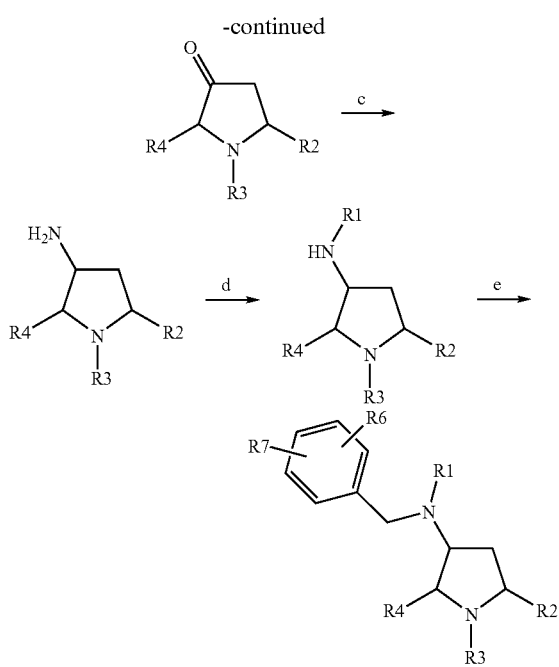

In step a) Removal of R8 can be effected by standard functional group manipulation as well known in the art or as specifically described herein.

In step b) standard methods to oxidize the alcohol are employed, such as the use of a chromium complex (e.g. PDC, PCC or $Na_2Cr_2O_7$), $Pr_4NRuO_4$, Raney nickel, NCS/TEMPO, a hypervalent iodine reagent (e.g. Dess-Martin periodinane, $PhI(OAc)_2$/TEMPO), NCS/DMS/base or a DMSO based reagent (e.g. DMSO/DCC/$H_3PO_4$, DMSO/oxalyl chloride/base or DMSO/$SO_3$/pyridine).

In step c) standard methods for the introduction of the primary amine are employed, such as using:
- an $NH_3$ equivalent [e.g. $NH_3$/EtOH, $NH_4Cl$, $NH_4OH$], a hydride reagent [e.g. $NaBH(OAc)_3$, $NaBH_3CN$ or a combination of $Ti(OiPr)_4$ with hydride agents such as $NaBH_4$]
- i) either simultaneous treatment with or stepwise treatment via imine formation with $BnNH_2$, a hydride reagent (see above), ii) cat. Hydrogenation
- a treatment with $BnNH_2$ under cat. Hydrogenation condition
- i) either simultaneous treatment with or stepwise treatment via imine formation with $PMBNH_2$, hydride reagent (see above), ii) CAN or DDQ (oxidative debenzylation) or TFA
- i) either simultaneous treatment with or stepwise treatment via imine formation with $Ph_2CHNH_2$ (benzhydrylamine), hydride reagent (see above), ii) deprotection with TFA/$Et_3$SiH or cat. Hydrogenation
- i) $RONH_2$ [oxime formation] ii) Na or $BH_3$ or cat. hydrogenation (e.g. Ra—Ni, Pd—C, Pt—C) [reduction of oxime] whereby R is for example benzyl, p-methoxybenzyl, or allyl.
- i) a hydride reagent [reduction to alcohol] ii) Mitsunobu condition using $PPh_3$, DEAD, $N_3$ anion or mesylation with MsCl and base then $N_3$ anion or bromination with conditions such as NBS/$PPh_3$, $PBr_3$/$PPh_3$, $CBr_4$/$PPh_3$ then $N_3$ anion or $PBr_3$/$PPh_3$ then $N_3$ anion iii) $PR_3$ or cat. Hydrogenation [reduction of azide] whereby R is for example ethyl or phenyl In steps d) and e), group R1 or the substituted benzyl ring, respectively, are introduced by usual functional group manipulation in the amine, such as alkylation, carbamate formation, urea formation, $S_{RN}1$ substitution, aryl amination and reductive amination for step d) and preferably alkylation and reductive amination for step e).

The group R3 may be modified at an appropriate stage to have the desired definition as set forth in the claims by standard nitrogen protecting group chemistry as known in the art or as described herein.

1.16. Route AXVI:

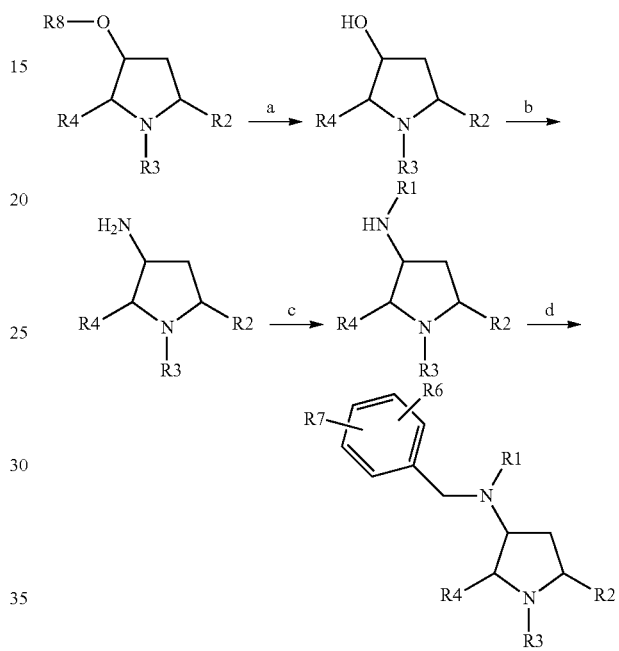

In step a) Removal of R8 can be effected by standard functional group manipulation as well known in the art or as specifically described herein.

In step b) standard methods for the introduction of the primary amine are employed, such as using: i) Mitsunobu condition using $PPh_3$, DEAD, $N_3$ anion or mesylation with MsCl and base then $N_3$ anion or bromination with conditions such as NBS/$PPh_3$, $PBr_3$/$PPh_3$, $CBr_4$/$PPh_3$ then $N_3$ anion or $PBr_3$/$PPh_3$ then $N_3$ anion ii) $PR_3$ or cat. Hydrogenation [reduction of azide]

In steps c) and d), group R1 or the substituted benzyl ring, respectively, are introduced by usual functional group manipulation in the amine, such as alkylation, carbamate formation, urea formation, $S_{RN}1$ substitution, aryl amination and reductive amination for step c) and preferably alkylation and reductive amination for step d).

2. General Procedure B: Using Nitropyrrolidine B1

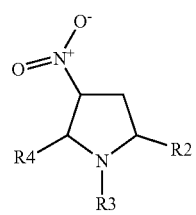
(B1)

Compounds of formula (B1) can be prepared following the synthetic route outlined in Synlett, 2007, No. 15, pp. 2355-2358 either directly or analogously.

Using the above route, the nitropyrrolidine B1 can be converted into the compound of formula (I) such as using the route BI shown below.

2.1. Route BI:

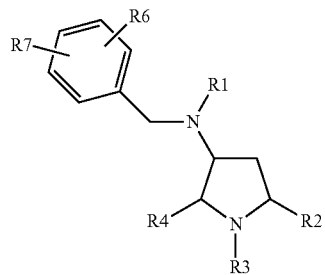
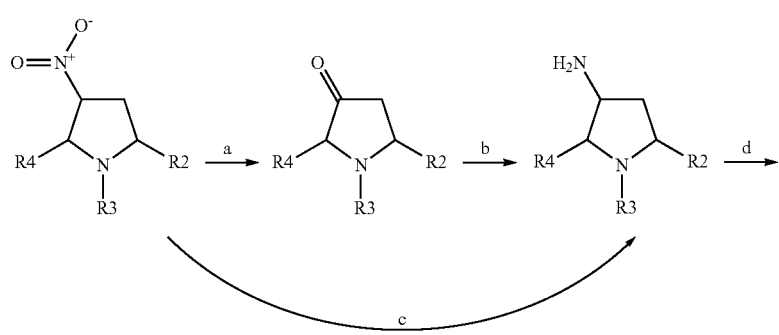

In step a) standard methods for the Nef reaction are employed, such as using a oxidizing agent (e.g. KMNO4, Oxone) and H2O or a base followed by a protic acid (e.g. HCl, H2SO4, AcOH) and H2O.

In step b) standard methods for the introduction of the primary amine are employed as described above in the procedure A.

In step c) standard methods for the reduction of nitro group to give the corresponding primary amine are employed, such as using Zn/HCl, SmI2, NiCl2/NaBH4, Et3SiH/RhCl(PPh3)3, or Pd/C.

In step d) this pyrrolidine can also be further reacted to form a compound of formula (I) by alkylation methods and nitrogen protecting group manipulations as described above in the procedure A.

3. General Procedure C: Using Ynoate Chemistry

Compounds of formula (I) can be prepared following the synthetic route outlined in Synlett, 2004, No. 1, pp. 119-121, The Journal of Organic Chemistry, 2005, Vol. 70, No. 5, pp. 1791-1795 or The Journal of Organic Chemistry, 1992, Vol. 57, No. 5, pp. 1323-1324 either directly or analogously.

4. General Procedure D: Using N-Acyliminium Ion Chemistry

Compounds of formula (I) can be prepared following the synthetic route outlined in Chemistry Letters, 1991, Vol. 20, No. 1, pp. 81-84 either directly or analogously.

5. General Procedure E: Preparation from Substituted Pyrrole

Compounds of formula (I) can be prepared from substituted pyrrole analogously and converting the obtained pyrrolidine by methods outlined in e.g. routes AXIV, AXV, AXVI or BI above. An illustrative example of substituted pyrrolidine from pyrrole is outlined in Journal of Organic Chemistry, 2002, Vol. 67, No. 10, pp. 3479-3486.

6. General Procedure F: Using 1,3-dipolar Cycloaddition Chemistry

Compounds of formula (I) can be prepared from an azomethine ylides and a enamine analogously. An illustrative example of this chemistry is outlined in Tetrahedron, 1999, Vol. 55, No. 31, pp. 9535-9558.

General Procedure G: Using □,γ-diamino acid Chemistry

Compounds of formula (I) can be prepared from nitroolefin and □-amino ester (or □-amino amide) followed by hydrogenolysis analogously and converting the obtained pyrrolidine by methods outlined in e.g. routes AXIV, AXV, AXVI or BI above. An illustrative example of this chemistry is outlined in Chemical Communications, 2001, No. 2, pp. 207-208.

Racemates and diastereomer mixtures obtained can be separated into the pure isomers or racemates in a known manner on the basis of the physicochemical differences of the components, for example by fractional crystallization or by chiral chromotography or HPLC separation utilizing chiral stationery phases. Racemates obtained may furthermore be resolved into the optical antipodes by known methods, for example by recrystallization from an optically active solvent, chromatography on chiral adsorbents, with the aid of suitable microorganisms, by cleavage with specific immobilized enzymes, via the formation of inclusion compounds, for example using chiral crown ethers, only one enantiomer being complexed, or by conversion into diastereomeric salts, for example by reaction of a basic final substance racemate with an optically active acid, such as a carboxylic acid, for example tartaric or malic acid, or sulfonic acid, for example camphorsulfonic acid, and separation of the diastereomer mixture obtained in this manner, for example on the basis of its differing solubilities, into the diastereomers from which the desired enantiomer can be liberated by the action of suitable agents. The more active enantiomer is advantageously isolated.

The present invention includes all pharmaceutically acceptable isotopically-labeled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^{2}$H and $^{3}$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Substitution with heavier isotopes such as deuterium, i.e. $^{2}$H, may afford certain therapeutic advantages resulting from greater metabolic stability, for example, increased in vivo half-life or reduced dosage requirements, and hence may be preferred in some circumstances.

Isotopically-labeled compounds of formula (I) can generally be prepared by conventional techniques known to those skilled in the art or by processes analogous to those described in the accompanying Examples and Preparations Sections using an appropriate isotopically-labeled reagent in place of the non-labeled reagent previously employed.

In starting compounds and intermediates which are converted to the compounds of the invention in a manner described herein, functional groups present, such as amino, thiol, carboxyl and hydroxy groups, are optionally protected by conventional protecting groups that are common in preparative organic chemistry. Protected amino, thiol, carboxyl and hydroxy groups are those that can be converted under mild conditions into free amino thiol, carboxyl and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, room temperature or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers etc.

Preferably, the pharmaceutical compositions are tablets and gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable compositions for transdermal application include an effective amount of a compound of the invention with carrier. Advantageous carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

The present invention further provides anhydrous pharmaceutical compositions and dosage forms comprising the compounds of the present invention as active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The invention likewise relates to a combination of a compound of formula (I), (IA) or (IB), respectively, or a pharmaceutically acceptable salt thereof with a further active principle.

The combination may be made for example with the following active principles, selected from the group consisting of a:
  (i) HMG-Co-A reductase inhibitor or a pharmaceutically acceptable salt thereof,
  (ii) angiotensin II receptor antagonist or a pharmaceutically acceptable salt thereof,
  (iii) angiotensin converting enzyme (ACE) Inhibitor or a pharmaceutically acceptable salt thereof,
  (iv) calcium channel blocker or a pharmaceutically acceptable salt thereof,
  (v) aldosterone synthase inhibitor or a pharmaceutically acceptable salt thereof,
  (vi) aldosterone antagonist or a pharmaceutically acceptable salt thereof,
  (vii) dual angiotensin converting enzyme/neutral endopeptidase (ACE/NEP) inhibitor or a pharmaceutically acceptable salt thereof,
  (viii) endothelin antagonist or a pharmaceutically acceptable salt thereof,
  (ix) renin inhibitor or a pharmaceutically acceptable salt thereof,
  (x) diuretic or a pharmaceutically acceptable salt thereof, and
  (xi) an ApoA-I mimic.

An angiotensin II receptor antagonist or a pharmaceutically acceptable salt thereof is understood to be an active ingredients which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

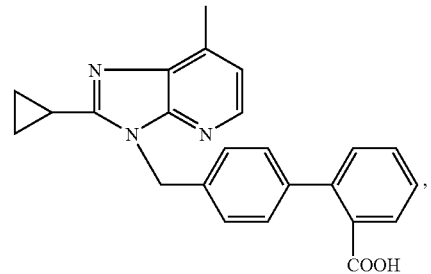 [SMILES: Cc1ccnc2c1nc(C1CC1)n2Cc1ccc(-c2ccccc2C(=O)O)cc1]

the compound with the designation SC-52458 of the following formula

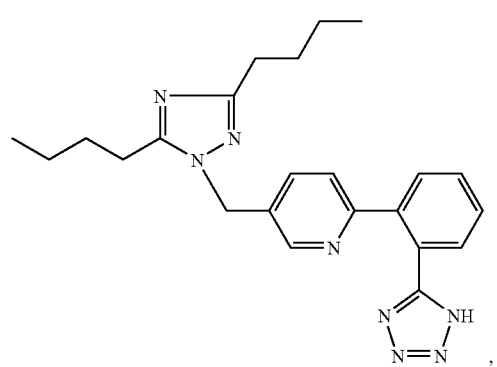 [SMILES: CCCCc1nc(CCCC)n(Cc2ccc(-c3ccccc3-c3nnn[nH]3)nc2)n1 ; ","]

and the compound with the designation ZD-8731 of the following formula

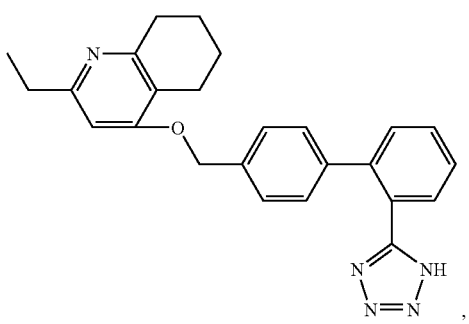 [SMILES: CCc1cc(OCc2ccc(-c3ccccc3-c3nnn[nH]3)cc2)c2c(n1)CCCC2 ; ","]

or, in each case, a pharmaceutically acceptable salt thereof.

Preferred $AT_1$-receptor antagonist are those agents which have been marketed, most preferred is valsartan or a pharmaceutically acceptable salt thereof.

HMG-Co-A reductase inhibitors (also called β-hydroxy-β-methylglutaryl-co-enzyme-A reductase inhibitors) are understood to be those active agents that may be used to lower the lipid levels including cholesterol in blood.

The class of HMG-Co-A reductase inhibitors comprises compounds having differing structural features. For example, mention may be made of the compounds that are selected from the group consisting of atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, in each case, a pharmaceutically acceptable salt thereof.

Preferred HMG-Co-A reductase inhibitors are those agents which have been marketed, most preferred is fluvastatin and pitavastatin or, in each case, a pharmaceutically acceptable salt thereof.

The interruption of the enzymatic degradation of angiotensin I to angiotensin II with so-called ACE-inhibitors (also called angiotensin converting enzyme inhibitors) is a successful variant for the regulation of blood pressure and thus also makes available a therapeutic method for the treatment of congestive heart failure.

The class of ACE inhibitors comprises compounds having differing structural features. For example, mention may be made of the compounds which are selected from the group consisting alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, in each case, a pharmaceutically acceptable salt thereof.

Preferred ACE inhibitors are those agents that have been marketed, most preferred are benazepril and enalapril.

The class of CCBs essentially comprises dihydropyridines (DHPs) and non-DHPs such as diltiazem-type and verapamil-type CCBs.

A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs.

Preferred CCBs comprise amlodipine, diltiazem, isradipine, nicardipine, nifedipine, nimodipine, nisoldipine, nitrendipine, and verapamil, or, e.g. dependent on the specific CCB, a pharmaceutically acceptable salt thereof. Especially preferred as DHP is amlodipine or a pharmaceutically acceptable salt, especially the besylate, thereof. An especially preferred representative of non-DHPs is verapamil or a pharmaceutically acceptable salt, especially the hydrochloride, thereof.

Aldosterone synthase inhibitor is an enzyme that converts corticosterone to aldosterone to by hydroxylating corticosterone to form 18-OH-corticosterone and 18-OH-corticosterone to aldosterone. The class of aldosterone synthase inhibitors is known to be applied for the treatment of hypertension and primary aldosteronism comprises both steroidal and non-steroidal aldosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. For example, mention may be made of the compounds which are selected from the group consisting of the non-steroidal aromatase inhibitors anastrozole, fadrozole (including the (+)-enantiomer thereof), as well as the steroidal aromatase inhibitor exemestane, or, in each case where applicable, a pharmaceutically acceptable salt thereof.

The most preferred non-steroidal aldosterone synthase inhibitor is the (+)-enantiomer of the hydrochloride of fadrozole (U.S. Pat. Nos. 4,617,307 and 4,889,861) of formula

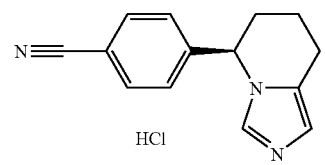

A preferred steroidal aldosterone antagonist is eplerenone of the formula

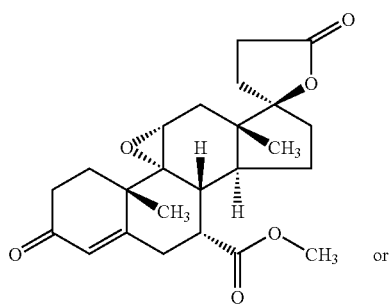

spironolactone.

A preferred dual angiotensin converting enzyme/neutral endopeptidase (ACE/NEP) inhibitor is, for example, omapatrilate (cf. EP 629627), fasidotril or fasidotrilate, or, if appropriate, a pharmaceutically acceptable salt thereof.

A preferred endothelin antagonist is, for example, bosentan (cf. EP 526708 A), furthermore, tezosentan (cf. WO 96/19459), or in each case, a pharmaceutically acceptable salt thereof.

A renin inhibitor is, for example, a non-peptidic renin inhibitor such as the compound of formula

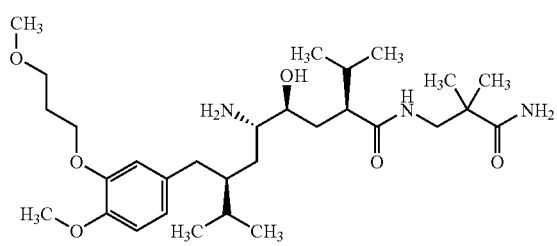 [SMILES: COCCCOc1cc(C[C@@H](C[C@H](N)[C@@H](O)C[C@H](C(=O)NCC(C)(C)C(N)=O)C(C)C)C(C)C)ccc1OC]

chemically defined as 2(S),4(S),5(S),7(S)-N-(3-amino-2,2-dimethyl-3-oxopropyl)-2,7-di(1-methylethyl)-4-hydroxy-5-amino-8-[4-methoxy-3-(3-methoxy-propoxy)phenyl]-octanamide. This representative is specifically disclosed in EP 678503A. Especially preferred is the hemi-fumarate salt thereof.

A diuretic is, for example, a thiazide derivative selected from the group consisting of chlorothiazide, hydrochlorothiazide, methylclothiazide, and chlorothalidon. The most preferred is hydrochlorothiazide.

An ApoA-I mimic is, for example, D4F peptide, especially of formula D-W-F-K-A-F-Y-D-K-V-A-E-K-F-K-E-A-F Preferably, the jointly therapeutically effective amounts of the active agents according to the combination of the present invention can be administered simultaneously or sequentially in any order, separately or in a fixed combination.

The structure of the active agents identified by generic or tradenames may be taken from the actual edition of the standard compendium "The Merck Index" or from databases, e.g. IMS LifeCycle (e.g. IMS World Publications). Any person skilled in the art is fully enabled to identify the active agents and, based on these references, likewise enabled to manufacture and test the pharmaceutical indications and properties in standard test models, both in vitro and in vivo.

Furthermore, the combinations as described above can be administered to a subject via simultaneous, separate or sequential administration (use). Simultaneous administration (use) can take place in the form of one fixed combination with two or more active ingredients, or by simultaneously administering two or more compounds that are formulated independently. Sequential administration (use) preferably means administration of one (or more) compounds or active ingredients of a combination at one time point, other compounds or active ingredients at a different time point, that is, in a chronically staggered manner, preferably such that the combination shows more efficiency than the single compounds administered independently (especially showing synergism). Separate administration (use) preferably means administration of the compounds or active ingredients of the combination independently of each other at different time points, preferably meaning that two compounds are administered such that no overlap of measurable blood levels of both compounds are present in an overlapping manner (at the same time).

Also combinations of two or more of sequential, separate and simultaneous administrations are possible, preferably such that the combination compound-drugs show a joint therapeutic effect that exceeds the effect found when the combination compound-drugs are used independently at time intervals so large that no mutual effect on their therapeutic efficiency can be found, a synergistic effect being especially preferred.

Additionally, the present invention provides:
a pharmaceutical composition or combination of the present invention for use as a medicament;
the use of a pharmaceutical composition or combination of the present invention for the delay of progression and/or treatment of a disorder or disease mediated by CETP or responsive to the inhibition of CETP.
the use of a pharmaceutical composition or combination of the present invention for the delay of progression and/or treatment of a disorder or disease selected from hyperlipidemia, arteriosclerosis, atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorder, coronary heart disease, coronary artery disease, coronary vascular disease, angina, ischemia, heart ischemia, thrombosis, cardiac infarction such as myocardial infarction, stroke, peripheral vascular disease, reperfusion injury, angioplasty restenosis, hypertension, congestive heart failure, diabetes such as type II diabetes mellitus, diabetic vascular complications, obesity or endotoxemia etc.

The pharmaceutical composition or combination of the present invention can be in unit dosage of about 1-1000 mg of active ingredients for a subject of about 50-70 kg, preferably about 5-500 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, preferably between about 1-100 mg/kg.

The CETP inhibitory effect of the compounds of the present invention can be determined by using the test models or assays known in the art. For example, EP1115695B1 describes both the in vitro and in vivo CETP activity assays. In particular, the following assays are used.

(1) CETP In vitro Assay:

CETP Activity Kit (#RB-RPAK) was purchased from Roar Biochemical, Inc. (New York, N.Y., USA). To each well of a 96-well NBS half-area plate (costar #3686), 1.2 ng/well of the donor solution, 1 µL of the acceptor solution and 5 µL compound solution diluted in 100% DMSO were added in a 38 µL of buffer containing 10 mM Tris, 150 mM NaCl and 2 mM EDTA, pH 7.4. Then, the plate was sealed with Themowell™ Sealers (costar #6524) and followed by a mixing on a plate shaker by MICROPLATE MIXER MPX-96 (IWAKI) at power 3 for 10 sec at room temperature. After 10-min incubation at 37° C., the reaction was started by adding 5 µL of rhCETP solution (Cardiovascular Target, New York, N.Y., USA) and mixed on the plate shaker for 10 sec, then the fluorescence intensity at 0 min was measured by a ARVO SX (Perkin Elmerr, USA) at excitation wavelength of 465 nm and emission wavelength of 535 nm. After 120 min-incubation at 37° C., fluorescence intensity was measured again. The inhibition of rhCETP activity by a compound was calculated by the following calculation. Inhibition %={1−(F120−F0)/(f120−f0)}×100 F: measured fluorescence intensity with compound at 0 or 120 min. f: measured fluorescence intensity of without compound at 0 or 120 min.

The $IC_{50}$ values are determined from the dose-effect curve by Origin software. $IC_{50}$ values, especially from about 0.1 nM to about 50 μM, are determined for the compounds of the present invention or a pharmaceutically acceptable salt thereof.

(2) Effects on Plasma HDL Levels in Hamster:

Effects of compounds on HDL-cholesterol level in hamsters are investigated by the method reported previously with some modifications (Eur, J. Pharmacol, 466 (2003) 147-154). In brief, male Syrian hamsters (10-11 week-old age, SLC, Shizuoka, Japan) are fed a high cholesterol diet for two weeks. Then, the animals are dosed singly with the compound suspended with carboxylmethyl cellulose solution. HDL-cholesterol levels are measured by using commercially available kit (Wako Pure Chemical, Japan) after the precipitation of apolipoprotein B (apoB)-containing lipoproteins with 13% polyethylene glycol 6000.

(3) Preparation of Human Pro-Apolipoprotein Al (Pro-apoAl)

The cDNA of human pro-apoAl (NCBI accession number: NM_000039) is cloned from human liver Quick-Clone™ cDNA (Clontech, CA) and inserted to a pET28a vector (Novagen, Germany) for bacterial expression. Expressed protein as a fusion protein with 6×His-tag at N-terminus in BL-21 Gold (DE3) (Strategene, CA) is purified using HiTrap Chelating (GE Healthcare, CT).

(4) Preparation of Donor Microemulsion

Pro-apoAl containing microemulsion as a donor particle is prepared following previous reports (J. Biol. Chem., 280: 14918-22). Glyceryl trioleate (62.5 ng, Sigma, Mo.), 3-sn-phosphatidylcholine (583 ng, Wako Pure Chemical Industries, Japan), and cholesteryl BODIPY® FL $C_{12}$ (250 ng, Invitrogen, CA) are dissolved in 1 mL of chloroform. The solution is evaporated, then residual solvent is removed in vacuum for more than 1 hr. The dried lipid mixture is dissolved in 500 μL of the assay buffer (50 mM Tris-HCl (pH7.4) containing 150 mM NaCl and 2 mM EDTA) and sonicated at 50° C. with a microtip (MICROSON™ ULTRASONIC CELL DISRUPTOR, Misonix, Farmingdale, N.Y.) at output power 006 for 2 min. After sonication, the solution is cooled to 40° C., added to 100 μg of human pro-apoAl, and sonicated at output power 004 for 5 min at 40° C. The solution, BODIPY-CE microemulsion as a donor molecule is stored at 4° C. after filtration through a 0.45 μm PVDF filter.

(5) In vitro CETP Activity Assay in Human Plasma

Human EDTA plasma samples from healthy men are purchased from New Drug Development Research Center, Inc. Donor solution is prepared by a dilution of donor microemulsion with assay buffer. Human plasma (50 μL), assay buffer (35 μL) and test compound dissolved in dimethylsulfoxide (1 μL) are added to each well of 96 well half area black flat bottom plate. The reaction is started by the addition of donor solution (14 μL) into each well. Fluorescence intensities are measured every 30 min at 37° C. with excitation wave length of 485 nm and emission wavelength of 535 nm. The CETP activity (Fl/min) is defined as the changes of fluorescence intensity from 30 to 90 min. The $IC_{50}$ value is obtained by the logistic equation (Y=Bottom+(Top−Bottom)/(1+(x/$IC_{50}$)^Hill slope) using Origin software, version 7.5 SR3. The compounds of formula I exhibit inhibitory activity with an IC50 value in the range from approximately from 0.001 to 100 μM, especially from 0.01 to 10 μM.

The compounds of the present invention or a pharmaceutically acceptable salt thereof have superior CETP inhibitory activity in mammals (e.g., human, monkey, bovine, horse, dog, cat, rabbit, rat, mouse and the like), and can be used as CETP activity inhibitors. In addition, utilizing the superior CETP inhibitory activity of a compound of the present invention or a pharmaceutically acceptable salt thereof, the compounds of the present invention are useful as pharmaceutical agents effective for the prophylaxis or treatment of or delay progression to overt to diseases in which CETP is involved (e.g., hyperlipidemia, arteriosclerosis, atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorder, coronary heart disease, coronary artery disease, coronary vascular disease, angina, ischemia, heart ischemia, thrombosis, cardiac infarction such as myocardial infarction, stroke, peripheral vascular disease, reperfusion injury, angioplasty restenosis, hypertension, congestive heart failure, diabetes such as type II diabetes mellitus, diabetic vascular complications, obesity or endotoxemia etc.), particularly as prophylactic or therapeutic agents for hyperlipidemia or arteriosclerotic diseases.

TABLE 1

Inhibitory Activity of Compounds

| Example No | IC50 (nM) |
|---|---|
| 5-3 | 92 |
| 6 | 23 |
| 6-1 | 69 |
| 6-2 | 47 |
| 7-4 | 60 |
| 7-6 | 46 |
| 9 | 53 |
| 9-1 | 41 |
| 9-2 | 59 |
| 9-3 | 70 |
| 9-4 | 21 |
| 9-5 | 54 |
| 9-6 | 70 |
| 11 | 72 |
| 14 | 34 |
| 16 | 39 |
| 16-2 | 25 |
| 17 | 32 |
| 18 | 63 |
| 23-6 | 110 |
| 23-10 | 30 |
| 32 | 77 |
| 33-2 | 130 |

Abbreviations
Ac: Acetyl
aq: aqueous
Ar: aromatic
BBN: borabicyclo[3.3.1]nonane
dba: dibenzylideneacetone
Bn: benzyl
Boc: tert-butoxycarbonyl
Bu: n-butyl
CAN: ceric ammonium nitrate
DDQ: 2,3-dichloro-5,6-dicyano-p-benzoquinone
DEAD: diethyl azodicarboxylate
DIPEA: N,N-diisopropylethylamine
DMAP: N,N-dimethylaminopyridine
DME: 1,2-dimethoxyethane
DMF: N,N-dimethylformamide
DMSO: dimethyl sulfoxide
dppf: 1,1-bis(diphenylphosphino)ferrocene EDTA: ethylenediaminetetraacetic acid
ESI: electrospray ionization
Et: ethyl
EtOAc: ethyl acetate
h: hours
HCl: hydrogen chloride
HOAt: 1-hydroxy-7-azabenzotriazole
HOBt: 1-hydroxybenzotriazole
HPLC: high pressure liquid chromatography
IPA: 2-propanol
iPr: isopropyl
IR: infrared
KHMDS: potassium hexamethyldisilazanide
LC: liquid chromatography
LDA: lithium diisopropylamide
LHMDS: lithium hexamethyldisilazanide
Me: methyl
min: minutes
MS: mass spectrometry
Ms: mesyl, methanesulfonyl
NBS: N-bromosuccinimide
NMR: nuclear magnetic resonance
Ph: phenyl
PMB: p-methoxybenzyl
RP: reverse phase
RT: room temperature
s-Bu: sec-butyl
Sia: siamyl
SFC: supercritical fluid chromatography
Tf: triflate
TFA: trifluoroacetic acid
THF: tetrahydrofuran
TLC: thin layer chromatography
Ts: tosyl
tBu: tert-butyl
tol: tolyl
WSCD: water soluble carbodiimide, 1-ethyl-3-(3-dimethylamino propyl) carbodiimide

EXAMPLES

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. The compounds in the following examples have been found to have $IC_{50}$ values in the range of about 0.1 nM to about 10,000 nM for CETP.

The conditions for measuring the retention times are as follows:
Condition A (HPLC)
Column: ACQUITY UPLCTM BEH C18 1.7 um, 50×2.1 mm.
Flow rate: 0.5 ml/min
Mobile phase: A) TFA/water (0.1/100, v/v), B) TFA/acetonitrile (0.1/100, v/v)
Gradient: 5% B in 0.5 min, then linear gradient from 5% B to 100% B in 1.5 min then 100% B in 1 min
Detection: UV at 215 nm
Condition B (HPLC)
Column: ACQUITY UPLCTM BEH C18 1.7 um, 50×2.1 mm.
Flow rate: 0.5 ml/min
Mobile phase: A) TFA/water (0.1/100, v/v), B) TFA/acetonitrile (0.1/100, v/v)
Gradient: 5% B in 0.5 min, then linear gradient from 5% B to 100% B in 5.0 min then 100% B in 1.5 min
Detection: UV at 215 nm
Condition C(HPLC)
Column: CombiScreen ODS-AM, 50×4.6 mm.
Flow rate: 2.0 ml/min
Mobile phase: A) TFA/water (0.1/100, v/v), B) TFA/acetonitrile (0.1/100, v/v)
Gradient: linear gradient from 5% B to 100% B in 5 min then 100% B in 2 min
Detection: UV at 215 nm Example 1

Synthesis of (2S,3S,5R)-2-Benzyl-3-[(3,5-bis-trifluoromethyl-benzyl)-methoxycarbonyl-amino]-5-ethyl-pyrrolidine-1-carboxylic acid tert-butyl ester

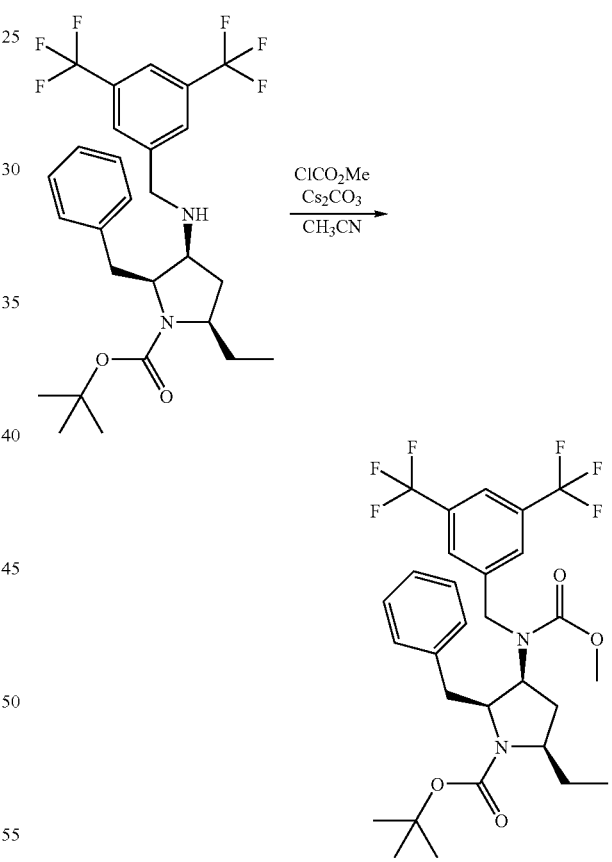

To a solution of (2S,3S,5R)-2-benzyl-3-(3,5-bis-trifluoromethyl-benzylamino)-5-ethyl-pyrrolidine-1-carboxylic acid tert-butyl ester (0.0377 mmol; 20 mg) and cesium carbonate (0.113 mmol; 36.8 mg) in acetonitrile (0.38 mL) is added methyl chloroformate (0.0754 mmol; 5.9 mg) at room temperature. The reaction mixture is warmed to 80° C. and stirred for 3.5 hours. Additional methyl chloroformate (0.0754 mmol; 5.9 mg) is added to the mixture, and the mixture is stirred for additional 0.5 hours, and then cooled to room temperature. To the mixture is added brine and EtOAc.

The organic layer is separated, dried over Na2SO4, filtered, and concentrated under reduced pressure. The residue is purified by preparative thin layer chromatography on silica gel (eluent: n-hexane/EtOAc) to give (2S,3S,5R)-2-Benzyl-3-[(3,5-bis-trifluoromethyl-benzyl)-methoxycarbonyl-amino]-5-ethyl-pyrrolidine-1-carboxylic acid tert-butyl ester (11.5 mg, 52%); ESI-MS m/z: 589 [M+1]+, Retention time 2.63 min (condition A).

Example 2

Synthesis of (2S,3S,5R)-2-Benzyl-3-[(5-bromo-pyrimidin-2-yl)-(3-chloro-5-trifluoromethyl-benzyl)-amino]-5-ethyl-pyrrolidine-1-carboxylic acid isopropyl ester

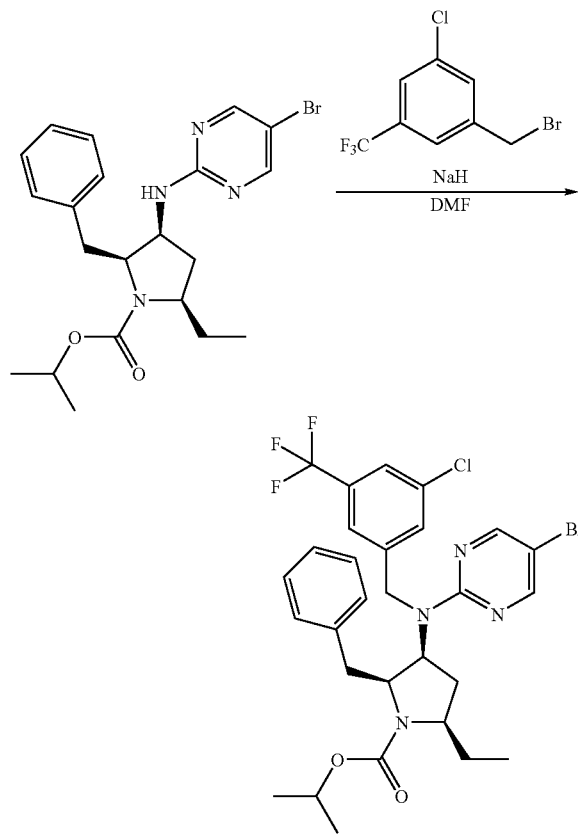

To a suspension of (2S,3S,5R)-2-benzyl-3-(5-bromo-pyrimidin-2-ylamino)-5-ethyl-pyrrolidine-1-carboxylic acid isopropyl ester (0.064 mmol; 28.6 mg) and sodium hydride (60% dispersion in mineral oil, 0.19 mmol; 7.6 mg) in DMF (0.6 mL) is added 3-chloro-5-trifluoromethylbenzyl bromide (0.13 mmol; 35.6 mg) at room temperature under N2. After 3.5 hours, additional sodium hydride (60% dispersion in mineral oil, 0.19 mmol; 7.6 mg) is added to the suspension. The reaction mixture is stirred for 20 minutes, and quenched with water and saturated aqueous ammonium chloride solution. The product is extracted three times with EtOAc. The combined organic layer is washed with brine, dried over Na2SO4, filtered, and concentrated under reduced pressure. The residue is purified by column chromatography on silica gel (eluent: n-hexane/EtOAc) to give (2S,3S,5R)-2-Benzyl-3-[(5-bromo-pyrimidin-2-yl)-(3-chloro-5-trifluoromethyl-benzyl)-amino]-5-ethyl-pyrrolidine-1-carboxylic acid isopropyl ester (30.0 mg, 73%); ESI-MS m/z: 639 [M+1]+, Retention time 2.68 min (condition A).

Example 3

Synthesis of (2S,3S,5R)-2-Benzyl-3-{(3-chloro-5-trifluoromethyl-benzyl)-[5-(1-methyl-1H-pyrazol-4-yl)-pyrimidin-2-yl]-amino}-5-ethyl-pyrrolidine-1-carboxylic acid isopropyl ester

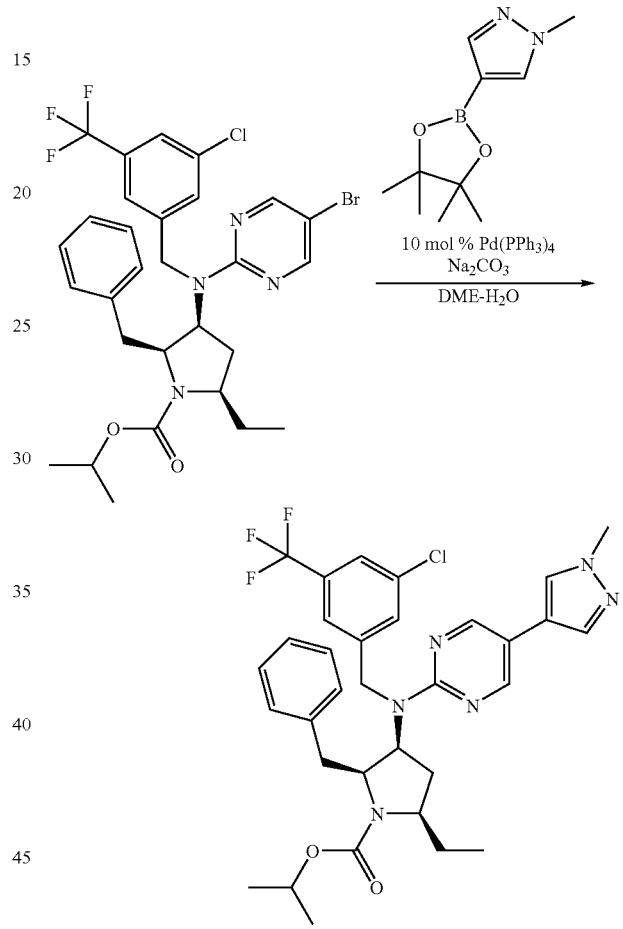

(2S,3S,5R)-2-Benzyl-3-[(5-bromo-pyrimidin-2-yl)-(3-chloro-5-trifluoromethyl-benzyl)-amino]-5-ethyl-pyrrolidine-1-carboxylic acid isopropyl ester (0.042 mmol; 27 mg), tetrakis(triphenylphosphine) palladium (0.0042 mmol; 4.9 mg), 1-methylpyrazol-4-boronic acid pinacol ester (0.063 mmol; 13 mg) and sodium carbonate (0.084 mmol; 8.9 mg) are dissolved in 1,2-dimethoxyethane (0.8 mL) and water (0.08 mL) at room temperature. The mixture is stirred at 90° C. for 17 hours, and then cooled to ambient temperature. To the mixture is added brine and the solution is extracted three times with EtOAc. The combined organic layer is washed with brine, dried over Na2SO4, filtered, and concentrated under reduced pressure. The obtained residue is purified by silica gel column chromatography (eluent: n-hexane/EtOAc) to give (2S,3S,5R)-2-Benzyl-3-{(3-chloro-5-trifluoromethyl-benzyl)-[5-(1-methyl-1H-pyrazol-4-yl)-pyrimidin-2-yl]-amino}-5-ethyl-pyrrolidine-1-carboxylic acid isopropyl ester (13.6 mg, 51%); ESI-MS m/z: 641 [M+1]+, Retention time 2.62 min (condition A).

The following compounds are prepared following the procedure of Example 3.

Example 3-1: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid tert-butyl ester

| No. | Product | ESI-MS m/z [M + 1]⁺ | Retention time (min) | Starting Material |
|---|---|---|---|---|
| 3-1 |  | 599 | 2.37 (condition A) |  |

Example 4

Synthesis of (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 4-carboxy-cyclohexyl ester

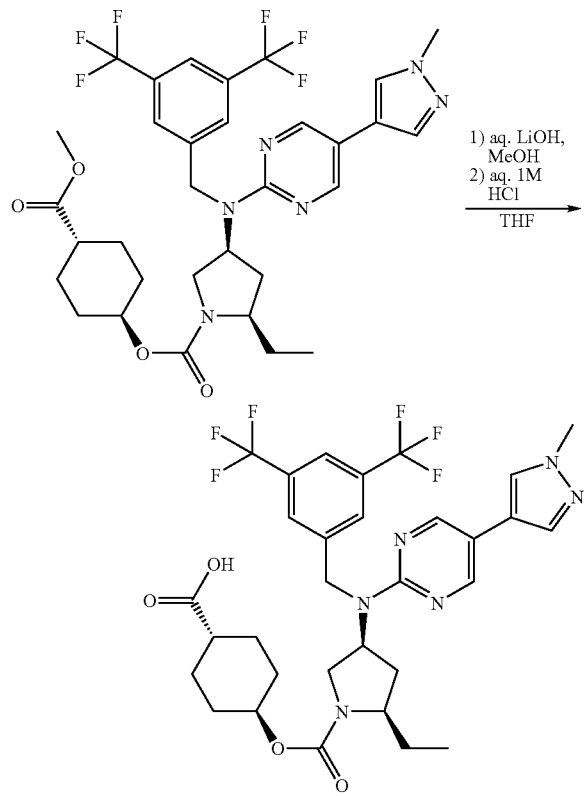

(2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid trans-4-methoxycarbonyl-1-cyclohexyl ester (0.101 mmol; 69 mg) and lithium hydroxide monohydrate (0.381 mmol; 16 mg) are dissolved in THF (1 mL), water (0.5 mL) and MeOH (0.1 mL). The solution is stirred for 3 hours at room temperature. The reaction mixture is quenched with aqueous 1M HCl (0.95 mL) and stirred for 15 minutes. To the mixture is added dichloromethane and the organic layer is separated and then concentrated under reduced pressure. The desired product, (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 4-carboxy-cyclohexyl ester, is obtained in 90% yield (60 mg); ESI-MS m/z: 669 [M+1]⁺, Retention time 2.13 min (condition A).

The following compounds are prepared following the procedure of Example 4.

Example 4-1: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 4-carboxy-cyclohexyl ester Example 4-2: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 2-carboxy-2-methyl-propyl ester Example 4-3: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 3-carboxy-3-methyl-butyl ester Example 4-4: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 3-carboxy-cyclobutyl ester Example 4-5: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 4-carboxy-cyclohexylmethyl ester Example 4-6: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 3-carboxy-cyclobutyl ester Example 4-7: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 1-carboxy-cyclopentylmethyl ester Example 4-8: 4-{[((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carbonyl)-ethyl-amino]-methyl}-cyclohexanecarboxylic acid Example 4-9: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 4-carboxymethyl-cyclohexylmethyl ester Example 4-10: (S)-1-((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carbonyl)-pyrrolidine-2-carboxylic acid Example 4-11: (S)-1-((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carbonyl)-piperidine-2-carboxylic acid Example 4-12: 4-[((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carbonyl)-amino]-cyclohexanecarboxylic acid Example 4-13: 4-[((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carbonyl)-methyl-amino]-cyclohexanecarboxylic acid

| No. | Product | ESI-MS m/z [M + 1]$^+$ | Retention time (min) | Starting Material |
|---|---|---|---|---|
| 4-1 | | 669 | 2.09 (condition A) | |
| 4-2 | | 643 | 2.11 (condition A) | |
| 4-3 | | 657 | 4.26 (condition B) | |
| 4-4 | | 641 | 2.06 (condition A) | |

-continued

| No. | Product | ESI-MS m/z [M + 1]+ | Retention time (min) | Starting Material |
|---|---|---|---|---|
| 4-5 | | 683 | 2.19 (condition A) | |
| 4-6 | | 641 | 4.01 (condition B) | |
| 4-7 | | 669 | 4.85 (condition B) | |
| 4-8 | | 710 | 4.20 (condition B) | |

-continued

| No. | Product | ESI-MS m/z [M + 1]+ | Retention time (min) | Starting Material |
|---|---|---|---|---|
| 4-9 | | 697 | 2.20 (condition A) | |
| 4-10 | | 639 | 2.01 (condition A) | |
| 4-11 | | 654 | 2.06 (condition A) | |
| 4-12 | | 668 | 3.83 (condition B) | |

| No. | Product | ESI-MS m/z [M + 1]+ | Retention time (min) | Starting Material |
|---|---|---|---|---|
| 4-13 | | 682 | 3.89 (condition B) | |

Example 5

Synthesis of ((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidin-1-yl)-oxo-acetic acid ethyl ester

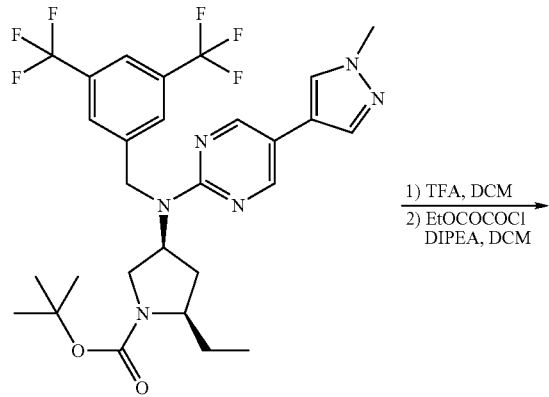

To a solution of (2R,4S)-4-{(3,5-bis-trifluoromethyl-benzyl)-[5-(1-methyl-1H-pyrazol-4-yl)-pyrimidin-2-yl]-amino}-2-ethyl-pyrrolidine-1-carboxylic acid tert-butyl ester (0.117 mmol; 70 mg) in dichloromethane (1.2 mL) is added trifluoroacetic acid (0.4 mL). The mixture is stirred for 1 hour, and then concentrated under reduced pressure. To a solution of the obtained residue and N,N-diisopropylethylamine (0.468 mmol; 60.5 mg) in dichloromethane (0.4 mL) is added ethyl chloroglyoxylate (0.234 mmol; 31.9 mg). The mixture is stirred for 1 hour at room temperature, and then diluted with water and dichloromethane. The organic layer is separated to concentrated under reduced pressure. The obtained residue is purified by silica gel column chromatography (eluent: n-hexane/EtOAc) to give ((2R,4S)-4-{(3,5-Bis-trifluoromethyl-benzyl)-[5-(1-methyl-1H-pyrazol-4-O-pyrimidin-2-yl]-amino}-2-ethyl-pyrrolidin-1-yl)-oxo-acetic acid ethyl ester (51 mg, 73%); ESI-MS m/z: 599 [M+1]+, Retention time 2.15 min (condition A).

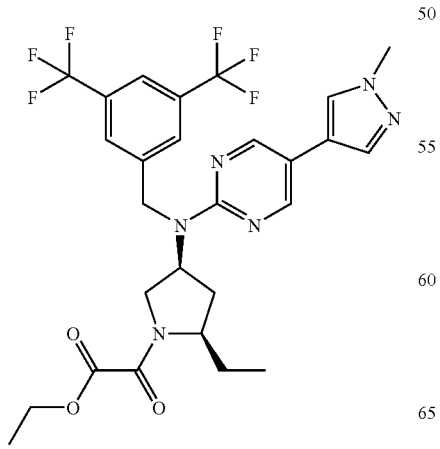

The following compounds are prepared following the procedure of Example 5 using corresponding acid chlorides.

Example 5-1: 1-((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidin-1-yl)-ethanone Example 5-2: 1-((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidin-1-yl)-3-methyl-butan-1-one Example 5-3: ((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidin-1-yl)-cyclohexyl-methanone

| No | Product | ESI-MS m/z [M + 1]+ | Retention time (min) | Starting Material | Starting Material |
|---|---|---|---|---|---|
| 5-1 | | 541 | 2.02 (condition A) | acetyl chloride | |
| 5-2 | | 583 | 2.32 (condition A) | 3-methylbutanoyl chloride | |
| 5-3 | | 609 | 2.08 (condition A) | cyclohexanecarbonyl chloride | |

Example 6

Synthesis of (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid isopropyl ester

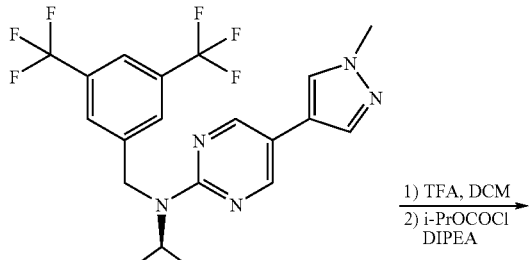

To a solution of (2R,4S)-4-{(3,5-bis-trifluoromethyl-benzyl)-[5-(1-methyl-1H-pyrazol-4-yl)-pyrimidin-2-yl]-amino}-2-ethyl-pyrrolidine-1-carboxylic acid tert-butyl ester (0.200 mmol; 120 mg) in dichloromethane (2.0 mL) is added trifluoroacetic acid (0.7 mL). The mixture is stirred for 1 hour, and then concentrated under reduced pressure. To a mixture of the obtained residue and N,N-diisopropylethylamine (1.6 mmol; 207 mg) is added isopropyl chloroformate (0.4 mmol; 49 mg). The mixture is stirred for 1 hour at room temperature, and then diluted with water and dichloromethane. The organic layer is separated to concentrated under reduced pressure. The obtained residue is purified by silica gel column chromatography (eluent: n-hexane/EtOAc) to give (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid isopropyl ester (51 mg, 73%); ESI-MS m/z: 599 [M+1]$^+$, Retention time 2.15 min (condition A).

1H NMR (400 MHz, CHLOROFORM-d) □ ppm 0.82 (t, J=7.30 Hz, 3 H), 1.23 (d, J=5.54 Hz, 6 H), 1.47-1.58 (m, 1 H), 1.66-1.74 (m, 1 H), 1.97 (br. s., 1 H), 2.26-2.33 (m, 1 H), 3.13 (t, J=10.58 Hz, 1 H), 3.78-3.85 (m, 1 H), 3.89-4.00 (m, 4 H), 4.87-4.98 (m, 3 H), 5.17-5.26 (m, 1 H), 7.54 (s, 1 H), 7.66 (s, 3 H), 7.76 (s, 1 H), 8.44 (s, 2 H)

The following compounds are prepared following the procedure of Example 6 using corresponding chloroformates.

Example 6-1: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid isobutyl ester Example 6-2: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 2,2-dimethyl-propyl ester

| No. | Product | ESI-MS m/z [M + 1]$^+$ | Retention time (min) | Starting Material | Starting Material |
|-----|---------|------------------------|----------------------|-------------------|-------------------|
| 6-1 | | 599 | 4.84 (condition B) | | |

| No. | Product | ESI-MS m/z [M + 1]+ | Retention time (min) | Starting Material | Starting Material |
|---|---|---|---|---|---|
| 6-2 | | 613 | 2.66 (condition A) | | |

Example 6-1

1H NMR (400 MHz, CHLOROFORM-d) ☐ ppm 0.83 (t, J=7.56 Hz, 3 H), 0.92 (d, J=6.52 Hz, 6 H), 1.48-1.60 (m, 1 H), 1.68-1.76 (m, 1 H), 1.88-2.10 (m, 2 H), 2.28-2.34 (m, 1 H), 3.15 (t, J=10.58 Hz, 1 H), 3.82-3.86 (m, 7 H), 4.89-4.98 (m, 2 H), 5.17-5.26 (m, 1 H), 7.54 (s, 1 H), 7.67 (br. s., 3 H), 7.76 (s, 1 H), 8.44 (s, 2 H)

Example 6-2

1H NMR (400 MHz, CHLOROFORM-d) ☐ ppm 0.84 (t, J=7.55 Hz, 3 H), 0.93 (br. s., 9 H), 1.47-1.60 (m, 1 H), 1.68-1.84 (m, 2 H), 1.91-2.10 (m, 1 H), 2.27-2.39 (m, 1 H), 3.16 (t, J=10.58 Hz, 1 H), 3.71-3.89 (m, 3 H), 3.95 (s, 3 H), 4.94 (s, 2 H), 5.15-5.28 (m, 1 H), 7.54 (s, 1 H), 7.67 (s, 3 H), 7.76 (s, 1 H), 8.44 (s, 2 H)

Example 7

Synthesis of (2R,4S)-4-{(3,5-bis-trifluoromethyl-benzyl)-[5-(1-methyl-1H-pyrazol-4-yl)-pyrimidin-2-yl]-amino}-2-ethyl-pyrrolidine-1-carboxylic acid cis-4-methoxycarbonylcyclohexyl ester

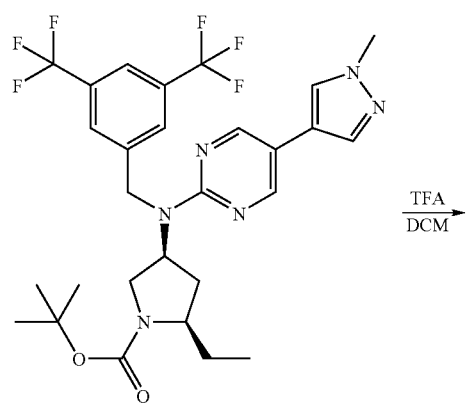

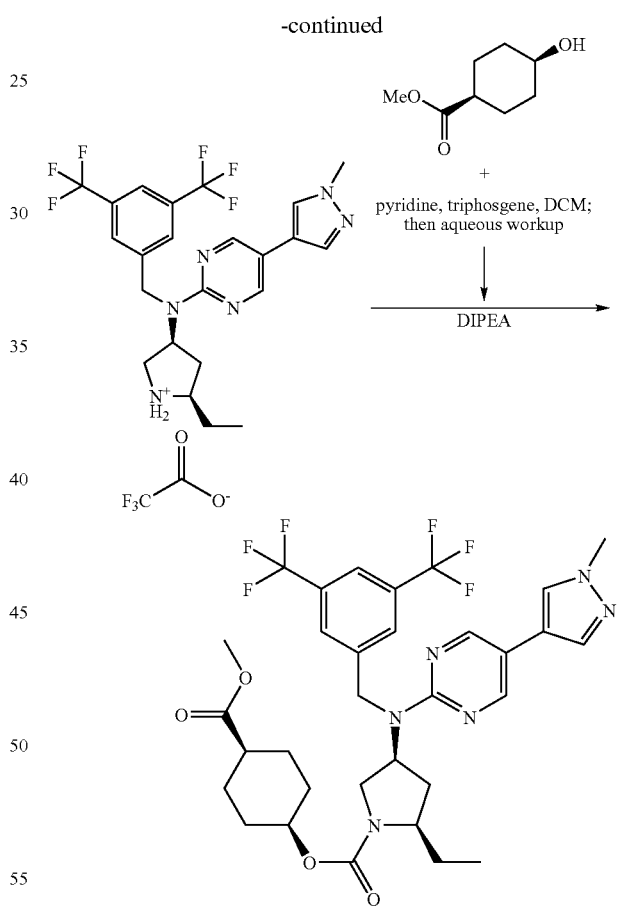

To a solution of (2R,4S)-4-{(3,5-bis-trifluoromethyl-benzyl)-[5-(1-methyl-1H-pyrazol-4-yl)-pyrimidin-2-yl]-amino}-2-ethyl-pyrrolidine-1-carboxylic acid tert-butyl ester (0.117 mmol; 70 mg) in dichloromethane (1.2 mL) is added trifluoroacetic acid (0.4 mL). The mixture is stirred for 1 hour, and then concentrated under reduced pressure to give the crude ammonium trifluoroacetate; ESI-MS m/z: 499 [M-CF3COO+1]+, Retention time 1.82 min (condition A).

To a solution of cis-4-Hydroxycyclohexanecarboxylic acid methyl ester (4.05 mmol; 640 mg) and triphosgene (2.70 mmol; 801 mg) in dichloromethane (20 mL) is slowly added a solution of pyridine (4.25 mmol; 336 mg) in dichloromethane (20 mL) at 0° C. The reaction mixture is stirred for 4 hours at room temperature, and then quenched with saturated aqueous ammonium chloride solution, extracted twice with dichloromethane. The combined organic layer is washed with brine, dried over Na2SO4, filtered, concentrated under reduced pressure to give the crude material (848 mg).

Next, a mixture of 52 mg of the obtained residue and the full volume of the crude ammonium trifluoroacetate and N,N-diisopropylethylamine (0.936 mmol; 121 mg) is stirred for 2 hours at room temperature. The mixture is diluted with dichloromethane and water. The organic layer after drying is separated to concentrated under reduce pressure. The obtained residue is purified by silica gel column chromatography (eluent: n-hexane/EtOAc) to give (2R,4S)-4-{(3,5-bis-trifluoromethyl-benzyl)-[5-(1-methyl-1H-pyrazol-4-yl)-pyrimidin-2-yl]-amino}-2-ethyl-pyrrolidine-1-carboxylic acid cis-4-methoxycarbonylcyclohexyl ester (76 mg, 95%); ESI-MS m/z: 683 [M+1]$^+$, Retention time 2.26 min (condition A).

The following compounds are prepared following the procedure of Example 7 using corresponding alcohols.

Example 7-1: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 2-methoxycarbonyl-2-methyl-propyl ester Example 7-2: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 1-ethoxycarbonyl-1-methyl-ethyl ester Example 7-3: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 3-ethoxycarbonyl-3-methyl-butyl ester Example 7-4: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid tetrahydro-pyran-4-yl ester Example 7-5: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 3-methoxycarbonyl-phenyl ester Example 7-6: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid tetrahydro-pyran-4-ylmethyl ester Example 7-7: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 3-methoxycarbonyl-cyclobutyl ester Example 7-8: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 3-methoxycarbonyl-cyclobutyl ester Example 7-9: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 4-methoxycarbonyl-cyclohexylmethyl ester Example 7-10: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid cyclohexylmethyl ester Example 7-11: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 1-methoxycarbonyl-cyclopentylmethyl ester Example 7-12: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 4-ethoxycarbonylmethyl-cyclohexylmethyl ester

| No. | Product | ESI-MS m/z [M + 1]$^+$ | Retention time (min) | alcohol | Starting Material |
|---|---|---|---|---|---|
| 7-1 | | 657 | 2.26 (condition A) | | |
| 7-2 | | 657 | 2.32 (condition A) | | |

-continued

| No. | Product | ESI-MS m/z [M + 1]+ | Retention time (min) | alcohol | Starting Material |
|---|---|---|---|---|---|
| 7-3 | | 685 | 4.83 (condition B) | | |
| 7-4 | | 627 | 2.18 (condition A) | | |
| 7-5 | | 677 | 2.28 (condition A) | | |
| 7-6 | | 641 | 4.39 (condition B) | | |
| 7-7 | | 655 | 2.21 (condition A) | | |

-continued

| No. | Product | ESI-MS m/z [M + 1]+ | Retention time (min) | alcohol | Starting Material |
|---|---|---|---|---|---|
| 7-8 | | 655 | 4.45 (condition B) | | |
| 7-9 | | 697 | 2.36 (condition A) | | |
| 7-10 | | 639 | 2.66 (condition A) | | |
| 7-11 | | 683 | 5.13 (condition B) | | |

| No. | Product | ESI-MS m/z [M + 1]⁺ | Retention time (min) | alcohol | Starting Material |
|---|---|---|---|---|---|
| 7-12 | | 725 | 2.47 (condition A) | | |

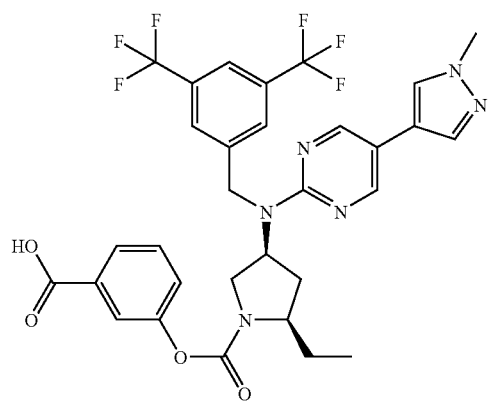

Example 7-4

1H NMR (400 MHz, CHLOROFORM-d) ☐ ppm 0.84 (t, J=7.30 Hz, 3 H), 1.51-1.77 (m, 4 H), 1.92-2.12 (m, 3 H), 2.29-2.31 (m, 1 H), 3.16 (t, J=10.58 Hz, 1 H), 3.53-3.58 (m, 2 H), 3.80-4.00 (m, 7 H), 4.88-4.99 (m, 3 H), 5.17-5.26 (m, 1 H), 7.54 (s, 1 H), 7.67 (s, 3 H), 7.77 (s, 1 H), 8.45 (s, 2 H)

Example 7-6

1H NMR (400 MHz, CHLOROFORM-d) ☐ ppm 0.83 (t, J=7.56 Hz, 3 H), 1.32-1.43 (m, 2 H), 1.47-1.63 (m, 3 H), 1.69-1.77 (m, 1 H), 1.82-2.12 (m, 2 H), 2.27-2.34 (m, 1 H), 3.15 (t, J=10.32 Hz, 1 H), 3.36-3.41 (m, 2 H), 3.81-4.00 (m, 9 H), 4.85-5.06 (m, 2 H), 5.16-5.25 (m, 1 H), 7.54 (s, 1 H), 7.66 (s, 3 H), 7.77 (s, 1 H), 8.44 (s, 2 H)

Example 8

Synthesis of (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 3-carboxy-phenyl ester

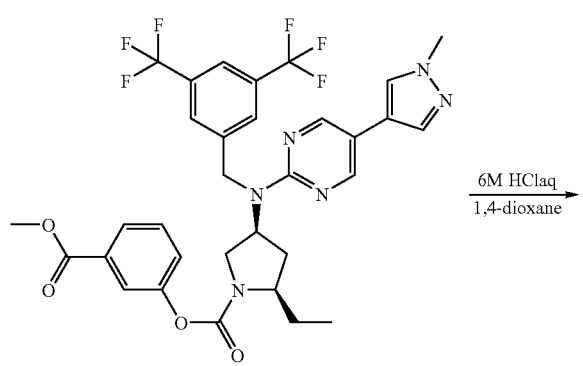

A mixture of (2R,4S)-4-{(3,5-bis-trifluoromethyl-benzyl)-[5-(1-methyl-1H-pyrazol-4-yl)-pyrimidin-2-yl]-amino}-2-ethyl-pyrrolidine-1-carboxylic acid 3-methoxycarbonylphenyl ester (0.037 mmol; 25 mg), aqueous 6M HCl (0.5 mL) and 1,4-dioxane (0.1 mL) is stirred at 100° C. for 19 hours. The mixture is cooled to ambient temperature, then diluted with water and Et2O. The product is extracted three times with Et2O. The combined organic layer is washed with brine, dried over Na2SO4, filtered, concentrated under reduced pressure. The obtained residue is purified by silica gel column chromatography (eluent: dichloromethane/methanol) to give (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 3-carboxyphenyl ester (8.0 mg, 33%); ESI-MS m/z: 663 [M+1]⁺, Retention time 2.14 min (condition A).

Example 9

Synthesis of (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 3-methyl-oxetan-3-ylmethyl ester

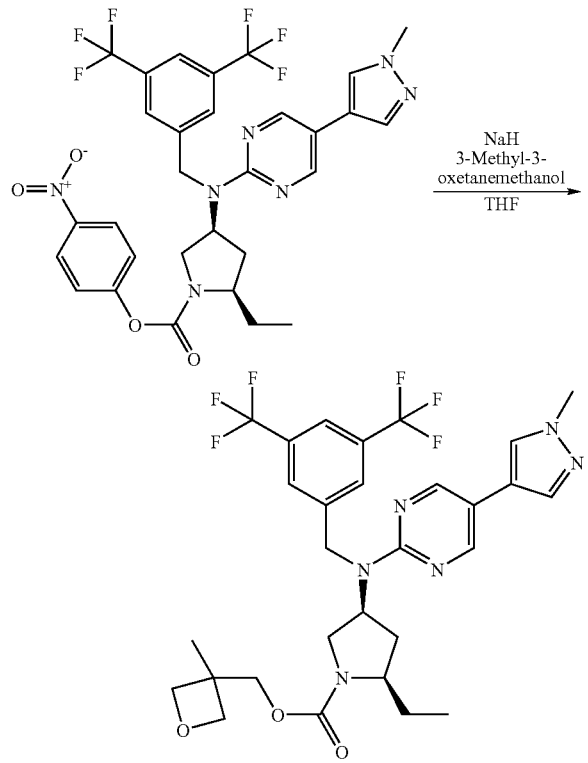

To a mixture of 3-methyl-3-oxetanemethanol (0.202 mmol; 20.6 mg) and sodium hydride (60% oil dispersion in mineral oil, 0.202 mmol; 8.1 mg) in THF (0.5 mL) is added a solution of (2R,4S)-4-{(3,5-bis-trifluoromethyl-benzyl)-[5-(1-methyl-1H-pyrazol-4-yl)-pyrimidin-2-yl]-amino}-2-ethyl-pyrrolidine-1-carboxylic acid 4-nitro-phenyl ester (0.101 mmol; 67 mg) in THF (0.5 mL). The reaction mixture is stirred for 1 hour at room temperature, then quenched with saturated aqueous ammonium chloride. The product is extracted three times with EtOAc. The combined organic layer is washed with brine, dried over Na2SO4, filtered, concentrated under reduced pressure. The obtained residue is purified by silica gel column chromatography (eluent: n-hexane/EtOAc), followed by another silica gel column chromatography (eluent: dichloromethane/methanol) to give (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 3-methyl-oxetan-3-ylmethyl ester (40.7 mg, 64%); ESI-MS m/z: 626 [M+1]$^+$, Retention time 2.19 min (condition A).

1H NMR (400 MHz, CHLOROFORM-d) □ ppm 0.84 (t, J=7.30 Hz, 3 H) 1.32 (br s, 3 H) 1.50-1.60 (m, 1 H), 1.71-1.79 (m, 1 H) 1.84-2.15 (m, 1 H) 2.31 (br s, 1 H) 3.16-3.21 (m, 1 H) 3.81-3.95 (m, 5 H), 4.15 (br s, 2 H) 4.36-4.39 (m, 2 H) 4.51-4.54 (m, 2 H) 4.89-4.99 (m, 2 H) 5.17-5.26 (m, 1 H) 7.54 (s, 1 H) 7.66 (s, 3 H) 7.77 (s, 1 H) 8.44 (s, 2 H)

The following compounds are prepared following the procedure of Example 9 using corresponding alcohols.

Example 9-1: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 1-ethyl-propyl ester Example 9-2: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 2,2,2-trifluoro-ethyl ester Example 9-3: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid cyclopentyl ester Example 9-4: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid (R)-sec-butyl ester Example 9-5: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid (S)-sec-butyl ester Example 9-6: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 3-ethyl-oxetan-3-ylmethyl ester

| No. | Product | ESI-MS m/z [M + 1]$^+$ | Retention time (min) | Starting Material | Starting Material |
|---|---|---|---|---|---|
| 9-1 | | 613 | 2.46 (condition A) | | |

-continued
| No. | Product | ESI-MS m/z [M + 1]+ | Retention time (min) | Starting Material | Starting Material |
|---|---|---|---|---|---|
| 9-2 | 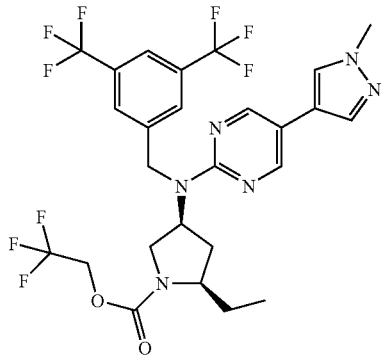 [SMILES: CC[C@@H]1C[C@H](N(Cc2cc(C(F)(F)F)cc(C(F)(F)F)c2)c2ncc(-c3cnn(C)c3)cn2)CN1C(=O)OCC(F)(F)F] | 625 | 2.30 (condition A) | 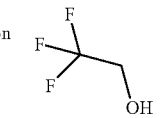 | 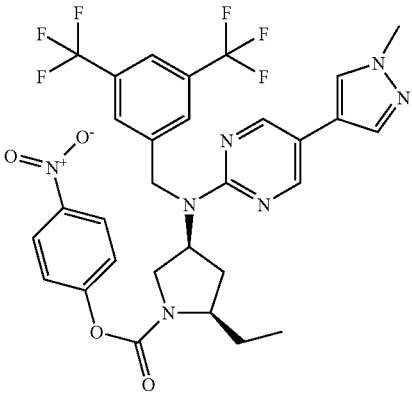 [SMILES: CC[C@@H]1C[C@H](N(Cc2cc(C(F)(F)F)cc(C(F)(F)F)c2)c2ncc(-c3cnn(C)c3)cn2)CN1C(=O)Oc1ccc([N+](=O)[O-])cc1] |
| 9-3 | 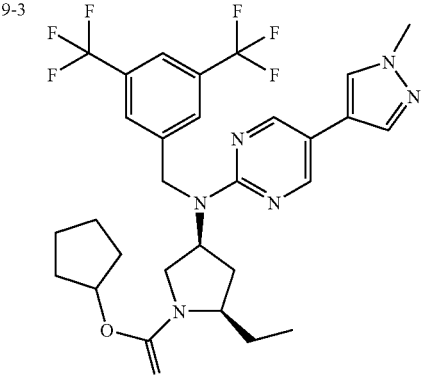 | 611 | 2.42 (condition A) | 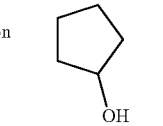 | 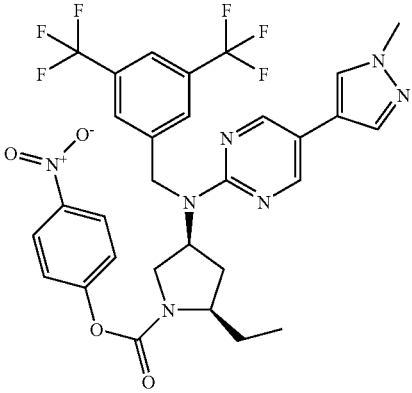 [SMILES: CC[C@@H]1C[C@H](N(Cc2cc(C(F)(F)F)cc(C(F)(F)F)c2)c2ncc(-c3cnn(C)c3)cn2)CN1C(=O)Oc1ccc([N+](=O)[O-])cc1] |
| 9-4 | 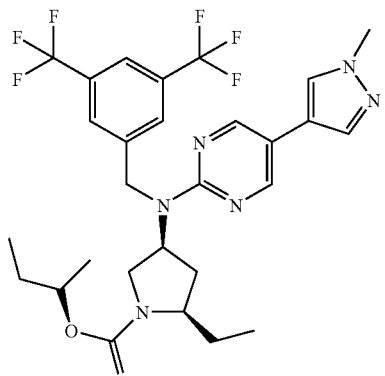 | 599 | 2.41 (condition A) | 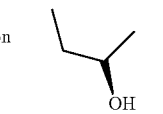 | 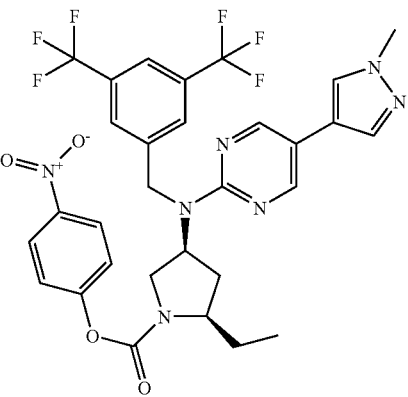 [SMILES: CC[C@@H]1C[C@H](N(Cc2cc(C(F)(F)F)cc(C(F)(F)F)c2)c2ncc(-c3cnn(C)c3)cn2)CN1C(=O)Oc1ccc([N+](=O)[O-])cc1] |

-continued

| No. | Product | ESI-MS m/z [M + 1]+ | Retention time (min) | Starting Material | Starting Material |
|---|---|---|---|---|---|
| 9-5 | 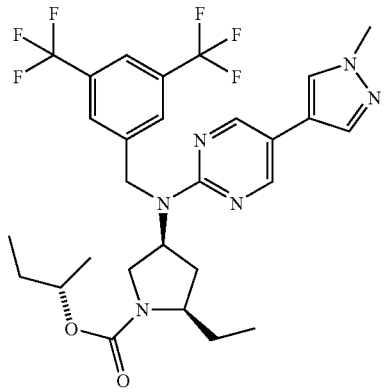 | 599 | 4.89 (condition B) | 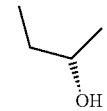 | 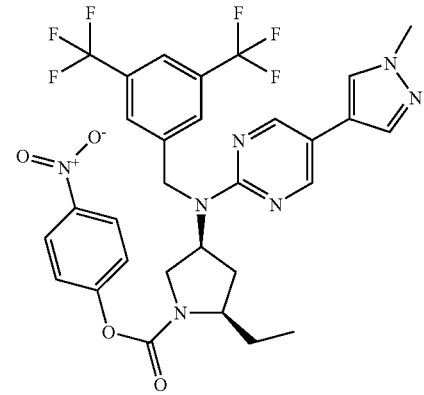 [SMILES: CC[C@@H]1C[C@H](N(Cc2cc(C(F)(F)F)cc(C(F)(F)F)c2)c2ncc(-c3cnn(C)c3)cn2)CN1C(=O)Oc1ccc([N+](=O)[O-])cc1] |
| 9-6 | 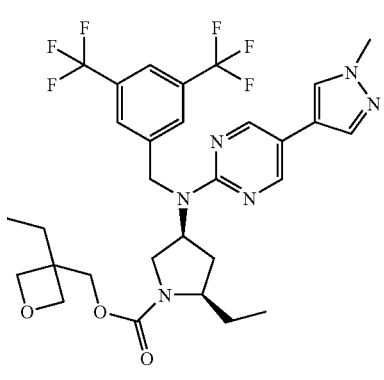 [SMILES: CC[C@@H]1C[C@H](N(Cc2cc(C(F)(F)F)cc(C(F)(F)F)c2)c2ncc(-c3cnn(C)c3)cn2)CN1C(=O)OCC1(CC)COC1] | 641 | 2.24 (condition A) |  | 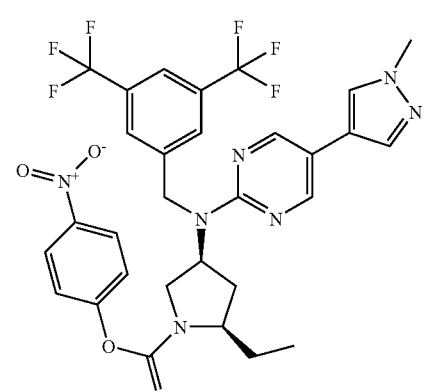 |

Reactions (No. 1, 4, & 5 in the above table) is performed at 60° C.

Example 9-1

1H NMR (400 MHz, CHLOROFORM-d) □ ppm 0.83 (t, J=7.56 Hz, 3 H), 0.89 (t, J=7.56 Hz, 6H), 1.56-1.61 (m, 5 H), 1.70-1.74 (m, 1 H), 1.96 (br s, 1 H), 2.27-2.34 (m, 1 H), 3.15 (t, J=10.58 Hz, 1 H), 3.79-3.98 (m, 5 H), 4.65 (br s, 1 H), 4.89-4.98 (m, 2 H), 5.17-5.26 (m, 1 H), 7.54 (s, 1 H), 7.66 (s, 3 H), 7.76 (s, 1 H), 8.44 (s, 2 H)

Example 9-2

1H NMR (400 MHz, CHLOROFORM-d): 2 rotamers at 23° C. □ ppm 0.84 (t, J=7.56 Hz, 3 H), 1.56 (br s, 1 H), 1.74-1.82 (m, 1 H), 1.88 and 2.04 (m, 1H, rotamers), 2.31 (br s, 1 H), 3.21-3.24 (m, 1 H), 3.86-4.00 (m, 5 H), 4.44 and 4.58 (m, 2H, rotamers) 4.86-5.02 (m, 2 H), 5.20 (br s, 1 H), 7.55 (s, 1 H), 7.67 (s, 3 H), 7.77 (s, 1 H), 8.45 (s, 2 H)

Example 9-3

1H NMR (400 MHz, CHLOROFORM-d) □ ppm 0.82 (t, J=7.54 Hz, 3 H), 1.48-1.74 (m, 8 H), 1.80-1.85 (m, 3 H), 2.25-2.32 (m, 1 H), 3.12 (t, J=10.32 Hz, 1 H), 3.78-4.00 (m, 5 H), 4.87-4.97 (m, 2 H) 5.11 (br. s., 1 H) 5.16-5.25 (m, 1 H) 7.54 (s, 1 H) 7.66 (s, 3 H) 7.76 (s, 1 H) 8.44 (s, 2 H)

Example 9-4

1H NMR (400 MHz, CHLOROFORM-d) □ ppm 0.82 (t, J=7.54 Hz, 3 H), 0.88-0.91 (m, 3 H), 1.21 (d, J=6.56 Hz, 3 H), 1.50-1.61 (m, 3 H), 1.67-1.75 (m, 1 H), 1.83-2.12 (m, 1 H), 2.27-2.33 (m, 1 H), 3.14 (t, J=10.32 Hz, 1 H), 3.78-4.00 (m, 5 H), 4.72-4.77 (m, 1 H), 4.88-4.98 (m, 2 H), 5.18-5.27 (m, 1 H), 7.54 (s, 1 H), 7.66 (s, 3 H), 7.76 (s, 1 H), 8.44 (s, 2 H)

Example 9-5

1H NMR (400 MHz, CHLOROFORM-d) □ ppm 0.83 (t, J=7.30 Hz, 3 H), 0.90 (t, J=7.54 Hz, 3H), 1.21 (d, J=6.56 Hz, 3 H), 1.48-1.64 (m, 3 H), 1.67-1.75 (m, 1 H), 1.83-2.10 (m, 1 H), 2.27-2.33 (m, 1 H), 3.14 (t, J=10.56 Hz, 1 H), 3.78-4.00 (m, 5 H), 4.72-4.80 (m, 1 H), 4.88-4.98 (m, 2 H), 5.17-5.26 (m, 1 H), 7.54 (s, 1 H), 7.66 (s, 3 H), 7.76 (s, 1 H), 8.44 (s, 2H)

Example 9-6

1H NMR (400 MHz, CHLOROFORM-d) □ ppm 0.84 (t, J=7.30 Hz, 3 H), 0.91 (t, J=7.56 Hz, 3H), 1.51-1.58 (m, 1 H), 1.70-1.79 (m, 3 H), 1.84-2.16 (m, 1 H), 2.31 (br s, 1 H), 3.18 (t, J=10.32 Hz, 1 H), 3.81-4.00 (m, 5 H), 4.20 (br s, 2 H), 4.34-4.39 (m, 2 H), 4.47-4.49 (m, 2 H), 4.89-4.99 (m, 2 H), 5.17-5.26 (m, 1 H), 7.54 (s, 1 H), 7.67 (s, 3 H), 7.77 (s, 1 H), 8.44 (s, 2 H)

Example 10

Synthesis of diasteromers of (5R)-3-{(3,5-Bis-trifluoromethyl-benzyl)-[5-(1-methyl-1H-pyrazol-4-yl)-pyrimidin-2-yl]-amino}-5-ethyl-2-oxo-pyrrolidine-1-carboxylic acid tert-butyl ester

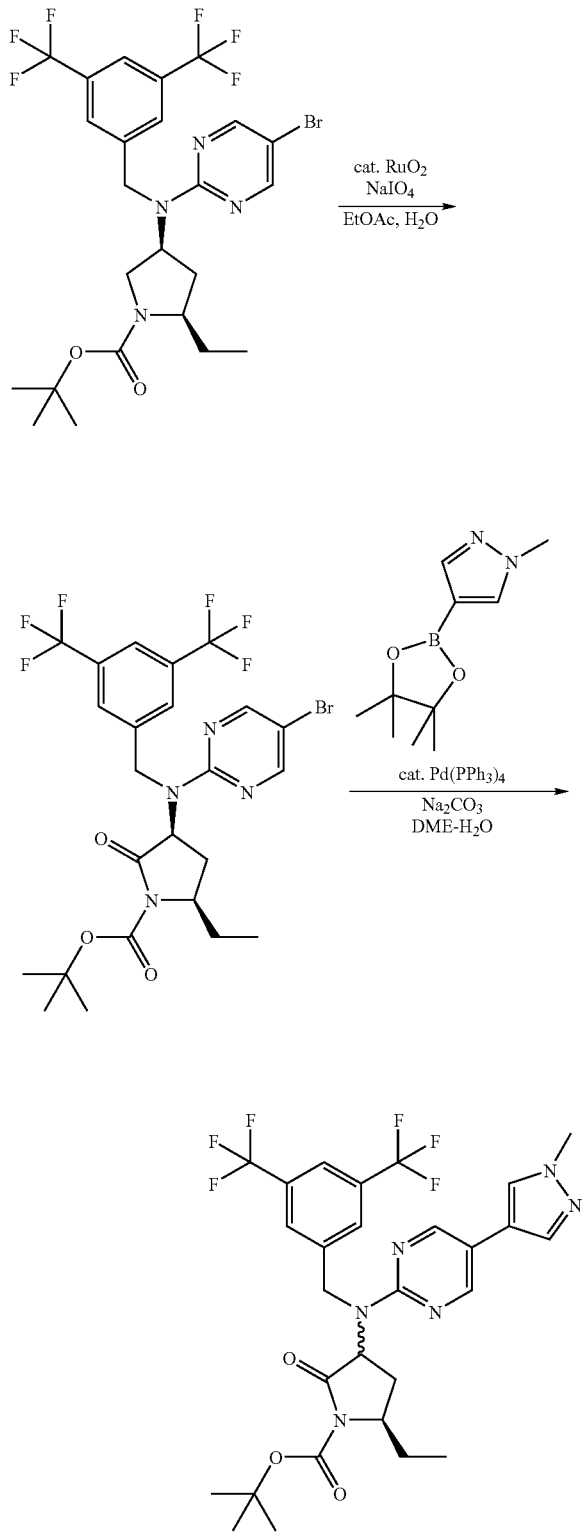

To a suspension of ruthenium(IV) oxide hydrate (10 mg) and sodium periodate (3.0 mmol; 642 mg) in water (12 mL) is added a solution of (2R,4S)-4-[(3,5-bis-trifluoromethyl-benzyl)-(5-bromo-pyrimidin-2-yl)-amino]-2-ethyl-pyrrolidine-1-carboxylic acid tert-butyl ester (0.5 mmol; 300 mg) in EtOAc (12 mL) at 0° C. After stirring for 2 hours at 0° C. and then stirred for 1.5 hours at room temperature, another sodium periodate (3.0 mmol; 642 mg) is added to the mixture. After stirring for additional 16.5 hours at room temperature, the reaction mixture is diluted with EtOAc and water. The product is extracted three times with EtOAc. The combined organic layer is washed with brine, dried over Na2SO4, filtered, concentrated under reduced pressure. The obtained residue is purified by silica gel column chromatography (eluent: dichloromethane/methanol) to give (3S,5R)-4-[(3,5-bis-trifluoromethyl-benzyl)-(5-bromo-pyrimidin-2-yl)-amino]-2-ethyl-2-oxopyrrolidine-1-carboxylic acid tert-butyl ester (28 mg, 9%); ESI-MS m/z: 511 [M-tBuOCO+2]$^+$, Retention time 2.43 min (condition A). (3S,5R)-4-[(3,5-bis-trifluoromethyl-benzyl)-(5-bromo-pyrimidin-2-yl)-amino]-2-ethyl-2-oxopyrrolidine-1-carboxylic acid tert-butyl ester (0.043 mmol; 26 mg), tetrakis(triphenylphosphine) palladium (0.0043 mmol; 5.0 mg), 1-methylpyrazol-4-boronic acid pinacol ester (0.060 mmol; 12.5 mg) and aqueous 2M sodium carbonate (0.043 mL) are dissolved in 1,2-dimethoxyethane (0.2 ml) at room temperature. The mixture is stirred at 90° C. for 7 hours, and then cooled to ambient temperature. To the mixture is added brine and the solution is extracted with EtOAc. The organic layer is washed with brine, dried over Na2SO4, filtered, and concentrated under reduced pressure. The obtained residue is subjected to column chromatography on silica gel (eluent: n-hexane/EtOAc) to give a mixture of pinacol and diastereomers of (5R)-3-{3,5-bis-trifluoromethyl-benzyl)-[5-(1-methyl-1H-pyrazol-4-yl)-pyrimidin-2-yl]-amino}-5-ethyl-2-oxo-pyrrolidine-1-carboxylic acid tert-butyl ester.

To a suspension of the crude and silica gel (0.81 g) in EtOAc (3.9 mL) is added aqueous 0.65 M sodium periodate solution (0.78 mL). After stirring for 17 hours, another silica gel (4.05 g) and EtOAc (5.6 mL) are added. After stirring for 10 min., the mixture is subjected to short column chromatography on silica gel to give pure (5R)-3-{(3,5-bis-trifluoromethyl-benzyl)-[5-(1-methyl-1H-pyrazol-4-yl)-pyrimidin-2-yl]-amino}-5-ethyl-2-oxo-pyrrolidine-1-carboxylic acid tert-butyl ester (16 mg, 61%) as a diastereomixture (dr=62:38); ESI-MS m/z: 613 [M+1]$^+$, Retention time 4.59 min (condition B).

Example 11

Synthesis of (2R,4S)-4-{(3,5-Bis-trifluoromethyl-benzyl)-[5-((S)-3-hydroxy-pyrrolidin-1-yl)-pyrimidin-2-yl]-amino}-2-ethyl-pyrrolidine-1-carboxylic acid isopropyl ester

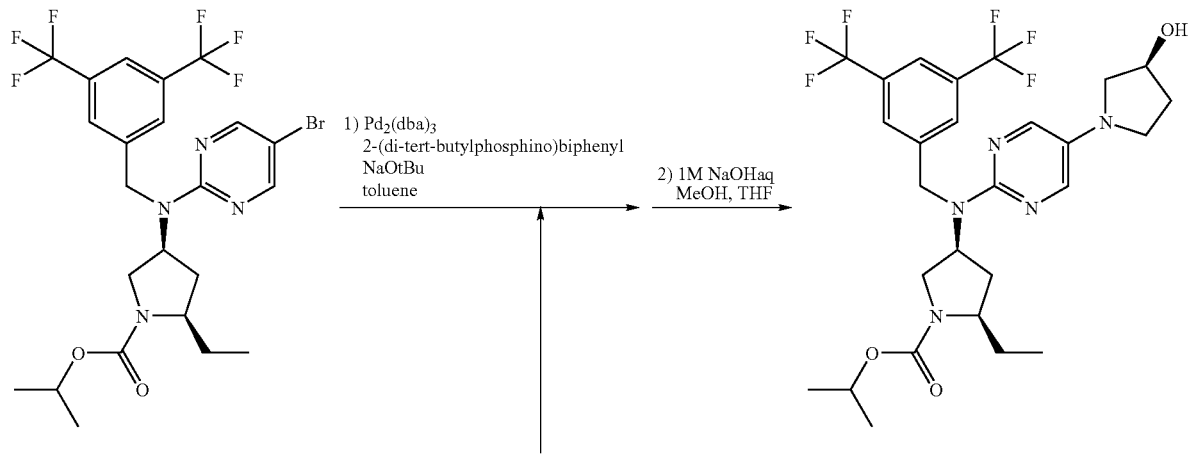

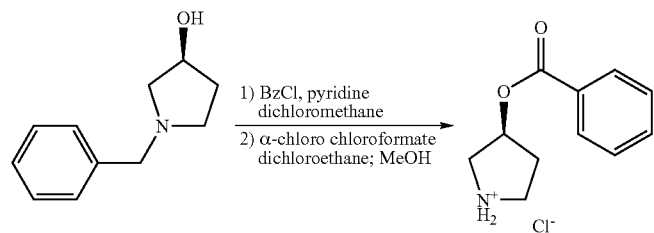

To a mixture of (S)-(−)-1-benzyl-3-pyrrolidinol (2.84 mmol; 0.50 g) in dichloromethane (5 ml) and pyridine (5.68 mmol; 449 mg) is added benzoyl chloride (3.41 mmol; 479 mg) at 0° C., and the mixture is stirred for 1 hour while warming to room temperature. After addition of saturated aqueous NaHCO3 solution, the product is extracted with EtOAc. The combined organic layer after dried over MgSO4 is concentrated under reduced pressure. The resulting benzoic acid (S)-1-benzyl-pyrrolidin-3-yl ester is used in next step without further purification.

To a solution of the crude product (0.45 mmol; 127 mg) in 1,2-dichloroethane (1.5 mL) is added α-chloroethyl chloroformate (0.59 mmol; 84 mg) at room temperature, and the mixture is heated at 90° C. for 3 hours. After addition of another α-chloroethyl chloroformate (1.18 mmol; 168 mg), the mixture is stirred for additional 8 hours at the same temperature. After cooling to ambient temperature, the reaction mixture is concentrated, and then the resulting mixture is diluted with MeOH (1 ml). The reaction mixture is refluxed for 1 hour. After cooling to ambient temperature, solvent are concentrated. The resulting benzoic acid (S)-pyrrolidin-3-yl ester hydrochloride is used in next step without further purification.

The resulting benzoic acid (S)-pyrrolidin-3-yl ester hydrochloride (0.45 mmol), (2R,4S)-4-[(3,5-bis-trifluoromethyl-benzyl)-(5-bromo-pyrimidin-2-yl)-amino]-2-ethyl-pyrrolidine-1-carboxylic acid isopropyl ester (0.196 mmol; 114 mg), tris(dibenzylideneacetone)dipalladium(0) (0.0098 mmol; 9.0 mg), 2-(di-tert-butylphosphino)biphenyl (0.0196 mmol; 5.8 mg) and sodium tert-butoxide (0.784 mmol; 75.3 mg) are dissolved in toluene (1 mL). The mixture is stirred for 2.5 hours at 100° C. To the mixture are added aqueous 1 M NaOH (5 mL), MeOH (10 mL) and THF (3 mL) at room temperature. After stirring for 5 hours, the reaction mixture is quenched with saturated aqueous ammonium chloride solution. The product is extracted three times with EtOAc. The combined organic layer is washed with brine, dried over Na2SO4, filtered, concentrated under reduced pressure. The obtained residue is purified by silica gel column chromatography (eluent: n-hexane/EtOAc) to give (2R,4S)-4-{(3,5-bis-trifluoromethyl-benzyl)-[5-((S)-3-hydroxy-pyrrolidin-1-yl)-pyrimidin-2-yl]-amino}-2-ethyl-pyrrolidine-1-carboxylic acid isopropyl ester (82 mg, 71%); ESI-MS m/z: 590 [M+1]$^+$, Retention time 2.15 min (condition A).

1H NMR (400 MHz, CHLOROFORM-d) □ ppm 0.81 (t, J=7.56 Hz, 3 H), 1.23 (d, J=6.04 Hz, 6 H), 1.45-1.56 (m, 1 H), 1.61-1.69 (m, 1 H), 1.87-2.08 (m, 3 H), 2.14-2.22 (m, 1 H), 2.23-2.30 (m, 1 H), 3.08 (t, J=10.6 Hz, 1 H), 3.20-3.28 (m, 2 H), 3.41-3.49 (m, 2 H), 3.76-3.82 (m, 1 H), 3.89 (br s, 1 H), 4.58-4.65 (m, 1 H), 4.78-4.93 (m, 3 H), 5.07-5.16 (m, 1H), 7.66 (s, 2 H), 7.73 (s, 1 H), 7.85 (s, 2 H)

Example 12

Synthesis of (2R,4S)-4-[(3,5-Bis-trifluoromethyl-benzyl)-(5-morpholin-4-yl-pyrimidin-2-yl)-amino]-2-ethyl-pyrrolidine-1-carboxylic acid tert-butyl ester

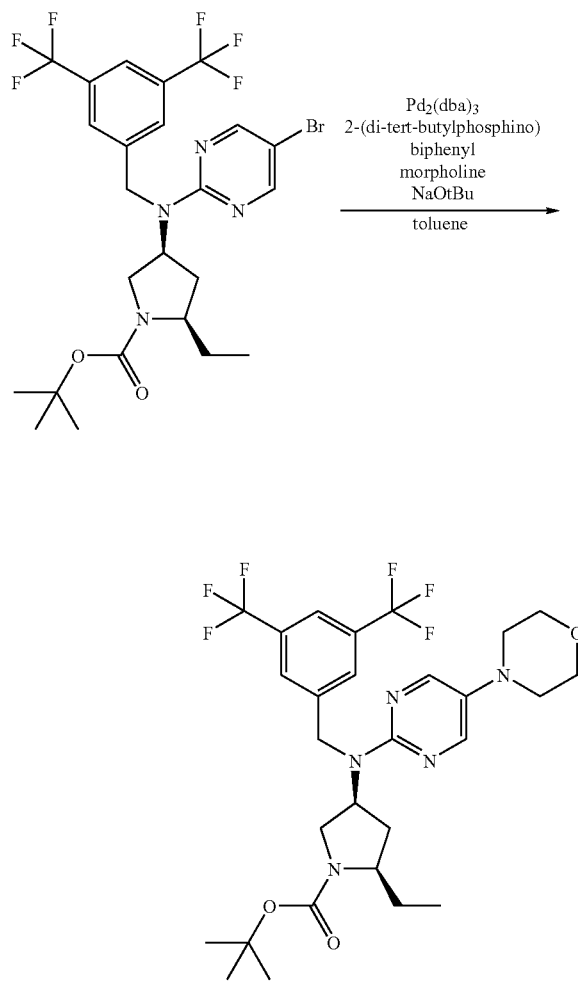

(2R,4S)-4-[(3,5-Bis-trifluoromethyl-benzyl)-(5-bromo-pyrimidin-2-yl)-amino]-2-ethyl-pyrrolidine-1-carboxylic acid tert-butyl ester (0.50 mmol; 299 mg), morpholine (1.0 mmol; 87 mg), tris(dibenzylideneacetone)dipalladium(0) (0.025 mmol; 22.9 mg), 2-(di-tert-butylphosphino)biphenyl (0.05 mmol; 14.9 mg) and sodium tert-butoxide (1.0 mmol; 96 mg) are dissolved in toluene (2.5 mL). The mixture is stirred for 3 hours at 100° C., and then cooled to ambient temperature. The reaction mixture is quenched with saturated aqueous ammonium chloride solution. The product is extracted three times with EtOAc. The combined organic layer is washed with brine, dried over Na2SO4, filtered, concentrated under reduced pressure. The obtained residue is purified by silica gel column chromatography (eluent: n-hexane/EtOAc) to give (2R,4S)-4-[(3,5-Bis-trifluoromethyl-benzyl)-(5-morpholin-4-yl-pyrimidin-2-yl)-amino]-2-ethyl-pyrrolidine-1-carboxylic acid tert-butyl ester (247 mg, 82%); ESI-MS m/z: 604 [M+1]$^+$, Retention time 4.91 min (condition C).

Example 13

Synthesis of (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 2-carbamoyl-2-methyl-propyl ester

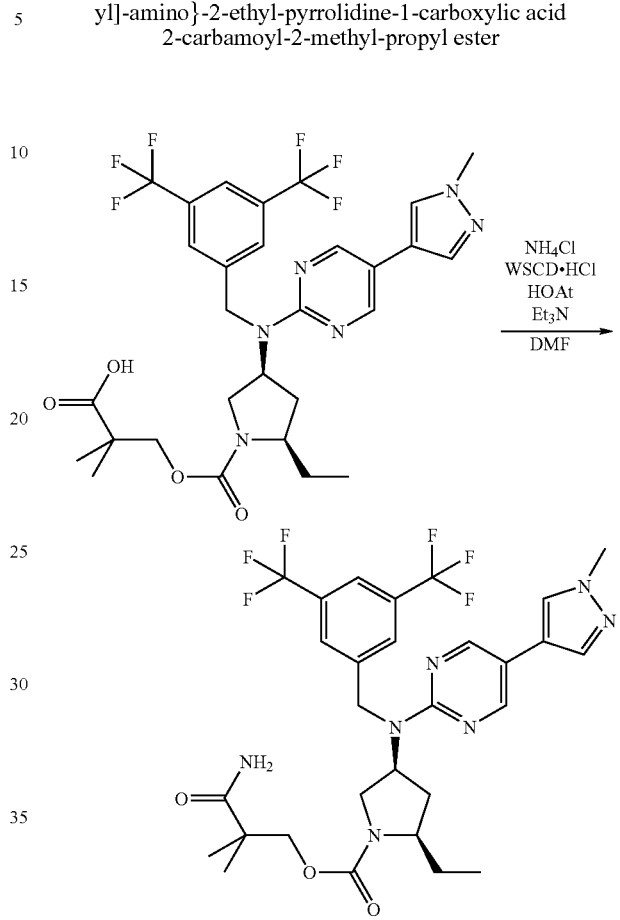

To a solution of (2R,4S)-4-{(3,5-bis-trifluoromethyl-benzyl)-[5-(1-methyl-1H-pyrazol-4-yl)-pyrimidin-2-yl]-amino}-2-ethyl-pyrrolidine-1-carboxylic acid 2-carboxy-2-methylpropyl ester (0.016 mmol; 10 mg), ammonium chloride (0.032 mmol; 1.7 mg), WSCD hydrochloride (0.032 mmol; 7.3 mg), HOAt (0.032 mmol; 4.4 mg) in DMF (0.4 ml) is added triethylamine (0.080 mol; 8.1 mg) at room temperature. The reaction mixture is stirred for 18.5 hours at the same temperature, and then quenched with water. The product is extracted three times with EtOAc. The combined organic layer is washed with brine, dried over Na2SO4, filtered, concentrated under reduced pressure. The obtained residue is purified by preparative thin layer chromatography on silica gel (eluent: dichloromethane/MeOH) to give (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 2-carbamoyl-2-methyl-propyl ester (4.1 mg, 40%); ESI-MS m/z: 642 [M+1]$^+$, Retention time 2.04 min (condition A).

The following compounds are prepared following the procedure of Example 13 using corresponding amines.

Example 13-1: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 2-methyl-2-methylcarbamoyl-propyl ester Example 13-2: (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid 1-dimethylcarbamoyl-1-methyl-ethyl ester

| No. | Product | ESI-MS m/z [M + 1]+ | Retention time (min) | Starting Material | Starting Material |
|---|---|---|---|---|---|
| 13-1 | | 656 | 2.08 (condition A) | H₂N— | |
| 13-2 | | 656 | 4.20 (condition B) | | |
Example 14
Synthesis of (2R,4S)-4-{(3,5-Bis-trifluoromethyl-benzyl)-[5-(1H-pyrazol-4-yl)-pyrimidin-2-yl]-amino}-2-ethyl-pyrrolidine-1-carboxylic acid isopropyl ester
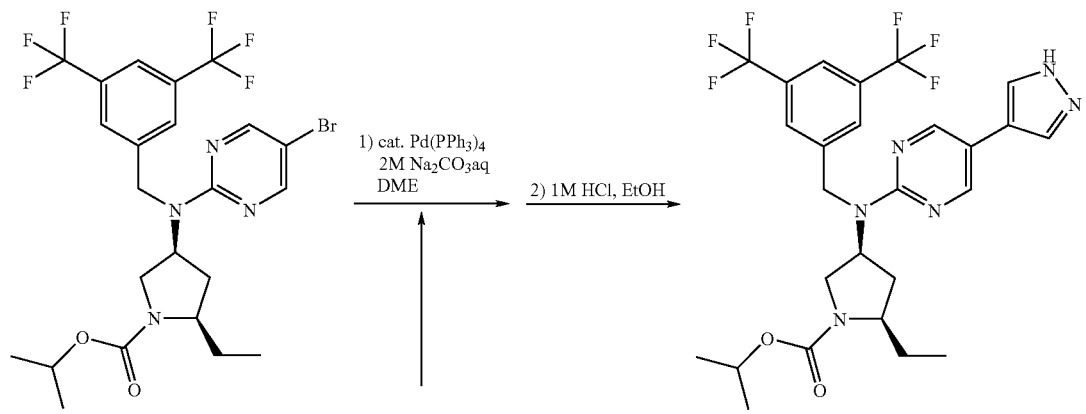

-continued

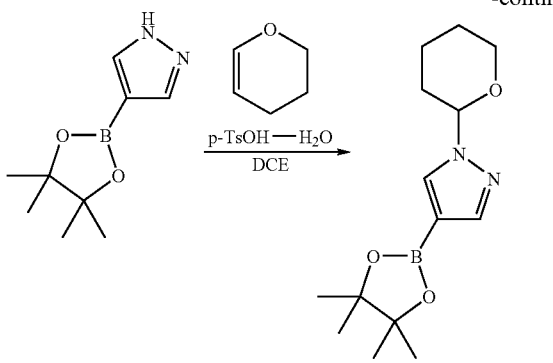

A solution of 4-(4,4,5,5-tetramethyl-1,3,2-dioxaborolan-2-yl)-1H-pyrazole (5 mmol; 970 mg) and 3,4-dihydro-2H-pyran (10 mmol; 841 mg) and p-toluenesulfonic acid monohydrate (0.5 mmol; 95 mg) in 1,2-dichloroethane (25 mL) is stirred at 40° C. for 2 hours. The reaction mixture is cooled to ambient temperature, and then quenched with saturated aqueous NaHCO3 solution. The product is extracted with dichloromethane. The organic layer is washed with brine, dried over Na2SO4, filtered, concentrated under reduced pressure. The resulting material is used in the next step without further purification.

The obtained 1-(tetrahydro-pyran-2-yl)-4-(4,4,5,5-tetramethyl-1,3,2-dioxaborolan-2-yl)-1H-pyrazole (ca. 0.269 mmol; 112 mg), (2R,4S)-4-[(3,5-bis-trifluoromethyl-benzyl)-(5-bromo-pyrimidin-2-yl)-amino]-2-ethyl-pyrrolidine-1-carboxylic acid isopropyl ester (0.192 mmol; 112 mg), tetrakis(triphenylphosphine) palladium (0.019 mmol; 21.9 mg), and aqueous 2M sodium carbonate (0.2 mL) are dissolved in 1,2-dimethoxyethane (1 mL) at room temperature. The mixture is stirred at 90° C. for 13 hours, and then cooled to ambient temperature. To the mixture is added brine and the solution is extracted three times with EtOAc. The organic layer is washed with brine, dried over Na2SO4, filtered, and concentrated under reduced pressure. The obtained residue is subjected to column chromatography on silica gel (eluent: n-hexane/EtOAc) to give a diastereomeric mixture of (2R, 4S)-4-((3,5-bis-trifluoromethyl-benzyl)-{5-[1-(tetrahydro-pyran-2-yl)-1H-pyrazol-4-yl]-pyrimidin-2-yl}-amino)-2-ethyl-pyrrolidine-1-carboxylic acid isopropyl ester (99 mg).

A solution of the obtained material and 1 M HCl (2 mL) in ethanol is stirred for 4 hours. Another 1 M HCl (2 mL) in ethanol is added to the mixture to stir additional 40 minutes. The solution is concentrated under reduced pressure, and Et2O is added to the residue. The solids are isolated by filtration, washed with Et2O and dried under vacuum to provide (2R,4S)-4-{(3,5-Bis-trifluoromethyl-benzyl)-[5-(1H-pyrazol-4-yl)-pyrimidin-2-yl]-amino}-2-ethyl-pyrrolidine-1-carboxylic acid isopropyl ester as a HCl salt (80 mg, 69%); ESI-MS m/z: 571 [M+1]+, Retention time 2.28 min (condition A).

1H NMR (400 MHz, DMSO-d6): HCl salt □ ppm 0.75 (t, J=7.55 Hz, 3 H), 1.16 (d, J=6.04 Hz, 6 H), 1.49 (br s, 1 H), 1.68-2.00 (m, 2 H), 2.14-2.25 (m, 1 H), 3.03-3.19 (m, 1 H), 3.62-4.80 (m, 5 H), 4.96-5.19 (m, 3 H), 7.88 (s, 2 H), 7.98 (s, 1 H), 8.04-8.12 (m, 2 H), 8.71 (s, 2 H)

Example 15

Synthesis of 2-((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidin-1-O-oxazole-4-carboxylic acid ethyl ester

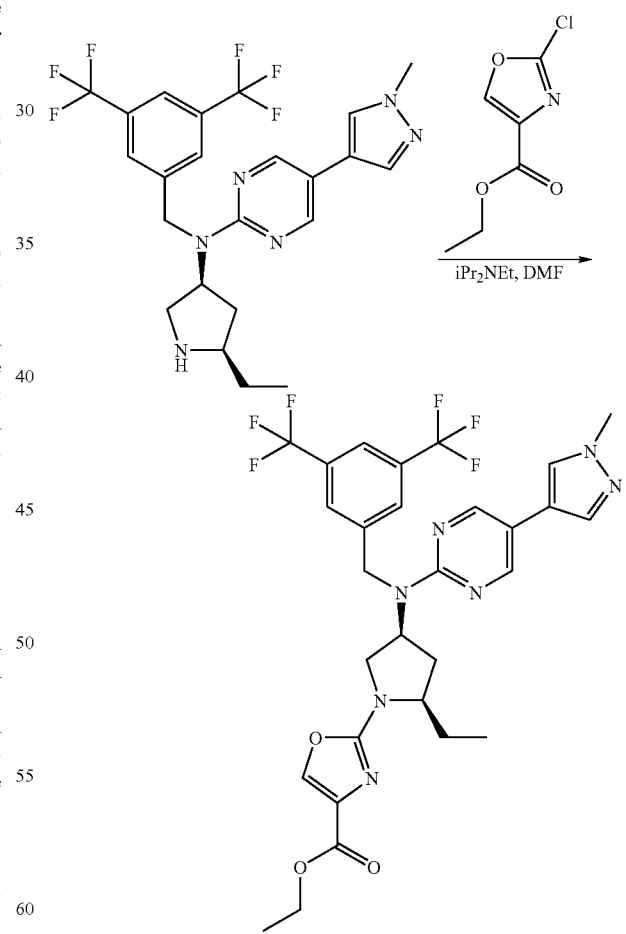

A solution of [3,5-bis(trifluoromethyl)benzyl]-(5-ethyl-pyrrolidin-3-yl)-[5-(1-methyl-1H-pyrazol-4-yl)-pyrimidin-2-yl]-amine (0.025 mmol, 12.5 mg), 2-chloro-oxazole-5-carboxylic acid ethyl ester (0.03 mmol, 5 mg) and N,N-diisopropylethylamine (0.03 mmol, 5 uL) in DMF (0.1 mL) is allowed to warm to 120° C. and stirred for 3 hours. The mixture is cooled to room temperature, then added with water. The mixture is extracted with CH$_2$Cl$_2$. The combined organic layer is dried over Na$_2$SO$_4$, filtrated, and concentrated under reduced pressure. The obtained residue is purified by silica gel column chromatography (eluent: n-hexane/EtOAc) to give 2-((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidin-1-yl)-oxazole-4-carboxylic acid ethyl ester (7.4 mg, 46%); ESI-MS m/z: 638 [M+1]$^+$, Retention time 2.20 min (condition A).

Example 16

Synthesis of ((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidin-1-yl)-pyrrolidin-1-yl-methanone

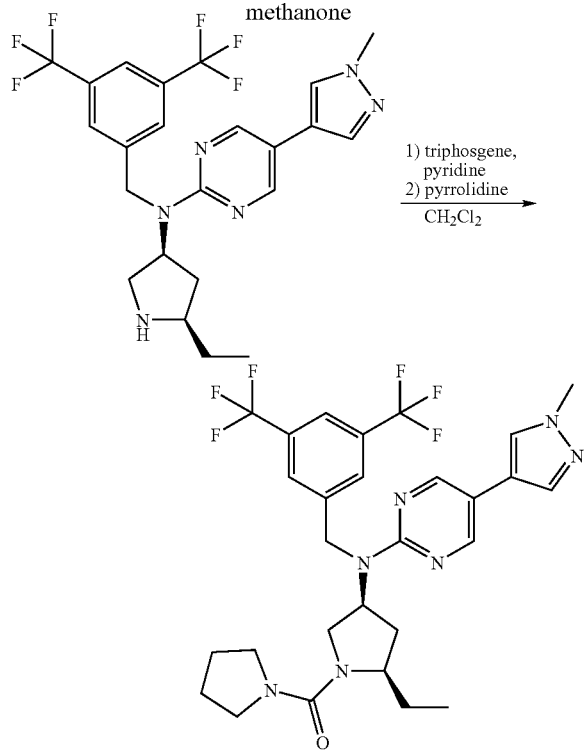

[3,5-Bis(trifluoromethyl)benzyl]-((3S,5R)-5-ethyl-pyrrolidin-3-yl)-[5-(1-methyl-1H-pyrazol-4-yl)-pyrimidin-2-yl]-amine (84 mg, 0.17 mmol) and triphosgene (71 mg, 0.24 mmol) are dissolved in CH$_2$Cl$_2$ (2 mL). The reaction mixture is stirred at room temperature for 1 hour after addition of pyridine (15 mg, 0.19 mmol). Saturated aqueous NH$_4$Cl and EtOAc are added, then extracted with EtOAc. The combined organic layer is dried over Na$_2$SO$_4$ then concentrated under reduced pressure. The resulting residue is dissolved in CH$_2$Cl$_2$ (1.5 mL) and then pyrrolidine (60 mg, 0.85 mmol) is added. The reaction mixture is stirred at room temperature for 12 hours. Saturated aqueous NH$_4$Cl and CH$_2$Cl$_2$ are added, then extracted with CH$_2$Cl$_2$. The combined organic layer is dried over MgSO$_4$, then concentrated under reduced pressure. The obtained residue is purified by silica gel column chromatography (eluent: n-hexane/EtOAc) to give ((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidin-1-yl)-pyrrolidin-1-yl-methanone (45 mg, 36%); ESI-MS m/z: 596 [M+1]$^+$, Retention time 4.52 min (condition B).

1H NMR (400 MHz, CHLOROFORM-d) □ ppm 0.82 (t, J=7.55 Hz, 3 H) 1.31-1.44 (m, 1 H) 1.61-1.68 (m, 1 H) 1.69-1.78 (m, 2 H) 1.80-1.93 (m, 2 H) 2.13-2.22 (m, 1 H) 3.16-3.26 (m, 3 H) 3.31-3.39 (m, 2 H) 3.49 (d, J=4.03 Hz, 1 H) 3.58-3.63 (m, 1 H) 3.95 (s, 3 H) 4.00-4.09 (m, 1 H) 4.84-5.06 (m, 2 H) 5.17-5.28 (m, 1 H) 7.54 (s, 1 H) 7.66 (s, 1 H) 7.69 (s, 2H) 7.77 (s, 1 H) 8.44 (s, 2 H)

The following compounds are prepared following the procedure of Example 16 using corresponding amines.

Example 16-1: 4-{[((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carbonyl)-ethyl-amino]-methyl}-cyclohexanecarboxylic acid methyl ester Example 16-2: ((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidin-1-yl)-piperidin-1-yl-methanone Example 16-3: (S)-1-((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carbonyl)-piperidine-3-carboxylic acid ethyl ester Example 16-4: (S)-1-((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carbonyl)-piperidine-2-carboxylic acid methyl ester Example 16-5: ((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidin-1-yl)-cyclohexyl-methanone Example 16-6: 1-[4-((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carbonyl)-piperazin-1-yl]-ethanone Example 16-7: ((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidin-1-yl)-(2-cyclohexyl-pyrrolidin-1-yl)-methanone Example 16-8: 4-((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carbonyl)-piperazin-2-one

| No. | Product | ESI-MS m/z [M + 1]$^+$ | Retention time (min) | amine | Starting Material |
|---|---|---|---|---|---|
| 16-1 | | 724 | 4.56 (condition B) | | |

| No. | Product | ESI-MS m/z [M + 1]+ | Retention time (min) | amine | Starting Material |
|---|---|---|---|---|---|
| 16-2 | | 609 | 2.24 (condition A) | | |
| 16-3 | | 682 | 2.24 (condition A) | | |
| 16-4 | | 668 | 2.22 (condition A) | | |
| 16-5 | | 626 | 1.95 (condition A) | | |

| No. | Product | ESI-MS m/z [M + 1]+ | Retention time (min) | amine | Starting Material |
|---|---|---|---|---|---|
| 16-6 | 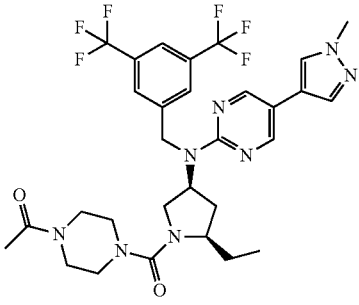 [SMILES: CC[C@@H]1C[C@H](N(Cc2cc(C(F)(F)F)cc(C(F)(F)F)c2)c2ncc(-c3cnn(C)c3)cn2)CN1C(=O)N1CCN(C(C)=O)CC1] | 653 | 1.95 (condition A) | 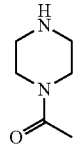 | 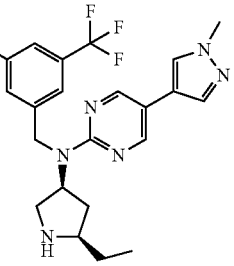 |
| 16-7 | 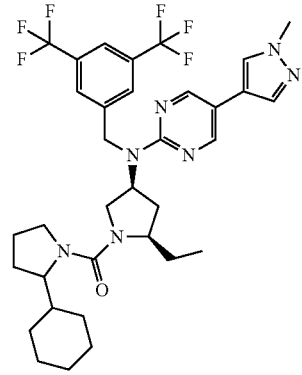 diastereomixture | 678 | 2.49, 2.57 (condition A) | 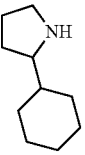 | 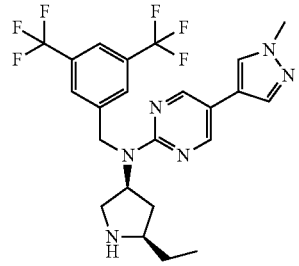 [SMILES: CC[C@@H]1C[C@H](N(Cc2cc(C(F)(F)F)cc(C(F)(F)F)c2)c2ncc(-c3cnn(C)c3)cn2)CN1] |
| 16-8 | 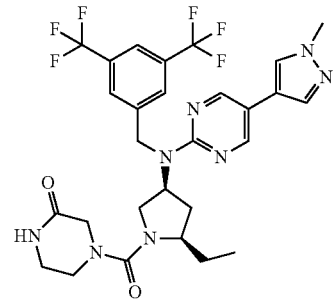 [SMILES: CC[C@@H]1C[C@H](N(Cc2cc(C(F)(F)F)cc(C(F)(F)F)c2)c2ncc(-c3cnn(C)c3)cn2)CN1C(=O)N1CCNC(=O)C1] | 625 | 3.56 (condition B) | 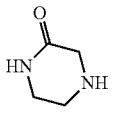 | 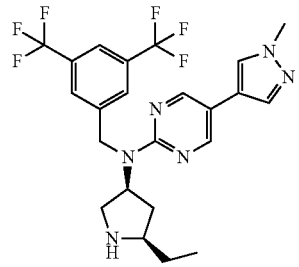 [SMILES: CC[C@@H]1C[C@H](N(Cc2cc(C(F)(F)F)cc(C(F)(F)F)c2)c2ncc(-c3cnn(C)c3)cn2)CN1] |
Example 16-2
1H NMR (400 MHz, CHLOROFORM-d) ppm 0.82 (t, J=7.45 Hz, 3 H) 1.35-1.53 (m, 7 H) 1.62-1.72 (m, 1 H) 1.74-1.81 (m, 1 H) 2.13-2.22 (m, 1 H) 3.14-3.19 (m, 4 H) 3.20-3.26 (m, 1 H) 3.95 (s, 3 H) 4.05-4.15 (m, 1 H) 4.87-5.04 (m, 2 H) 5.16-5.26 (m, 1 H) 7.54 (s, 1H) 7.66 (s, 1 H) 7.68 (s, 2 H) 7.77 (s, 1 H) 8.44 (s, 2 H)

Example 17

Synthesis of ((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidin-1-yl)-morpholin-4-yl-methanone

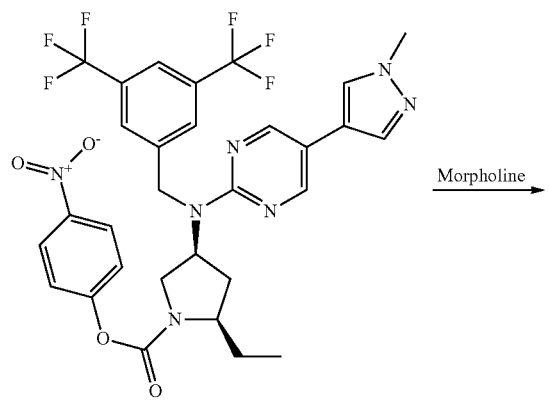

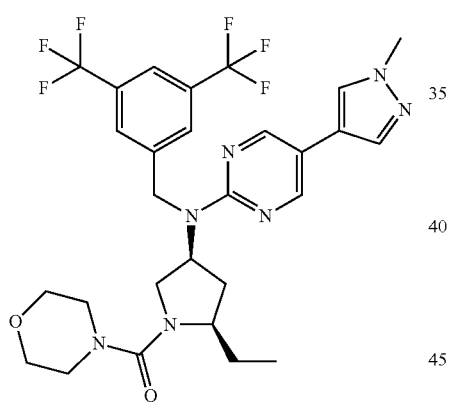

A mixture of (2R,4S)-4-{(3,5-bis-trifluoromethyl-benzyl)-[5-(1-methyl-1H-pyrazol-4-yl)-pyrimidin-2-yl]-amino}-2-ethyl-pyrrolidine-1-carboxylic acid 4-nitro-phenyl ester (0.1 mmol; 66 mg) and morpholine (1.15 mmol; 1.00 g) is stirred for 20 hours at 80° C. The reaction mixture is purified by silica gel column chromatography (eluent: n-hexane/EtOAc) to give ((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidin-1-yl)-morpholin-4-yl-methanone (45 mg; 73%) %); ESI-MS m/z: 612 [M+1]$^+$, Retention time 2.07 min (condition A).

1H NMR (400 MHz, CHLOROFORM-d) □ ppm 0.83 (t, J=7.56 Hz, 3 H), 1.35-1.46 (m, 1 H), 1.67-1.75 (m, 1 H), 1.76-1.85 (m, 1 H), 2.15-2.21 (m, 1 H), 3.15-3.34 (m, 5 H), 3.57-3.70 (m, 5 H), 3.95 (s, 3 H), 4.08-4.15 (m, 1 H), 4.88-5.04 (m, 2 H), 5.13-5.22 (m, 1 H), 7.55 (s, 1 H), 7.67-7.68 (m, 3 H), 7.78 (s, 1 H), 8.45 (s, 2 H)

Example 18

Synthesis of (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid dimethylamide

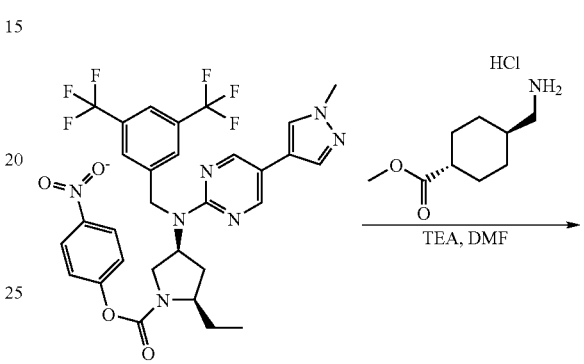

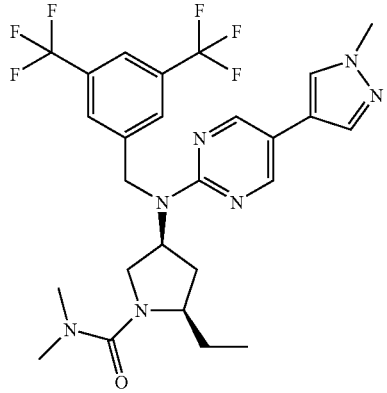

To a solution of (2R,4S)-4-{(3,5-bis-trifluoromethyl-benzyl)-[5-(1-methyl-1H-pyrazol-4-yl)-pyrimidin-2-yl]-amino}-2-ethyl-pyrrolidine-1-carboxylic acid 4-nitro-phenyl ester (0.03 mmol, 20 mg) in 1 mL of DMF are added trans-4-(aminomethyl)cyclohexanecarboxylic acid methyl ester hydrochloride (0.04 mmol, 8 mg) and triethylamine (0.07 mmol, 0.01 mL). The mixture is stirred under microwave irradiation (150° C., 5 bar), then cooled to room temperature. The mixture is poured into a saturated aqueous ammonium chloride and extracted with dichloromethane. The combined organic phases is washed by water and brine, dried over anhydrous Na$_2$SO$_4$ and evaporated. The obtained residue is purified by column chromatography on silica gel (eluent: n-hexane-ethyl acetate) to obtain 12.3 mg (59%) of (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid dimethylamide as colorless oil. ESI-MS m/z: 570 [M+1]⁺, Retention time 4.05 min (condition B).

Example 19

Synthesis of (S)-3-{(3-Chloro-5-trifluoromethyl-benzyl)-[5-(1-methyl-1H-pyrazol-4-yl)-pyrimidin-2-yl]-amino}-pyrrolidine-1-carboxylic acid isopropyl ester

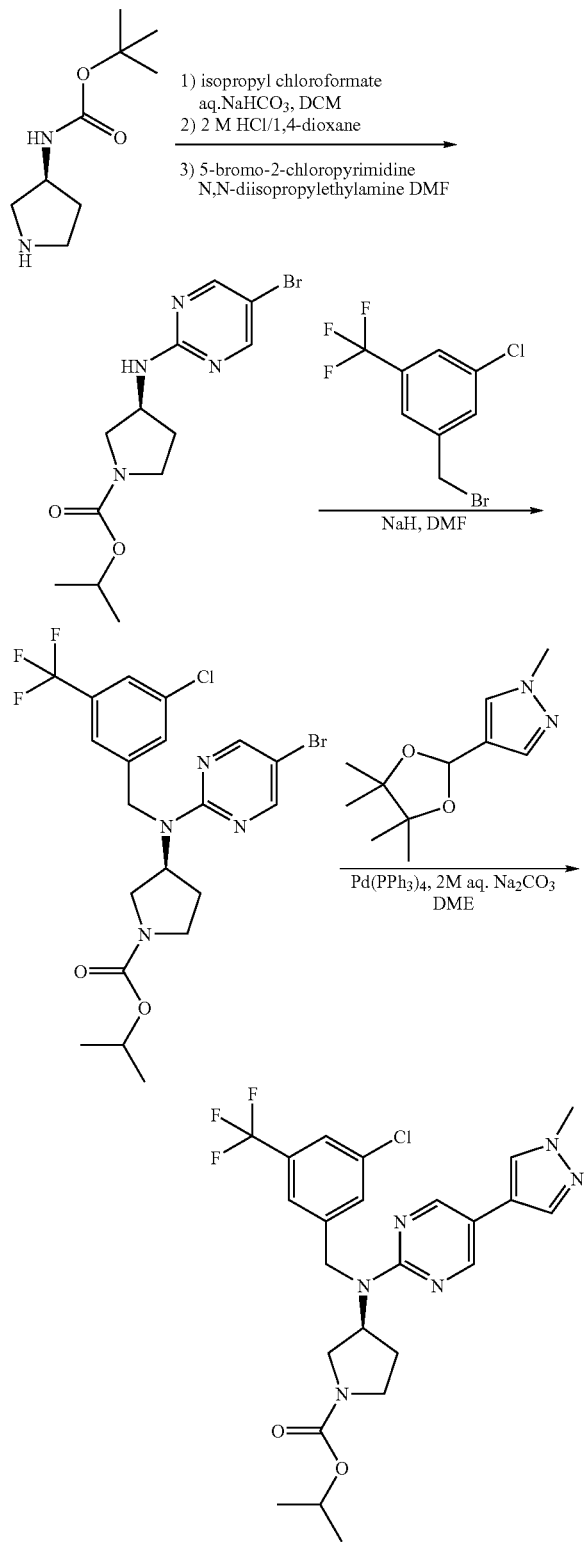

To a mixture of (S)-pyrrolidin-3-yl-carbamic acid tert-butyl ester (5.37 mmol, 1 g) in CH₂Cl₂ (5 mL) and aqueous NaHCO₃ solution (5 mL) is added isopropyl chloroformate (6.44 mmol, 0.74 mL) at 0° C. and the mixture is stirred for 1 hours at room temperature. The organic phase is separated, dried over Na₂SO₄, filtrated, and concentrated under reduced pressure to give a pale yellow oil (1.6 g). To a solution of the obtained oil in 1,4-dioxane (15 mL) is added 4M HCl solution in 1,4-dioxane (15 mL) at 0° C. and the mixture is stirred for 17 hours at room temperature. The mixture is concentrated under reduced pressure, then basified with 1M aqueous NaOH. The mixture is extracted with CH₂Cl₂. The combined organic layer is dried over Na₂SO₄, filtrated, and concentrated under reduced pressure to give a pale brown oil (1.05 g). A mixture of the obtained oil, 5-bromo-2-chloro-pyrimidine and N,N-diisopropylethylamine (6.44 mmol, 1.1 mL) in DMF (16 mL) is allowed to warm to 120° C. and stir for 3 hours. The mixture is cooled to room temperature, then added water. The mixture is extracted with EtOAc. The combined organic layer is dried over Na₂SO₄, filtrated, and concentrated under reduced pressure. The obtained residue is purified by silica gel column chromatography (eluent: hexane/EtOAc) to give (S)-3-(5-bromo-pyrimidin-2-ylamino)-pyrrolidine-1-carboxylic acid isopropyl ester (1.41 g, 80%); ESI-MS m/z: 329 [M+1]⁺, Retention time 1.82 min (condition A).

To a solution of (S)-3-(5-bromo-pyrimidin-2-ylamino)-pyrrolidine-1-carboxylic acid isopropyl ester (4.3 mmol, 1.41 g) in DMF (20 mL) is added sodium hydride (60% oil suspension, 8.6 mmol, 344 mg) at 0° C. and stirred at room temperature for 30 minutes. To the mixture is added 1-bromomethyl-3,5-bis-(trifluoromethyl)benzene (6.45 mmol, 0.87 mL) at 0° C. and stirred at room temperature for 2 hours. The mixture is added water and extracted with EtOAc. The combined organic layer is dried over Na₂SO₄, filtrated, and concentrated under reduced pressure. The obtained residue is purified by silica gel column chromatography (eluent: n-hexane/EtOAc) to give (S)-3-{(5-bromo-pyrimidin-2-yl)-[3-chloro-5-(trifluoromethyl)benzyl]-amino}-pyrrolidine-1-carboxylic acid isopropyl ester (1.9 g, 85%); ESI-MS m/z: 521 [M+1]⁺, Retention time 2.43 min (condition A).

To a mixture of (S)-3-{(5-bromo-pyrimidin-2-yl)-[3-chloro-5-(trifluoromethyl)benzyl]-amino}-pyrrolidine-1-carboxylic acid isopropyl ester (0.19 mmol, 100 mg), 1-methylpyrazol-3-yl-4,4,5,5-tetramethyl-[1,3,2]dioxaborolane (0.23 mmol, 48 mg), tetrakis(triphenylphosphine)palladium (0) (0.02 mmol, 22 mg) and 2M aqueous sodium hydrogen carbonate (0.19 mL) in 1,2-dimethoxy-ethane (0.6 mL) is allowed to warm to 95° C. and stirred for 3 hours. The mixture is cooled to room temperature and then added water. The mixture is extracted with CH₂Cl₂. The combined organic layer is dried over Na₂SO₄, filtrated, and concentrated under reduced pressure. The obtained residue is purified by silica gel column chromatography (eluent: CH₂Cl₂/EtOAc). To the obtained mixture in CH₂Cl₂ (1 mL) is added saturated aqueous sodium carbonate (0.04 mL) and NaIO₄ (82 mg). The mixture is stirred at room temperature for 3 hours. The mixture is concentrated under reduced pressure. The obtained residue is purified by silica gel column chromatography (eluent: n-hexane/EtOAc) to give (S)-3-{(3-Chloro-5-trifluoromethyl-benzyl)-[5-(1-methyl-1H-pyrazol-4-yl)-pyrimidin-2- yl]-amino}-pyrrolidine-1-carboxylic acid isopropyl ester (67 mg, 67%); ESI-MS m/z: 523 [M+1]+, Retention time 2.16 min (condition A).

Example 20

Synthesis of 2-{2-(3,5-Bis-trifluoromethyl-phenyl)-1-[(3R,5R)-5-ethyl-1-(2-methoxymethyl-4-trifluoromethyl-phenyl)-pyrrolidin-3-yl]-ethyl}-5-(1-methyl-1H-pyrazol-4-yl)-pyrimidine

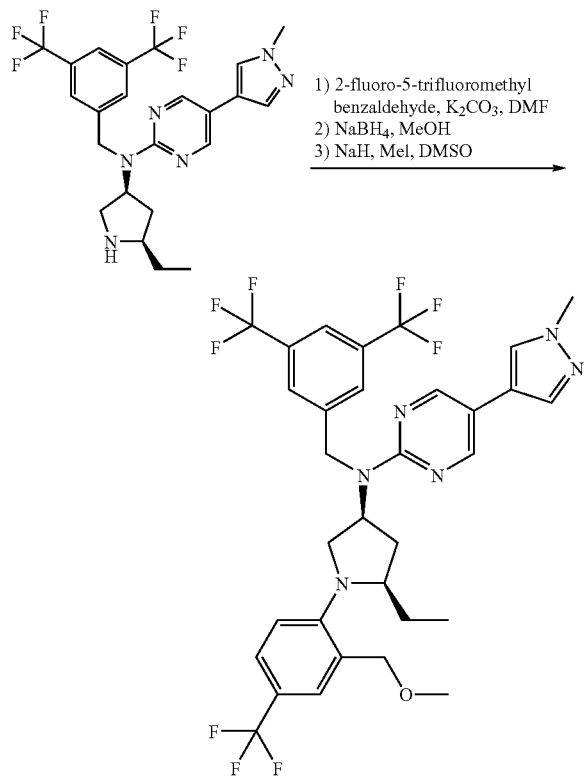

A mixture of [3,5-bis(trifluoromethyl)benzyl]-((3S,5R)-5-ethyl-pyrrolidin-3-yl)-[5-(1-methyl-1H-pyrazol-4-yl)-pyrimidin-2-yl]-amine (75 mg, 0.15 mmol), 2-fluoro-5-trifluoromethyl-benzaldehyde (44 mg, 0.23 mmol) and K₂CO₃ (42 mg, 0.30 mmol) in DMF (1.5 mL) is heated at 130° C. and stirred for 2 hours. After the mixture is cooled down until room temperature, H₂O and EtOAc is added and then extracted with EtOAc. The combined organic layer is dried over MgSO₄, then concentrated under reduced pressure. The obtained residue is purified by silica gel column chromatography (eluent: n-hexane/EtOAc) to give 2-((2R,4S)-4-{[3,5-bis(trifluoromethyl)benzyl]-[5-(1-methyl-1H-pyrazol-4-yl)-pyrimidin-2-yl]-amino}-2-ethyl-pyrrolidin-1-yl)-5-trifluoromethyl-benzaldehyde as a colorless oil (77 mg, 74%). ESI-MS m/z: 670 [M+1]+, Retention time 2.75 min (condition A).

To a mixture of 2-((2R,4S)-4-{[3,5-bis(trifluoromethyl)benzyl]-[5-(1-methyl-1H-pyrazol-4-yl)-pyrimidin-2-yl]-amino}-2-ethyl-pyrrolidin-1-yl)-5-trifluoromethyl-benzaldehyde (75 mg, 0.11 mmol) in MeOH (2.0 mL) is added sodium borohydride (6 mg, 0.17 mmol). The reaction mixture is stirred at room temperature for 15 minutes. After addition of saturated aqueous sodium hydrogen carbonate, and the mixture is extracted with EtOAc. The combined organic layer is dried over MgSO₄ then concentrated under reduced pressure. The obtained residue is purified by silica gel column chromatography (eluent: n-hexane/EtOAc) to give [2-((2R,4S)-4-{[3,5-bis(trifluoromethyl)benzyl]-[5-(1-methyl-1H-pyrazol-4-yl)-pyrimidin-2-yl]-amino}-2-ethyl-pyrrolidin-1-yl)-5-trifluoromethyl-phenyl]-methanol as a colorless oil (72 mg, 96%). ESI-MS m/z: 672 [M+1]+, Retention time 2.36 min (condition A).

To a solution of [2-((2R,4S)-4-{[3,5-bis(trifluoromethyl)benzyl]-[5-(1-methyl-1H-pyrazol-4-yl)-pyrimidin-2-yl]-amino}-2-ethyl-pyrrolidin-1-yl)-5-trifluoromethyl-phenyl]-methanol (67 mg, 0.10 mmol) in DMSO (1.5 mL) is added NaH (60% in oil, 6 mg, 0.15 mmol) at room temperature. The reaction mixture is stirred at room temperature for 5 minutes. After addition of methyl iodide (9.6 uL 0.15 mmol), the mixture is stirred for 30 minutes. H₂O and EtOAc are added, then extracted with EtOAc. The combined organic layer is dried over MgSO₄, and then concentrated under reduced pressure. The obtained residue is purified by silica gel column chromatography (eluent: n-hexane/EtOAc) to give 2-{2-(3,5-Bis-trifluoromethyl-phenyl)-1-[(3R,5R)-5-ethyl-1-(2-methoxymethyl-4-trifluoromethyl-phenyl)-pyrrolidin-3-yl]-ethyl}-5-(1-methyl-1H-pyrazol-4-yl)-pyrimidine as a colorless oil (52 mg, 75%). ESI-MS m/z: 686 [M+1]+, Retention time 2.72 min (condition A).

Example 21

Synthesis of (2R,4S)-4-[(3,5-Bis-trifluoromethyl-benzyl)-(5-bromo-pyrimidin-2-yl)-amino]-2-ethyl-pyrrolidine-1-carboxylic acid isopropyl ester

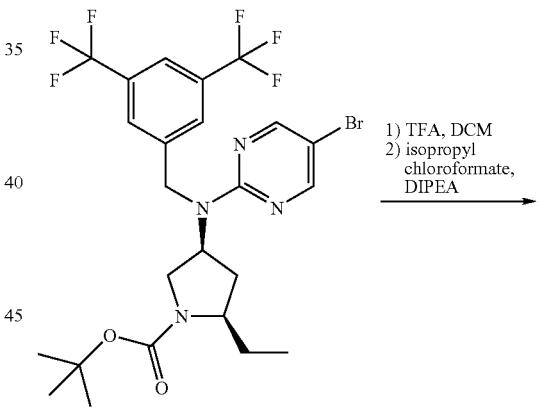

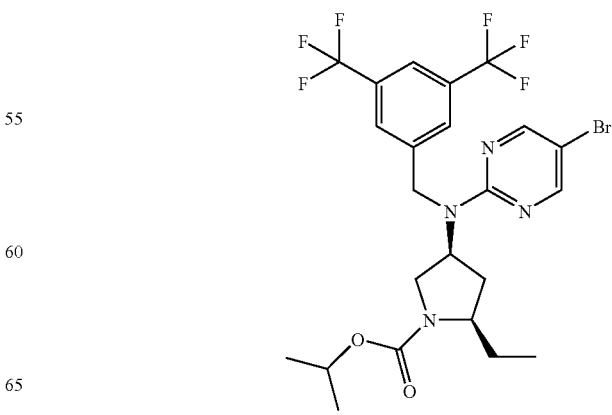

To a solution of (2R,4S)-4-[(3,5-bis-trifluoromethyl-benzyl)-(5-bromo-pyrimidin-2-yl)-amino]-2-ethyl-pyrrolidine-1-carboxylic acid tert-butyl ester (0.20 mmol; 120 mg) in dichloromethane (2.0 mL) is added TFA (0.7 mL). The reaction mixture is stirred for 30 minutes, and concentrated under reduced pressure. The residue is soluted in 10 ml of dichloromethane, followed by neutralization with 2 ml of saturated aqueous NaHCO₃ solution. After stirring for 15 minutes, the product is extracted with dichloromethane. The organic layer after dried is separated and concentrated under reduced pressure.

A mixture of the obtained residue, N,N-diisopropylethylamine (1.6 mmol; 207 mg) and isopropyl chloroformate (0.4 mmol; 49.0 mg) is stirred for 11.5 hours at room temperature. The reaction mixture is diluted with dichloromethane and then quenched with saturated ammonium chloride solution. The product is extracted with dichloromethane. The organic layer after dried is separated and concentrated under reduced pressure. The obtained residue is purified by silica gel column chromatography (eluent: n-hexane/EtOAc) to give (2R,4S)-4-[(3,5-Bis-trifluoromethyl-benzyl)-(5-bromo-pyrimidin-2-yl)-amino]-2-ethyl-pyrrolidine-1-carboxylic acid isopropyl ester (112 mg, 96%).

The following compounds are prepared following the procedure of Example 21.

Example 21-1: (2R,4S)-4-[(3,5-Bis-trifluoromethyl-benzyl)-(5-morpholin-4-yl-pyrimidin-2-yl)-amino]-2-ethyl-pyrrolidine-1-carboxylic acid isopropyl ester

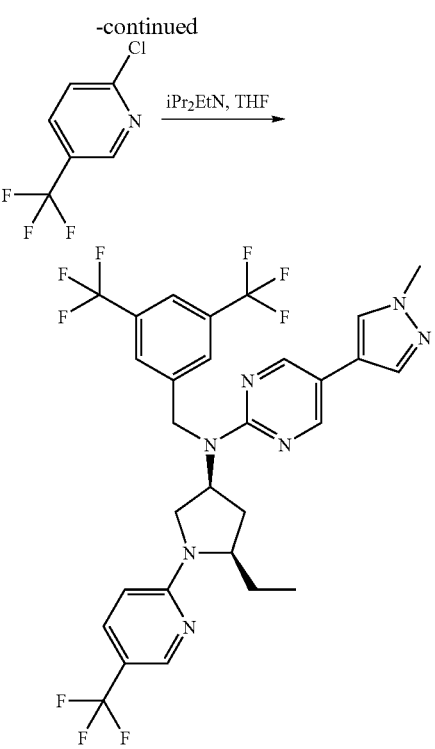

| No. | Product | ESI-MS m/z [M + 1]⁺ | Retention time (min) | Starting Material |
|---|---|---|---|---|
| 21-1 | | 590 | 2.31 (condition A) | |

Example 22
Synthesis of (3,5-Bis-trifluoromethyl-benzyl)-[(3S,5R)-5-ethyl-1-(5-trifluoromethyl-pyridin-2-yl)-pyrrolidin-3-yl]-[5-(1-methyl-1H-pyrazol-4-yl)-pyrimidin-2-yl]-amine

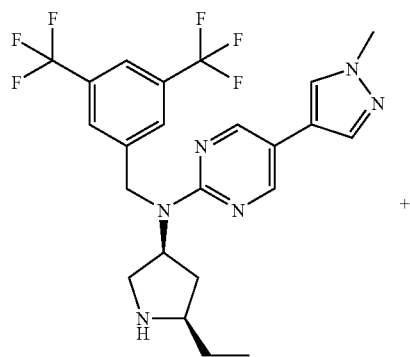

A mixture of [3,5-bis(trifluoromethyl)benzyl]-((3S,5R)-5-ethyl-pyrrolidin-3-yl)-[5-(1-methyl-1H-pyrazol-4-yl)-pyrimidin-2-yl]amine (45 mg, 0.09 mmol), 2-chloro-5-trifluoromethyl-pyridine (50 mg, 0.27 mmol) and iPr₂EtN (45 uL 0.27 mmol) in THF (1.5 mL) is stirred at 120° C. under microwave irradiation. The mixture is concentrated under reduced pressure. The obtained residue is purified by silica gel column chromatography (eluent: hexane/EtOAc) to give (3,5-Bis-trifluoromethyl-benzyl)-[(3S,5R)-5-ethyl-1-(5-trifluoromethyl-pyridin-2-yl)-pyrrolidin-3-yl]-[5-(1-methyl-1H-pyrazol-4-yl)-pyrimidin-2-yl]-amine as a colorless oil (38 mg, 66%). ESI-MS m/z: 643 [M+1]+, Retention time 2.45 min (condition A).

The following compounds are prepared following the procedure of Example 22 using corresponding chloroformates.

Example 22-1: (3,5-Bis-trifluoromethyl-benzyl)-[3S,5R)-1-(6-chloro-pyrimidin-4-yl)-5-ethyl-pyrrolidin-3-yl]-[5-(1-methyl-1H-pyrazol-4-yl)-pyrimidin-2-yl]-amine

| No. | Product | ESI-MS m/z [M + 1]+ | Retention time (min) | Starting Material | Starting Material |
|---|---|---|---|---|---|
| 22-1 | | 611 | 2.26 (condition A) | | |

Example 23

Synthesis of 1-[2-((3,5-bis-trifluoromethyl-benzyl)-{(3S,5R)-1-[5-chloro-2-(4-hydroxy-piperidin-1-yl)-pyrimidin-4-yl]-5-ethyl-pyrrolidin-3-yl}-amino)-pyrimidin-5-yl]-3-methyl-imidazolidin-2-one

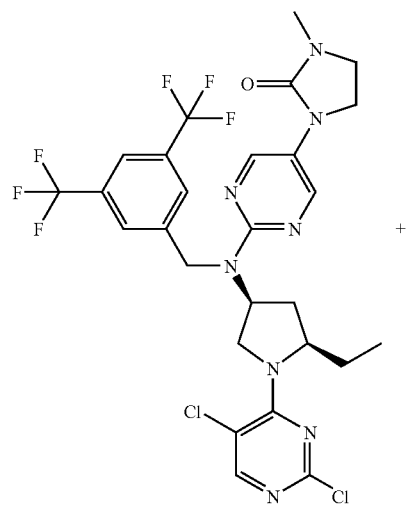

+

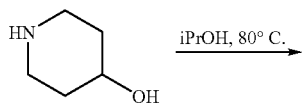

iPrOH, 80° C.

-continued

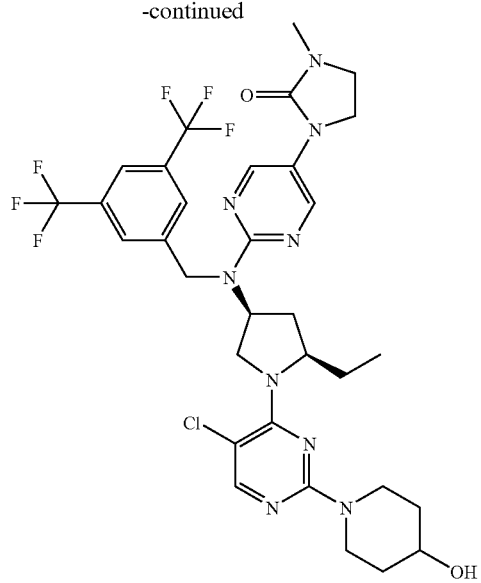

To a mixture of 1-(2-{(3,5-bis-trifluoromethyl-benzyl)-[(3S,5R)-1-(2,5-dichloro-pyrimidin-4-yl)-5-ethyl-pyrrolidin-3-yl]-amino}-pyrimidin-5-yl)-3-methyl-imidazolidin-2-one (30 mg, 0.05 mmol) in i-PrOH (1 mL) is added piperidin-4-ol (23 mg, 0.23 mmol). The reaction mixture is stirred at 80° C. for 12 hours. After removal of solvent, the mixture is washed with brine and extracted with EtOAc. The combined organic layer is dried over MgSO$_4$ then concentrated under reduced pressure to give 1-[2-((3,5-bis-trifluoromethyl-benzyl)-{(3S,5R)-1-[5-chloro-2-(4-hydroxy-piperidin-1-yl)-pyrimidin-4-yl]-5-ethyl-pyrrolidin-3-yl}-amino)-pyrimidin-5-yl]-3-methyl-imidazolidin-2-one (26 mg, 79%) after purification by silica gel column chromatography (eluent: EtOAc:MeOH=20:1).

$^1$H NMR (400 MHz, chloroform-d) δ ppm 0.84 (t, J=7.5 Hz, 3 H), 1.4-1.8 (m, 6 H), 1.85-2.01 (m, 4 H), 2.28 (dt, J=5.8, 11.6 Hz, 1 H), 2.89 (s, 3 H), 3.14-3.23 (m, 2 H), 3.5 (dt, J=2.3, 7.3 Hz, 2 H), 3.50 (t, J=10.5 Hz, 1 H), 3.74 (dt, J=2.3, 7.3 Hz, 2 H), 3.85-3.90 (m, 1 H), 3.95 (dd, J=7.6, 10.5 Hz, 1 H), 4.20-4.40 (m, 3 H), 4.90 (d, J=17.0 Hz, 1 H), 5.01 (d, J=17.0 Hz, 1 H), 5.15-5.30 (m, 1 H), 7.70 (s, 2 H), 7.76 (s, 1 H), 7.86 (s, 1 H), 8.54 (s, 2 H); ESI-MS m/z: 728 [M]+, Retention time 3.62 min (condition A).

The following compounds are prepared following the procedure of Example 23 using corresponding amine.

| No. | Product | ESI-MS m/z [M + 1]+ | Retention time (min) | Starting Material | Starting Material |
|---|---|---|---|---|---|
| 23-1 | | 689 | 1.88 (condition A) | | |
| 23-2 | | 715 | 1.93 (condition A) | | |
| 23-3 | | 715 | 3.60 (condition B) | | |

| No. | Product | ESI-MS m/z [M + 1]+ | Retention time (min) | Starting Material | Starting Material |
|---|---|---|---|---|---|
| 23-4 | | 714 | 3.47 (condition B) | | |
| 23-5 | | 747 | 3.42 (condition B) | | |
| 23-6 | | 715 | 3.51 (condition B) | | |

| No. | Product | ESI-MS m/z [M + 1]+ | Retention time (min) | Starting Material | Starting Material |
|---|---|---|---|---|---|
| 23-7 | | 694 | 2.12 (condition A) | piperidine | |
| 23-8 | | 737 | 1.93 (condition A) | 1-acetylpiperazine | |
| 23-9 | | 717 | 4.10 (condition B) | piperidine | |

-continued
| No. | Product | ESI-MS m/z [M + 1]+ | Retention time (min) | Starting Material | Starting Material |
|---|---|---|---|---|---|
| 23-10 | 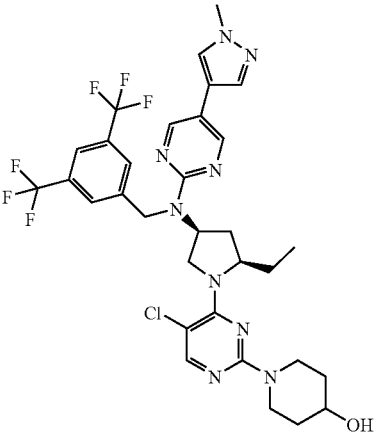 [SMILES: CC[C@@H]1C[C@H](N(Cc2cc(C(F)(F)F)cc(C(F)(F)F)c2)c2ncc(-c3cnn(C)c3)cn2)CN1c1nc(N2CCC(O)CC2)ncc1Cl] | 710 | 1.94 (condition A) | 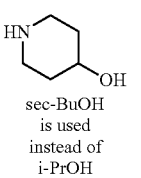 sec-BuOH is used instead of i-PrOH | 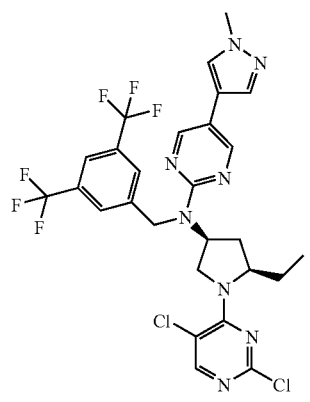 [SMILES: CC[C@@H]1C[C@H](N(Cc2cc(C(F)(F)F)cc(C(F)(F)F)c2)c2ncc(-c3cnn(C)c3)cn2)CN1c1nc(Cl)ncc1Cl] |
| 23-11 | 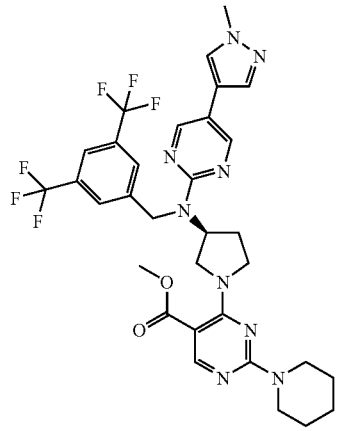 [SMILES: COC(=O)c1cnc(N2CCCCC2)nc1N1CC[C@H](N(Cc2cc(C(F)(F)F)cc(C(F)(F)F)c2)c2ncc(-c3cnn(C)c3)cn2)C1] | 699 | 1.97 (condition A) |  | 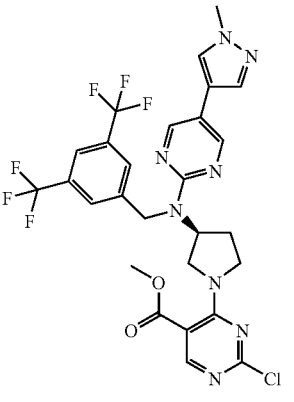 [SMILES: COC(=O)c1cnc(Cl)nc1N1CC[C@H](N(Cc2cc(C(F)(F)F)cc(C(F)(F)F)c2)c2ncc(-c3cnn(C)c3)cn2)C1] |
| 23-12 | 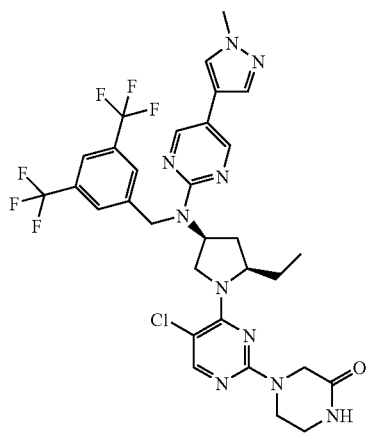 [SMILES: CC[C@@H]1C[C@H](N(Cc2cc(C(F)(F)F)cc(C(F)(F)F)c2)c2ncc(-c3cnn(C)c3)cn2)CN1c1nc(N2CCNC(=O)C2)ncc1Cl] | 709 | 2.12 (condition A) | 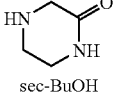 sec-BuOH is used instead of i-PrOH | 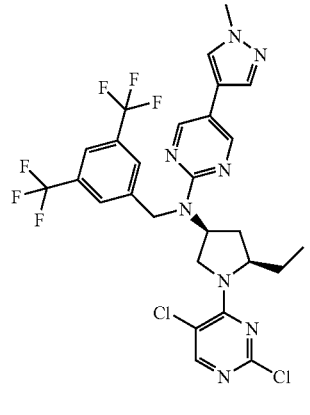 [SMILES: CC[C@@H]1C[C@H](N(Cc2cc(C(F)(F)F)cc(C(F)(F)F)c2)c2ncc(-c3cnn(C)c3)cn2)CN1c1nc(Cl)ncc1Cl] |

-continued

| No. | Product | ESI-MS m/z [M + 1]+ | Retention time (min) | Starting Material | Starting Material |
|---|---|---|---|---|---|
| 23-13 | | 683 | 1.75 (condition A) | piperidin-4-ol | |
| 23-14 | | 669 | 1.88 (condition A) | morpholine | |
| 23-15 | | 730 | 2.12 (condition A) | 4,4-fluoropiperidine·HCl<br>sec-BuOH is used instead of i-PrOH | |

| No. | Product | ESI-MS m/z [M + 1]+ | Retention time (min) | Starting Material | Starting Material |
|---|---|---|---|---|---|
| 23-16 | | 697 | 1.93 (condition A) | | |
| 23-17 | | 716 | 1.99 (condition A) | | |
| 23-18 | | 727 | 1.882 (condition A) | | |

| No. | Product | ESI-MS m/z [M + 1]+ | Retention time (min) | Starting Material | Starting Material |
|---|---|---|---|---|---|
| 23-19 | | 635 | 1.91 (condition A) | | |

Example 24

Synthesis of 1-[4-((2R,4S)-4-{(3,5-bis-trifluoromethyl-benzyl)-[5-(3-methyl-2-oxo-imidazolidin-1-yl)-pyrimidin-2-yl]-amino}-2-ethyl-pyrrolidin-1-yl)-5-chloro-pyrimidin-2-yl]-piperidine-4-carboxylic acid

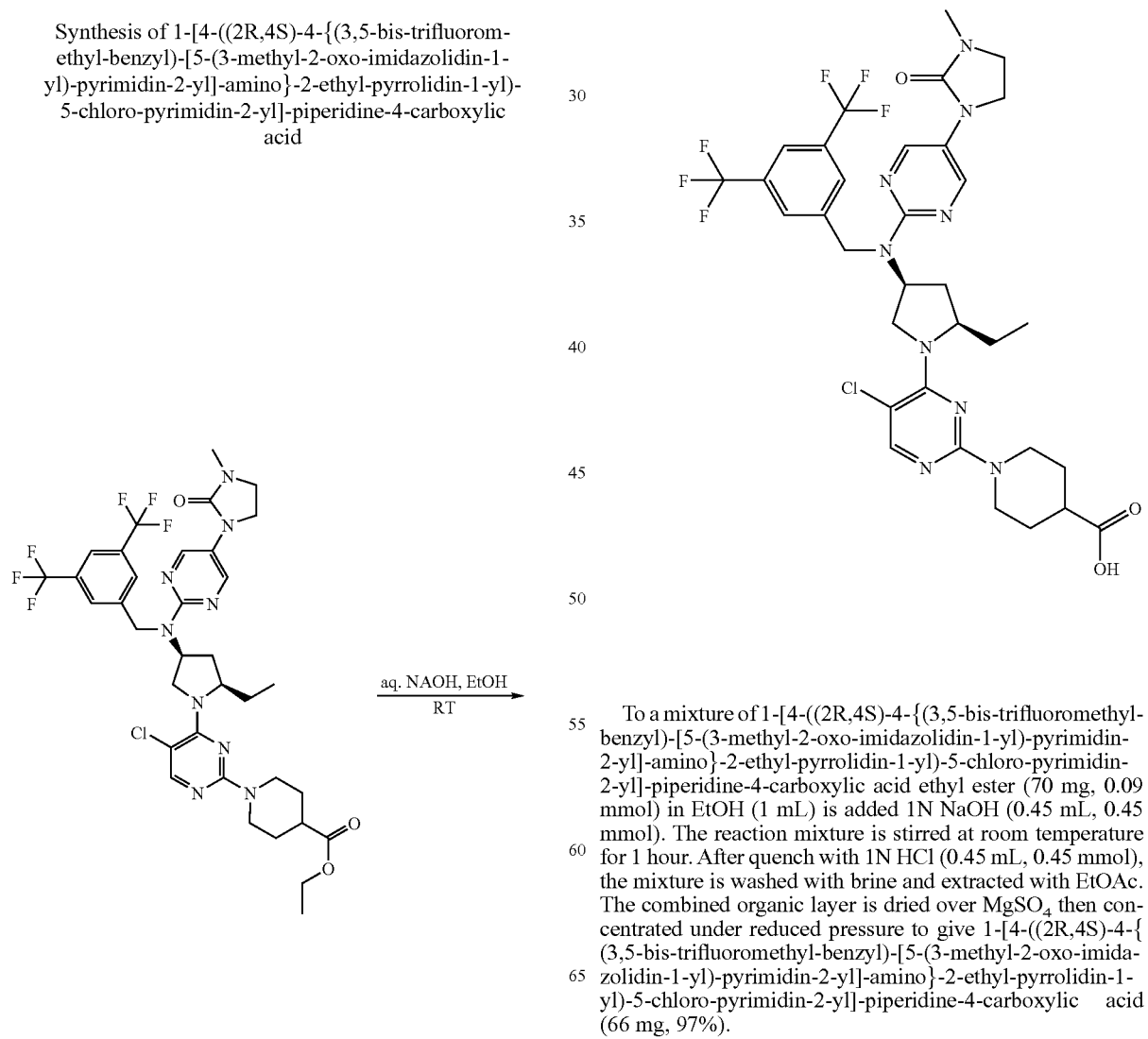

To a mixture of 1-[4-((2R,4S)-4-{(3,5-bis-trifluoromethyl-benzyl)-[5-(3-methyl-2-oxo-imidazolidin-1-yl)-pyrimidin-2-yl]-amino}-2-ethyl-pyrrolidin-1-yl)-5-chloro-pyrimidin-2-yl]-piperidine-4-carboxylic acid ethyl ester (70 mg, 0.09 mmol) in EtOH (1 mL) is added 1N NaOH (0.45 mL, 0.45 mmol). The reaction mixture is stirred at room temperature for 1 hour. After quench with 1N HCl (0.45 mL, 0.45 mmol), the mixture is washed with brine and extracted with EtOAc. The combined organic layer is dried over MgSO₄ then concentrated under reduced pressure to give 1-[4-((2R,4S)-4-{(3,5-bis-trifluoromethyl-benzyl)-[5-(3-methyl-2-oxo-imidazolidin-1-yl)-pyrimidin-2-yl]-amino}-2-ethyl-pyrrolidin-1-yl)-5-chloro-pyrimidin-2-yl]-piperidine-4-carboxylic acid (66 mg, 97%).

¹H NMR (400 MHz, chloroform-d) δ ppm 0.84 (t, J=7.3 Hz, 3 H), 1.40-1.46 (m, 2 H), 1.61-1.80 (m, 4 H), 1.85-1.95 (m, 4 H), 2.28 (dt, J=5.8, 11.6 Hz, 1 H), 2.58 (ddt, J=4.3, 7.1, 10.5 Hz, 1 H), 2.89 (s, 3 H), 2.95-3.03 (m, 2 H), 3.50 (dt, J=2.8, 7.6 Hz, 2 H), 3.60 (t, J=10.5 Hz, 1 H), 3.73 (dt, J=2.8, 7.3 Hz, 2 H), 3.95 (dd, J=2.8, 7.6 Hz, 1 H), 4.32-4.40 (m, 1 H), 4.44-4.51 (m, 2 H), 4.90 (d, J=17.2 Hz, 1 H), 5.02 (d, J=17.2 Hz, 1 H), 5.16-5.27 (m, 1 H), 7.69 (s, 2 H), 7.76 (s, 1 H), 7.87 (s, 1 H), 8.54 (s, 2 H); ESI-MS m/z: 717 [M]+, Retention time 3.20 min (condition A).

The following compounds are prepared following the procedure of Example 24.

| No. | Product | ESI-MS m/z [M + 1]+ | Retention time (min) | Starting Material |
|---|---|---|---|---|
| 24-1 | | 717 | 1.74 (condition B) | |

Example 25

Synthesis of 1-[4-((2R,4S)-4-{(3,5-bis-trifluoromethyl-benzyl)-[5-(1H-pyrazol-4-yl)-pyrimidin-2-yl]-amino}-2-ethyl-pyrrolidin-1-yl)-5-chloro-pyrimidin-2-yl]-piperidin-4-ol

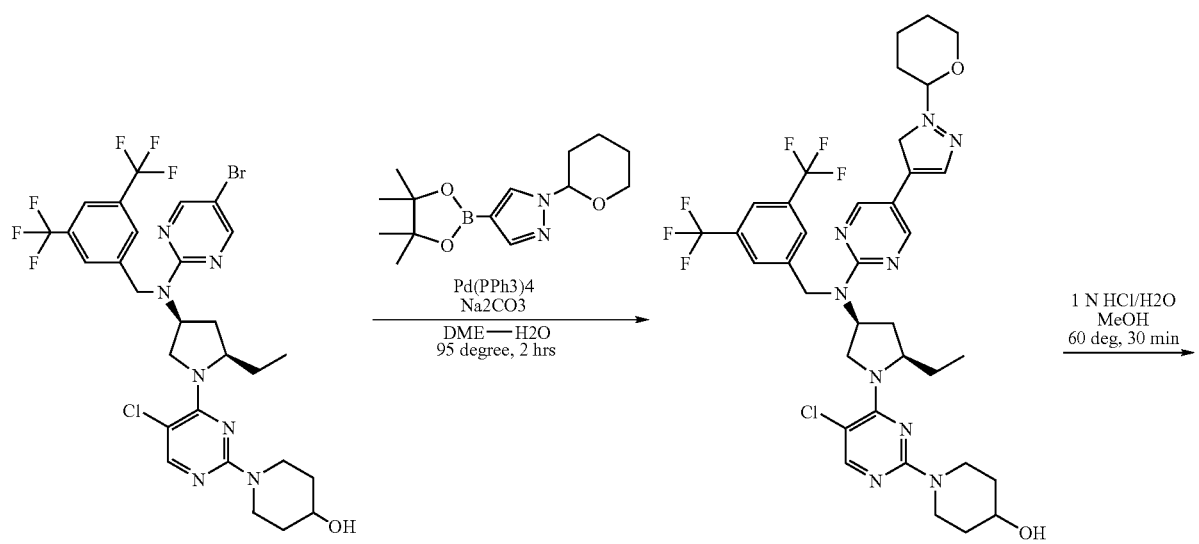

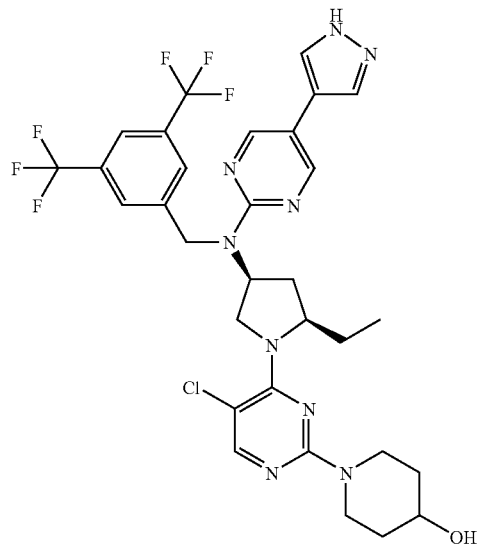

A 25 ml round-bottom flask is charged with 1-(tetrahydro-pyran-2-yl)-4-(4,4,5,5-tetramethyl-[1,3,2]dioxaborolan-2-yl)-1H-pyrazole (56 mg, 0.2 mmol), 1-(4-{(2R,4S)-4-[(3,5-bis-trifluoromethyl-benzyl)-(5-bromo-pyrimidin-2-yl)-amino]-2-ethyl-pyrrolidin-1-yl}-5-chloro-pyrimidin-2-yl)-piperidin-4-ol (110 mg, 0.15 mmol) under $N_2$. Pd(PPh3)4 (34 mg, 0.03 mmol) is added promptly and the flask is recharged with $N_2$. Then DME (0.5 ml), $Na_2CO_3$ (1 M in $H_2O$, 0.3 ml, 0.3 mmol) are added. The mixture is then heated to 95 degree for 2 hours. After cooling down to rt, $NaIO_4$ (103 mg, 0.48 mmol) is added into reaction mixture. Stirring is continued for 1 h to give white suspension. $H_2O$ and dichloromethane are added, then organic layer is collected with phase separator. Removal of solvent gave 1-{4-[(2R,4S)-4-((3,5-bis-trifluoromethyl-benzyl)-{5-[1-(tetrahydro-pyran-2-yl)-1H-pyrazol-4-yl]-pyrimidin-2-yl}-amino)-2-ethyl-pyrrolidin-1-yl]-5-chloro-pyrimidin-2-yl}-piperidin-4-ol which is used without further purification.

A 25 ml round-bottom flask is charged with 1-{4-[(2R,4S)-4-((3,5-bis-trifluoromethyl-benzyl)-{5-[1-(tetrahydro-pyran-2-yl)-1H-pyrazol-4-yl]-pyrimidin-2-yl}-amino)-2-ethyl-pyrrolidin-1-yl]-5-chloro-pyrimidin-2-yl}-piperidin-4-ol (0.15 mmol), 1N HCl (0.8 ml, 0.8 mmol) and MeOH (2 ml). The mixture is then heated to 60 degree for 30 minutes. After cooling down to rt, sat. $NaHCO_3$ and dichloromethane are added, then organic layer is collected. Removal of solvent and purification with reverse phase column chromatography give 1-[4-((2R,4S)-4-{(3,5-Bis-trifluoromethyl-benzyl)-[5-(1H-pyrazol-4-yl)-pyrimidin-2-yl]-amino}-2-ethyl-pyrrolidin-1-yl)-5-chloro-pyrimidin-2-yl]-piperidin-4-ol (11.3 mg, 0.015 mmol, 10% for 2 steps).

1H NMR (400 MHz, chloroform-d) δ ppm 0.84 (t, J=8 Hz, 3 H), 1.43-1.54 (m, 2 H), 1.62-1.67 (m, 1 H), 1.79 (q, J=12 Hz, 2 H), 1.92-1.97 (m, 2 H), 2.26-2.33 (m, 1 H), 3.44-3.50 (m, 1 H), 3.55-3.66 (m, 2 H), 3.71-3.84 (m, 2 H), 3.91-4.04 (m, 2 H), 4.37-4.41 (m, 1 H), 4.92-5.09 (m, 2 H), 5.24-5.30 (m, 1 H), 7.71 (s, 2 H), 7.77 (s, 3 H), 7.86 (s, 1 H), 8.48 (s, 2 H). ESI-MS m/z: 696 [M+1]+, Retention time 1.89 min (condition A).

Example 26

Synthesis of 1-[4-((2R,4S)-4-{(3,5-bis-trifluoromethyl-benzyl)-[5-(1H-pyrazol-4-yl)-pyrimidin-2-yl]-amino}-2-ethyl-pyrrolidin-1-yl)-5-chloro-pyrimidin-2-yl]-piperidine-4-carboxylic acid

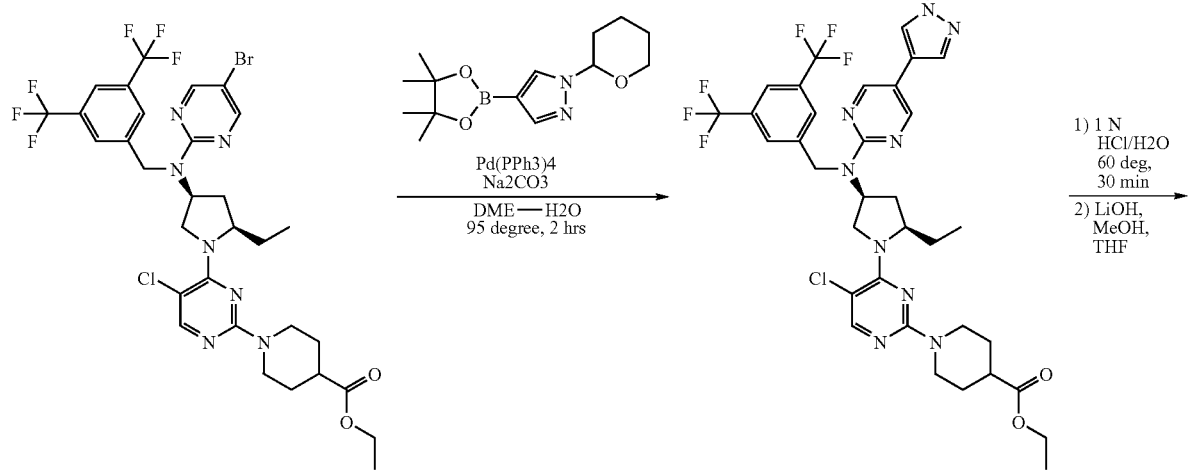

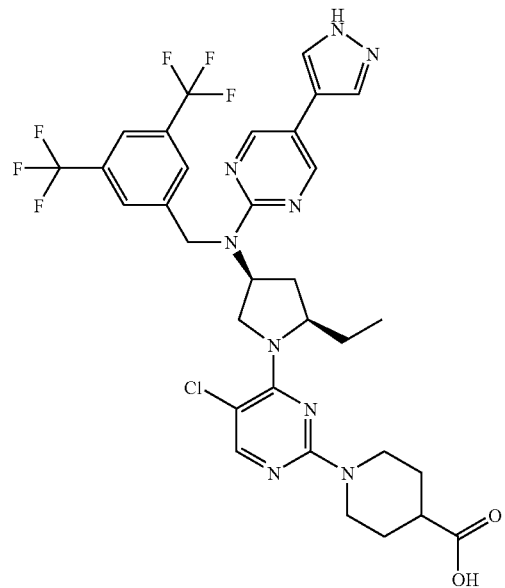

A 25 ml round-bottom flask is charged with 1-(tetrahydro-pyran-2-yl)-4-(4,4,5,5-tetramethyl-[1,3,2]dioxaborolan-2-yl)-1H-pyrazole (83 mg, 0.3 mmol), 1-(4-{(2R,4S)-4-[(3,5-bis-trifluoromethyl-benzyl)-(5-bromo-pyrimidin-2-yl)-amino]-2-ethyl-pyrrolidin-1-yl}-5-chloro-pyrimidin-2-yl)-piperidine-4-carboxylic acid ethyl ester (178 mg, 0.23 mmol) under $N_2$. Pd(PPh3)$_4$ (57 mg, 0.05 mmol) is added promptly and the flask is recharged with $N_2$. Then DME (1 ml), $Na_2CO_3$ (1 M in $H_2O$, 0.45 ml, 0.45 mmol) are added. The mixture is then heated to 95 degree for 2 hrs. After cooling down to rt, $NaIO_4$ (140 mg, 0.72 mmol) is added into reaction mixture. Stirring is continued for 1 h to give white suspension. $H_2O$ and dichloromethane are added, and then organic layer is collected. Removal of solvent give 1-{4-[(2R,4S)-4-((3,5-bis-trifluoromethyl-benzyl)-{5-[1-(tetrahydro-pyran-2-yl)-1H-pyrazol-4-yl]pyrimidin-2-yl}-amino)-2-ethyl-pyrrolidin-1-yl]-5-chloro-pyrimidin-2-yl}-piperidine-4-carboxylic acid ethyl ester which is used without further purification.

A 25 ml round-bottom flask was charged with 1-{4-[(2R, 4S)-4-((3,5-bis-trifluoromethyl-benzyl)-{5-[1-(tetrahydro-pyran-2-yl)-1H-pyrazol-4-yl]-pyrimidin-2-yl}amino)-2-ethyl-pyrrolidin-1-yl]-5-chloro-pyrimidin-2-yl}-piperidine-4-carboxylic acid ethyl ester (70 mg, 0.084 mmol), 1N HCl (0.8 ml, 0.8 mmol) and MeOH (2 ml). The mixture is then heated to 60 degree for 30 minutes. After cooling down to rt, Saturated $NaHCO_3$ and dichloromethane are added, then organic layer is collected. Removal of solvent give 1-[4-((2R,4S)-4-{(3,5-bis-trifluoromethyl-benzyl)-[5-(1H-pyrazol-4-yl)-pyrimidin-2-yl]-amino}-2-ethyl-pyrrolidin-1-yl)-5-chloro-pyrimidin-2-yl]-piperidine-4-carboxylic acid ethyl ester and it is used for the next step without further purification.

A 15 ml round-bottom flask is charged with 1-[4-((2R,4S)-4-{(3,5-bis-trifluoromethyl-benzyl)-[5-(1H-pyrazol-4-yl)-pyrimidin-2-yl]-amino}-2-ethyl-pyrrolidin-1-yl)-5-chloro-pyrimidin-2-yl]-piperidine-4-carboxylic acid ethyl ester, 2N LiOH (0.4 ml, 0.8 mmol) THF (0.5 ml) and MeOH (1 ml). The mixture is then stirred at rt for 1 hour. PH is adjusted to 6 using 1 N HCl and resulted solution is extracted with EtOAc. The organic layer is dried over $Na_2SO_4$ and removal of solvent, purification with reverse phase column give 1-[4-((2R, 4S)-4-{(3,5-bis-trifluoromethyl-benzyl)-[5-(1H-pyrazol-4-yl)-pyrimidin-2-yl]-amino}-2-ethyl-pyrrolidin-1-yl)-5-chloro-pyrimidin-2-yl]-piperidine-4-carboxylic acid (13 mg, 0.017 mmol, 20% for 3 steps).

1H NMR (400 MHz, chloroform-d) δ ppm 0.84 (t, J=8 Hz, 3H), 1.41-1.46 (m, 1H), 1.67-1.82 (m, 3H), 1.95-1.97 (m, 3H), 2.28-2.31 (m, 1H), 2.57-2.63 (m, 1H), 2.97-3.04 (m, 3H), 3.63 (t, J=8 Hz, 1H), 3.97 (dd, J=8 Hz, 8 Hz, 1H), 4.37-4.40 (m, 1H), 4.50 (d, J=12 Hz, 2H), 4.91-5.09 (m, 2H), 5.25-5.31 (m, 1H), 7.71 (s, 2H), 7.77 (s, 3H), 7.88 (s, 1H), 8.47 (s, 2H). ESI-MS m/z: 724 [M+1]+, Retention time 1.87 min (condition A).

Example 27

Synthesis of 1-(4-{(2R,4S)-4-[(3,5-bis-trifluoromethyl-benzyl)-(5-imidazol-1-yl-pyrimidin-2-yl)-amino]-2-ethyl-pyrrolidin-1-yl}-5-chloro-pyrimidin-2-yl)-piperidin-4-ol

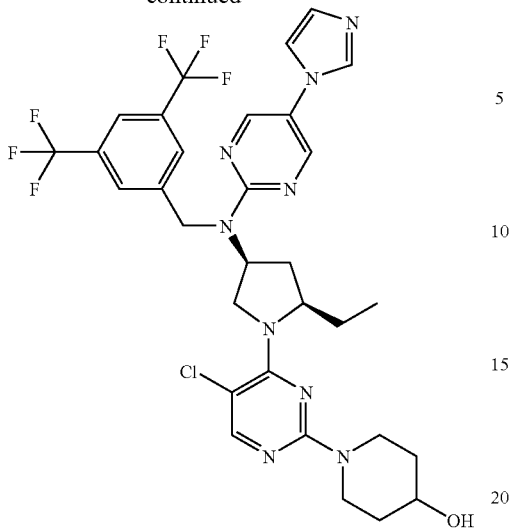

A 15 ml round-bottom tube is charged with 1-(4-{(2R,4S)-4-[(3,5-bis-trifluoromethyl-benzyl)-(5-bromo-pyrimidin-2-yl)-amino]-2-ethyl-pyrrolidin-1-yl}-5-chloro-pyrimidin-2-yl)-piperidin-4-ol (32 mg, 0.044 mmol), imidazole (6 mg, 0.088 mmol), CuI (9 mg, 0.044 mmol), K₂CO₃ (12 mg, 0.088 mmol), N,N-dimethyl glycine (5 mg, 0.044 mmol) and DMSO (0.5 ml). Then the tube is sealed and heated to 110 degree for 18 hours. After cooling to rt, saturated NH₃/H₂O, EtOAc is added and then filtered through Celite pad. The solution is extracted with EtOAc and organic layer was dried over MgSO₄. Removal of solvent and purification with reverse phase column give 1-(4-{(2R,4S)-4-[(3,5-bis-trifluoromethyl-benzyl)-(5-imidazol-1-yl-pyrimidin-2-yl)-amino]-2-ethyl-pyrrolidin-1-yl}-5-chloro-pyrimidin-2-yl)-piperidin-4-ol (6.5 mg, 0.009 mmol, 20%).

1H NMR (400 MHz, chloroform-d) δ ppm 0.86 (dt, J=4 Hz, 8 Hz, 3H), 1.43-1.54 (m, 2H), 1.81 (q, J=12 Hz, 3H), 1.90-1.98 (m, 3H), 2.29-2.35 (m, 1H), 3.44-3.50 (m, 1H), 3.56-3.60 (m, 1H), 3.63-3.69 (td, 1H), 3.79-3.82 (m, 2H), 3.83-4.10 (m, 2H), 4.39-4.43 (m, 1H), 4.94-5.10 (m, 2H), 5.23-5.29 (m, 1H), 7.14 (s, 1H), 7.24 (s, 1H), 7.70 (s, 3H), 7.80 (s, 1H), 7.87 (s, 1H), 8.40 (s, 2H). ESI-MS m/z: 696 [M+1]+, Retention time 1.73 min (condition A).

Example 28

Synthesis of 1-[4-((2R,4S)-4-{(3,5-bis-trifluoromethyl-benzyl)-[5-(4-hydroxy-piperidin-1-yl)-pyrimidin-2-yl]-amino}-2-ethyl-pyrrolidin-1-yl)-5-chloro-pyrimidin-2-yl]-piperidine-4-carboxylic acid

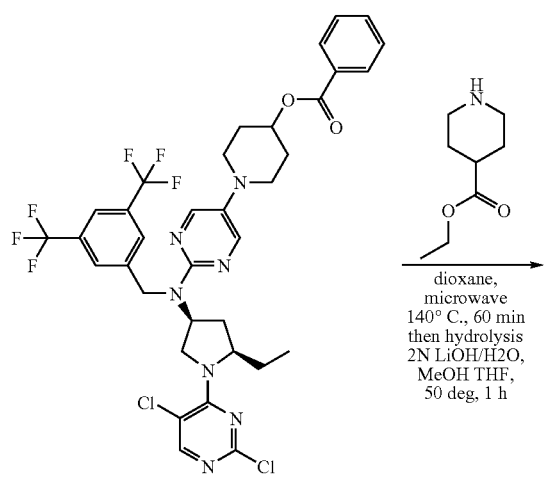

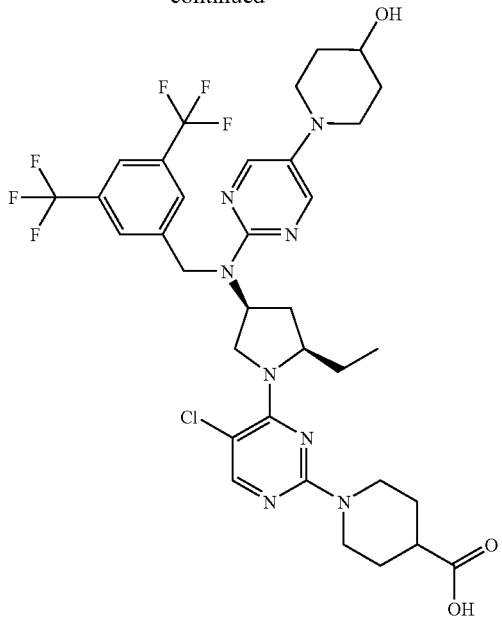

A 5 ml test tube for microwave reactor is charged with ethyl piperidine 4-carboxylate (104 ul, 0.68 mmol), benzoic acid 1-(2-{(3,5-bis-trifluoromethyl-benzyl)-[3S,5R)-1-(2,5-dichloro-pyrimidin-4-yl)-5-ethyl-pyrrolidin-3-yl]-amino}-pyrimidin-5-yl)-piperidin-4-yl ester (110 mg, 0.17 mmol) and dioxane (1.5 ml). Then the test tube is set into microwave reactor at 140 degrees for 2 hours. After cooling to rt, reaction mixture is transferred into a 25 ml round-bottom flask and solvent is removed under evaporator. Then into the flask is added 2N LiOH (0.8 ml, 1.6 mmol) THF (2 ml) and MeOH (4 ml). The mixture is heated to 50 degree for 1 h. PH is adjusted to 6-7 using 1 N HCl and resulted solution is extracted with EtOAc. The organic layer is dried over MgSO4 and removal of solvent, purification with reverse phase column give 1-[4-((2R,4S)-4-{(3,5-bis-trifluoromethyl-benzyl)-[5-(4-hydroxy-piperidin-1-yl)-pyrimidin-2-yl]-amino}-2-ethyl-pyrrolidin-1-yl)-5-chloro-pyrimidin-2-yl]-piperidine-4-carboxylic acid (36.6 mg, 0.048 mmol, 30% for 2 steps).

1H NMR (400 MHz, chloroform-d) δ ppm 0.91 (t, J=8 Hz, 3H), 1.62-1.72 (m, 2H), 1.75-1.81 (m, 3H), 1.91-1.96 (m, 1H), 2.03-2.11 (m, 5H), 2.38 (br, 1H), 2.68-2.72 (m, 1H), 3.06-3.19 (m, 2H), 3.31-3.36 (m, 3H), 3.43-3.46 (m, 1H), 3.53-3.56 (m, 1H), 3.87 (br, 1H), 3.99-4.02 (m, 1H), 4.19-4.21 (br, 1H), 4.35 (br, 1H), 5.13-5.19 (m, 3H), 7.86 (s, 3H), 7.91 (s, 1H), 8.48-8.49 (m, 2H). 2H). ESI-MS m/z: 757 [M+1]+, Retention time 1.84 min (condition A).

The following compounds are prepared following the procedure of Example 28 using corresponding amine.

| No. | Product | ESI-MS m/z [M + 1]+ | Retention time (min) | Starting Material | Starting Material |
|---|---|---|---|---|---|
| 28-1 | | 724 | 1.73 (condition A) | | |
| 28-2 | | 729 | 1.86 (condition A) | | |

Example 29

Synthesis of (3,5-bis-trifluoromethyl-benzyl)-[(3S,5R)-5-ethyl-1-(2-ethyl-4-trifluoromethyl-phenyl)-pyrrolidin-3-yl]-[5-(1-methyl-1H-pyrazol-4-yl)-pyrimidin-2-yl]-amine

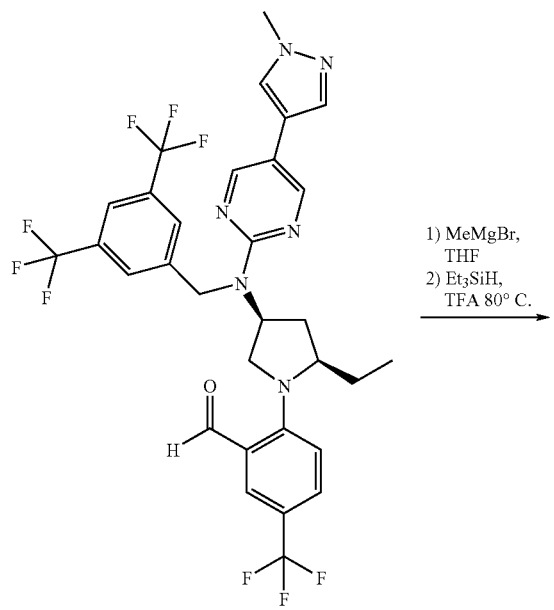

1) MeMgBr, THF
2) Et₃SiH, TFA 80° C.

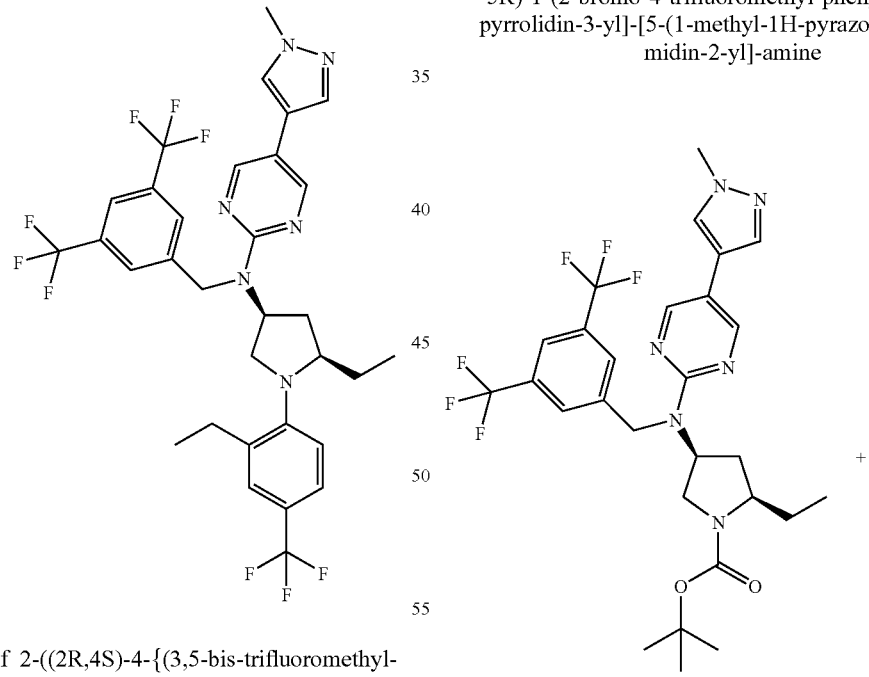

To a mixture of 2-((2R,4S)-4-{(3,5-bis-trifluoromethyl-benzyl)-[5-(1-methyl-1H-pyrazol-4-yl)-pyrimidin-2-yl]-amino}-2-ethyl-pyrrolidin-1-yl)-5-trifluoromethyl-benzaldehyde (120 mg, 0.17 mmol) in THF (3 mL) is added MeMgBr (0.24 mL, 0.23 mmol) in THF solution (0.97M). The reaction mixture is stirred at room temperature for 0.5 hour. After addition of saturated NH₄Cl aq., the mixture is extracted with EtOAc. The combined organic layer is dried over MgSO₄ then concentrated under reduced pressure to give 1-[2-((2R,4S)-4-{(3,5-bis-trifluoromethyl-benzyl)-[5-(1-methyl-1H-pyrazol-4-yl)-pyrimidin-2-yl]-amino}-2-ethyl-pyrrolidin-1-yl)-5-trifluoromethyl-phenyl]-ethanol as a colorless oil (122 mg, quant.). ESI-MS m/z: 687 [M+1]+, Retention time 2.05 min (condition A).

To a mixture of 1-[2-((2R,4S)-4-{(3,5-bis-trifluoromethyl-benzyl)-[5-(1-methyl-1H-pyrazol-4-yl)-pyrimidin-2-yl]-amino}-2-ethyl-pyrrolidin-1-yl)-5-trifluoromethyl-phenyl]-ethanol (29 mg, 0.04 mmol) in TFA (1 mL) and DCE (1 mL) is added triethylsilane (1 mL, 6.3 mmol) The reaction mixture is stirred at 80° C. for 4 hours. After removal of solvent and triethylsilane, the mixture is washed with brine and extracted with EtOAc. The combined organic layer is dried over MgSO₄ then concentrated under reduced pressure to give (3,5-bis-trifluoromethyl-benzyl)-[(3S,5R)-5-ethyl-1-(2-ethyl-4-trifluoromethyl-phenyl)-pyrrolidin-3-yl]-[5-(1-methyl-1H-pyrazol-4-yl)-pyrimidin-2-yl]-amine as a colorless oil (2 mg, 7%) after purification by silica gel column chromatography (eluent: n-hexane/EtOAc);

1H NMR (400 MHz, chloroform-d) δ ppm 0.81 (t, 3H), 1.13 (t, 3H), 1.24-1.27 (m, 1H), 1.60-1.71 (m, 2H), 2.41-2.50 (m, 2H), 2.61-2.67 (m, 1H), 3.12 (t, 1H), 3.39 (dd, 1H), 3.60-3.63 (m, 1H), 3.94 (s, 3H), 5.05 (d, 1H), 5.08 (d, 1H), 5.49-5.52 (m, 1H), 7.04 (d, 1H), 7.38 (d, 1H), 7.52 (s, 1H), 7.65 (s, 1H), 7.71 (s, 2H), 7.77 (s, 1H), 8.42 (s, 1H). ESI-MS m/z: 672 [M+1]+, Retention time 2.38 min (condition A).

Example 30

Synthesis of (3,5-bis-trifluoromethyl-benzyl)-[(3S,5R)-1-(2-bromo-4-trifluoromethyl-phenyl)-5-ethyl-pyrrolidin-3-yl]-[5-(1-methyl-1H-pyrazol-4-yl)-pyrimidin-2-yl]-amine

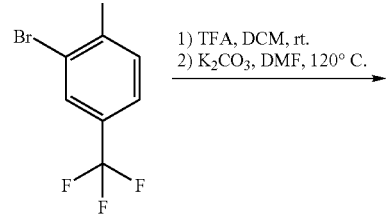

1) TFA, DCM, rt.
2) K₂CO₃, DMF, 120° C.

-continued

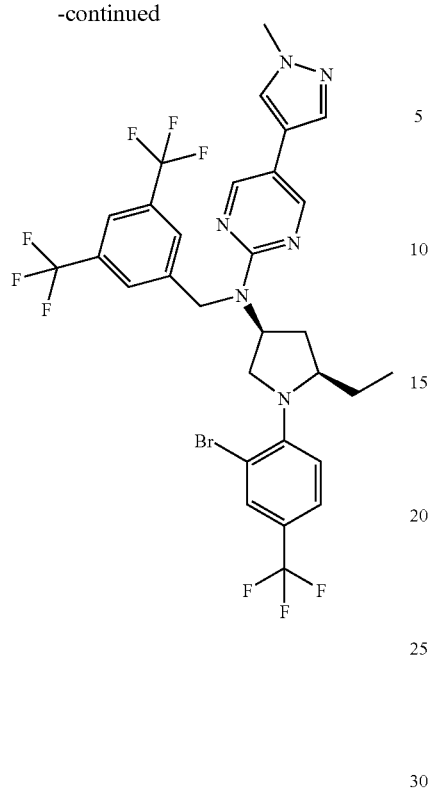

To a mixture of (2R,4S)-4-{(3,5-bis-trifluoromethyl-benzyl)-[5-(1-methyl-1H-pyrazol-4-yl)-pyrimidin-2-yl]amino}-2-ethyl-pyrrolidine-1-carboxylic acid tert-butyl ester (1.40 g, 6 mmol) in dichloromethane (28 mL) is added TFA (9 mL) at room temperature. The mixture is stirred for 0.5 hour, and diluted with dichloromethane. After addition of saturated NaHCO3 aq., the layers are separated, and the aqueous layer is extracted with dichloromethane. The combined organic layers (dried with MgSO$_4$) are concentrated. The resulting crude (3,5-bis-trifluoromethyl-benzyl)-((3S,5R)-5-ethyl-pyrrolidin-3-yl)-[5-(1-methyl-1H-pyrazol-4-yl)-pyrimidin-2-yl]-amine was used in next step without purification.

A mixture of [3,5-bis(trifluoromethyl)benzyl]-((3S,5R)-5-ethyl-pyrrolidin-3-yl)-[5-(1-methyl-1H-pyrazol-4-yl)-pyrimidin-2-yl]-amine (45 mg, 0.27 mmol), 2-chloro-5-trifluoromethyl-pyridine (196 mg, 0.81 mmol) and K$_2$CO$_3$ (111 mg, 0.81 mmol) in THF (2.0 mL) in a sealed tube is stirred at 120° C. for 2 hours. The mixture is concentrated under reduced pressure. The obtained residue is purified by silica gel column chromatography (eluent: hexane/EtOAc) to give (3,5-bis-trifluoromethyl-benzyl)-[(3S,5R)-1-(2-bromo-4-trifluoromethyl-phenyl)-5-ethyl-pyrrolidin-3-yl]-[5-(1-methyl-1H-pyrazol-4-yl)-pyrimidin-2-yl]-amine as a colorless oil (36 mg, 18%).

1H NMR (400 MHz, chloroform-d) δ ppm 0.81 (t, 3H), 1.31-1.35 (m, 1H), 1.63-1.69 (m, 1H), 1.74 (q, 1H), 2.40-2.43 (m, 1H), 3.20 (dd, 1H), 3.76-3.83 (m, 1H), 3.88 (dd, 1H), 3.95 (s, 3H), 5.02 (d, 1H), 5.16 (d, 2H), 5.45-5.50 (m, 1H), 6.98 (d, 1H), 7.46 (dd, 1H), 7.52 (s, 1H), 7.66 (s, 1H), 7.72 (s, 2H), 7.75 (d, 2H), 8.42 (s, 2H). ESI-MS m/z: 722 [M+1]+, Retention time 2.48 min (condition A).

Example 31

Synthesis of (3,5-bis-trifluoromethyl-benzyl)-[(3S,5R)-5-ethyl-1-(5-methoxymethyl-2-piperidin-1-yl-pyrimidin-4-yl)-pyrrolidin-3-yl]-[5-(1-methyl-1H-pyrazol-4-yl)-pyrimidin-2-yl]-amine

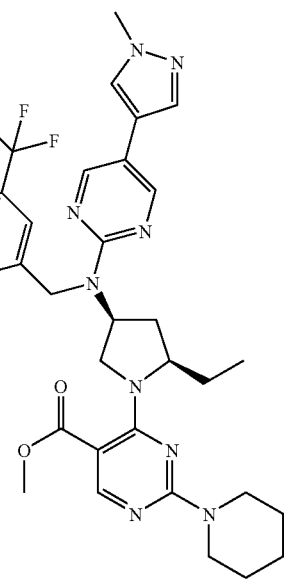

LAH, THF

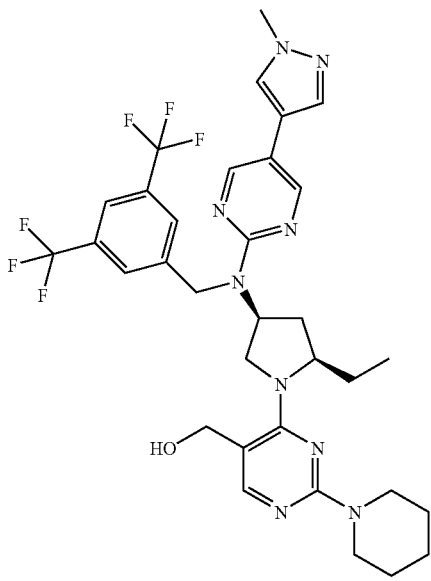

MeI, NaH
DMF

127 -continued

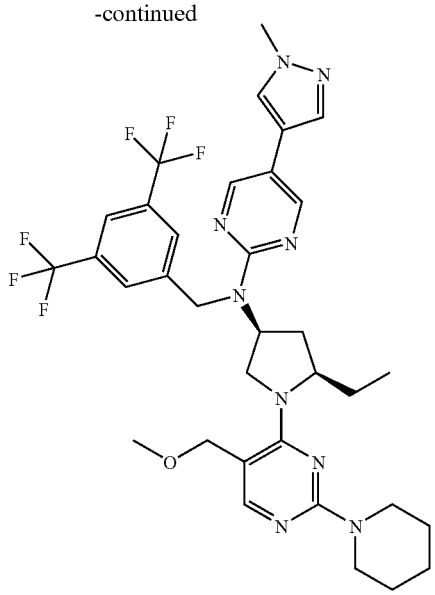

To a solution of 4-((2R,4S)-4-{(3,5-bis-trifluoromethyl-benzyl)-[5-(1-methyl-1H-pyrazol-4-yl)-pyrimidin-2-yl]-amino}-2-ethyl-pyrrolidin-1-yl)-2-piperidin-1-yl-pyrimidine-5-carboxylic acid methyl ester (250 mg, 0.33 mmol) in 1.5 mL of THF is added LAH (24 mg, 0.66 mmol). After stirred at room temperature for 3.5 hours, the reaction is quenched by Glauber's salt. The mixture is filtered on celite, and the filtrate is concentrated. The obtained residue is purified by silica gel column chromatography (eluent: hexane/EtOAc) to give [4-((2R,4S)-4-{(3,5-bis-trifluoromethyl-benzyl)-[5-(1-methyl-1H-pyrazol-4-yl)-pyrimidin-2-yl]-amino}-2-ethyl-pyrrolidin-1-yl)-2-piperidin-1-yl-pyrimidin-5-yl]-methanol (40 mg, 20% yields); ESI-MS m/z: 690 [M+1]+, Retention time 5.79 min (condition B).

To a solution of [4-((2R,4S)-4-{(3,5-bis-trifluoromethyl-benzyl)-[5-(1-methyl-1H-pyrazol-4-yl)-pyrimidin-2-yl]-amino}-2-ethyl-pyrrolidin-1-yl)-2-piperidin-1-yl-pyrimidin-5-yl]-methanol (40 mg, 0.06 mmol) and methyl iodide (0.004 mL, 0.7 mmol) in 1 mL of DMF is added sodium hydride (2.8 mg, 0.07 mmol) and stirred at room temperature for 1 day. Saturated NH4Cl aqueous solution is added at room temperature and then extracted twice with 50 mL of EtOAc. The combined organic layer is washed with brine, dried over Na2SO4 and concentrated. Column chromatography (eluent: hexane/EtOAc) give (3,5-bis-trifluoromethyl-benzyl)-[3S, 5R)-5-ethyl-1-(5-methoxymethyl-2-piperidin-1-yl-pyrimidin-4-yl)-pyrrolidin-3-yl]-[5-(1-methyl-1H-pyrazol-4-yl)-pyrimidin-2-yl]-amine (15 mg, 37% yields) as white solid.

1H NMR (400 MHz, CDCl3) δ ppm 0.84 (s, 3H), 1.45-1.70 (m, 5H), 1.93-2.05 (m, 2H), 1.93-2.05 (s, 2H), 2.28-2.35 (m, 2H), 3.10 (s, 3H), 3.45-3.55 (m, 1H), 3.65-3.75 (m, 4H), 3.95 (s, 3H), 4.09 (s, 2H), 4.13-4.23 (s, 1H), 4.33-4.45 (s, 1H), 4.99 (d, 2H), 5.15-5.25 (m, 1H), 7.54 (s, 1H), 7.66 (s, 1H), 7.70 (s, 1H), 7.77 (s, 1H), 7.82 (s, 1H), 8.43 (s, 2H). ESI-MS m/z: 704 [M+1]+, Retention time 4.17 min (condition B).

128

Example 32

Synthesis of 1-[5-chloro-4-(2R,4S)-4-{([3,5-bis(trifluoromethyl)-benzyl]-[5-(1-methyl-1H-pyrazol-4-yl)-pyrimidin-2-yl]-amino}-2-ethyl-pyrrolidin-1-yl)-pyrimidin-2-yl]-piperidine-4-carboxylic acid

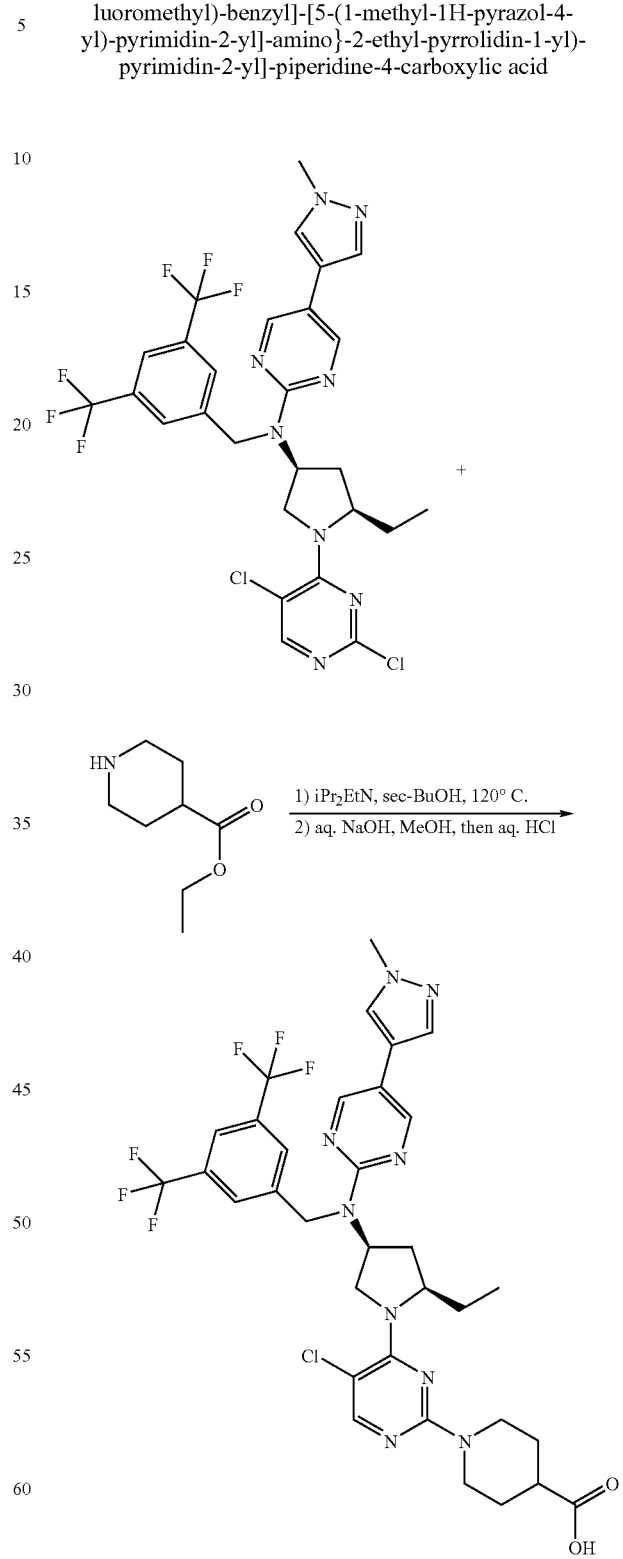

A mixture of 3,5-bis(trifluoromethyl)benzyl-[(3S,5R)-1-(2,5-dichloro-pyrimidin-4-yl)-5-ethyl-pyrrolidin-3-yl]-[5-(1-methyl-1H-pyrazol-4-yl)-pyrimidin-2-yl]-amine (50.6 mg, 0.0784 mmol), ethyl isonipecotate (31 μL, 0.196 mmol) and diisopropyl-ethylamine (21 μL, 0.118 mmol) in sec-butanol (2 mL) is stirred at 120° C. for 10 hour. After addition of ethyl isonipecotate (12 μL, 0.0784 mmol) and diisopropyl-ethylamine (27 μL, 0.157 mmol), the mixture is stirred for additional 8 hours. The mixture is diluted with dichloromethane and washed with waterm 1N HCl aq, and the brine, dried over sodium sulfate and concentrated in vacuo. The obtained residue is purified by silica gel column chromatography (n-hexane:AcOEt=1:2 to 5% MeOH in AcOEt) to give (1-[5-chloro-4-((2R,4S)-4-{[3,5-bis(trifluoromethyl)-benzyl]-[5-(1-methyl-1H-pyrazol-4-yl)-pyrimidin-2-yl]-amino}-2-ethyl-pyrrolidin-1-yl)-pyrimidin-2-yl]-piperidine-4-carboxylic acid ethyl ester, 34.7 mg). The obtained solid is dissolved in MeOH (2.5 mL), 1N NaOH aq (225 μL, 0.225 mmol) and water (0.3 mL), and the resulting mixture was stirred at room temperature for 18 hour. 1N HCl (225 μL, 0.225 mmol) and then MeOH were added to the mixture and the solvent was removed by evaporation. The residue was dissolved in dichloromethane and then filtered. The filtrate was evaporated to give 1-[5-chloro-4-((2R,4S)-4-{[3,5-bis (trifluoromethyl)-benzyl]-[5-(1-methyl-1H-pyrazol-4-yl)-pyrimidin-2-yl]-amino}-2-ethyl-pyrrolidin-1-yl)-pyrimidin-2-yl]-piperidine-4-carboxylic acid (29.2 mg, 51%).

1H NMR (400 MHz, chloroform-d) δ ppm: 0.84 (t, 3H), 1.38-1.50 (m, 1H), 1.61-1.80 (m, 4H), 1.90-2.01 (m, 3H), 2.24-2.34 (m, 1H), 2.55-2.65 (m, 1H), 2.94-3.06 (m, 2H), 3.57-3.67 (m, 1H), 3.93-4.01 (m, 1H), 3.95 (s, 3H), 4.2-4.43 (m, 1H), 4.44-4.53 (m, 2H), 4.94 (d, 1H), 5.06 (d, 1H), 5.22-5.33 (m, 1H), 7.53 (s, 1H), 7.66 (s, 1H), 7.71 (s, 2H), 7.78 (s, 1H), 7.88 (s, 1H), 8.44 (s, 2H). ESI-MS m/z: 738 [M+1]+, Retention time 1.96 min (condition A).

Example 33

Synthesis of 1-[4-((2S,4S)-4-{(3,5-bis-trifluoromethyl-benzyl)-[5-(1-methyl-1H-pyrazol-4-yl)-pyrimidin-2-yl]-amino}-2-methoxymethyl-pyrrolidin-1-yl)-5-chloro-pyrimidin-2-yl]-piperidine-4-carboxylic acid

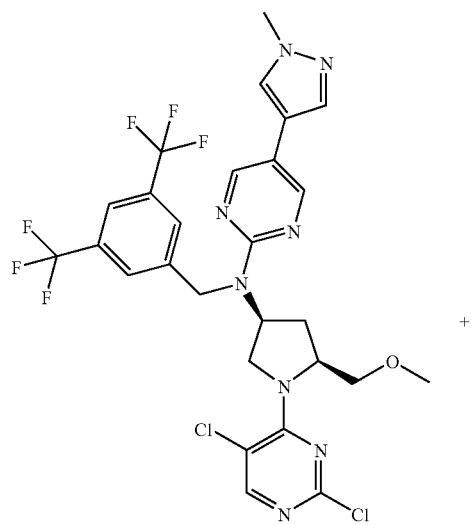

+

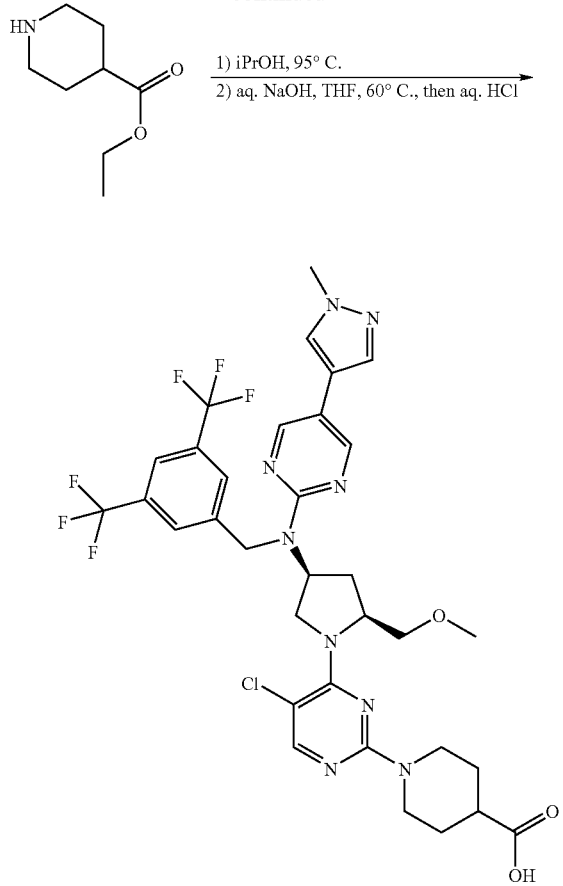

A 5 ml test tube for microwave reactor is charged with ethyl piperidine 4-carboxylate (202 mg, 1.28 mmol), (3,5-bis-trifluoromethyl-benzyl)-[(3S,5S)-1-(2,5-dichloro-pyrimidin-4-yl)-5-methoxymethyl-pyrrolidin-3-yl]-[5-(1-methyl-1H-pyrazol-4-yl)-pyrimidin-2-yl]-amine (170 mg, 0.26 mmol) and isopropanol (1.5 ml). Then, the test tube is set into microwave reactor at 95 degree for 2 hours. After cooling to rt, reaction mixture is transferred into a 25 ml round-bottom flask and solvent is removed under reduced pressure. Then, into the flask is added 1N NaOH (1.28 ml, 1.28 mmol). The mixture is stirred for 1 hour, and pH is adjusted to 6-7 using 1.5 N HCl. The resulted solution is extracted with EtOAc and the organic layer is dried over MgSO4. The solvent is removed under reduced pressure, and the obtained residue is purified with reverse phase column to give 1-[4-((2S,4S)-4-{ (3,5-bis-trifluoromethyl-benzyl)-[5-(1-methyl-1H-pyrazol-4-yl)-pyrimidin-2-yl]-amino}-2-methoxymethyl-pyrrolidin-1-yl)-5-chloro-pyrimidin-2-yl]-piperidine-4-carboxylic acid (78 mg, 0.74 mmol, 58% for 2 steps).

1H NMR (400 MHz, chloroform-d) δ ppm 1.73-1.79 (m, 2H), 1.96-2.06 (m, 2H), 2.13-2.21 (m, 1H), 2.25-2.31 (m, 1H), 2.61-2.66 (m, 1H), 3.14-3.19 (m, 2H), 3.31 (s, 3H), 3.53-3.62 (m, 3H), 3.95 (s, 3H), 4.20-4.25 (m, 1H), 4.43-4.49 (m, 2H), 4.70 (bs, 1H), 4.95 (d, 1H), 5.09 (d, 1H), 5.34-5.38 (m, 1H), 7.54 (s, 1H), 7.66 (s, 1H), 7.70 (s, 2H), 7.77 (s, 1H), 7.90 (s, 1H), 8.44 (s, 2H). ESI-MS m/z: 755 [M+1]+, Retention time 1.90 min (condition A).

The following compounds are prepared following the procedure of Example 33 using corresponding amine.

| No. | Product | ESI-MS m/z [M + 1]+ | Retention time (min) | Starting Material | Starting Material |
|---|---|---|---|---|---|
| 33-1 | | 663 | 1.91 (condition A) | | |
| 33-2 | | 744 | 1.99 (condition A) | | |
| 33-3 | | 717 | 1.90 (condition A) | | |

Example 34

Synthesis of (2R,4S)-4-{(3,5-bis-trifluoromethyl-benzyl)-[5-(2-methoxycarbonyl-ethyl)-pyrimidin-2-yl]-amino}-2-ethyl-pyrrolidine-1-carboxylic acid tert-butyl ester

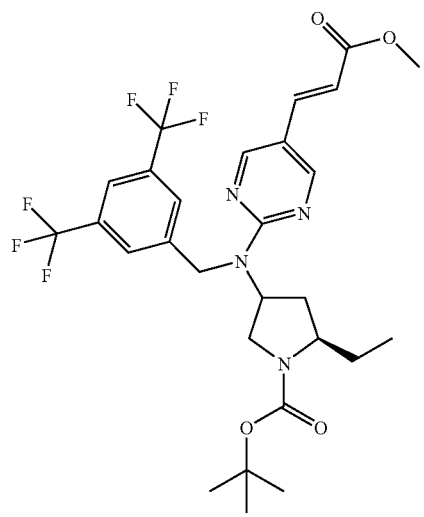

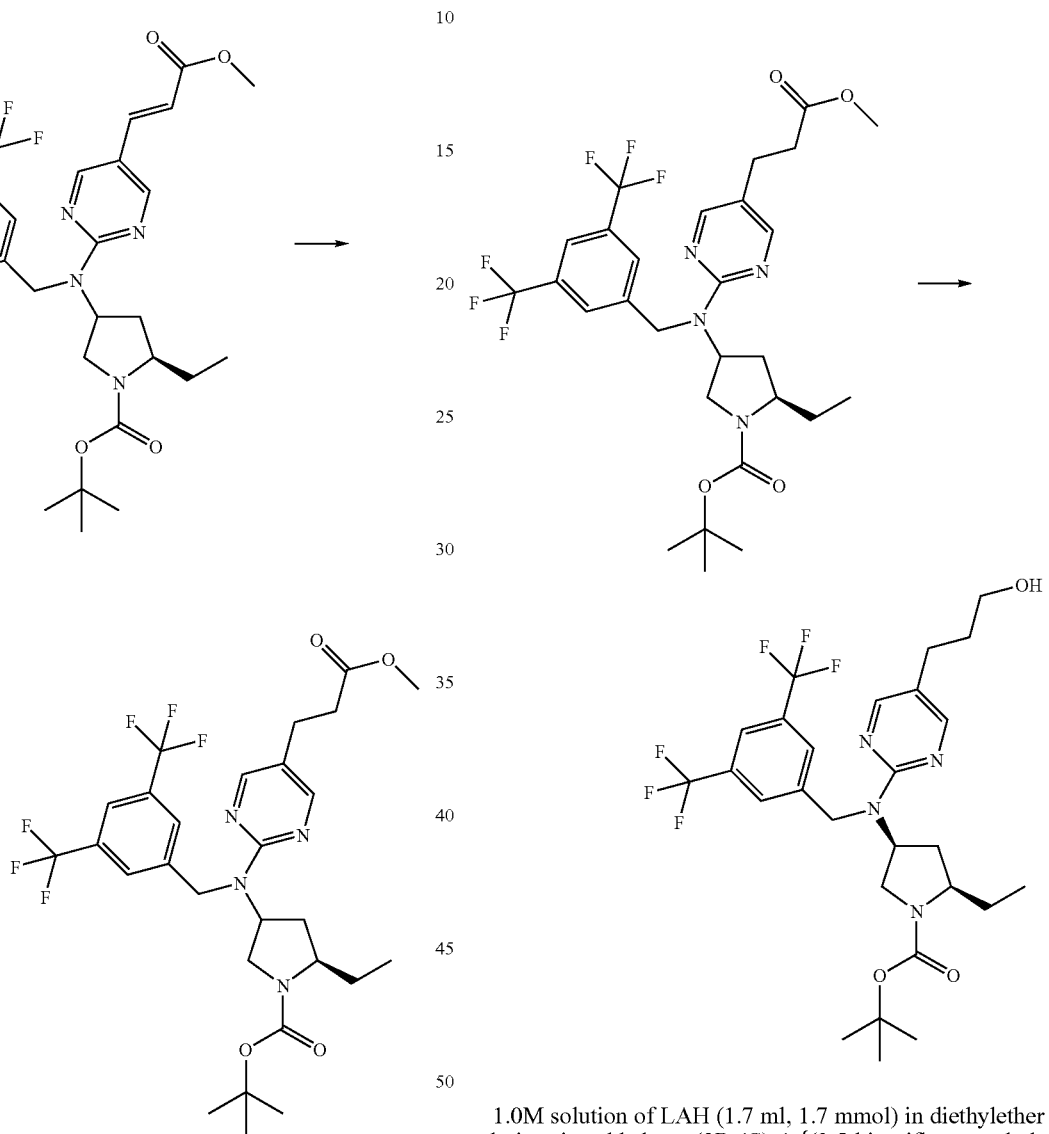

(2R,4S)-4-{(3,5-Bis-trifluoromethyl-benzyl)-[5-((E)-2-methoxycarbonyl-vinyl)-pyrimidin-2-yl]-amino}-2-ethyl-pyrrolidine-1-carboxylic acid tert-butyl ester (200 mg, 0.33 mmol) is dissolved in EtOH (5 mL) and hydrogenation reaction with 10% Pd/C. The residue is purified by column chromatography on silica gel (eluent: n-hexane/EtOAc) to give (2R,4S)-4-{(3,5-bis-trifluoromethyl-benzyl)-[5-(2-methoxycarbonyl-ethyl)-pyrimidin-2-yl]-amino}-2-ethyl-pyrrolidine-1-carboxylic acid tert-butyl ester (198 mg, 99%).

1H NMR (400 MHz, chloroform-d) δ ppm 0.80 (t, 3H), 1.44-1.49 (m, 1H), 1.60-1.68 (m, 1H), 1.90 (bs, 1H), 2.25-2.28 (m, 1H), 2.58 (t, 2H), 2.79 (t, 2H), 3.05 (t, 1H), 3.67 (s, 3H), 3.72-3.90 (m, 2H), 4.88 (s, 2H), 5.17-5.21 (1H), 7.63 (s, 2H), 7.74 (s, 1H), 8.20 (s, 2H). ESI-MS m/z: 605 [M+1]+, Retention time 2.47 min (condition A).

Example 35

Synthesis of (2R,4S)-4-{(3,5-bis-trifluoromethyl-benzyl)-[5-(3-hydroxy-propyl)-pyrimidin-2-yl]-amino}-2-ethyl-pyrrolidine-1-carboxylic acid tert-butyl ester 1.0M solution of LAH (1.7 ml, 1.7 mmol) in diethylether solution is added to (2R,4S)-4-{(3,5-bis-trifluoromethyl-benzyl)-[5-(2-methoxycarbonyl-ethyl)-pyrimidin-2-yl]-amino}-2-ethyl-pyrrolidine-1-carboxylic acid tert-butyl ester (350 mg, 0.58 mmol) in diethylether (8 ml) at 0° C., and this mixture is stirred for 0.5 hour at the same temperature. The reaction mixture is quenched with saturated ammonium chloride solution. The product is extracted three times with EtOAc. The combined organic layer is washed with 1N HCl, sat NaHCO₃ aq. and brine, dried over Na₂SO₄, filtered, and concentrated under reduced pressure. The residue is purified by column chromatography on silica gel (eluent: n-hexane/EtOAc) to give (2R,4S)-4-{(3,5-bis-trifluoromethyl-benzyl)-[5-(3-hydroxy-propyl)-pyrimidin-2-yl]-amino}-2-ethyl-pyrrolidine-1-carboxylic acid tert-butyl ester (0.25 g, 74%).

1H NMR (400 MHz, chloroform-d) δ ppm 0.81 (t, 3H), 1.30 (t, 1H), 1.44-1.49 (m, 1H), 1.60-1.66 (m, 1H), 1.79-1.86

(m, 2H), 2.24-2.29 (m, 1H), 2.57 (t, 2H), 3.06 (t, 1H), 3.66-3.71 (m, 2H), 3.74-3.85 (m, 2H), 4.88 (s, 2H), 5.15-5.23 (m, 1H), 7.64 (s, 2H), 7.74 (s, 1H), 8.20 (s, 2H). ESI-MS m/z: 577 [M+1]+, Retention time 2.33 min (condition A).

Example 36

Synthesis of (2R,4S)-4-[(3,5-bis-trifluoromethyl-benzyl)-(2-methyl-2H-tetrazol-5-yl)-amino]-2-ethyl-pyrrolidine-1-carboxylic acid tert-butyl ester

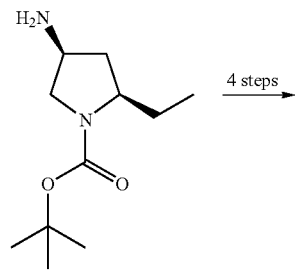

4 steps

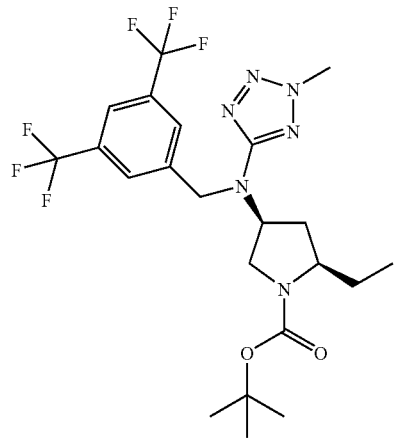

To a solution of (2R,4S)-4-amino-2-ethyl-pyrrolidine-1-carboxylic acid tert-butyl ester (150 mg, 0.7 mmol) in methanol (2 mL) is added to 3,5-bis-trifluoromethyl-benzaldehyde (340 mg, 1.4 mmol), and the reaction mixture is stirred at room temperature. After stirring for overnight, sodium borohydride (53 mg, 1.4 mmol) is added. After stirring for additional 1 hour, The product is extracted three times with EtOAc. The combined organic layer is washed with brine, dried over Na₂SO₄, filtered, and concentrated under reduced pressure to give crude (2R,4S)-4-(3,5-bis-trifluoromethyl-benzylamino)-2-ethyl-pyrrolidine-1-carboxylic acid tert-butyl ester (250 mg).

A solution of the crude product (82 mg 0.18 mmol), bromonitrile (60 mg, 0.56 mmol) and sodium carbonate (59 mg, 0.56 mmol) in methanol (2 mL) is stirred at room temperature for 1 hour. The reaction mixture is quenched with saturated ammonium chloride solution. The product is extracted three times with EtOAc. The combined organic layer is washed with brine, dried over Na₂SO₄, filtered, and concentrated under reduced pressure. The obtained residue is passed through silica pad (eluent: n-hexane/EtOAc) to give crude (2R,4S)-4-[(3,5-bis-trifluoromethyl-benzyl)-cyano-amino]-2-ethyl-pyrrolidine-1-carboxylic acid tert-butylester (52 mg).

A solution of the crude (2R,4S)-4-[(3,5-bis-trifluoromethyl-benzyl)-cyano-amino]-2-ethyl-pyrrolidine-1-carboxylic acid tert-butylester (52 mg, 0.11 mmol), sodium azide (72 mg, 1.11 mmol) ammonium chloride (60 mg, 1.11 mmol) in DMF (2 mL) is stirred at 90° C. for 12 hours. The reaction mixture is diluted with water after letting it cool to room temperature. The product is extracted twice with EtOAc. The combined organic layer is washed with water and brine, dried over Na₂SO₄, filtered, and concentrated under reduced pressure. The obtained residue is passed through silica pad (eluent: n-hexane/EtOAc) to give crude (2R,4S)-4-[(3,5-bis-trifluoromethyl-benzyl)-(2H-tetrazol-5-yl)-amino]-2-ethyl-pyrrolidine-1-carboxylic acid tert-butyl ester (52 mg).

A solution of the crude (2R,4S)-4-[(3,5-bis-trifluoromethyl-benzyl)-(2H-tetrazol-5-yl)-amino]-2-ethyl-pyrrolidine-1-carboxylic acid tert-butyl ester (52 mg, 0.10 mmol), methyl iodide (90 mg, 0.51 mmol) and potassium carbonate (28 mg, 0.20 mmol) in DMF (1.3 mL) is stirred at 50° C. for 2 hours. The reaction mixture is quenched with saturated ammonium chloride solution. The product is extracted three times with EtOAc. The combined organic layer is washed with brine, dried over Na₂SO₄, filtered, and concentrated under reduced pressure. The residue is purified by column chromatography on silica gel (eluent: n-hexane/EtOAc) to give (2R,4S)-4-[(3,5-bis-trifluoromethyl-benzyl)-(2-methyl-2H-tetrazol-5-yl)-amino]-2-ethyl-pyrrolidine-1-carboxylic acid tert-butyl ester (45 mg, 44% overall yield in 4 steps).

1H NMR (400 MHz, chloroform-d) δ ppm 0.83 (t, 3H), 1.44 (s, 9H), 1.47-1.53 (m, 1H), 1.75-1.83 (m, 1H), 1.95 (bs, 1H), 2.27-2.34 (m, 1H), 3.19 (t, 1H), 3.73-3.75 (m, 1H), 3.89 (bs, 1H), 4.16 (s, 3H), 4.48-4.53 (m, 1H), 4.74 (t, 2H), 7.70 (s, 2H), 7.78 (s, 1H). ESI-MS m/z: 523 [M+1]+, Retention time 2.26 min (condition A).

Example 37

Synthesis of (2R,4S)-4-{(3,5-bis-trifluoromethyl-benzyl)-[5-((E)-2methoxycarbonyl-vinyl)-pyrimidin-2-yl]-amino}-2-ethyl-pyrrolidine-1-carboxylic acid tert-butyl ester

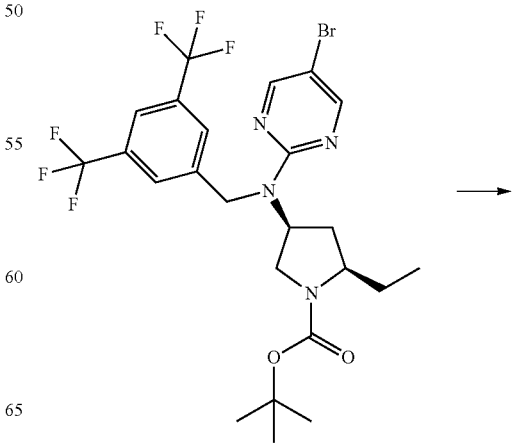

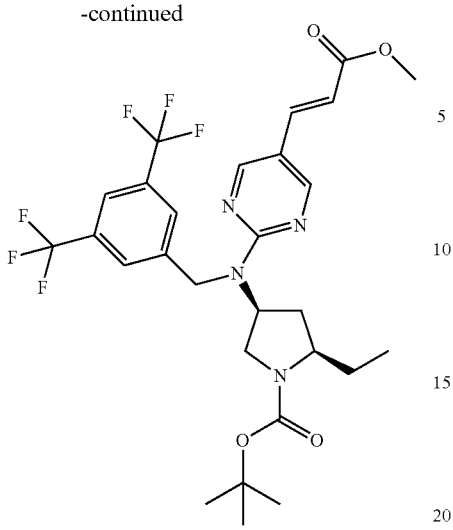

(2R,4S)-4-[(3,5-Bis-trifluoromethyl-benzyl)-(5-bromo-pyrimidin-2-yl)-amino]-2-ethyl-pyrrolidine-1-carboxylic acid tert-butyl ester (300 mg, 0.5 mmol), palladium(II) acetate (15 mg, 0.05 mmol), tri(o-tolyl)phosphine (36 mg, 0.1 mmol), triethylamine (0.2 mL, 1.5 mmol), and methyl acrylate (0.15 mL, 1.5 mmol) are dissolved in DMF (5 mL) and heated in a microwave at 150° C. for 30 minutes. The reaction mixture is filtered through Celite with EtOAc and concentrated under reduced pressure. The residue is purified by column chromatography on silica gel (eluent: n-hexane/EtOAc) to give (2R,4S)-4-{(3,5-bis-trifluoromethyl-benzyl)-[5-((E)-2methoxycarbonyl-vinyl)-pyrimidin-2-yl]-amino}-2-ethyl-pyrrolidine-1-carboxylic acid tert-butyl ester (225 mg, 75%).

1H NMR (400 MHz, chloroform-d) δ ppm 0.81 (t, 3H), 1.44-1.51 (m, 1H), 1.64-1.67 (m, 1H), 1.94 (bs, 1H), 2.26-2.32 (m, 1H), 3.10 (t, 1H), 3.73-3.86 (m, 2H), 3.84 (s, 3H), 4.94 (t, 2H), 5.20-5.26 (m, 1H), 6.34 (d, 1H), 7.52 (d, 1H), 7.62 (s, 2H), 7.77 (s, 1H), 8.50 (s, 2H). ESI-MS m/z: 603 [M+1]+, Retention time 2.51 min (condition A).

Preparation of the starting materials can be done as follows.

To a solution (2S,5R)-2-benzyl-5-ethyl-3-oxo-pyrrolidine-1-carboxylic acid tert-butyl ester (0.038 mmol; 25.1 mg) and 3,5-bis(trifluoromethyl)benzylamine (0.166 mmol; 40.4 mg) in MeOH (0.4 mL) is added titanium(IV) isopropoxide (0.1 mmol; 28.4 mg). After stirring for 6 hours, NaBH$_4$ (0.125 mmol; 4.8 mg) is added to the reaction mixture at 0° C. After stirring for 1.5 hours at room temperature, another NaBH$_4$ (0.041 mmol; 1.6 mg) is added to the mixture at the same temperature. After stirring for additional 45 minutes, H$_2$O is added to the mixture. The mixture is filtered and concentrated under reduced pressure. Water and dichloromethane are added to the residue. The organic layer after dried is separated, concentrated under reduced pressure. The residue is purified by column chromatography on silica gel (eluent: n-hexane/EtOAc) to give (2S,3S,5R)-2-benzyl-3-(3,5-bis-trifluoromethyl-benzylamino)-5-ethyl-pyrrolidine-1-carboxylic acid tert-butyl ester (25.8 mg, 59%); ESI-MS m/z: 531 [M+1]+, Retention time 4.55 min (condition B).

Example 38

Synthesis of (2S,3S,5R)-2-benzyl-3-(3,5-bis-trifluoromethyl-benzylamino)-5-ethyl-pyrrolidine-1-carboxylic acid tent-butyl ester

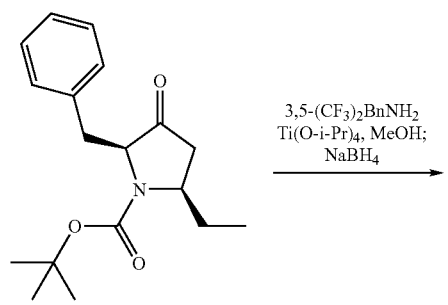

Example 39

Synthesis of (2S,3S,5R)-2-benzyl-3-(5-bromo-pyrimidin-2-ylamino)-5-ethyl-pyrrolidine-1-carboxylic acid isopropyl ester

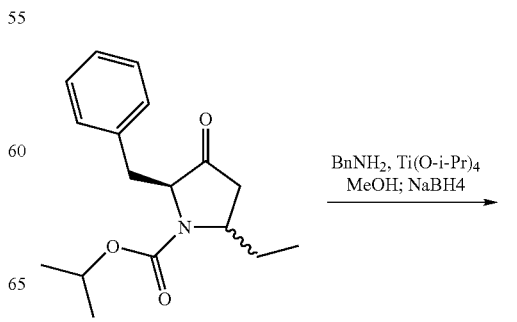

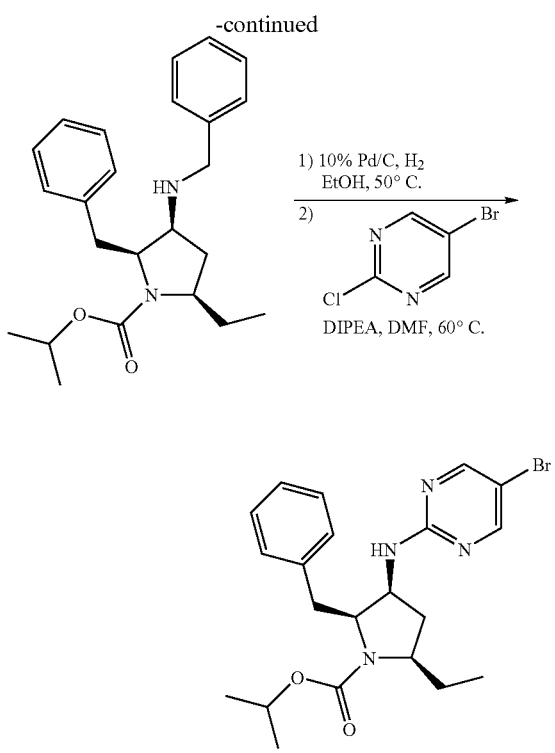

To a solution of a diastereomeric mixture of (2S)-2-benzyl-5-ethyl-3-oxo-pyrrolidine-1-carboxylic acid isopropyl ester (0.29 mmol; 84 mg) and benzylamine (0.58 mmol; 62.1 mg) in MeOH (1.5 mL) is added titanium(IV) isopropoxide (0.58 mmol; 165 mg) at room temperature under nitrogen. After stirring for 5 hours, NaBH$_4$ (0.58 mmol; 22 mg) is added to the mixture at 0° C. The mixture is stirred for 2 hours at room temperature and then diluted with water and aqueous 0.1 M NaOH solution. The solution is filtered and concentrated under reduced pressure. To the residue is added water and dichloromethane. The product is extracted twice with dichloromethane. The combined organic layer is washed with brine, dried over Na$_2$SO$_4$, filtered, and concentrated under reduced pressure. The residue is purified by column chromatography on silica gel (n-hexane/EtOAc) to give (2S,3S,5R)-2-benzyl-3-benzylamino-5-ethyl-pyrrolidine-1-carboxylic acid isopropyl ester (61 mg, 55%); ESI-MS m/z: 381 [M$^+$+1], Retention time 1.77 min (condition A).

A solution of (2S,3S,5R)-2-benzyl-3-benzylamino-5-ethyl-pyrrolidine-1-carboxylic acid isopropyl ester (0.16 mmol; 61 mg) in ethanol (5 mL) is hydrogenated over 10% palladium on carbon (6 mg) at 50° C. and atmospheric pressure. After 9.5 hours, the suspension is cooled to ambient temperature and purged with nitrogen. The reaction mixture is filtered and concentrated under reduced pressure. A mixture of the obtained material (46 mg), 5-bromo-2-chloropyrimidine (0.18 mmol; 34.8 mg) and DIPEA (0.32 mmol; 41.4 mg) in DMF (0.8 mL) is stirred at 100° C. for 4 hours and then at 120° C. for 8.5 hours, and cooled to ambient temperature. The solution is diluted with brine and EtOAc. The product is extracted three times with EtOAc. The combined organic layer is washed with brine, dried over Na$_2$SO$_4$, filtered, and concentrated under reduced pressure. The residue is purified by column chromatography on silica gel (n-hexane/EtOAc) to give (2S,3S,5R)-2-benzyl-3-(5-bromo-pyrimidin-2-ylamino)-5-ethyl-pyrrolidine-1-carboxylic acid isopropyl ester (28.6 mg, 40% in 2 steps); ESI-MS m/z: 447 [M$^+$+1], Retention time 2.36 min (condition A).

Example 40

Synthesis of (2S,5R)-2-benzyl-5-ethyl-3-oxo-pyrrolidine-1-carboxylic acid tert-butyl ester

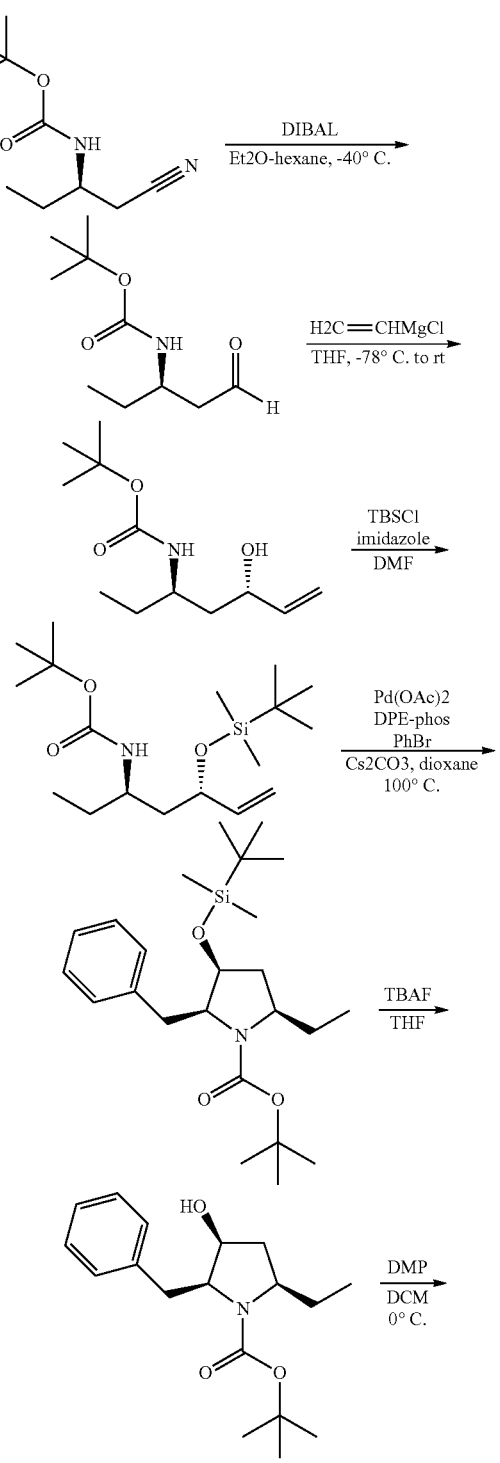

-continued

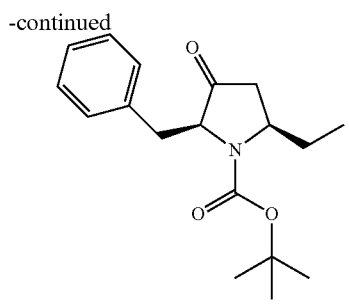

To a solution of ((R)-2-cyano-1-ethyl-ethyl)-carbamic acid tert-butyl ester (10 mmol; 1.98 g) in Et₂O (50 mL) is slowly added a 0.97 M n-hexane solution (40 mmol; 41 mL) of DIBAL under nitrogen at −78° C. The reaction mixture is warmed to −40° C. and stirred for an additional 3.5 hours. Another 1.00 M n-hexane solution (30 mmol; 30 mL) of DIBAL is added to the suspension at the same temperature. After stirring for additional 1.5 hours, the solution is quenched by careful addition of 1 ml of MeOH then immediately poured into 25 ml of saturated aqueous ammonium chloride solution in a separatory funnel. Shake mixture and leave until it reaches room temperature. Aqueous 1M HCl is added to reach a pH of 3-4. The solution is extracted three times with EtOAc and the combined organic layer is washed with an aqueous 1M HCl/brine (1:1) solution and twice with a saturated aqueous NaHCO3/brine (1:1) solution, dried over Na₂SO₄, filtered and concentrated under reduced pressure and purified by column chromatography on silica gel (eluent; n-hexane/EtOAc) to give ((R)-1-ethyl-3-oxo-propyl)-carbamic acid tent-butyl ester (590 mg, 29%); ESI-MS m/z: 146 [M⁺−tBu+2], Retention time 2.17 min (condition A).

To a solution of ((R)-1-ethyl-3-oxo-propyl)carbamic acid tert-butyl ester (2.9 mmol; 584 mg) in THF (20 mL) is added a 1.44 M THF solution (11.6 mmol; 8.1 mL) of vinylmagnesium chloride under nitrogen at −78° C. After stirring for 30 minutes, the reaction mixture is warmed to room temperature and stirred for an additional 1.5 hours. Another 1.44 M THF solution (2.9 mmol; 2 mL) of vinylmagnesium chloride is added to the reaction mixture at room temperature. After stirring for additional 15 minutes, the solution is quenched by saturated aqueous ammonium chloride solution and extracted three times with EtOAc. The combined organic layer is washed with brine, dried over Na₂SO₄, filtered, and concentrated under reduced pressure. The residue is purified by column chromatography on silica gel (eluent; n-hexane/EtOAc) to give ((1R,3S)-1-ethyl-3-hydroxy-pent-4-enyl)-carbamic acid tert-butyl ester (130 mg, 20%); ESI-MS m/z: 174 [M⁺−tBu+2], Retention time 4.13 min (condition B).

To a solution of ((1R,3S)-1-ethyl-3-hydroxy-pent-4-enyl)-carbamic acid tert-butyl ester (0.541 mmol; 124 mg) and imidazole (2.164 mmol; 147 mg) in DMF (1.8 mL) is added tert-butyldimethylsilyl chloride (1.623 mmol; 245 mg) at room temperature under N₂. After 12 hours, the reaction mixture is quenched with water, extracted three times with EtOAc. The combined organic layer is washed with brine, dried over Na₂SO₄, filtered, concentrated under reduced pressure. The residue is purified by column chromatography on silica gel (eluent; n-hexane/EtOAc) to give [(1R,3S)-3-(tert-butyl-dimethyl-silanyloxy)-1-ethyl-pent-4-enyl]-carbamic acid tert-butyl ester (160 mg, 86%); ESI-MS m/z: 288 [M⁺−tBu+2], Retention time 5.77 min (condition B).

give [(1R,3S)-3-(tert-butyl-dimethyl-silanyloxy)-1-ethyl-pent-4-enyl]-carbamic acid tert-butyl ester (0.38 mmol; 138 mg), palladium(II) acetate (0.038 mmol; 8.5 mg), (Oxidi-2,1-phenylene)bis(diphenylphosphine) (0.076 mmol; 41 mg), bromobenzene (0.57 mmol; 89 mg), and Cs₂CO₃ (1.14 mmol; 371 mg) are dissolved in 1,4-dioxane (1.9 mL) at room temperature. The mixture is stirred at 100° C. for 15 hours, and cooled to room temperature. To the mixture is added saturated aqueous ammonium chloride solution and the solution is extracted three times with EtOAc. The combined organic layer is washed with brine, dried over Na₂SO₄, filtered, and concentrated under reduced pressure. The obtained residue is purified by silica gel column chromatography to give (2S,3S,5R)-2-benzyl-3-(tert-butyl-dimethyl-silanyloxy)-5-ethyl-pyrrolidine-1-carboxylic acid tert-butyl ester (102 mg, 64%); ESI-MS m/z: 364 [M⁺−tBu+2] Retention time 6.22 min (condition B).

To a solution of (2S,3S,5R)-2-benzyl-3-(tert-butyl-dimethyl-silanyloxy)-5-ethyl-pyrrolidine-1-carboxylic acid tert-butyl ester (0.243 mmol; 102 mg) in THF is added 1.0 M THF solution (0.36 mL) of tetra-n-butylammonium fluoride under nitrogen at room temperature. After 3 hours, The reaction mixture is quenched with saturated aqueous ammonium chloride solution, extracted three times with EtOAc. The combined organic layer is washed with brine, dried over Na₂SO₄, filtered, concentrated under reduced pressure. The residue is purified by column chromatography on silica gel (eluent; n-hexane/EtOAc) to give (2S,3S,5R)-2-benzyl-5-ethyl-3-hydroxy-pyrrolidine-1-carboxylic acid tert-butyl ester (74.4 mg, 99%); ESI-MS m/z: 250 [M⁺−tBu+2], Retention time 2.34 min (condition A).

To a solution of (2S,3S,5R)-2-benzyl-5-ethyl-3-hydroxy-pyrrolidine-1-carboxylic acid tert-butyl ester (0.138 mmol; 42 mg) in dichloromethane (1.4 mL) is added Dess-Martin periodinane (0.166 mmol; 70.4 mg) at 0° C. The mixture is stirred at the same temperature for 1.5 hours. To the mixture, brine and EtOAc are added. The organic layer is separated, washed with saturated aqueous Na₂S₂O₃ solution, dried over Na₂SO₄, filtered, concentrated under reduced pressure. The residue is purified by column chromatography on silica gel (eluent; n-hexane/EtOAc) to give (2S,5R)-2-benzyl-5-ethyl-3-oxo-pyrrolidine-1-carboxylic acid tert-butyl ester (29.8 mg, 71%); ESI-MS m/z: 248 [M⁺−tBu+2], Retention time 2.49 min (condition A).

Example 41

Synthesis of diastereomers of (2S)-2-benzyl-5-ethyl-3-oxo-pyrrolidine-1-carboxylic acid isopropyl ester

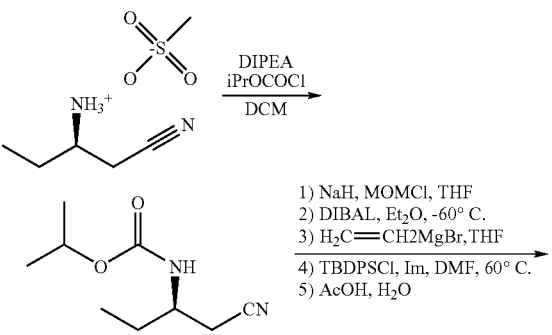

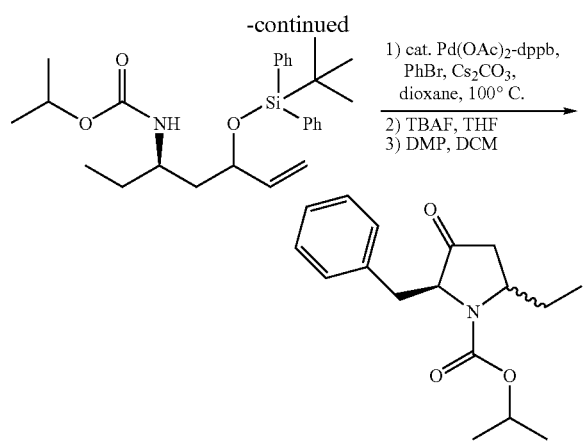

To a solution of (R)-2-cyano-1-ethylethylammonium methanesulfonate (50 mmol; 9.72 g) and DIPEA (105 mmol; 13.6 g) in dichloromethane (100 mL) is added isopropyl chloroformate (52.5 mmol; 6.43 g) at 0° C. The solution is warmed to room temperature and stirred for 4 hours. The reaction mixture is quenched with brine and extracted with dichloromethane. The organic layer is washed with aqueous 0.1M HCl, saturated aqueous $NaHCO_3$ solution and then brine, dried over $MgSO_4$, filtered concentrated under reduced pressure to give ((R)-2-cyano-1-ethyl-ethyl)-carbamic acid isopropyl ester (8.75 g, 95%); ESI-MS m/z: 185 [M$^+$+1], Retention time 1.60 min (condition A).

To a suspension of ((R)-2-cyano-1-ethyl-ethyl)-carbamic acid isopropyl ester (20 mmol; 3.68 g) and sodium hydride (60% dispersion in mineral oil, 40 mmol; 1.60 g) in THF (80 mL) is added chloromethyl methyl ether at 0° C. The reaction mixture is stirred at room temperature for 15 hours. The reaction mixture is quenched with brine and saturated aqueous ammonium chloride solution, and extracted three times with $Et_2O$. The combined organic layer is washed with brine, dried over $Na_2SO_4$, filtered, concentrated under reduced pressure. To a solution of the obtained residue (5.75 g) in $Et_2O$ (200 ml) is added 1.0 M n-hexane solution of DIBAL (25 mmol; 25 ml) dropwise over 10 minutes at −78° C. under $N_2$. The solution is stirred for 1 hour at the same temperature, then warmed to −60° C. for 3 hours. Another 15 mL of DIBAL (1.0 M in n-hexane) is added after 18.5 hours. After stirring for additional 2 hours, the reaction mixture is quenched by careful addition of 2 ml of MeOH then immediately poured on saturated aqueous ammonium chloride solution in a separatory funnel. Shake the mixture and leave until it reaches room temperature. Aqueous 1M HCl is added to reach a pH of 2. The solution is extracted three times with $Et_2O$ and the combined organic layer is washed with aqueous 1M HCl/brine (1:1) solution and saturated aqueous $NaHCO_3$/brine (1:1) solution, dried over $Na_2SO_4$, filtered and concentrated under reduced pressure. To a solution of the obtained residue (4.27 g) in THF (87 ml) is added 1.44 M THF solution (19 mmol; 13.2 mL) of vinylmagnesium chloride under $N_2$ at −78° C. After stirring for 1.5 hours, another 1.44 M THF solution (38 mmol; 26.4 ml) of vinylmagnesium chloride is added in 1.5 hours to the reaction mixture at the same temperature. After stirring for additional 1 hour, another 1.44 M THF solution (19 mmol; 13.2 mL) of vinylmagnesium chloride is added to the reaction mixture at room temperature. The solution is quenched by water, saturated aqueous ammonium chloride solution, aqueous 0.1 M HCl and then aqueous 1 M HCl, and extracted twice with EtOAc. The combined organic layer is washed with brine, dried over $Na_2SO_4$, filtered, and concentrated under reduced pressure. To a solution of the obtained residue (4.44 g) and imidazole (42.5 mmol; 2.89 g) in DMF (50 mL) is added chloro tert-butyldiphenylchlorosilane (34 mmol; 9.35 g) at room temperature under nitrogen. After stirring for 2 hours at 60° C., the reaction is cooled down to ambient temperature, then quenched with saturated aqueous ammonium chloride solution and extracted twice with EtOAc. The combined organic layer is washed with brine, dried over $Na_2SO_4$, filtered, and concentrated under reduced pressure. A mixture of the obtained residue (13.4 g), acetic acid (100 mL) and water (20 mL) is stirred at 60° C. for 3 hours. The mixture is concentrated under reduced pressure and then diluted with $Et_2O$ and aqueous sodium hydroxide solution. The product is extracted three times with Et2O. The combined organic layer is washed with brine, dried over $Na_2SO_4$, filtered, and concentrated under reduced pressure. The residue is purified by column chromatography on silica gel (n-hexane/EtOAc) to give [(1R)-3-(tert-butyl-diphenyl-silanyloxy)-1-ethyl-pent-4-enyl]-carbamic acid isopropyl ester (3.43 g, 42% in 5 steps) as a diastereomeric mixture; ESI-MS m/z: 454 [M$^+$+1], Retention time 5.51 min (condition C).

Diastereomeric mixture of [(1R)-3-(tert-butyl-diphenyl-silanyloxy)-1-ethyl-pent-4-enyl]-carbamic acid isopropyl ester (1.54 mmol; 840 mg), palladium(II) acetate (0.154 mmol; 34.5 mg), 1,4-bis(diphenylphosphino)butane (0.308 mmol; 131 mg), bromobenzene (2.31 mmol; 363 mg), $Cs_2CO_3$ (4.62 mmol; 1.51 g) are dissolved in 1,4-dioxane (7.7 ml) at room temperature. The mixture is stirred at 100° C. for 28 hours, and cooled to ambient temperature. To the mixture is added water and the product is extracted three times with EtOAc. The combined organic layer is washed with brine, dried over $Na_2SO_4$, filtered, and concentrated under reduced pressure. The obtained residue is purified by silica gel column chromatography (n-hexane/EtOAc) to give the desired product. To a solution of the obtained product in THF (15 mL) is added a 1.0 M THF solution of tetrabutylammonium fluoride (1.5 mL) under $N_2$. The mixture is stirred for 13 hours at room temperature and quenched with saturated aqueous ammonium chloride solution. The product is extracted three times with EtOAc. The combined organic layer is washed with brine, dried over $Na_2SO_4$, filtered, and concentrated under reduced pressure. To a solution of the residue in dichloromethane (15 mL) is added Dess-Martin periodinane (1.54 mmol; 653 mg) at 0° C. After stirring for 1 hour at the same temperature, the reaction mixture is stirred at room temperature for 1 hour. To the mixture, another portion of Dess-Martin periodinane (3.08 mmol; 1.31 g) is added in 2 hours. The mixture is stirred for additional 2 hours, and then quenched with brine. The product is extracted twice with EtOAc. The combined organic layer is washed with saturated aqueous $Na_2S_2O_3$ solution and brine, dried over $Na_2SO_4$, filtered, and concentrated under reduced pressure. The obtained residue is purified by silica gel column chromatography (n-hexane/EtOAc). The product fractions are collected and washed with saturated aqueous $Na_2S_2O_3$ solution, saturated aqueous $NaHCO_3$ solution and brine, dried over $Na_2SO_4$, filtered, and concentrated under reduced pressure to give (2S)-2-benzyl-5-ethyl-3-oxo-pyrrolidine-1-carboxylic acid isopropyl ester (84 mg, 19% in 3 steps) as a diastereomeric mixture (cis/trans=71:29); ESI-MS m/z: 290 [M$^+$+1], Retention time 2.12 min (condition A).

Example 42

The following compounds are prepared following the procedure of Example 7.

| No. | Product | ESI-MS m/z [M + 1]⁺ | Retention time (min) | Alcohol | Starting Material |
|---|---|---|---|---|---|
| 42-1 | | 683 | 2.26 (condition A) | | |

Example 43

The following compounds are prepared following the procedure of Example 16 using corresponding amines.

| No. | Product | ESI-MS m/z [M + 1]⁺ | Retention time (min) | Amine | Starting Material |
|---|---|---|---|---|---|
| 43-1 | | 628 | 4.17 (condition B) | | |
| 43-2 | | 696 | 4.22 (condition B) | | |

| No. | Product | ESI-MS m/z [M + 1]⁺ | Retention time (min) | Amine | Starting Material |
|---|---|---|---|---|---|
| 43-3 | | 640 | 2.01 (condition A) | | |

Example 44

Synthesis of (3,5-bis-trifluoromethyl-benzyl)-((3S, 5R)-5-ethyl-pyrrolidin-3-yl)-[5-(1-methyl-1H-pyrazol-4-yl)-pyrimidin-2-yl]-amine

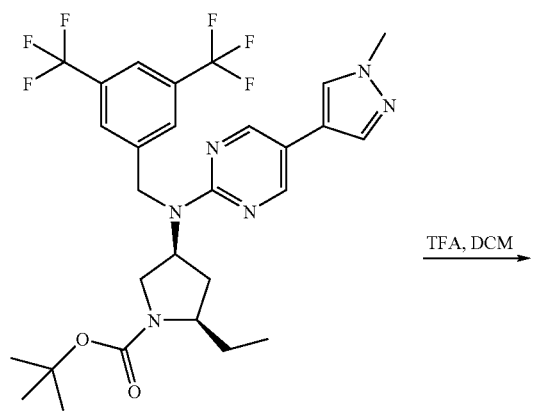

To a solution of (2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carboxylic acid tert-butyl ester (1.2 g, 2 mmol) in CH₂Cl₂ (20 mL) is added trifluoroacetic acid (7 mL) at room temperature. The reaction mixture is stirred at room temperature for 1.5 hours. The mixture is quenched with saturated aqueous NaHCO₃ solution, then extracted with CH₂Cl₂. The combined organic layer is washed by saturated aqueous NaHCO₃ solution, then dried over Na₂SO₄ and concentrated under reduced pressure to give (3,5-bis-trifluoromethyl-benzyl)-((3S,5R)-5-ethyl-pyrrolidin-3-yl)-[5-(1-methyl-1H-pyrazol-4-yl)-pyrimidin-2-yl]-amine as a yellow oil (1.01 g, quant.). ESI-MS m/z: 499 [M+1]+, Retention time 1.84 min (condition A).

Example 45

Synthesis of (2R,4S)-4-[(3,5-bis-trifluoromethyl-benzyl)-(5-bromo-pyrimidin-2-yl)-amino]-2-ethyl-pyrrolidine-1-carboxylic acid tert-butyl ester

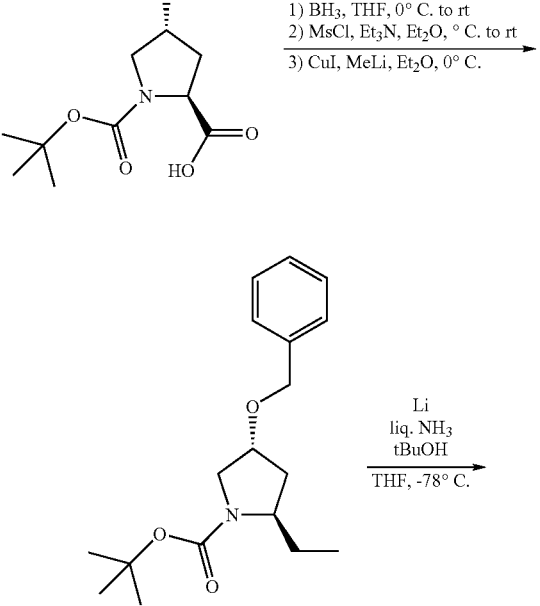

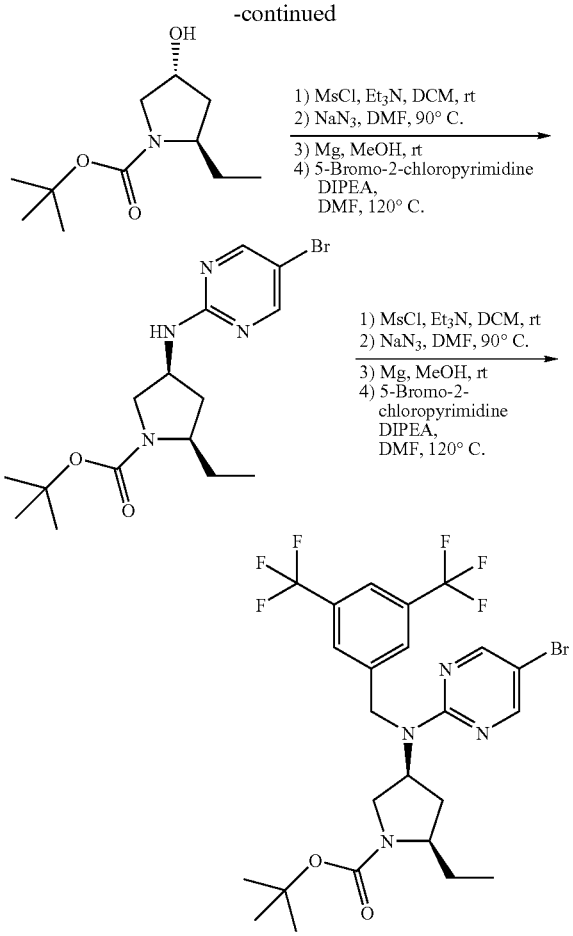

To a solution of (2S,4R)-4-benzyloxy-pyrrolidine-1,2-dicarboxylic acid 1-tert-butyl ester (77.8 mmol; 25.0 g) in THF (135 mL) is added 0.93 M THF solution of borane THF complex (116.7 mmol; 125 mL) at 0° C. under nitrogen. The solution is stirred for 1.5 hours at room temperature, quenched by dropwise addition of 40 ml of MeOH. After concentrating, the mixture is diluted with 400 ml of dichloromethane and 250 ml of saturated aqueous ammonium chloride solution. The product is extracted twice with 100 ml of dichloromethane. The combined organic layer is washed with 250 ml of brine, dried over MgSO$_4$, filtered, concentrated under reduced pressure to give the crude product (24.3 g).

To a solution of the crude product (24.3 g) and triethylamine (97.3 mmol; 9.85 g) in Et$_2$O (260 ml) is added MsCl (85.6 mmol; 9.81 g) at 0° C. under nitrogen. The reaction mixture is stirred for 13 hours and filtered. The filter cake is washed with additional Et$_2$O (250 mL). The filtrate is washed with 200 ml of a saturated aqueous ammonium chloride solution and 100 ml of brine, dried over MgSO$_4$, filtered, and concentrated under reduced pressure to give the crude product (29.8 g).

To a suspension of Cu (163 mmol; 31.0 g) in Et$_2$O (100 mL) is slowly added 1.09 M Et$_2$O solution of MeLi (300 mL) at 0° C. under nitrogen to give a clear solution. After stirring for 30 minutes, to the clear solution is slowly added a solution of the crude product (29.8 g) in Et$_2$O (100 mL) at 0° C. The reaction mixture is stirred for 3 hours at the same temperature, quenched with 800 mL of a saturated ammonium chloride solution. The product is extracted twice with 500 ml of Et$_2$O. The combined organic layer is washed with 400 ml of brine, dried over MgSO$_4$, filtered, concentrated under reduced pressure. The obtained residue is purified by silica gel column chromatography (eluent: n-hexane/EtOAc) to give (2R,4R)-4-benzyloxy-2-ethyl-pyrrolidine-1-carboxylic acid tent-butyl ester (8.91 g, 37% in 3 steps).

In a flask purged with ammonia gas, about 150 mL of liquid ammonia is collected with ammonia condenser at −78° C. To the liquid ammonia is added portion wise lithium metal (116 mmol; 805 mg) at the same temperature. To the deep blue solution is added a solution of (2R,4R)-4-benzyloxy-2-ethyl-pyrrolidine-1-carboxylic acid tert-butyl ester (29.1 mmol; 8.90 g) and tert-butanol (58.2 mmol; 4.31 g) in THF (30 mL). After stirring for 2 hours, the reaction mixture is quenched with MeOH, and then warmed to ambient temperature. The mixture is diluted with water, then aqueous 1M HCl is added to reach pH 8-9. The product is extracted three times with EtOAc. The combined organic layer is washed with brine, dried over MgSO$_4$, filtered, concentrated under reduced pressure to give (2R,4R)-4-hydroxy-2-ethyl-pyrrolidine-1-carboxylic acid tert-butyl ester (6.25 g, 99.8%).

To a solution of (2R,4R)-4-hydroxy-2-ethyl-pyrrolidine-1-carboxylic acid tert-butyl ester (21.5 mmol; 4.63 g) and Et$_3$N (32.3 mmol; 3.27 g) in dichloromethane (86 mL) is added MSCl (30.1 mmol; 3.45 g) at room temperature. The reaction mixture is stirred for 4 hours, and then quenched with saturated aqueous NaHCO$_3$ solution. The product is extracted three times with dichloromethane. The combined organic layer is washed with saturated aqueous ammonium chloride and then brine, dried over MgSO$_4$, filtered, concentrated under reduced pressure to give the crude product.

To a solution of the crude product in DMF (86 ml) is added sodium azide (30.1 mmol; 1.96 g) under nitrogen at room temperature. After stirring for 6 hours at 90° C., the reaction mixture is cooled to ambient temperature, then quenched with saturated ammonium chloride solution. The product is extracted twice with EtOAc. The combined organic layer is washed twice with aqueous 0.1 M HCl and then once with brine, dried over MgSO$_4$, filtered, concentrated under reduced pressure to give the crude product.

A suspension of the crude product and magnesium metal (107.5 mmol; 2.61 g) in MeOH (43 mL) is stirred for 7 hours. The suspension is filtered and concentrated. To the residue are added EtOAc and brine. The product is extracted twice with EtOAc. The combined organic layer is washed with brine, dried over K$_2$CO$_3$, filtered, concentrated under reduced pressure to give the crude product.

A solution of the crude product, 5-bromo-2-chloropyrimidine (25.8 mmol; 4.99 g) and N,N-diisopropylethylamine (43.0 mmol; 5.56 g) in DMF (72 mL) is stirred at 120° C. for 2 hours. The reaction mixture is cooled to ambient temperature, and then quenched with saturated ammonium chloride solution. The product is extracted three times with EtOAc. The combined organic layer is washed with brine, dried over Na$_2$SO$_4$, filtered, concentrated under reduced pressure. The obtained residue is purified by silica gel column chromatography (eluent: n-hexane/EtOAc) to give (2R,4S)-4-(5-bromo-pyrimidin-2-ylamino)-2-ethyl-pyrrolidine-1-carboxylic acid tert-butyl ester (5.56 g, 70% in 4 steps).

A mixture of (2R,4S)-4-(5-bromo-pyrimidin-2-ylamino)-2-ethyl-pyrrolidine-1-carboxylic acid tert-butyl ester (13.0 mmol; 4.84 g), 3,5-bis(trifluoromethyl)benzyl bromide (26.0 mmol; 7.98 g) and sodium hydride (60% dispersion in mineral oil, 39.0 mmol; 1.56 g) in DMF (52 mL) is stirred for 1.5 hours at room temperature under nitrogen. The reaction mixture is quenched with water then saturated ammonium chloride solution. The product is extracted twice with EtOAc. The combined organic layer is washed with brine, dried over MgSO₄, filtered, concentrated under reduced pressure. The obtained residue is purified by silica gel column chromatography (eluent: n-hexane/EtOAc) to give (2R,4S)-4-[(3,5-bis-trifluoromethyl-benzyl)-(5-bromo-pyrimidin-2-yl)-amino]-2-ethyl-pyrrolidine-1-carboxylic acid tent-butyl ester (5.57 g, 72%).

Example 46

The following compounds are prepared following the procedure of Example 6 using corresponding chloroformates.

| No. | Product | ESI-MS m/z [M + 1]⁺ | Retention time (min) | Starting Material | Starting Material |
|-----|---------|---------------------|----------------------|-------------------|-------------------|
| 46-1 | (structure) | 664 | 5.07 (condition B) | (structure) | (structure) |

¹H NMR (400 MHz, d₆ DMSO) δ ppm 0.96 (s, 6H), 1.47 (t, J=5.54 Hz, 2H), 3.43 (t, J=5.54 Hz, 2H)

To a solution of potassium 4-hydroxy-2,2-dimethylbutyrate (1.92 mmol; 327 mg) in DMF (6 mL) is added ethyl iodide (2.30 mmol; 359 mg). The reaction mixture is stirred for 2 hours, and quenched with saturated ammonium chloride solution. The product is extracted three times with EtOAc. The combined organic layer is washed with aqueous 0.1 M HCl then brine, dried over Na2SO4, filtered, concentrated under reduced pressure to give 4-Hydroxy-2,2-dimethylbutyric acid ethyl ester (520 mg) contaminated with DMF.

1H NMR (400 MHz, CHLOROFORM-d) δ ppm 1.22 (s, 6H) 1.26 (t, J=7.06 Hz, 3H) 1.82-1.85 (m, 2H) 1.91 (brs, 1H) 3.69 (t, J=6.55 Hz, 2H) 4.13 (q, J=7.06 Hz, 2H)

Example 47

Preparation of amines (for Example 16 and 43) and alcohols (for Example 7 and 9)

Example 47-1

4-Hydroxy-2,2-dimethylbutyric acid ethyl ester

Example 47-2 trans-3-hydroxy-cyclobutanecarboxylic acid methyl ester

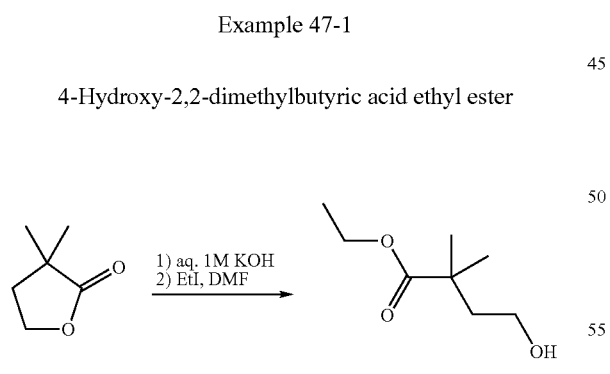

A mixture of dihydro-3,3-dimethyl-2(3H)-furanone (10 mmol; 1.14 g), aqueous 1 M KOH solution (10 mmol) and one drop of phenolphthalein indicator (0.5% w/v in EtOH/water (1:1)) is stirred at 105° C. for 3.5 hours. The mixture is cooled to ambient temperature and concentration under reduced pressure. To the residue is added 10 mL of EtOH. To the solution is added 50 ml of Et₂O, and the solid isolated by filtration and dried under 100 mbar at 50° C. to give potassium 4-hydroxy-2,2-dimethylbutyrate (1.21 g, 71%).

To a solution of cis-trans mixture of 3-hydroxy-cyclobutanecarboxylic acid methyl ester (1.30 g, 10 mmol) in DMF 13 mL is added NaH (50% in oil, 720 mg, 15 mmol) at 0° C.

After stirring at 0° C. for 15 minutes, benzyl bromide (1.43 ml, 12 mmol) is added at 0° C. The mixture is stirred at room temperature for 2 hours and quenched with H2O. The solution is extracted with EtOAc. The organic layer is washed with H2O and brine, dried over MgSO4 and concentrated under reduced pressure. The residue is purified by silica gel column chromatography (eluent; hexane/EtOAc) to give trans-3-benzyloxy-cyclobutanecarboxylic acid methyl ester (340 mg, 15.4%). TLC (hexane/EtOAc, 5:1) Rf 0.40.

1H NMR (400 MHz, chloroform-d) δ ppm 2.26-2.34 (m, 2H), 2.48-2.52 (m, 2H), 3.02-3.06 (m, 1H), 3.69 (s, 3H), 4.26-4.33 (m, 1H), 4.42 (s, 2H), 7.27-7.35 (m, 5H).

A solution of trans-3-benzyloxy-cyclobutanecarboxylic acid methyl ester (680 mg, 3.09 mmol) as 0.05 M solution in MeOH is pumped through the H-Cube™ flow hydrogenator fitted with a 10 mol % Pd/C catalyst cartridge heated to 40° C. at 10 bar. The flow rate is set at 1 ml/min. The solvent is removed under reduced pressure to give trans-3-hydroxy-cyclobutanecarboxylic acid methyl ester (380 mg, 94.5%); TLC (hexane/EtOAc, 1:1) Rf 0.38.

1H NMR (400 MHz, chloroform-d) δ ppm 2.18-2.25 (m, 2H), 2.55-2.61 (m, 2H), 3.01-3.08 (m, 1H), 3.70 (s, 3H), 4.53-4.61 (m, 1H).

Example 47-3 trans-3-hydroxy-cyclobutanecarboxylic acid methyl ester

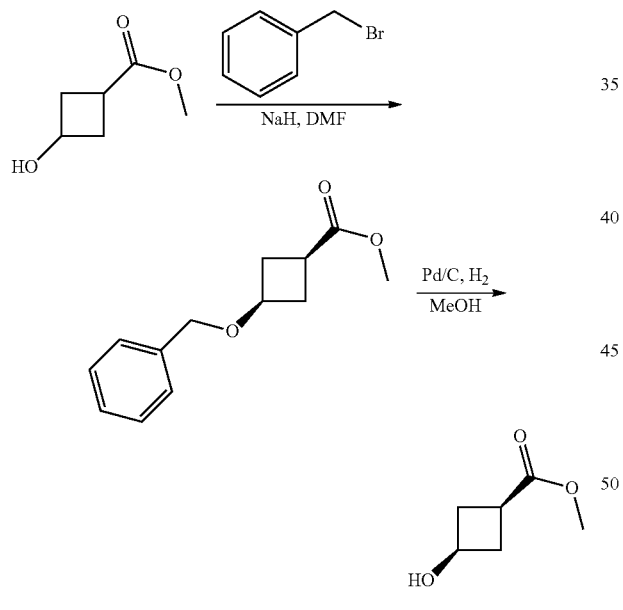

To a solution of cis-trans mixture of 3-hydroxy-cyclobutanecarboxylic acid methyl ester (1.30 g, 10 mmol) in DMF (13 mL) is added 50% NaH (720 mg, 15 mmol) at 0° C. After stirring at 0° C. for 15 min, benzyl bromide (1.43 ml, 12 mmol) is added at 0° C. The mixture is stirred at room temperature for 2 hours, and quenched with H$_2$O. The solution is extracted with EtOAc. The organic layer is washed with H$_2$O and brine, dried over MgSO$_4$ and concentrated under reduced pressure. The residue is purified by silica gel column chromatography to give trans-3-benzyloxy-cyclobutanecarboxylic acid methyl ester (750 mg, 34.1%); TLC (hexane/EtOAc, 5:1) R$_f$ 0.35.

1H NMR (400 MHz, chloroform-d) δ ppm 2.22-2.30 (m, 2H), 2.45-2.52 (m, 2H), 2.58-2.67 (m, 1H), 3.68 (s, 3H), 3.92-3.99 (m, 1H), 4.43 (s, 2H), 7.26-7.36 (m, 5H).

A solution of trans-3-benzyloxy-cyclobutanecarboxylic acid methyl ester (730 mg, 3.32 mmol) as a 0.05 M solution in MeOH is pumped through the H-Cube™ flow hydrogenator fitted with a 10 mol % Pd/C catalyst cartridge heated to 40° C. at 10 bar. The flow rate was set at 1 ml/min. The solvent is removed under reduced pressure to give trans 3-hydroxy-cyclobutanecarboxylic acid methyl ester (400 mg, 92.7%); TLC (hexane/AcOEt, 1:1) R$_f$ 0.38.

1H NMR (400 MHz, chloroform-d) δ ppm 2.14-2.22 (m, 2H), 2.56-2.64 (m, 3H), 3.69 (s, 3H), 4.16-4.23 (m, 1H).

Example 47-4

4-Hydroxymethyl-cyclohexanecarboxylic acid methyl ester

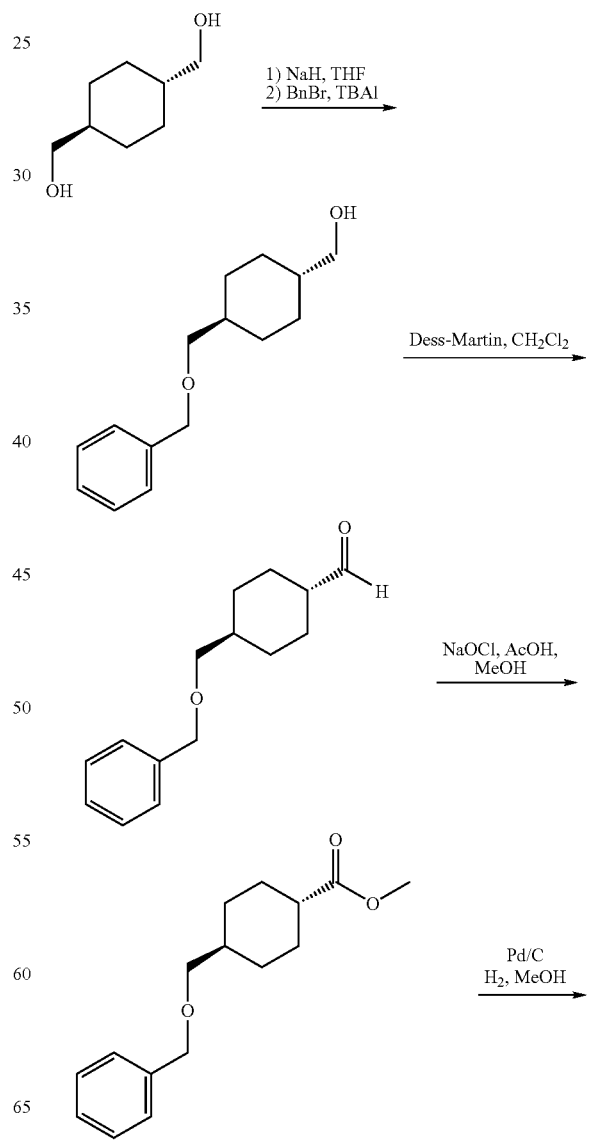

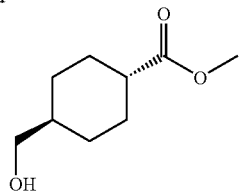

To a slurry of NaH (440 mg, 11 mmol) in THF (22 mL) is added trans-1,4-cyclohexanedimethanol (1.44 g, 10 mmol) at 0° C., and the mixture is stirred for 1 h while warming to room temperature. Benzyl bromide (1.2 mL, 10 mmol) is added dropwise followed by tetrabutylammonium iodide (185 mg, 0.5 mmol). The reaction is heated to 60° C. for 15 hours. After cooling to room temperature, H₂O is added and the aqueous layer is extracted with EtOAc. The combined organic layer (dried with MgSO₄) is concentrated. The desired product, (4-benzyloxymethyl-cyclohexyl)-methanol, is obtained (1.40 g, 60%) after purification using silica gel column chromatography (eluent: EtOAc/hexane).

To a mixture of (4-benzyloxymethyl-cyclohexyl)-methanol (1.40 g, 6 mmol) in dichloromethane (28 mL) is added Dess-Marin reagent (2.53 g, 6 mmol) at 0° C., and the mixture is stirred for 0.5 hour while warming to room temperature. After addition of saturated aqueous NaHCO₃, the aqueous layer is extracted with EtOAc. The combined organic layer (dried with MgSO₄) is concentrated. The desired product, 4-benzyloxymethyl-cyclohexanecarbaldehyde, is obtained (1.07 g, 79%) after purification using silica gel column chromatography (eluent: EtOAc/hexane).

4-Benzyloxymethyl-cyclohexanecarbaldehyde (1.70 g, 2.0 mmol) is dissolved in acetic acid (0.24 mL) and 2 mL of MeOH. The reaction mixture is cooled to 0-5° C. and stirred while 10% NaOCl solution (2.5 mL, 4 mmol) is added dropwise over 20 minutes. The cooling bath is removed and the mixture is allowed to come to room temperature. After addition of saturated aqueous NaHCO₃, the aqueous layer is extracted with EtOAc. The combined organic layer (dried with MgSO₄) is concentrated. The desired product, 4-benzyloxymethyl-cyclohexanecarboxylic acid methyl ester, is obtained (343 mg, 65%) after purification using silica gel column chromatography (eluent: EtOAc/hexane).

4-Benzyloxymethyl-cyclohexanecarboxylic acid methyl ester (340 mg, 1.30 mmol) is dissolved in MeOH (15 mL). In the presence of catalytic amount of 10% Pd/C, the reaction mixture is stirred for 3 hours under H₂ (10 bar). After removal of 10% Pd/C, solvent is evaporated. The desired product, 4-hydroxymethyl-cyclohexanecarboxylic acid methyl ester, is obtained (160 mg, 72%) after purification using silica gel column chromatography (eluent: EtOAc/hexane).

¹H-NMR (400 MHz, CDCl₃), δ (ppm): 0.99 (m, 2H), 1.47 (m, 3H), 1.88 (m, 2H), 2.02 (m, 2H), 2.23 (m, 1H), 3.46 (d, 2H), 3.66 (s, 3H).

Example 47-5

1-Hydroxymethyl-cyclopentanecarboxylic acid methyl ester

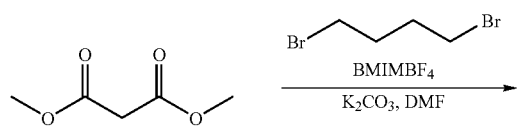

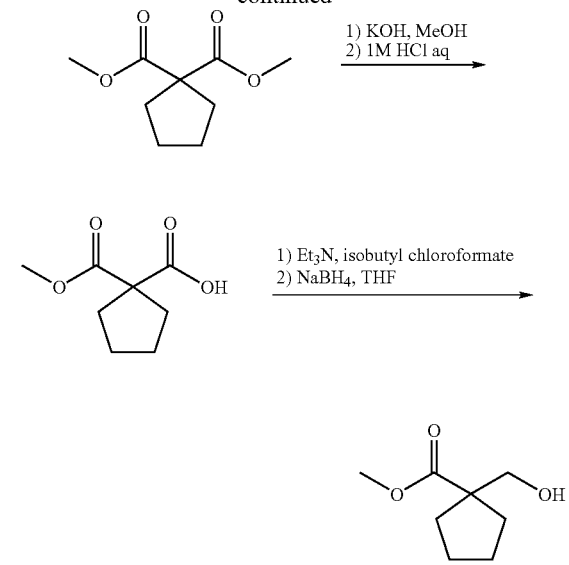

To a solution of malonic acid dimethyl ester (5.28 g, 40 mmol) in DMF (100 mL), 1,4-dibromo-butane (5.26 mL, 44 mmol), K₂CO₃ (13.8 g, 100 mmol), 1-butyl-3-methylimidazolium tetrafluoroborate (0.904 g, 4.0 mmol) are added at room temperature. The mixture is stirred at room temperature for 15 hours. To the mixture, water is added and the solution is extracted with EtOAc. The organic layer is washed with H₂O and brine, dried over MgSO₄, and concentrated under reduced pressure. The residue is purified by silica gel column chromatography to give cyclopentane-1,1-dicarboxylic acid dimethyl ester (6.13 g, 82%); TLC (hexane/AcOEt, 5:1) Rf 0.48.

1H NMR (400 MHz, chloroform-d) δ ppm 1.67-1.71 (m, 4H), 2.17-2.21 (m, 4H), 3.72 (s, 6H).

To a solution of cyclopentane-1,1-dicarboxylic acid dimethyl ester (4.0 g, 21.5 mmol) in MeOH (25 mL) is added potassium hydroxide (1.32 g, 23.7 mmol). The mixture is stirred at room temperature for 15 hours and concentrated under reduced pressure. To the obtained residue, aqueous 1M HCl (50 mL) is added and the solution is extracted with EtOAc. The organic layer is washed with H2O, dried over Na2SO4, and concentrated under reduced pressure to give cyclopentane-1,1-dicarboxylic acid methyl ester (3.72 g, quant.); TLC (dichloromethane/MeOH, 10:1) Rf 0.25.

1H NMR (400 MHz, chloroform-d) δ ppm 1.67-1.74 (m, 4H), 2.17-2.25 (m, 4H), 3.75 (s, 3H).

To a solution of cyclopentane-1,1-dicarboxylic acid methyl ester (1.00 g, 5.81 mmol) and triethylamine (808 uL, 5.81 mmol) in THF (15 mL) is added isobutyl chloroformate (750 uL, 5.81 mmol) at 0° C. The mixture is stirred at 0° C. for 20 minutes. The mixture is filtrated, and the filtrate is added to a suspension of NaBH4 (242 mg) in THF (15 mL) at 0° C. The mixture is stirred at 0° C. for 3 hours and at room temperature for 12 hours. To the mixture, H2O is added and the mixture is extracted with EtOAc. The organic layer is dried over MgSO4, and concentrated under reduced pressure. The obtained residue is purified by silica gel column chromatography to give 1-hydroxymethyl-cyclopentanecarboxylic acid methyl ester (433 mg, 47%); TLC (hexane/EtOAc, 1:1) Rf 0.43.

1H NMR (400 MHz, chloroform-d) δ ppm 1.61-1.77 (m, 6H), 1.93-2.00 (m, 2H), 2.53 (m, 1H), 3.57 (d, 2H), 3.72 (s, 3H).

Example 47-6 trans-4-(aminomethyl)cyclohexanecarboxylic acid methyl ester hydrochloride

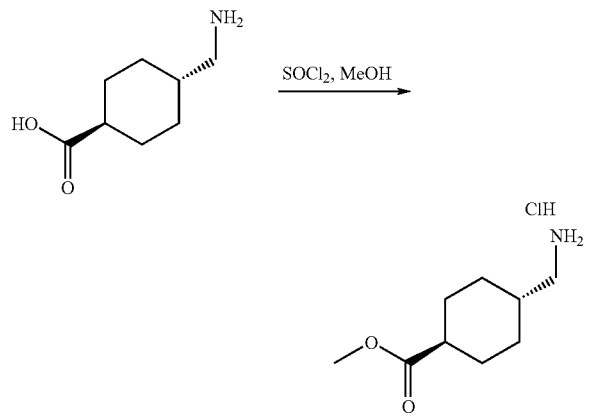

To a solution of trans-4-aminomethyl-1-cyclohexanecarboxylic acid (10 mmol, 1.57 g) in methanol (10 mL) is added of thionyl chloride (12 mmol, 0.88 mL) at 0° C. The mixture is stirred at room temperature for 24 hours and then concentrated under reduced pressure. The residue is washed with hexane to obtain 1.9 g (92%) of trans-4-(aminomethyl)cyclohexanecarboxylic acid methyl ester hydrochloride as white solid. ESI-MS m/z: 172 [M+1]$^+$, Retention time 2.12 min (condition B).

Example 47-7

(S)-Piperidine-2-carboxylic acid methyl ester

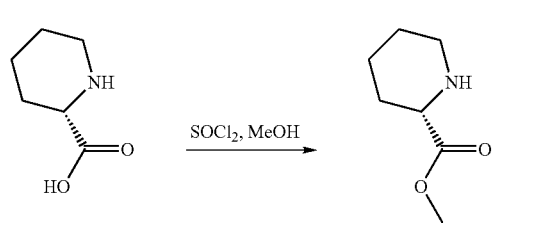

To a mixture of (S)-piperidine-2-carboxylic acid (10 mmol, 1.29 g) in MeOH (20 mL) is dropwise added thionyl chloride (30 mmol, 2.17 mL) at room temperature. The mixture is stirred at 2 hours, and then concentrated under reduced pressure. To the residue is added water (5 mL) and basified with potassium carbonate. The mixture is extracted with CH$_2$Cl$_2$. The combined organic layer is dried over Na$_2$SO$_4$, filtered, and concentrated under reduced pressure to give (S)-piperidine-2-carboxylic acid methyl ester as a pale brown oil (800 mg, 56%).

1H NMR (400 MHz, CHLOROFORM-d) δ ppm 1.40-1.61 (m, 4H) 1.74-1.85 (m, 1H) 1.92-2.01 (m, 1H) 2.62-2.71 (m, 1H) 3.05-3.11 (m, 1H) 3.37 (dd, J=9.73, 3.16 Hz, 1H) 3.64 (s, 1H) 3.72 (s, 3H).

Example 47-8 trans-4-aminocyclohexanecarboxylic acid methyl ester hydrochloride

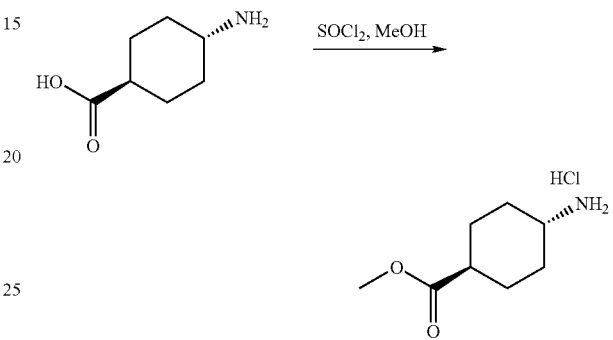

To a solution of trans-4-aminocyclohexanecarboxylic acid (20 mmol, 2.86 g) in methanol (20 mL) is added thionyl chloride (24 mmol, 1.76 mL) at 0° C. The mixture is stirred at room temperature for 12 hours then concentrated under reduced pressure. The residue is washed with hexane to obtain 3.5 g (90%) of trans-4-aminocyclohexanecarboxylic acid methyl ester hydrochloride as white solid. ESI-MS m/z: 157 [M+1]$^+$, Retention time 0.77 min (condition B).

Example 47-9 trans-4-(methylamino)cyclohexanecarboxylic acid methyl ester hydrochloride

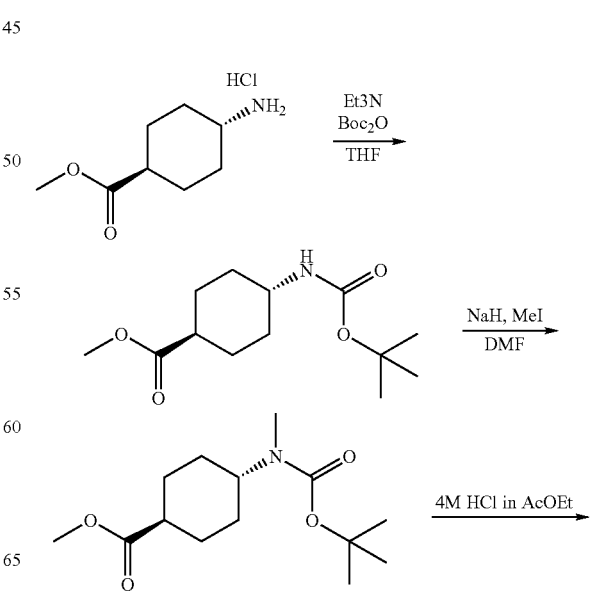

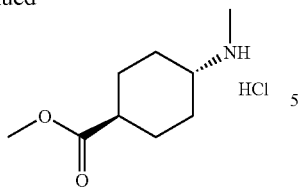

To a solution of trans-4-aminocyclohexanecarboxylic acid methyl ester hydrochloride (10 mmol, 1.94 g) in THF (30 mL) are added triethylamine (22 mmol, 3.1 mL) and di-tert-butyl dicarbonate (11 mmol, 2.4 g) at room temperature. The mixture is stirred at room temperature for 5 hours, poured into a saturated aqueous ammonium chloride, then extracted with ethyl acetate. The combined organic phase is washed with water and brine, dried over anhydrous $Na_2SO_4$ and concentrated under reduced pressure to obtain 2.6 g (quantitative) of trans-4-(tert-butoxycarbonylamino)cyclohexanecarboxylic acid methyl ester as white solid. ESI-MS m/z: 258 [M+1]$^+$, Retention time 3.16 min (condition B).

To a solution of trans-4-(tert-butoxycarbonylamino)cyclohexane carboxylic acid methyl ester (5 mmol, 1.3 g) in dimethylformamide (15 mL) is cooled to 0° C. and treated with of sodium hydride (60% in oil, 6 mmol, 240 mg) over 30 minutes. The mixture is stirred at room temperature for 1 hour, then cooled to 0° C. and treated with iodomethane (6 mmol, 0.38 mL). After stirring overnight at room temperature, the mixture is poured into a saturated aqueous ammonium chloride and extracted with ethyl acetate. The combined organic phase is washed with water and brine, dried over anhydrous $Na_2SO_4$ and concentrated under reduced pressure. The obtained residue is purified by column chromatography on silica gel (eluent: n-hexane-ethyl acetate 10:1) to obtain 1.3 g (96%) of trans-4-[(tert-Butoxycarbonyl)(methyl)amino]cyclohexane carboxylic acid methyl ester as colorless oil. ESI-MS m/z: 272 [M+1]$^+$, Retention time 3.57 min (condition B).

A solution of trans-4-[(tert-Butoxycarbonyl)(methyl) amino]cyclohexanecarboxylic acid methyl ester (3.69 mmol, 1.0 g) is dissolved in EtOAc (5 mL), cooled to 0° C. and treated with 4M HCl in ethyl acetate (5 mL). The mixture is stirred at room temperature for 5 hours. After the mixture is concentrated under reduced pressure, 100 mL of ethyl ether is added. The solid precipitate is filtrated, washed with ethyl ether and dried under reduced pressure to obtain 700 mg (91%) of trans-4-(methylamino)cyclohexanecarboxylic acid methyl ester hydrochloride as white solid. ESI-MS m/z: 171 [M+1]$^+$, Retention time 1.00 min (condition B).

Example 47-10 trans-4-(ethylamino)-1-cyclohexanecarboxylic acid methyl ester

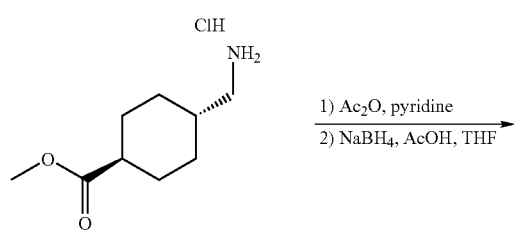

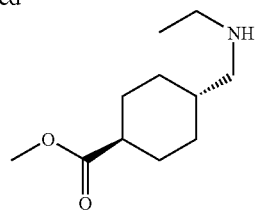

To a solution of trans-4-(aminomethyl)cyclohexanecarboxylic acid methyl ester hydrochloride (1.5 mmol, 310 mg) in pyridine (2 mL) is added acetic anhydride (1.8 mmol, 0.31 mL) at room temperature. The mixture is stirred at room temperature for 4 hours, poured into 1M HCl and ice-water, and then extracted with ethyl acetate. The combined organic phase is washed with water and brine, dried over anhydrous $Na_2SO_4$ and concentrated under reduced pressure to obtain trans-4-(acetamidomethyl)-1-cyclohexanecarboxylic acid methyl ester (330 mg) as colorless oil. ESI-MS m/z: 214 [M+1]$^+$, Retention time 1.97 min (condition B).

To a solution of trans-4-(acetamidomethyl)-1-cyclohexanecarboxylic acid methyl ester (1.5 mmol, 330 mg) and acetic acid (17.5 mmol, 1 mL) in THF (10 mL) is added sodium borohydride (7.5 mmol, 284 mg) at room temperature. The mixture is stirred at 75° C. for 4 hours, poured into ice-water, and extracted with ethyl acetate. The combined organic phase is washed with 1M NaOH aqueous solution, water, and brine, dried over anhydrous $Na_2SO_4$ and concentrated under reduced pressure to obtain 200 mg (67%) of trans-4-(ethylamino)-1-cyclohexanecarboxylic acid methyl ester as colorless oil. ESI-MS m/z: 200 [M+1]$^+$, Retention time 1.57 min (condition B).

Example 47-11 trans-(4-Hydroxymethylcyclohexyl)-acetic acid ethyl ester

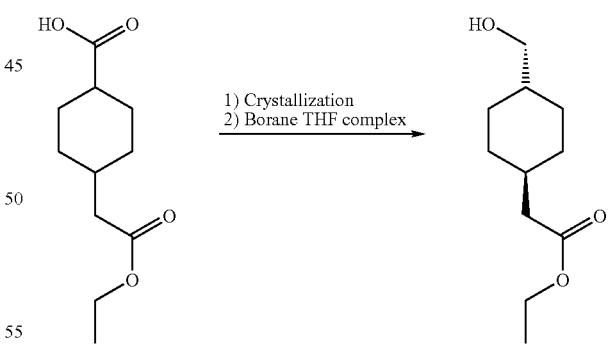

cis/trans mixture of 4-ethoxycarbonylmethyl-cyclohexanecarboxylic acid (112 g) is filtered to collect the solids. After washing with n-hexane, a suspension of the solids (27.2 g) in n-hexane (500 mL) is heated at 90° C. to be homogeneous solution. The solution is stirred for 30 min. and cooled to −25° C. for 1.5 hours. The solids are isolated by filtration, washed twice with 100 ml of n-hexane, and dried under reduced pressure to provide trans-4-ethoxycarbonylmethyl-cyclohexanecarboxylic acid (19.4 g, cis/trans=2: >98 determined by $^1$H NMR).

1H NMR (400 MHz, CHLOROFORM-d) δ ppm 0.98-1.08 (m, 2H), 1.26 (t, J=7.05 Hz, 3H), 1.42-1.53 (m, 2H), 1.74-1.87 (m, 3H), 2.00-2.05 (m, 2H), 2.20 (d, J=6.56 Hz, 2H), 2.26 (tt, J=3.52, 12.1 Hz, 1H), 1.91 (brs, 1H) 3.69 (t, J=6.55 Hz, 2H) 4.13 (q, J=7.05 Hz, 2H).

To a solution of trans-4-ethoxycarbonylmethyl-cyclohexanecarboxylic acid (1 mmol; 214 mg) in THF (3 mL) is added 1.0 M THF solution of borane THF complex (2 mmol; 2 mL) at 0° C. under nitrogen. The solution is stirred for 1.5 hours at room temperature, quenched by dropwise addition of 1 mL of MeOH. The mixture after concentration is diluted with dichloromethane and saturated aqueous ammonium chloride solution. The product is extracted with 100 ml of dichloromethane. The organic layer after dried is separated, concentrated under reduced pressure. The residue is purified by column chromatography on silica gel (n-hexane/EtOAc) to give trans-(4-hydroxymethylcyclohexyl)-acetic acid ethyl ester (166 mg, 83%); ESI-MS m/z: 201 [M++1], Retention time 1.67 min (condition A).

Example 48

(2R,4S)-4-{(3,5-bis-trifluoromethyl-benzyl)-[5-(3-methyl-2-oxo-imidazolidin-1-yl)-pyrimidin-2-yl]-amino}-2-ethyl-pyrrolidine-1-carboxylic acid tert-butyl ester

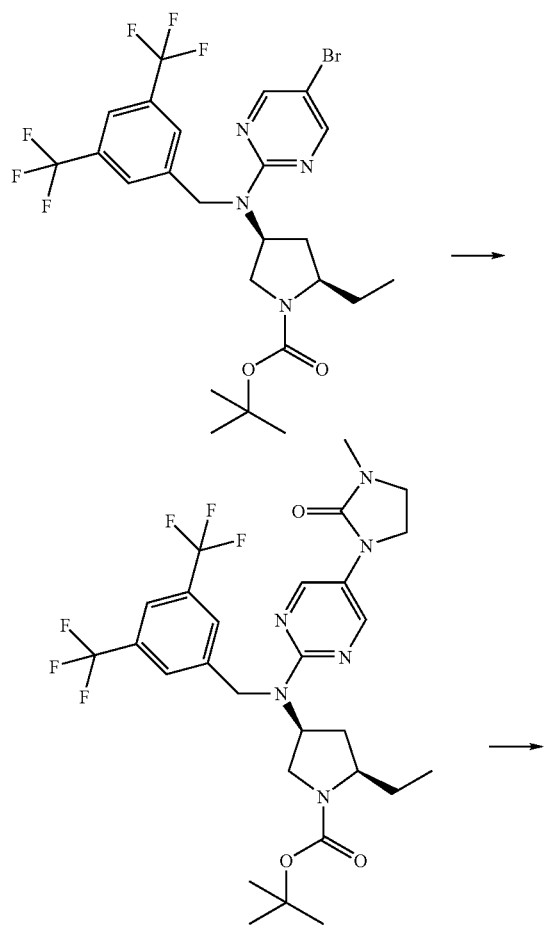

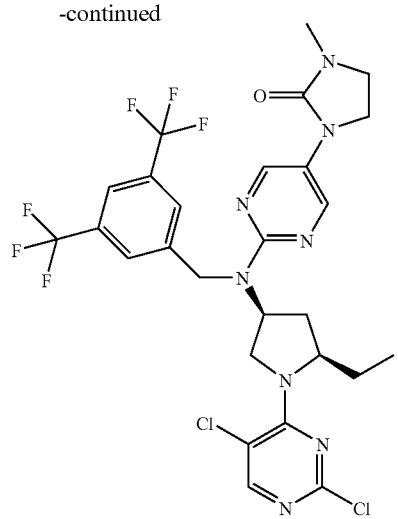

In a 2 mL glass microwave reaction vessel are placed in (2R,4S)-4-[(3,5-bis-trifluoromethyl-benzyl)-(5-bromo-pyrimidin-2-yl)-amino]-2-ethyl-pyrrolidine-1-carboxylic acid tert-butyl ester (200 mg, 0.32 mmol), 1-Methyl-imidazolidin-2-one (35 mg, 0.35 mmol), CuI (123.4 mg, 0.35 mmol), trans-1,2-cyclohexane (0.005 mL, 0.35 mmol), $K_2CO_3$ (88 mg, 0.64 mmol) in dry dioxane (2 mL). The reaction vessel is sealed and heated under microwave irradiation at 180° C. for 20 min. After completion of the reaction, the solvent is diluted with EtOAc and washed with sat. $NH_3$ (aq.), water, dried ($Na_2SO_4$), and concentrated under reduced pressure. The residue is purified by flash chromatography on silica gel to give (2R,4S)-4-{(3,5-bis-trifluoromethyl-benzyl)-[5-(3-methyl-2-oxo-imidazolidin-1-yl)-pyrimidin-2-yl]-amino}-2-ethyl-pyrrolidine-1-carboxylic acid tert-butyl ester (120 mg, 61%).

$^1$H NMR (400 MHz, chloroform-d) δ ppm 0.81 (t, 3H), 1.44 (s, 9H), 1.43-1.73 (m, 3H), 2.20-2.34 (m, 1H), 2.89 (s, 3H), 3.07 (brt, 2H), 3.51 (dd, 2H), 3.74 (dd, 2H), 3.80-3.90 (m, 1H). 4.88 (brs, 2H), 5.10-5.23 (m, 1H), 7.64 (brs, 2H), 7.74 (brs, 1H), 8.55 (s, 2H); ESI-MS m/z: 617 [M+1]+, Retention time 4.82 min (condition A).

To a mixture of (2R,4S)-4-{(3,5-bis-trifluoromethyl-benzyl)-[5-(3-methyl-2-oxo-imidazolidin-1-yl)-pyrimidin-2-yl]-amino}-2-ethyl-pyrrolidine-1-carboxylic acid tert-butyl ester (150 mg, 0.24 mmol) in EtOAc (1 mL) is added 4N HCl/EtOAc (2.4 mL, 2.44 mmol). After removal of solvent, the mixture is used without further purification. (2R,4S)-4-{(3,5-Bis-trifluoromethyl-benzyl)-[5-(3-methyl-2-oxo-imidazolidin-1-yl)-pyrimidin-2-yl]-amino}-2-ethyl-pyrrolidine is treated with 2,4,5-trichloro-pyrimide (67.1 mg, 0.37 mmol) and $Et_3N$ (0.07 mL, 0.49 mmol) in $CH_2Cl_2$ (1 mL) at RT for 12 hours. After adding sat. $NaHCO_3$ (aq.), the mixture is extracted with $CH_2Cl_2$, washed with brine and dried ($MgSO_4$). Concentration under vacuum and purification with silica gel column chromatography (eluent: n-hexane: EtOAc=1:1) gives 1-[2-((3,5-Bis-trifluoromethyl-benzyl)-{(3S,5R)-1-[5-chloro-2-(4-hydroxy-piperidin-1-yl)-pyrimidin-4-yl]-5-ethyl-pyrrolidin-3-yl}-amino)-pyrimidin-5-yl]-3-methyl-imidazolidin-2-one (110 mg, 68%)

$^1$H NMR (400 MHz, chloroform-d) δ ppm 0.85 (t, 3H), 1.79-1.97 (m, 1H), 2.27 (dt, 1H), 2.89 (s, 3H), 3.51 (dd, 2H), 3.67 (t, 3H), 3.75 (dd, 2H), 4.05-4.15 (m, 2H), 4.40-4.48 (m, 1H), 4.88 (d, 1H), 5.05 (d, 1H), 7.69 (brs, 2H), 7.78 (brs, 1H), 8.04 (brs, 1H), 8.56 (s, 2H); ESI-MS m/z: 663 [M]+, Retention time 4.90 min (condition A).

The following compounds are prepared following the procedure of Example 48 using corresponding amine.

| No. | Product | ESI-MS m/z [M + 1]+ | Retention time (min) | Starting Material | Starting Material |
|---|---|---|---|---|---|
| 48-1 | | 650 | 4.82 (condition B) | | |
| 48-2 | | 648 | 4.66 (condition B) | | |

Example 49

The following compounds are prepared following the procedure of Example 23 using corresponding amine.

| No. | Product | ESI-MS m/z [M + 1]+ | Retention time (min) | Starting Material | Starting Material |
|---|---|---|---|---|---|
| 49-1 | | 783 | 4.12 (condition B) | | |

-continued
| No. | Product | ESI-MS m/z [M + 1]+ | Retention time (min) | Starting Material | Starting Material |
|---|---|---|---|---|---|
| 49-2 | | 770 | 3.94 (condition B) | | |
| 49-3 | | 771 | 4.05 (condition B) | | |
Example 50
Synthesis of (3,5-bis-trifluoromethyl-benzyl)-(5-bromo-pyrimidin-2-yl)-[(3S,5R)-1-(2,5-dichloro-pyrimidin-4-yl)-5-ethyl-pyrrolidin-3-yl]-amine
-continued
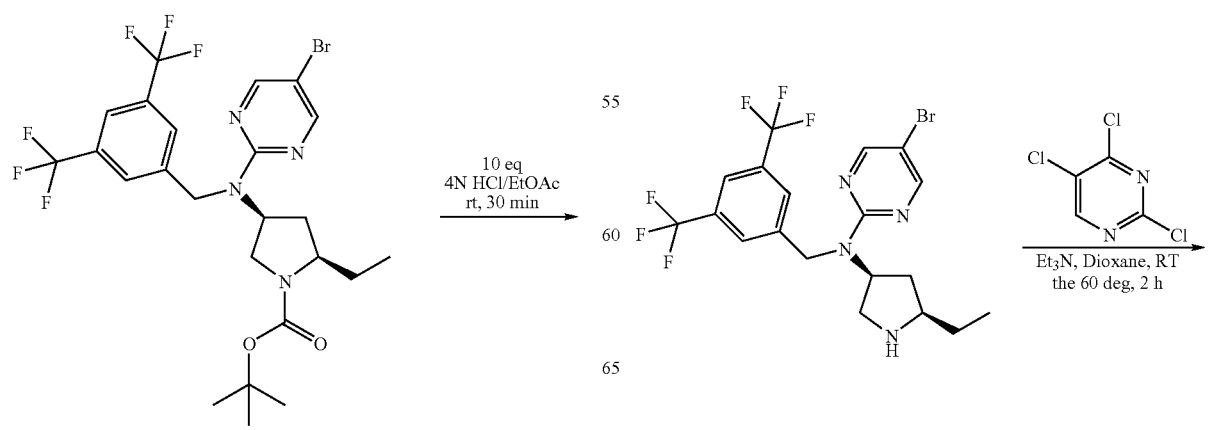

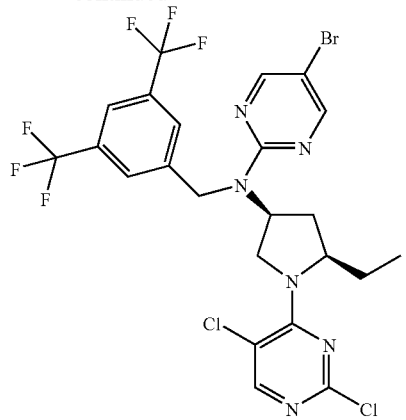

A 50 ml round-bottom flask is charged with (2R,4S)-4-[(3,5-bis-trifluoromethyl-benzyl)-(5-bromo-pyrimidin-2-yl)-amino]-2-ethyl-pyrrolidine-1-carboxylic acid tert-butyl ester (1.8 g, 3 mmol) and a stirbar under N₂. HCl/EtOAc (4 N, 7.5 ml) is added with stirring. TLC monitor showed that reaction completed after 30 minutes. Sat. Na₂CO₃ was added and extracted with dichloromethane. Filter through phase separator, removal of solvent give the BoC deprotected pyrrolidine which is used without further purification.

A 100 ml round-bottom flask is charged with the pyrrolidine (3 mmol), trichloropyrimidine (753 ul, 6 mmol), triethylamine (831 ul, 6 mmol) and a stirbar under N₂. 1,4-dioxane (20 ml) is added with stirring. The resulted pale yellow solution is then heated to 60 degree for 2 hours. After removal of solvent via evaporation, H₂O and dichloromethane is added and organic layer is collected filtering through phase separator. Removal of solvent and subsequent purification with Hex/EtOAc on column give (3,5-bis-trifluoromethyl-benzyl)-(5-bromo-pyrimidin-2-yl)-[(3S,5R)-1-(2,5-dichloro-pyrimidin-4-yl)-5-ethyl-pyrrolidin-3-yl]-amine (1.63 g, 90% for 2 steps). ESI-MS m/z: 645 [M]+, Retention time 2.65 min (condition A).

The following compounds are prepared following the procedure of Example 50 using corresponding pyrimidine.

| No. | Product | ESI-MS m/z [M + 1]⁺ | Retention time (min) | Starting Material | Starting Material |
|---|---|---|---|---|---|
| 50-1 | | 768 | 2.65 (condition A) | | |
| 50-2 | | 631 | 2.07 (condition A) | | |

-continued

| No. | Product | ESI-MS m/z [M + 1]+ | Retention time (min) | Starting Material | Starting Material |
|---|---|---|---|---|---|
| 50-3 | | 650 | 4.71 (condition A) | | |
| 50-4 | | 624 | 2.39 (condition A) | | |
| 50-5 | | 646 | 2.44 (condition A) | | |
| 50-6 | | 670 | 2.24 (condition A) | | |

| No. | Product | ESI-MS m/z [M + 1]+ | Retention time (min) | Starting Material | Starting Material |
|---|---|---|---|---|---|
| 50-7 | | 651 | 2.30 (condition A) | | |
| 50-8 | | 570 | 2.41 (condition A) | | |
| 50-9 | | 662 | 2.38 (condition A) | | |
| 50-10 | | 618 | 2.31 (condition A) | | |

-continued

| No. | Product | ESI-MS m/z [M + 1]+ | Retention time (min) | Starting Material | Starting Material |
|---|---|---|---|---|---|
| 50-11 | | 670 | 2.36 (condition A) | | |
| 50-12 | | 682 | 4.28 (condition B) | | |

Example 51

The following compound is prepared following the procedure of Example 11 using corresponding amine

| No. | Product | ESI-MS m/z [M + 1]+ | Retention time (min) | Starting Material | Starting Material |
|---|---|---|---|---|---|
| 1 | | 650 | 4.71 (condition B) | | |

Example 52

The following compounds are prepared following the procedure of Example 12 using corresponding amine.

| No. | Product | ESI-MS m/z [M + 1]+ | Retention time (min) | Starting Material | Starting Material |
|---|---|---|---|---|---|
| 52-1 | | 722 | 2.63 (condition A) | | |

Example 53

Synthesis of benzoic acid piperidin-4-yl ester

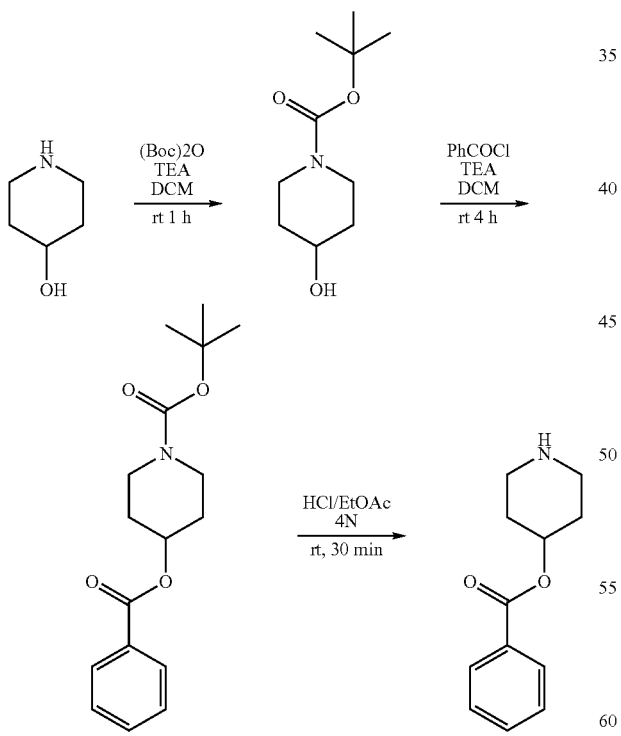

A 25 ml round-bottom flask is charged with 4-OH piperidine (303 mg, 3 mmol), TEA (500 ul, 3.6 mmol and $CH_2Cl_2$ (6 ml), then ice-cooled. BoC anhydride (786 mg, 3.6 mmol) is added slowly, and after removal of the ice bath, the mixture is stirred at rt for 1 hour. $H_2O$ and $CH_2Cl_2$ are added and organic layer is collected with phase separator. Removal of solvent under reduced pressure give a colorless oil which is used for the next step without further purification.

A 50 ml round-bottom flask is charged with the crude N-Boc-4-OH-piperidine (3 mmol), benzoyl chloride (495 ul, 3.9 mmol), TEA (540 ul, 3.9 mmol), DMAP (96 mg, 0.78 mmol), $CH_2Cl_2$ (9 ml), then ice-cooled. After removal of the ice bath, the mixture is stirred at rt for 4 hours. $H_2O$ and $CH_2Cl_2$ are added and organic layer was collected with phase separator. Removal of solvent under reduced pressure give a colorless oil which is purified with silica gel column to give 4-O-benzoyl N-BoC piperidine (700 mg, 0.23 mmol). ESI-MS m/z: 306 [M]+, Retention time 2.12 min (condition A).

A 25 ml round-bottom flask is charged with 4-O-Benzoyl N-BoC (700 mg, 0.23 mmol) under $N_2$. HCl/EtOAc (4 N, 0.6 ml) is added while stirring for 30 minutes. Saturated $Na_2CO_3$ is added and extracted with dichloromethane. Filter through phase separator, removal of solvent under reduced pressure give 4-O-benzoyl piperidine which is used without further purification.

Example 54

Synthesis of (2R,4S)-4-[(3,5-bis-trifluoromethyl-benzyl)-(5-imidazol-1-yl-pyrimidin-2-yl)-amino]-2-ethyl-pyrrolidine-1-carboxylic acid tert-butyl ester

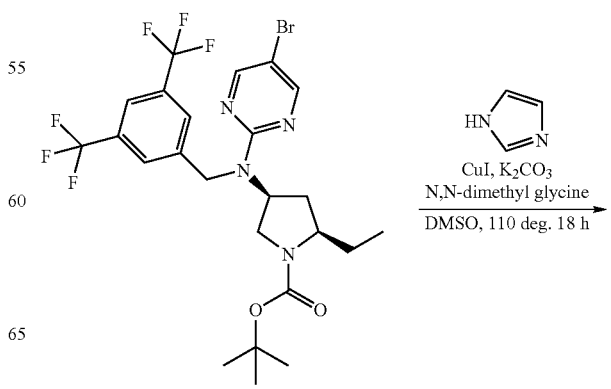

-continued

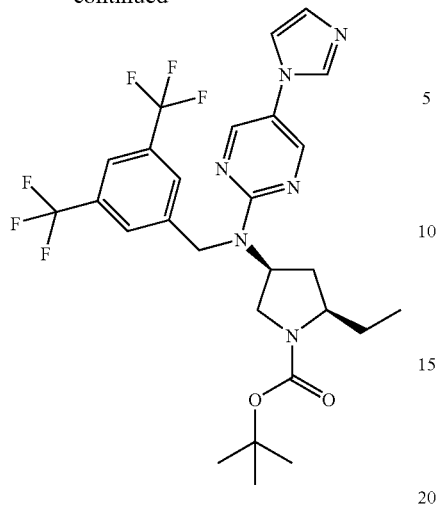

A 25 ml round-bottom tube is charged with (2R,4S)-4-[(3,5-bis-trifluoromethyl-benzyl)-(5-bromo-pyrimidin-2-yl)-amino]-2-ethyl-pyrrolidine-1-carboxylic acid tert-butyl ester (480 mg, 0.8 mmol), imidazole (82 mg, 1.2 mmol), CuI (152 mg, 0.8 mmol), $K_2CO_3$ (221 mg, 1.3 mmol), N,N-dimethyl glycine (82 mg, 0.8 mmol), and DMSO (4 ml). Then the tube is sealed and heated to 110 degree for 18 hours. After cooling to rt, saturated $NH_3/H_2O$ and EtOAc are added and then filtered through Celite pad. The solution is extracted with EtOAc and organic layer is dried over $MgSO_4$. Removal of solvent under reduced pressure and purification with reverse phase column give product (163 mg, 0.27 mmol, 35%). ESI-MS m/z: 585 [M]+, Retention time 2.07 min (condition A).

Example 55

The following compounds are prepared following the procedure of Example 30 using corresponding amine.

Example 56

Synthesis of (2S,4R)-4-benzyloxy-2-methoxymethyl-pyrrolidine-1-carboxylic acid tert-butyl ester

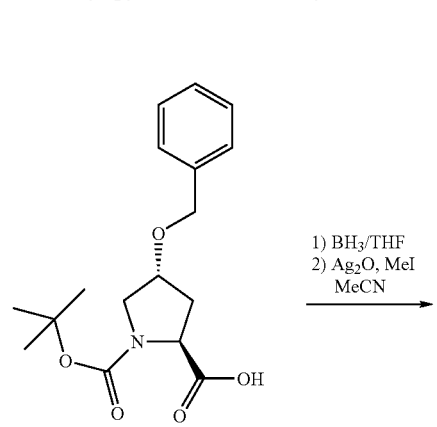

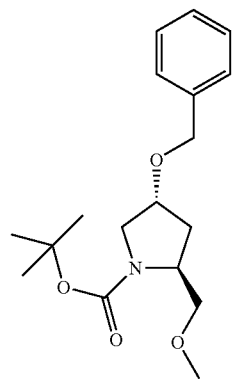

To a solution of (2S,4R)-4-benzyloxy-pyrrolidine-1,2-dicarboxylic acid 1-tert-butyl ester (15.5 mmol; 5.0 g) in THF (135 mL) is added 1 M THF solution of borane THF complex (31 mmol; 31 mL) at 0° C. under nitrogen. The solution is stirred for 1 hour at room temperature, quenched by dropwise addition of 15 ml of MeOH. After concentrating, the mixture is diluted with dichloromethane and saturated aqueous

| No. | Product | ESI-MS m/z [M + 1]+ | Retention time (min) | Starting Material | Starting Material |
|---|---|---|---|---|---|
| 55-1 | | 671 | 2.38 (condition A) | | | ammonium chloride solution. The product is extracted twice with dichloromethane. The combined organic layer is washed with brine, dried over MgSO$_4$, filtered, concentrated under reduced pressure to give the crude product. To a solution of crude material in MeCN (20 mL) were added Ag2O (46.5 mmol; 8.9 g) and MeI (155 mmol; 21.8 g) at room temperature, heated and stirred under reflux condition for 3 hours. After filtration and concentration, the resulting mixture is diluted with dichloromethane and saturated aqueous ammonium chloride solution. The product is extracted twice with dichloromethane. The combined organic layer is washed with brine, dried over MgSO$_4$, filtered, concentrated under reduced pressure to give the crude (2S,4R)-4-benzyloxy-2-methoxymethyl-pyrrolidine-1-carboxylic acid tert-butyl ester (3.1 g).

Example 57

Synthesis of (2S,4S)-4-{(3,5-bis-trifluoromethyl-benzyl)-[5-(1-methyl-1H-pyrazol-4-yl)-pyrimidin-2-yl]-amino}-2-methoxymethyl-pyrrolidine-1-carboxylic acid tert-butyl ester The following compound is prepared following the procedures of Example 3 and 45

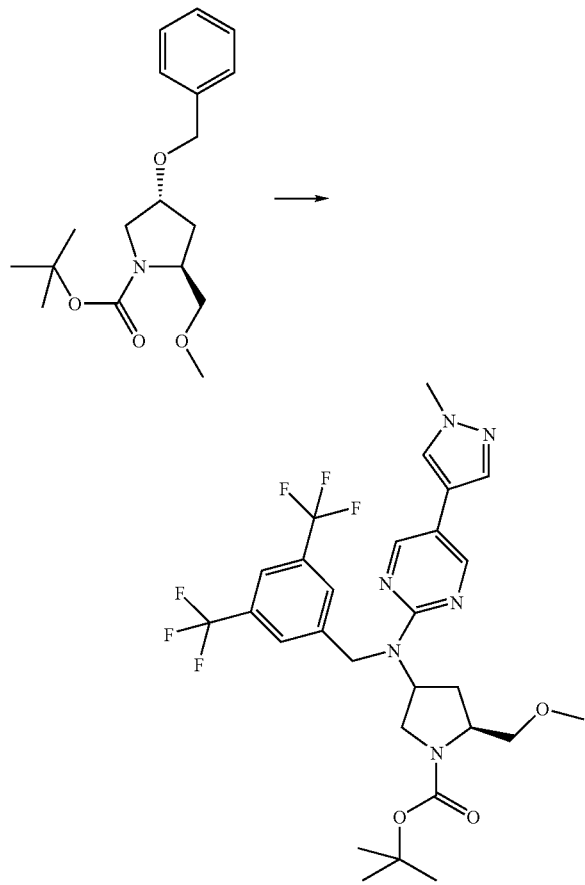

In a flask purged with ammonia gas, about 40 mL of liquid ammonia is collected with ammonia condenser at −78° C. To the liquid ammonia is added portionwise lithium metal (46 mmol; 320 mg) at the same temperature. To the deep blue solution is added a solution of (2S,4R)-4-benzyloxy-2-methoxymethyl-pyrrolidine-1-carboxylic acid tert-butyl ester (9.2 mmol; 3.1 g) and tert-butanol (18.4 mmol; 1.36 g) in THF (15 mL). After stirring for 2 hours, the reaction mixture is quenched with MeOH, and then warmed to ambient temperature. The mixture is diluted with water, and then aqueous 1M HCl is added to reach pH 8-9. The product is extracted three times with EtOAc. The combined organic layer is washed with brine, dried over MgSO$_4$, filtered, and concentrated under reduced pressure to give (2S,4R)-4-hydroxy-2-methoxymethyl-pyrrolidine-1-carboxylic acid tert-butyl ester (2.2 g).

To a solution of (2S,4R)-4-hydroxy-2-methoxymethyl-pyrrolidine-1-carboxylic acid tert-butyl ester (8.9 mmol; 2.2 g) and Et$_3$N (11.6 mmol; 1.6 mL) in diethylether (22 mL) is added MsCl (11.6 mmol; 0.90 mL) at room temperature. The reaction mixture is stirred for 4 hours, and then quenched with saturated aqueous NaHCO$_3$ solution. The product is extracted three times with dichloromethane. The combined organic layer is washed with saturated aqueous ammonium chloride and then brine, dried over MgSO$_4$, filtered, and concentrated under reduced pressure to give the crude product.

To a solution of the crude product in DMF (22 ml) is added sodium azide (14.3 mmol; 925 mg) under nitrogen at room temperature. After stirring for 8 hours at 90° C., the reaction mixture is cooled to ambient temperature, and then quenched with saturated ammonium chloride solution. The product is extracted twice with EtOAc. The combined organic layer is washed twice with aqueous 0.1 M HCl and then once with brine, dried over MgSO$_4$, filtered, and concentrated under reduced pressure to give the crude product.

A suspension of the crude product and magnesium metal (18 mmol; 1.1 g) in MeOH (18 mL) is stirred for 3 hours. The suspension is filtered and concentrated. To the residue are added EtOAc and brine. The product is extracted twice with EtOAc. The combined organic layer is washed with brine, dried over K$_2$CO$_3$, filtered, and concentrated under reduced pressure to give the crude product.

A solution of the crude product, 5-bromo-2-chloropyrimidine (14.3 mmol; 2.6 g) and N,N-diisopropylethylamine (17.8 mmol; 3.1 mL) in DMF (18 mL) is stirred at 120° C. for 3 hours. The reaction mixture is cooled to ambient temperature, and then quenched with saturated ammonium chloride solution. The product is extracted three times with EtOAc. The combined organic layer is washed with brine, dried over Na$_2$SO$_4$, filtered, and concentrated under reduced pressure. The obtained residue is passed through silica pad (eluent: n-hexane/EtOAc) to give (2S,4S)-4-(5-bromo-pyrimidin-2-ylamino)-2-methoxymethyl-pyrrolidine-1-carboxylic acid tert-butyl ester (1.8 g).

A mixture of ((2S,4S)-4-(5-bromo-pyrimidin-2-ylamino)-2-methoxymethyl-pyrrolidine-1-carboxylic acid tert-butyl ester (2.84 mmol; 1.1 g), 3,5-bis(trifluoromethyl)benzyl bromide (4.3 mmol; 0.78 mL) and sodium hydride (60% dispersion in mineral oil, 4.3 mmol; 0.17 g) in DMF (9 mL) is stirred for 1 hour at room temperature under nitrogen. The reaction mixture is quenched with water then saturated ammonium chloride solution. The product is extracted twice with EtOAc. The combined organic layer is washed with brine, dried over MgSO$_4$, filtered, and concentrated under reduced pressure. The obtained residue is passed though silica pad (eluent: n-hexane/EtOAc) to give (2S,4S)-4-[(3,5-bis-trifluoromethyl-benzyl)-(5-bromo-pyrimidin-2-yl)-amino]-2-methoxymethyl-pyrrolidine-1-carboxylic acid tert-butyl ester. To a mixture of (2S,4S)-4-[(3,5-Bis-trifluoromethyl-benzyl)-(5-bromo-pyrimidin-2-yl)-amino]-2-methoxymethyl-pyrrolidine-1-carboxylic acid tert-butyl ester, 1-methylpyrazol-3-yl-4,4,5,5-tetramethyl-[1,3,2]dioxaborolane (7.1 mmol, 1.48 g), tetrakis(triphenylphosphine)palladium(0) (0.43 mmol, 490 mg) and 2M aqueous sodium hydrogen carbonate (3.6 mL) in 1,2-dimethoxy-ethane (4 mL) is allowed to warm to 95° C. and stirred for 3 hours. The mixture is cooled to room temperature and then added water. The mixture is extracted with CH$_2$Cl$_2$, and the combined organic layer is dried over Na$_2$SO$_4$, filtrated, and concentrated under reduced pressure. The obtained residue is purified by silica gel column chromatography (eluent: n-hexane/EtOAc) to give (2S,4S)-4-{(3,5-bis-trifluoromethyl-benzyl)-[5-(1-methyl-1H-pyrazol-4-yl)-pyrimidin-2-yl]-amino}-2-methoxymethyl-pyrrolidine-1-carboxylic acid tert-butyl ester (1.3 g, 74% overall yield for 2 steps); ESI-MS m/z: 615 [M+1]$^+$, Retention time 2.12 min (condition A).

-continued

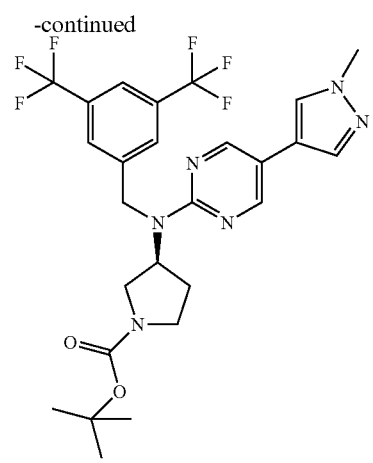

Example 58

Synthesis of (S)-3-{(3,5-bis-trifluoromethyl-benzyl)-[5-(1-methyl-1H-pyrazol-4-yl)-pyrimidin-2-yl]-amino}-pyrrolidine-1-carboxylic acid tert-butyl ester The following compound is prepared following the procedures of Example 2, 3 and 39

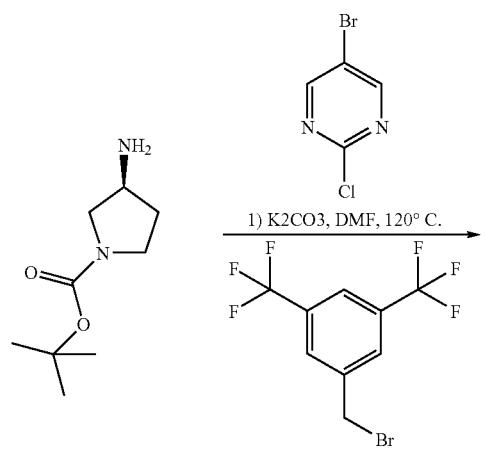

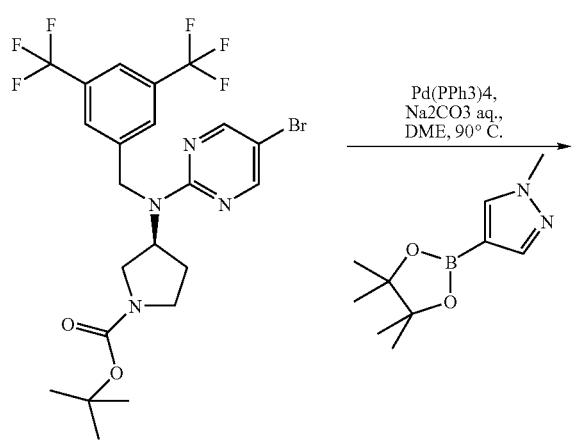

A solution of (S)-3-amino-pyrrolidine-1-carboxylicacid tert-butyl ester (10.7 mmol; 2.0 g), 5-bromo-2-chloropyrimidine (12.8 mmol; 2.4 g) and N,N-diisopropylethylamine (21.4 mmol; 2.98 g) in DMF (25 mL) is stirred at 120° C. for 2 hours. The reaction mixture is cooled to ambient temperature, and then quenched with saturated ammonium chloride solution. The product is extracted three times with EtOAc. The combined organic layer is washed with brine, dried over Na$_2$SO$_4$, filtered, and concentrated under reduced pressure. The obtained residue is passed through silica pad (eluent: n-hexane/EtOAc) to give crude product.

A mixture of the resulting crude product, 3,5-bis(trifluoromethyl)benzyl bromide (12 mmol; 4.0 g) and sodium hydride (60% dispersion in mineral oil, 18 mmol; 0.72 g) in DMF (25 mL) is stirred for 1 hours at room temperature under nitrogen. The reaction mixture is quenched with water then saturated ammonium chloride solution. The product is extracted twice with EtOAc. The combined organic layer is washed with brine, dried over MgSO$_4$, filtered, and concentrated under reduced pressure. The obtained residue is purified by silica gel column chromatography (eluent: n-hexane/EtOAc) to give (S)-3-[(3,5-bis-trifluoromethyl-benzyl)-(5-bromo-pyrimidin-2-yl)-amino]-pyrrolidine-1-carboxylic acid tert-butyl ester (4.14 g, 68% for 2 steps). ESI-MS m/z: 570 [M+1]$^+$, Retention time 2.48 min (condition A).

To a mixture of (S)-3-[(3,5-Bis-trifluoromethyl-benzyl)-(5-bromo-pyrimidin-2-yl)-amino]-pyrrolidine-1-carboxylic acid tert-butyl ester (2.2 mmol, 1.28 g), 1-methylpyrazol-3-yl-4,4,5,5-tetramethyl-[1,3,2]dioxaborolane (2.7 mmol, 0.72 g), tetrakis(triphenylphosphine)palladium(0) (0.22 mmol, 260 mg) and 2M aqueous sodium hydrogen carbonate (3.2 mL) in 1,2-dimethoxy-ethane (15 mL) is allowed to warm to 95° C. and stirred for 3 hours. The mixture is cooled to room temperature and then added water. The mixture is extracted with CH$_2$Cl$_2$. The combined organic layer is dried over Na$_2$SO$_4$, filtrated, and concentrated under reduced pressure. The obtained residue is purified by silica gel column chromatography (eluent: n-hexane/EtOAc) to give (S)-3-{(3,5-bis-trifluoromethyl-benzyl)-[5-(1-methyl-1H-pyrazol-4-yl)-pyrimidin-2-yl]amino}-pyrrolidine-1-carboxylic acid tert-butyl ester 766 mg, 61%). ESI-MS m/z: 571 [M+1]+, Retention time 2.25 min (condition A).

Example 59

Synthesis of 2,4-dichloro-pyrimidine-5-carboxylic acid dimethylamide

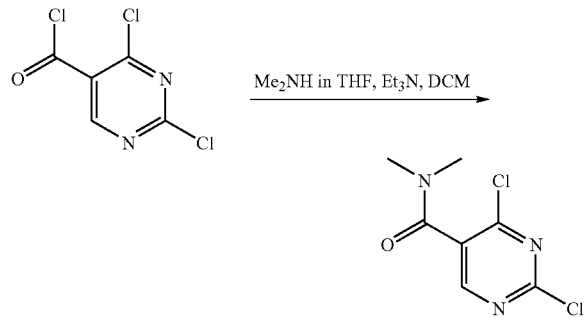

To a solution of 2,4-dichloro-pyrimidine-5-carbonyl chloride (197.7 mg, 0.94 mmol) in $CH_2Cl_2$ (9.4 mL) at RT is added $Me_2NH$ (2.0 M THF solution, 390 µL, 0.78 mmol) and $Et_3N$ (108.6 µL, 0.78 mmol) at 0° C. The reaction mixture is stirred overnight at RT. After adding water, the mixture is extracted with $CH_2Cl_2$. The organic layer is dried and concentration under reduce pressure give 2,4-dichloro-pyrimidine-5-carboxylic acid dimethylamide (272.5 mg, quant). ESI-MS m/z: 221 [M+1]+, Retention time 1.94 min (condition B).

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:
1. A compound of formula (I):

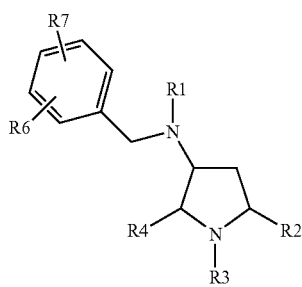

R1 is cycloalkyl, heterocyclyl, aryl, alkyl-O—C(O)—, or alkanoyl, wherein each cycloalkyl, heterocyclyl, or aryl is optionally substituted with one to three substituents selected from alkyl, aryl, haloalkyl, hydroxy, halogen, nitro, carboxy, thiol, cyano, $HSO_3$—, cycloalkyl, alkenyl, alkoxy, cycloalkoxy, alkenyloxy, alkyl-O—C(O)—, alkanoyl, carbamoyl, alkyl-S—, alkyl-SO—, alkyl-$SO_2$—, amino, monO—or di-substituted (alkyl, cycloalkyl, aryl and/or aryl-alkyl-) amino, $H_2N$-$SO_2$—, and heterocyclyl, and wherein each alkanoyl, alkyl-O—C(O)—, alkyl, alkoxy, or heterocyclyl is further optionally substituted with one to three substituents selected from hydroxy, alkyl, halogen, nitro, carboxy, thiol, cyano, HSO3—, cycloalkyl, alkenyl, alkoxy, cycloalkoxy, alkenyloxy, alkyl-O—C(O)—, alkanoyl, carbamoyl, alkyl-S-, alkyl-SO—, alkyl-$SO_2$—, amino, mono- or di-substituted (alkyl, cycloalkyl, aryl and/or aryl-alkyl-)amino, and $H_2N$—$SO_2$—, and heterocyclyl;

R2 is alkyl, cycloalkyl, or cycloalkyl-alkyl-, wherein each alkyl or cycloalkyl is optionally substituted with one to three substituents selected from alkyl, alkoxy and halogen;

R3 is R8-O—C(O)—, (R8)(R9)N—C(O)—, R8-C(O)—, aryl, heterocyclyl or heteroaryl, wherein R8 and R9 are independently hydrogen, alkyl, -C(O)O-alkyl, alkyl-O(O)C-alkyl-, amino-(O)C-alkyl-, cycloalkyl, aryl, heteroaryl, heterocyclyl, aryl-alkyl-, heteroaryl-alkyl-, heterocyclyl-alkyl- or cycloalkyl-alkyl-, wherein each alkyl, cycloalkyl, aryl, aryl-alkyl- or cycloalkyl-alkyl- is optionally substituted with one to three substituents selected from alkyl, hydroxy, halogen, nitro, carboxy, thiol, cyano, $HSO_3$—, cycloalkyl, alkenyl, alkoxy, cycloalkoxy, alkenyloxy, alkyl-haloalkyl, alkyl-O—C(O)—, alkanoyl, carbamimidoyl, alkyl-S—, alkyl-SO—, alkyl-$SO_2$—, amino, $H_2N$—$SO_2$—, and heterocyclyl, R8 and R9 may be taken together to form a 5 or 6-membered heterocyclyl or heteroaryl, which can be substituted with substituents selected from alkyl, hydroxy, halogen, nitro, carboxy, thiol, cyano, $HSO_3$—, cycloalkyl, alkenyl, alkoxy, cycloalkoxy, alkenyloxy, alkyl-haloalkyl, alkyl-O—C(O)—, alkanoyl, carbamimidoyl, alkyl-S—, alkyl-SO—, alkyl-$SO_2$—, amino, $H_2N$—$SO_2$—, and heterocyclyl;

R4 is hydrogen, alkyl, alkoxy, cycloalkyl, aryl, heteroaryl, aryl-alkyl-, cycloalkyl-alkyl-, or heteroaryl-alkyl-, wherein each alkyl, cycloalkyl, aryl, heteroaryl, aryl-alkyl-, cycloalkyl-alkyl-, or heteroaryl-alkyl- is optionally substituted with one to three substituents selected from alkyl, hydroxy, halogen, haloalkyl, nitro, carboxy, thiol, cyano, $HSO_3$—, cycloalkyl, alkenyl, alkoxy, cycloalkoxy, haloalkoxy, alkenyloxy, alkyl-O—C(O)—, alkanoyl, carbamimidoyl, alkyl-S—, alkyl-SO—, alkyl-$SO_2$—, amino, mono- or di-substituted (alkyl, cycloalkyl, aryl and/or aryl-alkyl-) amino, $H_2N$—$SO_2$—, and heterocyclyl;

R6 and R7 are independently hydrogen, alkyl, haloalkyl, halogen, cyano, nitro, hydroxy, amino, dialkylamino, or alkoxy, haloalkoxy; or R6 is aryl, heteroaryl, or alkyl-S(O)$_2$—, wherein each aryl or heteroaryl is optionally substituted with one to three substituents selected from alkyl, hydroxy, halogen, nitro, carboxy, thiol, cyano, $HSO_3$—, cycloalkyl, alkenyl, alkoxy, cycloalkoxy, alkenyloxy, alkyl-O—C(O)—, alkanoyl, carbamimidoyl, alkyl-S—, alkyl-SO—, alkyl-$SO_2$—, amino, and $H_2N$—$SO_2$— heterocyclyl;

or a pharmaceutically acceptable salt thereof; or an optical isomer thereof; or a mixture of optical isomers thereof.

2. The compound according to claim 1 wherein

R1 is cycloalkyl, heterocyclyl, aryl, alkyl-O—C(O)—, or alkanoyl, wherein each cycloalkyl, heterocyclyl, or aryl is optionally substituted with one to three substituents selected from alkyl, aryl, haloalkyl, hydroxy, halogen, nitro, carboxy, thiol, cyano, $HSO_3$—, cycloalkyl, alkenyl, alkoxy, cycloalkoxy, alkenyloxy, alkyl-O—C(O)—, carbamoyl, alkyl-S—, alkyl-SO—, alkyl-$SO_2$—, amino, alkylamino, $H_2N$—$SO_2$—, alkanoyl, or heterocyclyl; and wherein each alkanoyl, alkyl-O—C(O)—, alkyl, or heterocyclyl is further optionally substituted with one to three substituents selected from hydroxy, halogen, nitro, carboxy, thiol, cyano, HSO$_3$—, cycloalkyl, alkenyl, alkoxy, cycloalkoxy, alkenyloxy, alkyl-O—C(O)—, carbamoyl, alkyl-S—, alkyl-SO—, alkyl-SO$_2$—, amino, H$_2$N—SO$_2$—, alkanoyl, and heterocyclyl;

R2 is alkyl;

R3 is R8-O—C(O)—, (R8)(R9)N—C(O)—, R8-C(O)—, or heteroaryl;

R4 is hydrogen, aryl, alkyl, aryl-alkyl-, cycloalkyl, cycloalkyl-alkyl-, heteroaryl, or heteroaryl-alkyl-, wherein each aryl, aryl-alkyl-, cycloalkyl, cycloalkyl-alkyl-, heteroaryl, or heteroaryl-alkyl- is optionally substituted with one to three substituents selected from alkyl, haloalkyl, hydroxy, halogen, nitro, carboxy, thiol, cyano, HSO$_3$—, cycloalkyl, alkenyl, alkoxy, haloalkoxy, cycloalkoxy, alkenyloxy, alkoxycarbonyl, alkyl-S—, alkyl-SO—, alkyl-SO$_2$—, amino, mono- or di-substituted (alkyl, cycloalkyl, aryl and/or aryl-alkyl-) amino; H$_2$N—SO$_2$—, and alkanoyl;

R6 and R7 are independently hydrogen, alkyl, haloalkyl, halogen, cyano, nitro, hydroxy, dialkylamino, or alkoxy; or R6 is aryl, heteroaryl, or R8-S(O)$_2$—;

R8 is hydrogen, alkyl, cycloalkyl, aryl, aryl-alkyl- or cycloalkyl-alkyl-; or a pharmaceutically acceptable salt thereof; or an optical isomer thereof; or a mixture of optical isomers thereof.

3. The compound according to claim 1, wherein

R1 is alkyl-O—C(O)—, alkanoyl or heterocyclyl, wherein said heterocyclyl is optionally substituted with one to three substituents selected from halogen, dialkylamino, alkoxy and heterocyclyl, wherein the substituent heterocyclyl is further optionally substituted with one to three substituents selected from alkyl, hydroxy and alkanoyl, R2 is alkyl;

R3 is alkyl-O—C(O)—, cycloalkyl-C(O)—, or heteroaryl;

R4 is hydrogen, aryl-alkyl- optionally substituted by one to three alkyl or halogen; and R6 and R7 are independently halogen, alkyl, haloalkyl, alkoxy, or a pharmaceutically acceptable salt thereof; or an optical isomer thereof; or a mixture of optical isomers thereof.

4. The compound according to claim 1, 2 or 3, wherein

R1 is (C1-C7)alkyl-O—C(O)—, or 5- or 6-membered heterocyclyl, wherein said heterocyclyl is optionally substituted with one to three substituents selected from halogen, dialkylamino, (C1-C7) alkoxy, and 5- or 6-membered heterocyclyl, wherein said heterocyclyl is further optionally substituted with one to three substituents selected from (C1-C7)alkanoyl and hydroxy;

R2 is (C1-C7) alkyl;

R3 is (C1-C7)alkyl-O—C(O)—, 5- or 6-membered cycloalkyl-C(O)—, or heteroaryl;

R4 is hydrogen; and

R6 and R7 are independently halogen, (C1-C7) alkyl, (C1-C7) haloalkyl or (C1-C7) alkoxy, or a pharmaceutically acceptable salt thereof; or an optical isomer thereof; or a mixture of optical isomers thereof.

5. A method of inhibiting CETP activity in a subject, comprising:
administering to the subject a therapeutically effective amount of the compound of formula (I) according to claim 1.

6. A method of ameliorating or slowing or delaying the progression of a disorder or a disease in a subject mediated by CETP or responsive to inhibition of CETP, comprising:
administering to the subject a therapeutically effective amount of the compound of formula (I) according to any of claims 1 to 3 wherein the disorder or the disease is selected from hyperlipidemia, arteriosclerosis, atherosclerosis, peripheral vascular disease, hyperbetalipoproteinemia, hypoalphalipoproteinemia, hypercholesterolemia, hypertriglyceridemia, familial hypercholesterolemia, coronary heart disease, coronary artery disease, coronary vascular disease, angina, ischemia, heart ischemia, thrombosis, cardiac infarction such as myocardial infarction, stroke, peripheral vascular disease, reperfusion injury, angioplasty restenosis, hypertension, congestive heart failure, type II diabetes mellitus, diabetic vascular complications, obesity and endotoxemia.

7. A pharmaceutical composition, comprising:
a therapeutically effective amount of a compound of formula (I) according to any of claims 1 to 3, or a pharmaceutically acceptable salt thereof; or an optical isomer thereof; or a mixture of optical isomers thereof; and
a pharmaceutically acceptable carrier.

8. A pharmaceutical composition, comprising:
a therapeutically effective amount of the compound according to claim 1, or a pharmaceutically acceptable salt thereof; or an optical isomer thereof; or a mixture of optical isomers thereof; and
one or more therapeutically active agents selected from the group consisting of a:
(i) HMG-Co-A reductase inhibitor or a pharmaceutically acceptable salt thereof,
(ii) angiotensin II receptor antagonist or a pharmaceutically acceptable salt thereof,
(ii) angiotensin converting enzyme (ACE) Inhibitor or a pharmaceutically acceptable salt thereof,
(iv) calcium channel blocker or a pharmaceutically acceptable salt thereof,
(v) aldosterone synthase inhibitor or a pharmaceutically acceptable salt thereof,
(vi) aldosterone antagonist or a pharmaceutically acceptable salt thereof,
(vii) dual angiotensin converting enzyme/neutral endopeptidase (ACE/NEP) inhibitor or a pharmaceutically acceptable salt thereof,
(viii) endothelin antagonist or a pharmaceutically acceptable salt thereof,
(ix) renin inhibitor or a pharmaceutically acceptable salt thereof,
(x) diuretic or a pharmaceutically acceptable salt thereof, and
(xi) an ApoA-I mimic.

9. The compound according to claim 1 selected from the group consisting of
(2S,3S,5R)-2-Benzyl-3-[(3,5-bis-trifluoromethyl-benzyl)-methoxycarbonyl-amino]-5-ethyl-pyrrolidinr-1-carboxylic acid tert-butyl ester;
(2S,3S,5R)-2-Benzyl-3-[(5-bromo-pyrimidin-2-yl)-(3-chloro-5-trifluoromethyl-benzyl)-amino]-5-ethyl-pyrrolidine-1-carboxylic acid isopropyl ester;
(2S ,3S, 5R)-2-Benzyl-3-{(3-chloro-5-trifluoromethyl-benzyl)-[5-(1-methyl-1H-pyrazol-4-yl)-pyrimidin-2-yl]-amino}-5-ethyl-pyrrolidine-1-carboxylic acid isopropyl ester;

(2R,4S)-4-{(3,5-Bis-trtfluoromethyl-benzyl)-[5-(1-methyl-1H-pyrazol-4-yl)-pyrimidin-2-yl]-amino}-2-ethyl-pyrrolidine-1-carboxylic acid tert-butyl ester;

(2R,4S)-4-{(3,5-Bis-trtfluoromethyl-benzyl)[5-(1-methyl-1H-pyrazol-4-yl)-pyrimidin-2-yl]amino}-2-ethyl-pyrrolidine-1-carboxylic acid 4-carboxy-cyclohexyl ester;

(2R,4S)-4-{(3,5-Bis-trtfluoromethyl-benzyl)[5-(1-methyl-1H-pyrazol-4-yl)-pyrimidin-2-yl]amino}-2-ethyl-pyrrolidine-1-carboxylic acid 4-carboxy-cyclohexyl ester;

(2R,4S)-4-{(3,5-Bis-trtfluoromethyl-benzyl)[5-(1-methyl-1H-pyrazol-4-yl)-pyrimidin-2-yl]amino}-2-ethyl-pyrrolidine-1-carboxylic acid 2-carboxy-2-methyl-propyl ester;

(2R,4S)-4-{(3,5-Bis-trtfluoromethyl-benzyl)[5-(1-methyl-1H-pyrazol-4-yl)-pyrimidin-2-yl]-amino}-2-ethyl-pyrrolidine-1-carboxylic acid 3-carboxy-3-methyl-butyl ester;

(2R,4S)-4-{(3,5-Bis-trtfluoromethyl-benzyl)[5-(1-methyl-1H-pyrazol-4-yl)-pyrimidin-2-yl]-amino}-2-ethyl-pyrrolidine-1-carboxylic acid 3-carboxy-cyclobutyl ester;

(2R,4S)-4-{(3,5-Bis-trtfluoromethyl-benzyl)[5-(1-methyl-1H-pyrazol-4-yl)-pyrimidin-2-yl]-amino}-2-ethyl-pyrrolidine-1-carboxylic acid 4-carboxy-cyclohexylmethyl ester;

(2R,4S)-4-{(3,5-Bis-trfluoromethyl-benzyl)[5-(1-methyl-1H-pyrazol-4-yl)-pyrimidin-2-yl]amino}-2-ethyl-pyrrolidine-1-carboxylic acid 3-carboxy-cyclobutyl ester;

(2R,4S)-4-{(3,5-Bis-trtfluoromethyl-benzyl)[5-(1-methyl-1H-pyrazol-4-yl)-pyrimidin-2-yl]-amino}-2-ethyl-pyrrolidine-1-carboxylic acid 1-carboxy-cyclopentylmethyl ester;

4-{[(((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidine-1-carbonyl)-ethyl-amino]-methyl}-cyclohexanecarboxylic acid;

(2R,4S)-4-{(3,5-Bis-trtfluoromethyl-benzyl)[5-(1-methyl-1H-pyrazol-4-yl)-pyrimidin-2-yl]-amino}-2-ethyl-pyrrolidine-1-carboxylic acid 4-carboxymethyl-cyclohexylmethyl ester;

(S)-1-((2R,4S)-4-{(3,5-Bis-trifluoronnethyl-benzyl)[5-(1-methyl-1H-pyrazol-4-yl)-pyrimidin-2-yl]-amino}-2-ethyl-pyrrolidine-1-carbonyl)-pyrrolidine-2-carboxylic acid;

(S)-1-((2R,4S)-4-{(3,5-Bis-trifluoronnethyl-benzyl)-[5-(1-methyl-1H-pyrazol-4-yl)-pyrimidin-2-yl]-amino}-2-ethyl-pyrrolidine-1-carbonyl)-pyrrolidine-2-carboxylic acid;

4-[((2R,4S)-4-{(3,5-Bis-trifluoronnethyl-benzyl)-[5-(1-methyl-1H-pyrazol-4-yl)-pyrimidin-2-yl]-amino}-2-ethyl-pyrrolidine-1-carbonyl)-amino]-cyclohexanecarboxylic acid;

4-[((2R,4S)-4-{(3,5-Bis-trifluoronnethyl-benzyl)-[5-(1-methyl-1H-pyrazol-4-yl)-pyrimidin-2-yl]-amino}-2-ethyl-pyrrolidine-1-carbonyl)-methyl-amino]-cyclohexanecarboxylic acid;

((2R,4S)-4-{(3,5-Bis-trifluoromethyl-benzyl)-[5-(1-methyl-1H-pyrazol-4-yl)-pyrimidin-2-yl]-amino}-2-ethyl-pyrrolidin-1-yl)-oxo-acetic acid ethyl ester;

1-((2R,4S)-4-{(3,5-Bis-trifluoromethyl-benzyl)[5-(1-methyl-1H-pyrazol-4-yl)-pyrimidin-2-yl]-amino}-2-ethyl-pyrrolidin-1-yl)-ethanone;

1-((2R,4S)-4-{(3,5-Bis-trifluoromethyl-benzyl)[5-(1-methyl-1H-pyrazol-4-yl)-pyrimidin-2-yl]-amino}-2-ethyl-pyrrolidin-1-yl)-3-methyl-butan-1-one;

((2R,4S)-4-{(3,5-Bis-trifluoromethyl-benzyl)[5-(1-methyl-1H-pyrazol-4-yl)-pyrimidin-2-yl]-amino}-2-ethyl-pyrrolidin-1-yl)-cyclohexyl-methanone;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid isopropyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid isobutyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid 2,2-dimethyl-propyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid 4-methoxycarbonyl-cyclohexyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid 2-methoxycarbonyl-2-methyl-propyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid 1-ethoxycarbonyl-1-methyl-ethyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid 3-ethoxycarbonyl-3-methyl-butyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid tetrahydro-pyran-4-yl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid 3-methoxycarbonyl-phenyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid tetrahydro-pyran-4-ylmethyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid 3-methoxycarbonyl-cyclobutyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid 3-methoxycarbonyl-cyclobutyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid 4-methoxycarbonyl-cyclohexylmethyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid cyclohexylmethyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid 1-methoxycarbonyl-cyclopentylmethyl ester;

(2R,4S)-4-{(3,5-Bis-trifluoromethyl-benzyl)[5-(1-methyl-1H-pyrazol-4-yl)-pyrimidin-2-yl]-amino}-2- ethyl-pyrrolidine-1-carboxylic acid 4-ethoxycarbonyl-methyl-cyclohexylmethyl ester;

(2R,4S)-4-{(3,5-Bis-trfluoromethyl- benzyl)[5-(1-methyl-1H-pyrazol-4-yl)-pyrimidin-2-yl]-amino}-2-ethyl-pyrrolidine-1-carboxylic acid 3-carboxy-phenyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid 3-methyl-oxetan-3-ylmethyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid 1-ethyl-propyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid 2,2,2-trifluoro-ethyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid cyclopentyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid (R)-sec-butyl ester;

(2R,4S)-4-{(3,5-Bis-trifluoromethyl-benzyl)[5-(1 -methyl-1H-pyrazol-4-yl)-pyrimidin-2-yl]-amino}-2-ethyl-pyrrolidine-1-carboxylic acid (S)-sec-butyl ester;

(2R,4S)-4-{(3,5-Bis-trifluoromethyl-benzyl)[5-(1 -methyl-1H-pyrazol-4-yl)-pyrimidin-2-yl]-amino}-2-ethyl-pyrrolidine-1-carboxylic acid 3-ethyl-oxetan-3-ylmethyl ester;

(5R)-3-{(3,5-Bis-trifluoromethyl-benzyl)-[5-(1-methyl-1H-pyrazol-4-yl)-pyrimidin-2-yl]-amino}-5-ethyl-2-oxo-pyrrolidine-1-carboxylic acid tert-butyl ester;

(2R,4S)-4-{(3,5-Bis-trifluoromethyl-benzyl)[5-((S)-3-hydroxy-pyrrolidin- 1-yl)-pyrimidin-2-yl]-amino}-2-ethyl-pyrrolidine-1-carboxylic acid isopropyl ester;

(2R,4S)-4-[(3,5-Bis-trifluoromethyl-benzyl)-(5-morpholin-4-yl-pyrimidin-2-yl)-amino]-2-ethyl-pyrrolidine-1-carboxylic acid tert-butyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid 2-carbamoyl-2-methyl-propyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid 2-methyl-2-methylcarbamoyl-propyl ester;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid 1-dimethylcarbarnoyl-1-methyl-ethyl ester;

(2R,4S)-4-{(3,5-Bis-trfluoromethyl-benzyl)[5-(1H- pyrazol-4-yl)-pyrimidin-2-yl]-amino}-2-ethyl-pyrrolidine-1-carboxylic acid isopropyl ester;

2-((2R,4S)-4-{(3,5-Bis-trifluoromethyl-benzyl)[5-(1-methyl-1H-pyrazol-4-yl)-pyrimidin-2-yl]-amino}-2-ethyl-pyrrolidin-1-yl)-oxazole-4-carboxylic acid ethyl ester;

((b 2R,4S)-4-{(3,5-Bis-trifluoromethyl-benzyl)[5-(1-methyl-1H-pyrazol-4-yl)-pyrimidin-2-yl]-aminoino}-2-ethyl-pyrrolidin-1-yl)-pyrrolidin-1-yl-methanone;

4-{[((2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carbonyl)-ethyl-amino]methyl}-cyclohexanecarboxylic acid methyl ester;

R2R,4S)-4-{(3,5-Bis-trifluoronnethyl-benzyl)[5-(1-methyl-1H-pyrazol-4-yl)-pyrimidin-2-yl]-amino}-2-ethyl-pyrrolidin-1-yl)-piperidin-1-yl-methanone;

(S)-1((2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carbonyl)-piperidine-3-carboxylic acid ethyl ester;

(S)-1-((2R,4S)-4-{(3,5-Bis-trifluoronnethyl-benzyl)-[5-(1-methyl-1H-pyrazol-4-yl)-pyrimidin-2-yl]-amino}-2-ethyl-pyrrolidine-1-carbonyl)-piperidine-2-carboxylic acid methyl ester;

((2R,4S)-4-{(3,5-Bis-trifluoronnethyl-benzyl)[5-(1-methyl-1H-pyrazol-4-yl)-pyrimidin-2-yl]-amino}-2-ethyl-pyrrolidin-1-yl)-cyclohexyl-methanone;

1-[4-((2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carbonyl)-piperazin-1-yl]ethanone;

((2R,4S)-4-{(3,5-Bis-trifluoromethyl-benzyl)[5-(1-methyl-1H-pyrazol-4-yl)-pyrimidin-2-yl]-amino}-2-ethyl-pyrrolidin-1-yl)-(2-cyclohexyl-pyrrolidin-1-yl)-methanone;

4((2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carbonyl)-piperazin-2-one;

((2R,4S)-4-{(3,5-Bis-trifluoromethyl-benzyl)[5-(1-methyl-1H-pyrazol-4-yl)-pyrimidin-2-yl]-amino}-2-ethyl-pyrrolidin-1-yl)-morpholin-4-yl-methanone;

(2R,4S)-4-{(3,5-Bis-trifluoromethyl-benzyl)[5-(1-methyl-1H-pyrazol-4-yl)-pyrimidin-2-yl]-amino}-2-ethyl-pyrrolidine-1-carboxylic acid dimethylamide;

(S)-3-{(3-Chlor0-5-trifluoromethyl-benzyl)[5-(1-methyl-1H-pyrazol-4-yl)-pyrimidin-2-yl]-amino}-pyrrolidine-1-carboxylic acid isopropyl ester;

2-{2-(3,5-Bis-trifluoromethyl-phenyl)-1-[(3R, 5R)-5-ethyl-1-(2-methoxymethyl-4-trifluoromethyl-phenyl)-pyrrolidin-3-yl]-ethyl}-5-(1-methyl-1H-pyrazol-4-yl)-pyrimidine;

(2R,4S)-4-[(3,5-Bis-trifluoromethyl-benzyl)-(5-bromo-pyrimidin-2-yl)-amino]-2-ethyl-pyrrolidine-1-carboxylic acid isopropyl ester;

(2R,4S)-4-[(3,5-Bis-trifluoromethyl-benzyl)-(5-morpholin-4-yl-pyrimidin-2-yl)-amino]-2-ethyl-pyrrolidine-1-carboxylic acid isopropyl ester;

(3,5-Bis-trifluoromethyl-benzyl)-[(3S,5R)-5-ethyl-1-(5-trifluoromethyl-pyridin-2-yl)-pyrrolidin-3-yl]-[5-(1-methyl-1H-pyrazol-4-yl)-pyrimidin-2-yl]-amine;

(3,5-Bis-trifluoromethyl-benzyl)-[(3S ,5R)-1-(6-chloro-pyrimidin-4-yl)-5-ethyl-pyrrolidin-3-yl]-[5-(1-methyl-1H-pyrazol-4-yl)-pyrimidin-2-yl]-amine;

1[4-((2R,4S)-4-{(3,5-Bis-trifluoromethyl-benzyl)[5-((S)-3-hydroxy-pyrrolidin-1-yl)-pyrimidin-2-yl]-amino}-2-ethyl-pyrrolidin-1-yl)-5-chloro-pyrimidin-2-yl]-piperidin-4-ol;

1-[4((2R,4S)-4-{(3,5-Bis-trifluoromethyl-benzyl)[5-(1-methyl-1H-pyrazol-4-yl)-pyrimidin-2-yl]-amino}-2-ethyl-pyrrolidin-1-yl)-5-chloro-pyrimidin-2-yl]-piperidin-4-ol;

1-[5-chloro-4-((2R,4S)-4-{[3,5-Bis(trifluoromethyl)-benzyl]-[5-(1-methyl-1H-pyrazol-4-yl)-pyrimidin-2-yl]-amino}-2-ethyl-pyrrolidin-1-yl)-pyrimidin-2-yl)-piperidine-4-carboxylic acid; and 1-(4-{(2R,4R)-4-[2-(3,5-Bis-trifluoromethyl-phenyl)-1-(5-morpholin-4-yl-pyrimidin-2-yl)-ethyl]-2-ethyl-pyrrolidin-1-yl}-5-chloro-pyrimidin-2-yl)-piperidine-4-carboxylic acid; or a pharmaceutically acceptable salt thereof; or an optical isomer thereof; or a mixture of optical isomers thereof.

10. The compound according to claim 1, wherein R1 is selected from

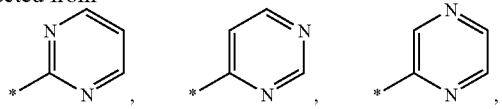

and pyridyl, wherein each is unsubstituted or substituted by $C_1$-$C_4$-alkyl, halo, $C_1$-$C_4$-alkoxy-carbonyl, $C_1$-$C_4$-alkyl-carbonyl, or hereocyclyl, or a pharmaceutically acceptable salt thereof; or an optical isomer thereof; or a mixture of optical isomers thereof.

11. The compound according to claim 10, wherein R1 is selected from

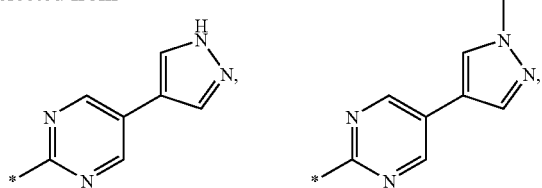

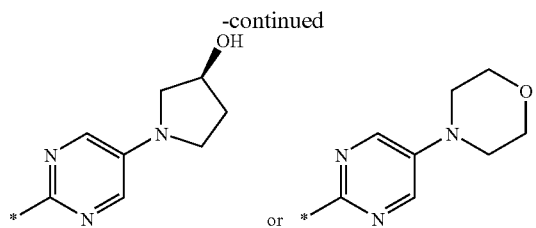

or a pharmaceutically acceptable salt thereof; or an optical isomer thereof; or a mixture of optical isomers thereof.

12. The method of claim 6, wherein the disorder or the disease is selected from atherosclerosis, hyperbetalipoproteinemia and hypoalphalipoproteinemia.

* * * * *